US010420789B2

(12) United States Patent
Pauza et al.

(10) Patent No.: US 10,420,789 B2
(45) Date of Patent: *Sep. 24, 2019

(54) METHODS AND COMPOSITIONS FOR THE ACTIVATION OF GAMMA-DELTA T-CELLS

(71) Applicant: American Gene Technologies International Inc., Rockville, MD (US)

(72) Inventors: Charles David Pauza, Baltimore, MD (US); Haishan Li, North Potomac, MD (US); Tyler Lahusen, Frederick, MD (US); Mei-Ling Liou, Germantown, MD (US)

(73) Assignee: American Gene Technologies International Inc., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/132,247

(22) Filed: Sep. 14, 2018

(65) Prior Publication Data

US 2019/0083523 A1 Mar. 21, 2019

Related U.S. Application Data

(63) Continuation of application No. 15/904,131, filed on Feb. 23, 2018, now Pat. No. 10,137,144, which is a continuation-in-part of application No. 15/652,080, filed on Jul. 17, 2017, now Pat. No. 9,914,938, which is a continuation of application No. PCT/US2017/013399, filed on Jan. 13, 2017.

(60) Provisional application No. 62/279,474, filed on Jan. 15, 2016.

(51) Int. Cl.
| | |
|---|---|
| *A61K 31/7105* | (2006.01) |
| *C12N 15/86* | (2006.01) |
| *C12N 15/113* | (2010.01) |
| *A61P 35/02* | (2006.01) |
| *A61K 47/68* | (2017.01) |
| *A61K 47/69* | (2017.01) |
| *A61K 31/675* | (2006.01) |
| *C12N 15/00* | (2006.01) |

(52) U.S. Cl.
CPC ........ *A61K 31/7105* (2013.01); *A61K 31/675* (2013.01); *A61K 47/6807* (2017.08); *A61K 47/6901* (2017.08); *A61P 35/02* (2018.01); *C12N 15/1137* (2013.01); *C12N 15/86* (2013.01); *C12Y 205/0101* (2013.01); *A61K 2300/00* (2013.01); *C12N 2310/14* (2013.01); *C12N 2310/531* (2013.01); *C12N 2330/51* (2013.01); *C12N 2740/16032* (2013.01); *C12N 2740/16043* (2013.01); *C12N 2740/16045* (2013.01); *C12N 2750/14143* (2013.01); *C12N 2810/6072* (2013.01)

(58) Field of Classification Search
None
See application file for complete search history.

(56) References Cited

U.S. PATENT DOCUMENTS

| 5,674,703 A | 10/1997 | Woo et al. |
|---|---|---|
| 6,156,514 A | 12/2000 | Acevedo et al. |
| 6,635,472 B1 | 10/2003 | Lauermann |
| 8,124,752 B2 | 2/2012 | Bumcrot et al. |
| 8,993,532 B2 | 3/2015 | Hannon et al. |
| 9,834,790 B1 | 12/2017 | Pauza et al. |
| 9,914,938 B2 | 3/2018 | Pauza et al. |
| 10,023,880 B2 | 7/2018 | Pauza et al. |
| 10,036,038 B2 | 7/2018 | Pauza et al. |
| 10,036,040 B2 | 7/2018 | Pauza et al. |
| 10,137,144 B2 | 11/2018 | Pauza et al. |
| 10,233,464 B2 | 3/2019 | Pauza et al. |
| 2002/0168345 A1 | 11/2002 | Dong et al. |
| 2003/0013196 A1 | 1/2003 | Engelman et al. |
| 2003/0096787 A1 | 5/2003 | Perridcaudet et al. |
| 2003/0119770 A1 | 6/2003 | Lai |
| 2003/0138444 A1 | 7/2003 | Zavitz et al. |
| 2004/0142416 A1 | 7/2004 | Laipis et al. |
| 2004/0161412 A1 | 8/2004 | Penn et al. |
| 2004/0192629 A1 | 9/2004 | Xu et al. |
| 2004/0214158 A1 | 10/2004 | Sethi et al. |
| 2005/0138677 A1 | 6/2005 | Pfister et al. |
| 2006/0183230 A1 | 8/2006 | Silla et al. |
| 2006/0246520 A1 | 11/2006 | Champagne et al. |
| 2007/0026521 A1 | 2/2007 | Colosi |
| 2007/0203333 A1 | 8/2007 | McSwiggen et al. |
| 2008/0003225 A1 | 1/2008 | Vie et al. |
| 2008/0003682 A1 | 1/2008 | Lois-Caballe et al. |
| 2008/0039413 A1 | 2/2008 | Morris et al. |
| 2008/0131940 A1 | 6/2008 | Chiu |
| 2008/0199961 A1 | 8/2008 | Rasko et al. |
| 2008/0293142 A1 | 11/2008 | Liu et al. |

(Continued)

FOREIGN PATENT DOCUMENTS

| BR | 2515 | 3/2019 |
|---|---|---|
| CN | 101805750 | 8/2010 |

(Continued)

OTHER PUBLICATIONS

Mason et al., "Inactivated Simian Immunodeficiency Virus-Pulsed Autologous Fresh Blood Cells as an Immunotherapy Strategy," Journal of Virology, vol. 83(3), pp. 1501-1510, (2009).
Blick et al., "Cyclophosphamide Enhances SB-728-T Engraftment to Levels Associated with HIV-RNA Control," CROI Conference on Retroviruses and Opportunistic Infections, Boston, Massachusetts, p. 141, (2014), (Abstract Only).
De Rose et al., "Safety, Immunogenicity and Efficacy of Peptide-Pulsed Cellular Immunotherapy in Macaques," Journal of Medical Primatology, vol. 27(2), pp. 69-78, (2008).

(Continued)

*Primary Examiner* — Sean McGarry
(74) *Attorney, Agent, or Firm* — Snell & Wilmer LLP

(57) ABSTRACT

The present invention relates generally to methods and compositions for gene therapy and immunotherapy that activate gamma delta T-cells, and in particular, can be used in the treatment of various cancers and infectious diseases.

20 Claims, 15 Drawing Sheets

Specification includes a Sequence Listing.

(56) References Cited

U.S. PATENT DOCUMENTS

| | | |
|---|---|---|
| 2009/0148936 A1 | 6/2009 | Stout et al. |
| 2009/0304688 A1 | 12/2009 | Fournie et al. |
| 2010/0017911 A1 | 1/2010 | Dawson et al. |
| 2010/0069372 A1 | 3/2010 | Kazantsev |
| 2010/0119511 A1 | 5/2010 | Wang et al. |
| 2010/0120155 A1 | 5/2010 | Brennan et al. |
| 2010/0286166 A1 | 11/2010 | Pey Rodriguez et al. |
| 2010/0316676 A1 | 12/2010 | Sanders |
| 2011/0008803 A1 | 1/2011 | Stockwell et al. |
| 2011/0207226 A1 | 8/2011 | Ni et al. |
| 2012/0053223 A1 | 1/2012 | Benkirane et al. |
| 2012/0027725 A1 | 2/2012 | Galvin et al. |
| 2012/0114607 A1 | 5/2012 | Lai et al. |
| 2012/0034197 A1 | 8/2012 | Young et al. |
| 2012/0201794 A1 | 8/2012 | Chen et al. |
| 2013/0090371 A1 | 4/2013 | Lu et al. |
| 2013/0142766 A1 | 6/2013 | Dodo et al. |
| 2013/0211380 A1 | 8/2013 | Aquino et al. |
| 2014/0155468 A1 | 6/2014 | Gregory et al. |
| 2014/0162894 A1 | 6/2014 | Hatchwell et al. |
| 2014/0178340 A1 | 6/2014 | Robbins et al. |
| 2014/0234958 A1 | 8/2014 | Kashara et al. |
| 2014/0248277 A1 | 9/2014 | Hoffman et al. |
| 2014/0336245 A1 | 11/2014 | Mingozzi et al. |
| 2015/0010578 A1 | 1/2015 | Balazs et al. |
| 2015/0018539 A1 | 1/2015 | Fellmann |
| 2015/0126580 A1 | 5/2015 | DePinho et al. |
| 2015/0132255 A1 | 5/2015 | Sorensen et al. |
| 2015/0176006 A1 | 6/2015 | Krause et al. |
| 2016/0060707 A1 | 3/2016 | Goldenberg et al. |
| 2016/0243169 A1 | 8/2016 | Chen et al. |
| 2017/0028036 A1 | 2/2017 | Mingozzi et al. |
| 2017/0335344 A1 | 11/2017 | Pauza et al. |
| 2018/0010147 A1 | 1/2018 | Pauza |
| 2018/0142257 A1 | 5/2018 | Pauza |
| 2018/0142258 A1 | 5/2018 | Pauza |
| 2018/0161455 A1 | 6/2018 | Pauza |
| 2018/0177866 A1 | 6/2018 | Pauza |
| 2018/0256624 A1 | 9/2018 | Pauza |
| 2018/0305716 A1 | 10/2018 | Pauza |
| 2019/0046633 A1 | 2/2019 | Pauza |
| 2019/0062786 A1 | 2/2019 | Pauza et al. |
| 2019/0078096 A1 | 3/2019 | Lahusen et al. |

FOREIGN PATENT DOCUMENTS

| | | |
|---|---|---|
| CN | 108883100 | 11/2018 |
| EP | 3402483 | 11/2018 |
| EP | 3413926 | 12/2018 |
| EP | 3426777 | 1/2019 |
| EP | 3468617 | 4/2019 |
| EP | 3468618 | 4/2019 |
| EP | 3481418 | 5/2019 |
| EP | 3481435 | 5/2019 |
| IN | 201947000153 | 2/2019 |
| JP | 2018-541270 | 4/2019 |
| WO | 2002020554 | 3/2002 |
| WO | 2004053137 | 6/2004 |
| WO | 2005033282 | 4/2005 |
| WO | 2006048215 | 5/2006 |
| WO | 2007133674 | 11/2007 |
| WO | WO2008/025025 | 2/2008 |
| WO | 2009100928 | 8/2009 |
| WO | 2009147445 | 12/2009 |
| WO | 2010051521 | 5/2010 |
| WO | 2011071476 | 6/2011 |
| WO | 2012048303 | 4/2012 |
| WO | 2012061075 | 5/2012 |
| WO | WO2012145624 | 10/2012 |
| WO | 2013096455 | 6/2013 |
| WO | 2014117050 | 7/2014 |
| WO | 2014187881 | 11/2014 |
| WO | 2015017755 | 2/2015 |
| WO | 2015042308 | 3/2015 |
| WO | 2015078999 | 6/2015 |
| WO | 2016046234 | 3/2016 |
| WO | 2016061232 | 4/2016 |
| WO | WO2016061232 | 4/2016 |
| WO | 2016200997 | 7/2016 |
| WO | 2017007994 | 1/2017 |
| WO | 2017100551 | 6/2017 |
| WO | 2017123918 | 7/2017 |
| WO | 2017139065 | 8/2017 |
| WO | 2017156311 | 9/2017 |
| WO | 2017213697 | 12/2017 |
| WO | 2017214327 | 12/2017 |
| WO | 2018009246 | 1/2018 |
| WO | 2018009847 | 1/2018 |
| WO | 2018017882 | 1/2018 |
| WO | 2018126112 | 7/2018 |
| WO | 2018129540 | 7/2018 |
| WO | 2018187231 | 10/2018 |
| WO | 2018232359 | 12/2018 |

OTHER PUBLICATIONS

Smith et al., "Developments in HIV-1 Immunotherapy and therapeutic Vaccination," F1000Prime Reports, vol. 6, p. 42, (2014).

Charron, "Gene Therapy for Phenylketonuria: Dominant-Negative Interference in a Recessive Disease," Dissertation, University of Florida 2005, http://etd.fcla.edu/UF/UFE0011392/charron_c.pdf>, (retrieved Jul. 26, 2018) (2005).

Ding et al., "Administration-Route and Gender-Independent Longterm Therapeutic Correction of Phenylketonuria (PKU) in a Mouse Model by Recombinant Adeno-Associated Virus 8 Pseudotyped Vector-Mediated Gene Transfer," Gene Therapy, vol. 13, pp. 583-587, (Dec. 1, 2005).

Nowacki et al., "The PAH Mutation Analysis Consortium Database: Update 1996," Nucleic Acid Research, vol. 25(1), pp. 139-142, (Jan. 1, 1997).

Condiotti et al., "Prolonged Liver-Specific Transgene Expression by a Non-Primate Lentiviral Vector," Biochemical and Biophysical Research Communications, vol. 320(3), pp. 998-1006, (Jul. 30, 2004).

PCT; International Search Report dated Sep. 24, 2018 in Application No. PCT/US2018/025733.

PCT; Written Opinion dated Sep. 24, 2018 in Application No. PCT/US2018/025733.

USPTO; Non-Final Office Action dated Oct. 19, 2018 in U.S. Appl. No. 15/736,284.

USPTO; Notice of Allowance dated Oct. 31, 2018 in U.S. Appl. No. 16/011,550.

Lin et al., "Up-Regulation of Bcl-2 is Required for the Progression of Prostate Cancer Cells from an Androgen-Dependent to an Androgen-Independent Growth Stage," Cell Research, vol. 17, pp. 531-536, (2007).

GenBank Sequence M65141.1 Retrieved from the Internet <URL: https://www.ncbi.nlm.nih.gov/nuccore/M65141.1. Especially Sequence, nt 301-420, (Retrieved Mar. 31, 2019).

PCT; International Search Report dated Apr. 12, 2019 in Application No. PCT/ US2018/053919.

PCT; Written Opinion dated Apr. 12, 2019 in Application No. PCT/US2018/053919.

USPTO; Non-Final Office Action dated Apr. 18, 2019 in U.S. Appl. No. 13/333,882.

Wang et al., "Butyrophilin 3A1 Plays an Essential Role in Prenyl Pyrophosphate Stimulation of Human Vg2Vd2 T Cells," Journal of Immunology, vol. 191(3), pp. 1029-1042, (Jul. 5, 2013).

Jiang et al., "A Novel EST-Derived RNAi Screen Reveals a Critical Role for Farnesyl Diphosphate Synthase in Beta2-Adrenergic Receptor Internalization and Down-Regulation," FASEB Journal, vol. 26(5), pp. 1-13, (Jan. 25, 2012).

Miettinen et al., "Mevalonate Pathway Regulates Cell Size Homeostasis and Proteostasis Through Autophagy," Cell Reports, vol. 13(11), pp. 2610-2620, (Dec. 2015).

Tolmachov, "Designing Lentiviral Gene Vectors," Viral Gene Therapy, Chapter 13, pp. 263-284, (2011).

Tracey, "Human DNA Sequence from Clone RP1-288M22 on Chromosome 6q 12-13," Complete Sequence, National Center for

(56) References Cited

OTHER PUBLICATIONS

Biotechnology. GenBank Entry. Retrieved from the internet: <https://www.ncbi.nlm.nih.gov/nucleotide/AL035467.23?report=genbank&log$=nucltop&blast_rank=1&RID=UUD4GX2D014>; pp. 1-34, (Jan. 24, 2013).
PCT; International Search Report dated Nov. 9, 2018 in Application No. PCT/US2018/037924.
PCT; Written Opinion dated Nov. 9, 2018 in Application No. PCT/US2018/037924.
USPTO; Advisory Action dated Nov. 16, 2018 in U.S. Appl. No. 13/333,882.
PCT; Invitation to Pay Additional Fees in Application No. PCT/US2018/053919 dated Feb. 22, 2019.
Gorziglia et al., "Elimination of Both E1 and E2A from Adenovirus Vectors Further Improves Prospects for In Vivo Human gene Therapy," Journal of Virology, vol. 70(6), pp. 4173-4178, (1996).
Vargas et al., "Novel Integrase-Defective Lentiviral Episomal Vectors for Gene Transfer," Human Gene Therapy, vol. 15(4), pp. 361-372, (Apr. 2004).
Wendelburg et al., "An Enhanced EBNA1 Variant with reduced IR3 Domain for Long-Term Episomal Maintenance and Transgene Expression of ORIP-Based Plasmids in Human Cells," GeneTherapy, vol. 5, pp. 1389-1399, (Oct. 1998).
Westerhout et al., "A Conditionally Replicating HIV-Based Vector that Stably Expresses an Antiviral shRNA Against HIV-1 Replication," Molecular Therapy: The Journal of the American Society of Gene Therapy, vol. 14(2), pp. 268-275, (May 2006).
Lam et al., "T-Cell Therapies for HIV," Immunotherapy, Future Medicine, vol. 5(4), pp. 407-414, (Apr. 2013).
Munoz et al., "Ex Vivo Expansion and Lentiviral Transduction of Macaca Nemestrina CD4 + T Cells," Journal of Medical Primatology, vol. 38(6), pp. 438-443, (Dec. 2009).
Porichis et al., "HIV-Specific CD4 T Cells and Immune Control of Viral Replication," Current Opinion in HIV and Aids, vol. 6(3), pp. 174-180, (May 2011).
Kavanagh et al., "Expansion of HIV-Specific CD4+ and CD8+ T Cells by Dendritic Cells Transfected with mRNA Encoding Cytoplasm- or Lysosome-Targeted Nef," Blood, American Society of Hematology, vol. 107(5), pp. 1963-1969, (Mar. 2006).
Akinsheye et al., "Fetal Hemoglobin in Sickle Cell Anemia," Blood, vol. 118(1), pp. 19-27, (2011).
USPTO; Non-Final Office Action dated Dec. 31, 2018 in U.S. Appl. No. 16/182,443.
EPO; Extended Search Report dated Dec. 12, 2018 in EP Application No. 16808223.8.
EPO; Extended Search Report dated Dec. 11, 2018 in EP Application No. 16822021.8.
Vargas, J. Jr. et al., "Conditionally Replicating Lentiviral-Hybrid Episomal Vectors for Suicide Gene Therapy," Antiviral Research, vol. 80(3), pp. 288-294, (2008).
Thompson et al., "Alkylamines Cause Vγ9Vδ2 T-Cell Activation and Proliferation by Inhibiting the Mevalonate Pathway," Blood, vol. 107, pp. 651-654, (2006).
Gober et al., "Human T Cell Receptor γδ Cells Recognize Endogenus Mevalonate Metabolites in Tumor Cells," Journal of Experimental Medicine, vol. 197, pp. 163-168, (2003).
Goepfert, et al., "Specificity and 6-Month Durability of Immune Responses Induced by DNA and Recombinant Modified Vaccinia Ankara Vaccines Expressing HIV-2 Virus-Like Particles," Journal of Infectious Diseases, vol. 210, pp. 99-110, (2014).
Human Papillomavirus Type 16 (HPV16), Complete Genome; GenBank: K02718.1; Publication [online], https://www.ncbi.nlm.nih.gov/nucleotide/333031?report=genbank&log$=nucltop&blast_rank=22&RID=H3E1THFU014; pp. 1-4 (1994).
{Long Control Regionγ [Human Papillomavirus, Type 16, Genomic, 860 nt]; Accession S60559. Publication [online]. https://www.ncbi.nlm.nih.gov/nucleotide/237343?report=genbank&log$=nucltop&blast_rank=1&RID=H3FCKA00014; p. 1, (1993).

Tebas, P. et al, "Antiviral Effects of Autologous CD4 T Cells Genetically Modified with a Conditionally Replicating Lentiviral Vector Expressing Long Antisense to HIV," Blood, vol. 121(9), pp. 1524-1533, (2013).
Tebas, P. et al., "Gene Editing of CCR5 in Autologous CD4 T Cells of Persons Infected with HIV," The New England Journal of Medicine, vol. 370(10), pp. 901-910, (2014).
Li et al., "Reduced Expression of the Mevalonate Pathway Enzyme Farnesyl Pyrophosphate Synthase Unveils Recognition of Tumor Cells by Vγ2Vδ2 T Cells," Journal of Immunology, vol. 182, pp. 8118-8124, (2009).
Wang et al., "Indirect Stimulation of Human Vγ2Vδ2 T Cells through Alterations in Isoprenoid Metabolism," Journal of Immunology, vol. 187, pp. 5099-5113, (2011).
Stunkel et al., "The Chromatin Structure of the Long Control Region of Human Papillomavirus Type 16 Repress Viral Oncoprotein Expression," Journal Of Virology, vol. 73(3), pp. 1918-1930, (1999).
Lu et al., "Anti-Sense-Mediated Inhibition of Human Immunodeficiency Virus (HIV) Replication by Use of an HIV Type 1-Based Vector Results in Severrly Attenuated Mutants Incapable of Developing Resistance," Journal of Virology, vol. 79(13), pp. 7079-7088, (2004).
Dieli et al., "Targeting Human γδ T Cells with Zoledronate and Interleukin-2 for Immunotherapy of Hormone-Refractory Prostate Cancer," Europe PMC Funders Group, Cancer Research, vol. 67(15), pp. 7450-1451, (2007).
GenBank Accession No. S60559 "(Long Control Region) [Human Papillomavirus, Type 16, Genomic, 860 nt]" https://ncbi.nlm.nih.gov/nuccore/S60559] entire DNA sequence, (1993).
GenBank Accession No. JG619773, MNESC1NG-T3-001_L15_6FEB2009_054 MNESC1NG Cell Culture from Mahonia Nervosa Berberis Nervosa cDNA, mRNA Sequence, (online). [Retrieved on Dec. 5, 2017]. Retrieved from the Internet :< URL: https://www.ncbi.nlm.nih.gov/nucest/JG619773 > entire document, (2014).
Moser et al., "γδ T Cells: Novel Initiators of Adaptive Immunity," Immunological Reviews, vol. 215, pp. 89-102, (2007).
Capietto, A. H. et al., "Stimulated γδ T Cells Increase the In Vivo Efficacy of Trastuzumab in HER-2+ Breast Cancer," Journal of Immunology, vol. 187(2), pp. 1031-1038, (2011).
Chen, Z. and M. S. Freedman, "CD16+ γδ T Cells Mediate Antibody Dependent Cellular Cytotoxicity: Potential Mechanism in the Pathogenesis of Multiple Sclerosis," Clinical Immunology, vol. 128(2), pp. 219-227, (2008).
Couzi, L. et al., "Antibody-Dependent Anti-Cytomegalovirus Activity of Human γδ T Cells Expressing CD16 (FcγRIIIa)," Blood, vol. 119(6), pp. 1418-1427, (2012).
Fisher, J. P. et al., "Effective Combination Treatment of GD2-Expressing Neuroblastoma and Ewing's Sarcoma Using Anti-GD2 ch14.18/CHO Antibody with Vγ9Vδ2+ γδT Cells," OncoImmunology, vol. 5(1), pp. e1025194, (2016).
Gertner-Dardenne, J. et al., "Bromohydrin Pyrophosphate Enhances Antibody-Dependent Cell-Mediated Cytotoxicity Induced by Therapeutic Antibodies," Blood 113(20), pp. 4875-4884, (2009).
Poonia, B. and C. D. Pauza, "Gamma Delta T Cells from HIV+ Donors can be Expanded In Vitro by Zoledronate/Interleukin-2 to Become Cytotoxic Effectors for Antibody-Dependent Cellular Cytotoxicity," Cytotherapy, vol. 14(2), pp. 173-181, (2012).
Schiller, C. B. et al., "CD19-Specific Triplebody SPM-1 Engages NK and γδ T Cells for Rapid and Efficient Lysis of Malignant B-Lymphoid Cells," Oncotarget, vol. 7(50), pp. 83392-83408, (2016).
Tokuyama, H. et al., "Vγ9Vδ2 T Cell Cytotoxicity Against Tumor Cells is Enhanced by Monoclonal Antibody Drugs—Rituximab and Trastuzumab," International Journal of Cancer, vol. 122(11), pp. 2526-2534, (2008).
Zufferey et al., "Self-Inactivating Lentivirus Vector for Safe and Efficient In Vivo Gene Delivery," Journal of Virology, vol. 72(12), pp. 9873-9880, (1998).
Ostertag et al., "Brain Tumor Eradication and Prolonged Survival from Intratumoral Conversion of 5-Fluorocytosine to 5-fluorouracil Using a Nonlytic Retroviral Replicating Vector," Neuro-Oncology, vol. 14(2), pp. 145-159, (2012).
Twitty et al., "Retroviral Replicating Vectors Deliver Cytosine Deaminase Leading to Targeted 5-Fluorouracil-Mediated Cytotoxic-

(56) References Cited

OTHER PUBLICATIONS ity in Multiple Human Cancer Types," Human Gene Therapy Methods, vol. 27(1), pp. 17-31, (2016).
Charron et al., "Dominant-Negative Interference in the Pahenu2 Mouse Model of PKU: Effectiveness of Vectors Expressing Either Modified Forms of Phenylalanine Hydroxylase (PAH) or Ribozymes Plus a Hardened PAH mRNA," Molecular Therapy, vol. 11, pp. S163-S164, (2005).
Fusetti, et al., "Structure of Tetrameric Human Phenylalanine Hydroxylase and Its Implications for Phenylketonuria," Journal of Biological Chemistry, vol. 273(27), pp. 16962-16958, (1998).
Hafid et al., "Phenylketonuria: A Review of Current and Future Treatments," Translational Pediatrics, vol. 4(4), pp. 304-317, (2015).
Blau et al., "Phenylketonuria," The Lancet, vol. 376(9750), pp. 1417-1427, (2010).
Chandler et al., "Vector Design Influences Hepatic Genotoxicity After Adeno-Associated Virus Gene Therapy," Journal of Clinical Investigation, vol. 125(2), pp. 870-880, (2015).
Christophersen et al., "A Technique of Transumbilical Portal Vein Catheterization in Adults," The Archives of Surgery, vol. 95(6), pp. 960-963, (1967). (Abstract Only).
Bartholome, "Genetics and Biochemistry of the Phenylketonuria-Present State," Human Genetics, vol. 51(3), pp. 241-245, (1979).
Donsante et al., "AAV Vector Integration Sites in Mouse Hepatocellular Carcinoma," Science, vol. 317, p. 477, (2007).
Eisensmith et al., "Multiple Origins for Phenylketonuria in Europe," American Journal of Human Genetics, vol. 51(6), pp. 1355-1365, (1992).
Fisher et al., "The Inhibition of Phenylalanine and Tyrosine Hydroxylases by High Oxygen Levels," Journal of Neurochemistry, vol. 19(5), pp. 1359-1365, (1972). (Abstract Only).
Grisch-Chan et al., "Low-Dose Gene Therapy for Murine PKU Using Episomal Naked DNA Vectors Expressing PAH from Its Endogenous Liver Promoter," Molecular Therapy Nucleic Acids, vol. 7, pp. 339-349, (2017).
Guldberg et al., "Aberrant Phenylalanine Metabolism in Phenylketonuria Heterozygotes," Journal of Inherited Metabolic Disease, vol. 21(4), pp. 365-372, (1998).
Kaufman et al., "A Model of Human Phenylalanine Metabolism in Normal Subjects and in Phenylketonuric Patients," Proceedings of the National Academy of Sciences USA, vol. 96(6), pp. 3160-3164, (1999).
Kaufman et al., "Phenylalanine Hydroxylase Activity in Liver Biopsies from Hyperphenylalaninemia Heterozygotes: Deviation from Proportionality with Gene Dosage," Pediatric Research, vol. 9(8), pp. 632-634, (1975).
Longo et al., "Single-Dose, Subcutaneous Recombinant Phenylalanine Ammonia Lyase Conjugated with Polyethylene Glycol in Adult Patients with Phenylketonuria: An Open-Label, Multicentre, Phase 1 Dose-Escalation Trial," The Lancet, vol. 384(9937), pp. 37-44, (2014).
Mochizuki et al., "Long-Term Correction of Hyperphenylalaninemia by AAV-Mediated Gene Transfer Leads to Behavioral Recovery in Phenylketonuria Mice," Gene Therapy, vol. 11(13), pp. 1081-1086, (2004).
Nault et al., "Adeno-Associated Virus Type 2 as an Oncogenic Virus in Human Hepatocellular Carcinoma," Molecular & Cellular Oncology, vol. 3(2), p. e1095271, 3 pages, (2016).
Oh et al., "Reversal of Gene Expression Profile in the Phenylketonuria Mouse Model After Adeno-Associated Virus Vector-Mediated Gene Therapy," Molecular Genetics and Metabolism, vol. 86(Supp. 1), pp. S124-S132, (2005).
Oh et al., "Long-Term Enzymatic and Phenotypic Correction in the Phenylketonuria Mouse Model by Adeno-Associated Virus Vector-Mediated Gene Transfer," Pediatric Research, vol. 56(2), pp. 278-284, (2004).
Pan et al., "Biodistribution and Toxicity Studies of VSVG-Pseudotyped Lentiviral Vector After Intravenous Administration in Mice with the Observation of in Vivo Transduction of Bone Marrow," Molecular Therapy, vol. 6(1), pp. 19-29, (2002).
Shedlovsky et al., "Mouse Models of Human Phenylketonuria," Genetics, vol. 134(4), pp. 1205-1210, (1993).
Yagi et al., "Complete Restoration of Phenylalanine Oxidation in Phenylketonuria Mouse by a Self-Complementary Adeno-Associated Virus Vector," Journal of Gene Medicine, vol. 13(2), pp. 114-122, (2011).
Yano et al., "Evaluation of Tetrahydrobiopterin Therapy with Large Neutral Amino Acid Supplementation in Phenylketonuria: Effects on Potential Peripheral Biomarkers, Melatonin and Dopamine, for Brain Monoamine Neurotransmitters," PLoS One, vol. 11(8), p. e0160892, 14 pages, (2016).
PCT: International Search Report dated Nov. 7, 2016 in Application No. PCT/US2016/036519.
PCT: Written Opinion dated Nov. 7, 2016 in Application No. PCT/US2016/036519.
PCT: International Search Report dated Oct. 19, 2016 in Application No. PCT/US2016/041456.
PCT: Written Opinion dated Oct. 19, 2016 in Application No. PCT/US2016/041456.
PCT: International Search Report dated Jul. 20, 2017 in Application No. PCT/US2017/043157.
PCT: Written Opinion dated Jul. 20, 2017 in application No. PCT/US2017/043157.
PCT: International Search Report dated Jun. 9, 2017 in Application No. PCT/US2016/066185.
PCT: Written Opinion dated Jun. 9, 2017 in Application No. PCT/US2016/066185.
PCT: International Search Report dated Jul. 17, 2017 in Application No. PCT/US2017/013019.
PCT: Written Opinion dated Jul. 17, 2017 in Application No. PCT/US2017/013019.
PCT: International Search Report dated May 26, 2017 in Application No. PCT/US2017/013399.
PCT: Written Opinion dated May 26, 2017 in Application No. PCT/US2017/013399.
PCT: International Search report dated Aug. 25, 2017 in Application No. PCT/US2017/021639.
PCT: Written Opinion dated Aug. 25, 2017 Application No. PCT/US2017/021639.
PCT: International Search Report dated Nov. 8, 2017 Application No. PCT/US2017/041168.
PCT: Written Opinion dated Nov. 8, 2017 in Application No. PCT/US2017/041168.
PCT: International Search Report dated Dec. 15, 2017 in Application No. PCT/US2017/36433.
PCT: Written Opinion dated Dec. 15, 2017 in Application No. PCT/US2017/36433.
PCT: International Search Report date Jul. 14, 2017 in Application No. PCT/US2017/013024.
PCT: Written Opinion dated Jul. 14, 2017 in application No. PCT/US2017/013024.
PCT: International Search Report dated May 29, 2018 in Application No. PCT/US2018/012998.
PCT: Written Opinion dated May 29, 2018 in Application No. PCT/US2018/012998.
USPTO; Notice of Allowance dated Oct. 13, 2017 in U.S. Appl. No. 14/706,481.
USPTO; Requirement for Restriction dated Oct. 23, 2017 in U.S. Appl. No. 15/668,223.
USPTO; Notice of Allowance dated Nov. 2, 2017 in U.S. Appl. No. 15/652,080.
USPTO; Non-Final Office Action dated Feb. 22, 2018 in U.S. Appl. No. 15/850,937.
USPTO; Non-Final Office Action dated Feb. 22, 2018 in U.S. Appl. No. 15/849,062.
USPTO; Non-Final Office Action dated Feb. 22, 2018 in U.S. Appl. No. 13/333,882.
USPTO; Notice of Allowance dated Mar. 26, 2018 in U.S. Appl. No. 15/668,223.
USPTO; Notice of Allowance dated Apr. 23, 2018 in U.S. Appl. No. 15/850,937.
USPTO; Notice of Allowance dated Apr. 26, 2018 in U.S. Appl. No. 15/849,062.

(56) References Cited

OTHER PUBLICATIONS

USPTO; Non-Final Office Action dated Jun. 15, 2018 in U.S. Appl. No. 15/904,131.
USPTO; Requirement for Restriction dated Jul. 12, 2018 in U.S. Appl. No. 15/736,284.
USPTO; Invitation to Pay Additional Fees and, where Applicable, Protest Fee dated Jul. 17, 2018 in Application No. PCT/US2018/25733.
USPTO; Requirement for Restriction dated Aug. 3, 2018 in U.S. Appl. No. 16/011,550.
USPTO; Notice of Allowance dated Aug. 10, 2018 in U.S. Appl. No. 15/904,131.
USPTO; Final Office Action dated Aug. 27, 2018 in U.S. Appl. No. 13/333,882.
USPTO; Non-Final Office Action dated Sep. 19, 2018 in U.S. Appl. No. 16/011,550.
USPTO; Invitation to Pay Additional Fees and, where Applicable, Protest Fee dated Sep. 11, 2018 in Application No. PCT/US2018/37924.
USPTO; Final Office Action dated May 2, 2019 in U.S. Appl. No. 15/736,284.
USPTO; Final Office Action dated May 2, 2019 in U.S. Appl. No. 16/182,443.
USPTO; Non-Final Office Action dated May 7, 2019 in U.S. Appl. No. 16/008,991.
USPTO; Non-Final Office Action dated May 24, 2019 in U.S. Appl. No. 16/218,010.
USPTO; Notice of Allowance dated Jul. 3, 2019 in U.S. Appl. No. 16/182,443.
EPO; Extended Search Report dated Jun. 6, 2019 in EP Application No. 17739028.3.

METHODS AND COMPOSITIONS FOR THE ACTIVATION OF GAMMA-DELTA T-CELLS

CROSS-REFERENCE TO RELATED APPLICATIONS

This application is a continuation of U.S. patent application Ser. No. 15/904,131 filed on Feb. 23, 2018 entitled "METHODS AND COMPOSITIONS FOR THE ACTIVATION OF GAMMA-DELTA T-CELLS", which is a continuation in part of U.S. patent application Ser. No. 15/652,080 filed on Jul. 17, 2017 entitled "METHODS AND COMPOSITIONS FOR THE ACTIVATION OF GAMMA-DELTA T-CELLS", which is a continuation of International Application No. PCT/US17/13399 filed on Jan. 13, 2017 entitled "METHODS AND COMPOSITIONS FOR THE ACTIVATION OF GAMMA-DELTA T-CELLS", which claims priority to U.S. Provisional Patent Application No. 62/279,474 filed on Jan. 15, 2016 entitled "METHODS AND COMPOSITIONS FOR THE ACTIVATION OF GAMMA-DELTA T-CELLS", the disclosures of which are incorporated herein by reference.

FIELD OF THE INVENTION

The present disclosure relates generally to the fields of gene therapy and immunotherapy, specifically in relation to increased activation and effector cell function of gamma delta ("GD") T cells.

BACKGROUND

Human T cells are distinguished on the basis of T cell receptor structure. The major populations, including CD4+ and CD8+ subsets, express a receptor composed of alpha and beta chains. A smaller subset expresses T cell receptor made from gamma and delta chains. Gamma delta ("GD") T cells make up 3-10% of circulating lymphocytes, and a Vδ2+ subset makes up 75% of GD T cells in blood. Vδ2+ cells recognize non-peptide epitopes and do not require antigen presentation by major histocompatibility complexes ("MHC") or human leukocyte antigen ("HLA"). The majority of Vδ2+ T cells also express a Vγ9 chain and are stimulated by exposure to 5-carbon pyrophosphate compounds that are intermediates in mevalonate and non-mevalonate sterol/isoprenoid synthesis pathways. The response to isopentenyl pyrophosphate (5-carbon) is universal among healthy human beings.

Another subset of GD T cells, Vδ1+, make up a much smaller percentage of the T cells circulating in the blood, but Vδ+1 cells are commonly found in the epithelial mucosa and the skin.

In general, GD T cells have several functions, including killing tumor cells and pathogen-infected cells. Stimulation through their unique T cell receptor ("TCRs") composed of two glycoprotein chains, γ and δ, improves the capacity for cellular cytotoxicity, cytokine secretion and other effector functions. The TCRs of GD T cells have unique specificities and the cells themselves occur in high clonal frequencies, thus allowing rapid innate-like responses to tumors and pathogens.

Bisphosphonate drugs and other inhibitors of farnesyl diphosphate synthase ("FDPS"), which are downstream from isopentenyl pyrophosphate ("IPP") in the mevalonate pathway (see, for e.g., FIG. 1), have been used to treat various diseases, including cancers, specifically those involving bone metastasis. Bisphosphonate drugs include, for example, Zometa® (Novartis) and Fosamax® (Merck).

Certain bisphosphonates have also been investigated for stimulation of GD T cells. This may be because when FDPS is inhibited in myeloid cells, IPP begins to accumulate and geranylgeranyl pyrophosphate ("GGPP"), a downstream product of FDPS that suppresses activation of the inflammasome pathway, is reduced. The reduction in GGPP removes an inhibitor of the caspase-dependent inflammasome pathway and allows secretion of mature cytokines including interleukin-beta and interleukin-18, the latter being especially important for gamma delta T cell activation.

Thus, when FDPS is blocked, the increased IPP and decreased GGPP combine to activate Vδ2+ T cells. Vδ2+ cells activated by IPP or bisphosphonates will proliferate rapidly, express a number of cytokines and chemokines, and can function to cytotoxically destroy tumor cells or cells infected with pathogenic microorganisms.

However, bisphosphonates are associated with inflammation and osteonecrosis, as well as having poor bioavailability due to their chemistry. Likewise, IPP has a very short half-life and is difficult to synthesize. Both types of compounds require systemic administration in an individual. Accordingly, both bisphosphonates in general, and IPP specifically, leave a great deal to be desired for therapeutic purposes involving activation of GD T cells.

SUMMARY OF THE INVENTION

In one aspect, a method of activating a GD T cell is provided. The method includes infecting, in the presence of the GD T cell, a target cell with a viral delivery system that encodes at least one genetic element. In embodiments, the at least one genetic element includes a small RNA capable of inhibiting production of an enzyme involved in the mevalonate pathway. In embodiments, the enzyme is FDPS. In embodiments, when the enzyme is inhibited in the target cell, the target cell subsequently activates the GD T cell. In embodiments, the target cell is a cancer cell or a cell that has been infected with an infectious agent. In a preferred embodiment, the activation of the GD T cell results in the GD T cell killing the cancer cell or the cell infected with an infectious agent. In embodiments, the at least one encoded genetic element includes a microRNA or a shRNA. In further embodiments, the target cell is also contacted with a bisphosphonate drug. In embodiments, the bisphosphonate drug is zoledronic acid.

In another aspect, a method of treating cancer in a subject is provided. The method includes administering to the subject a therapeutically-effective amount of a viral delivery system that encodes at least one genetic element. In embodiments, the at least one genetic element includes a small RNA capable of inhibiting production of an enzyme involved in the mevalonate pathway. In further embodiments, when the enzyme is inhibited in a cancer cell in the presence of a GD T cell, the cancer cell activates the GD T cell, to thereby treat the cancer. In embodiments, the enzyme is FDPS. In embodiments, the at least one encoded genetic element includes a microRNA or a shRNA. In further embodiments, the target cell is also contacted with a bisphosphonate drug. In embodiments, the bisphosphonate drug is zoledronic acid.

In another aspect, a method of treating an infectious disease in a subject is provided. The method includes administering to the subject a therapeutically-effective amount of a viral delivery system that encodes at least one genetic element. In embodiments, the at least one genetic element includes a small RNA capable of inhibiting production of an enzyme involved in the mevalonate pathway. In further embodiments, when the enzyme is inhibited in a cell that is infected with an infectious agent in the presence of a GD T cell, the infected cell activates the GD T cell, to thereby treat the infected cell, and the infectious disease. In embodiments, the enzyme is FDPS. In embodiments, the at least one encoded genetic element includes a microRNA or a shRNA. In further embodiments, the target cell is also contacted with a bisphosphonate drug. In embodiments, the bisphosphonate drug is zoledronic acid.

In another aspect, the at least one encoded genetic element includes a shRNA having at least 80%, or at least 85%, or at least 90%, or at least 95% percent identity with GTCCTGGAGTACAATGCCATTCTCGAGAATGGCATTGTACTCCAGGACTTTTT (SEQ ID NO: 1); GCAGGATTTCGTTCAGCACTTCTCGAGAAGTGCTGAACGAAATCCTGCTTTTT (SEQ ID NO: 2); GCCATGTACATGGCAGGAATTCTCGAGAA TTCCTGCCATGTACATGGCTTTTT (SEQ ID NO: 3); or GCAGAAGGAGGCTGAGAAAGTCTCGAGACTTTCTCAGCCTCCTTCTGCTTTTT (SEQ ID NO: 4). In a preferred embodiment, the shRNA includes GTCCTGGAGTACAATGCCATTCTCGAG AATGGCATTGTACTCCAGGACTTTTT (SEQ ID NO: 1); GCAGGATTTCGTTCA GCACTTCTCGAGAAGTGCTGAACGAAATCCTGCTTTTT (SEQ ID NO: 2); GCCA TGTACATGGCAGGAATTCTCGAGAATTCCTGCCATGTACATGGCTTTTT (SEQ ID NO: 3); or GCAGAAGGAGGCTGAGAAAGTCTCGAGACTTTCTCAGCCTCCTT CTGCTTTTT (SEQ ID NO: 4).

In another aspect, the at least one encoded genetic element includes a microRNA having at least 80%, or at least 85%, or at least 90%, or at least 95% percent identity with AAGGTATATTGCTGTTGACAGTGAGCGACACTTTCTCAGCCTCCTTCTGCGTGAAGC CACAGATGGCAGAAGGAGGCTGAGAAAGTGCTGCCTACTGCCTCGGACTTCAAGGG GCT (SEQ ID NO: 5); AAGGTATATTGCTGTTGACAGTGAGCGACACT TTCTCAGCCTCCTTCTGCGTGAAGCCACAGATGGCAGAAGGGCTGAGAAAGTGCTGC CTACTGCCTCGGACTTCAAGGGGCT (SEQ ID NO: 6); TGCTGTTGACAGTGAGCGACTTTCTCAGCCTCCTTCTGCGTGAAGCCACAGATGGCAGAAGGAGGCTGAG AAAGTTGCCTACTGCCTCGGA (SEQ ID NO: 7); CCTGGAGGCTTGCTGAAG GCTGTATGCTGACTTTCTCAGCCTCCTTCTGCTTTTGGCCACTGACTGAGCAGAAGGG CTGAGAAAGTCAGGACACAAGGCCTGTTACTAGCACTCA (SEQ ID NO: 8); CATCTCCATGGCTGTACCACCTTGTCGGGACTTTCTCAGCCTCCTTCTGCCTGTTGAA TCTCATGGCAGAAGGAGGCGAGAAAGTCTGACATTTTGGTATCTTTCATCTGACCA (SEQ ID NO: 9); or GGGCCTGGCTCGAGCAGGGGGCGAGGGATACTTTCT CAGCCTCCTTCTGCTGGTCCCCTCCCCGCAGAAGGAGGCTGAGAAAGTCCTTCCCTC CCAATGACCGCGTCTTCGTCG (SEQ ID NO: 10). In a preferred embodiment, the microRNA includes AAGGTATATTGCTGTTGACAGTGAGCGACACTTTCTCAGCCT CCTTCTGCGTGAAGCCACAGATGGCAGAAGGAGGCTGAGAAAGTGCTGCCTACTGC CTCGGACTTCAAGGGGCT (SEQ ID NO: 5); AAGGTATATTGCTGTTGACAGT GAGCGACACTTTCTCAGCCTCCTTCTGCGTGAAGCCACAGATGGCAGAAGGGCTGA GAAAGTGCTGCCTACTGCCTCGGACTTCAAGGGGCT (SEQ ID NO: 6); TGCTG TTGACAGTGAGCGACTTTCTCAGCCTCCTTCTGCGTGAAGCCACAGATGGCAGAAGG AGGCTGAGAAAGTTGCCTACTGCCTCGGA (SEQ ID NO: 7); CCTGGAGGCT TGCTGAAGGCTGTATGCTGACTTTCTCAGCCTCCTTCTGCTTTTGGCCACTGACTGAG CAGAAGGGCTGAGAAAGTCAGGACACAAGGCCTGTTACTAGCACTCA (SEQ ID NO: 8); CATCTCCATGGCTGTACCACCTTGTCGGGACTTTCTCAGCCTCCTT CTGCCTGTTGAATCTCATGGCAGAAGGAGGCGAGAAAGTCTGACATTTTGGTATCTT TCATCTGACCA (SEQ ID NO: 9); or GGGCCTGGCTCGAGCAGGGGGCGAGGG ATACTTTCTCAGCCTCCTTCTGCTGGTCCCCTCCCCGCAGAAGGAGGCTGAGAAAGT CCTTCCCTCCCAATGACCGCGTCTTCGTCG (SEQ ID NO: 10).

In another aspect, a viral vector comprising at least one encoded genetic element is provided. The at least one encoded genetic element includes a small RNA capable of inhibiting production of an enzyme involved in the mevalonate pathway. In embodiments, the enzyme involved in the mevalonate pathway is farnesyl diphosphate synthase (FDPS). In embodiments, the at least one encoded genetic element includes a microRNA or a shRNA.

In another aspect, the at least one encoded genetic element includes a shRNA having at least 80%, or at least 85%, or at least 90%, or at least 95% percent identity with v In a preferred embodiment, the shRNA includes SEQ ID NO: 1; SEQ ID NO: 2; SEQ ID NO: 3; or SEQ ID NO: 4.

In another aspect, the at least one encoded genetic element includes a microRNA having at least 80%, or at least 85%, or at least 90%, or at least 95% percent identity with SEQ ID NO: 5; SEQ ID NO: 6; SEQ ID NO: 7; SEQ ID NO: 8; SEQ ID NO: 9; or SEQ ID NO: 10. In a preferred embodiment, the microRNA includes SEQ ID NO: 5; SEQ ID NO: 6; SEQ ID NO: 7; SEQ ID NO: 8; SEQ ID NO: 9; or SEQ ID NO: 10.

In embodiments, the viral vector is comprised of any vector that can effectively transduce the small RNA into a target cell. In embodiments, the viral vector is a lentiviral vector. In other embodiments, the viral vector is an adeno-associated virus vector.

In another aspect, the viral vector includes a second encoded genetic element. In embodiments, the second genetic element includes at least one cytokine or chemokine. In embodiments, the at least one cytokine is selected from the group consisting of: IL-18, TNF-α, interferon-γ, IL-1, IL-2, IL-15, IL-17, and IL-12. In embodiments, the at least one chemokine is a CC chemokine or a CXC chemokine. In further embodiments, the at least one chemokine is RANTES.

In another aspect, a lentiviral vector system for expressing a lentiviral particle is provided. The system includes a lentiviral vector, at least one envelope plasmid for expressing an envelope protein optimized for infecting a cell; and at least one helper plasmid for expressing gag, pol, and rev genes. When the lentiviral vector, the at least one envelope plasmid, and the at least one helper plasmid are transfected into a packaging cell, a lentiviral particle is produced by the packaging cell. In embodiments, the lentiviral particle is capable of infecting a targeting cell, and inhibiting an enzyme involved in the mevalonate pathway within the target cell. In embodiments, the enzyme involved in the mevalonate pathway is FDPS. In embodiments, the lentiviral vector system includes a first helper plasmid for expressing the gag and pol genes, and a second helper plasmid for expressing the rev gene. In embodiments, the envelope protein is preferably optimized for infecting a target cell. In embodiments, the target cell is a cancer cell. In other embodiments, the target cell is a cell that is infected with an infectious agent.

In another aspect a pharmaceutical combination is disclosed which includes a bisphosphonate compound; and a lentiviral particle produced by a packaging cell and capable of infecting a target cell. The lentiviral particle comprises an envelope protein capable of infecting the target cell, and: at least one encoded shRNA capable of inhibiting production of an enzyme of the mevalonate pathway, wherein the at least one encoded shRNA comprises a sequence having at least 80% percent identity with SEQ ID NO: 1; SEQ ID NO: 2; SEQ ID NO: 3; or SEQ ID NO: 4; or at least one encoded microRNA capable of inhibiting production of an enzyme of the mevalonate pathway, wherein the at least one encoded microRNA comprises a sequence having at least 80% percent identity with SEQ ID NO: 5; SEQ ID NO: 6; SEQ ID NO: 7; SEQ ID NO: 8; SEQ ID NO: 9; or SEQ ID NO: 10, wherein the pharmaceutical combination is at least one of fixed and non-fixed. In embodiments, the at least one encoded shRNA comprises a sequence having at least 85% or at least 90% or at least 95% percent identity with SEQ ID NO: 1; SEQ ID NO: 2; SEQ ID NO: 3; or SEQ ID NO: 4; or the at least one encoded microRNA comprises a sequence having at least 85% percent identity with SEQ ID NO: 5; SEQ ID NO: 6; SEQ ID NO: 7; SEQ ID NO: 8; SEQ ID NO: 9; or SEQ ID NO: 10. In embodiments, the at least one encoded shRNA comprises SEQ ID NO: 1; SEQ ID NO: 2; SEQ ID NO: 3; or SEQ ID NO: 4 or the at least one encoded microRNA comprises SEQ ID NO: 5; SEQ ID NO: 6; SEQ ID NO: 7; SEQ ID NO: 8; SEQ ID NO: 9; or SEQ ID NO: 10. In embodiments, the pharmaceutical composition comprises a fixed combination. In embodiments, the pharmaceutical composition comprises a non-fixed combination. In embodiments, the bisphosphonate drug comprises zoledronic acid. In embodiments, the bisphosphonate drug and the lentiviral particle are present in synergistically effective amounts. In embodiments, the target cell is one or more cancer cells that are present in a cancer selected from one or more of a carcinoma, a leukemia, a lymphoma, a sarcoma, a myeloma, a mesothelioma, a mixed type, or mixtures thereof. In embodiments, the target cell is one or more cancer cells that are present in a hepatocellular carcinoma. In embodiments, the target cell is capable of activating a gamma delta T cell following infection with the lentiviral particle. In embodiments, the enzyme is FDPS.

In another aspect, a method of treating a cancer in a subject using an immunotherapy-based composition is disclosed. The method includes administering a therapeutically-effective amount of a bisphosphonate drug to the subject; and administering a therapeutically-effective amount of the immunotherapy-based composition to the subject, wherein the immunotherapy-based composition comprises a lentiviral particle. The lentiviral particle comprises an envelope protein capable of infecting one or more cancer cells, and at least one encoded shRNA capable of inhibiting production of an enzyme of the mevalonate pathway, wherein the at least one encoded shRNA comprises a sequence having at least 80% percent identity with SEQ ID NO: 1; SEQ ID NO: 2; SEQ ID NO: 3; or SEQ ID NO: 4 or at least one encoded microRNA capable of inhibiting production of an enzyme of the mevalonate pathway, wherein the at least one encoded microRNA comprises a sequence having at least 80% percent identity with SEQ ID NO: 5; SEQ ID NO: 6; SEQ ID NO: 7; SEQ ID NO: 8; SEQ ID NO: 9; or SEQ ID NO: 10. In embodiments, the at least one encoded shRNA comprises a sequence having at least 85% or at least 90% or at least 95% percent identity with SEQ ID NO: 1; SEQ ID NO: 2; SEQ ID NO: 3; or SEQ ID NO: 4, or at least one encoded microRNA comprises a sequence having at least 85% or at least 90% or at least 95% percent identity with SEQ ID NO: 5; SEQ ID NO: 6; SEQ ID NO: 7; SEQ ID NO: 8; SEQ ID NO: 9; or SEQ ID NO: 10. In embodiments, the at least one encoded shRNA comprises SEQ ID NO: 1; SEQ ID NO: 2; SEQ ID NO: 3; or SEQ ID NO: 4. In embodiments, the at least one encoded microRNA comprises SEQ ID NO: 5; SEQ ID NO: 6; SEQ ID NO: 7; SEQ ID NO: 8; SEQ ID NO: 9; or SEQ ID NO: 10. In embodiments, the one or more cancer cells are present in a cancer selected from one or more of a carcinoma, a leukemia, a lymphoma, a sarcoma, a myeloma, a mesothelioma, a mixed type, or mixtures thereof. In embodiments, the bisphosphonate drug comprises zoledronic acid. In embodiments, the bisphosphonate drug and the immunotherapy-based composition are administered in a fixed combination. In embodiments, the bisphosphonate drug and the immunotherapy-based composition are administered in a non-fixed combination. In embodiments, the bisphosphonate drug and the immunotherapy-based composition are administered simultaneously. In embodiments, the bisphosphonate drug and the immunotherapy-based composition are administered sequentially. In embodiments, the bisphosphonate drug and the immunotherapy-based composition are administered in synergistically effective amounts. In embodiments, the bisphosphonate drug and the immunotherapy-based composition are administered at a synergistically effective time interval. In embodiments, the one or more cancer cells are capable of activating a gamma delta T cell resident in the subject following infection of the one or more cancer cells with the immunotherapy-based composition. In embodiments, activating the gamma delta T cell comprises increasing tumor necrosis factor (TNF)-α expression by the gamma delta T cell. In embodiments, activating the gamma delta T cell comprises increasing expression and/or secretion of cytokines, chemokines, and/or cell death ligands including but not limited to FasL and TRAIL. In embodiments, the enzyme of the mevalonate pathway is farnesyl diphosphate synthase (FDPS).

DETAILED DESCRIPTION

Overview of Disclosure

Figure 1:
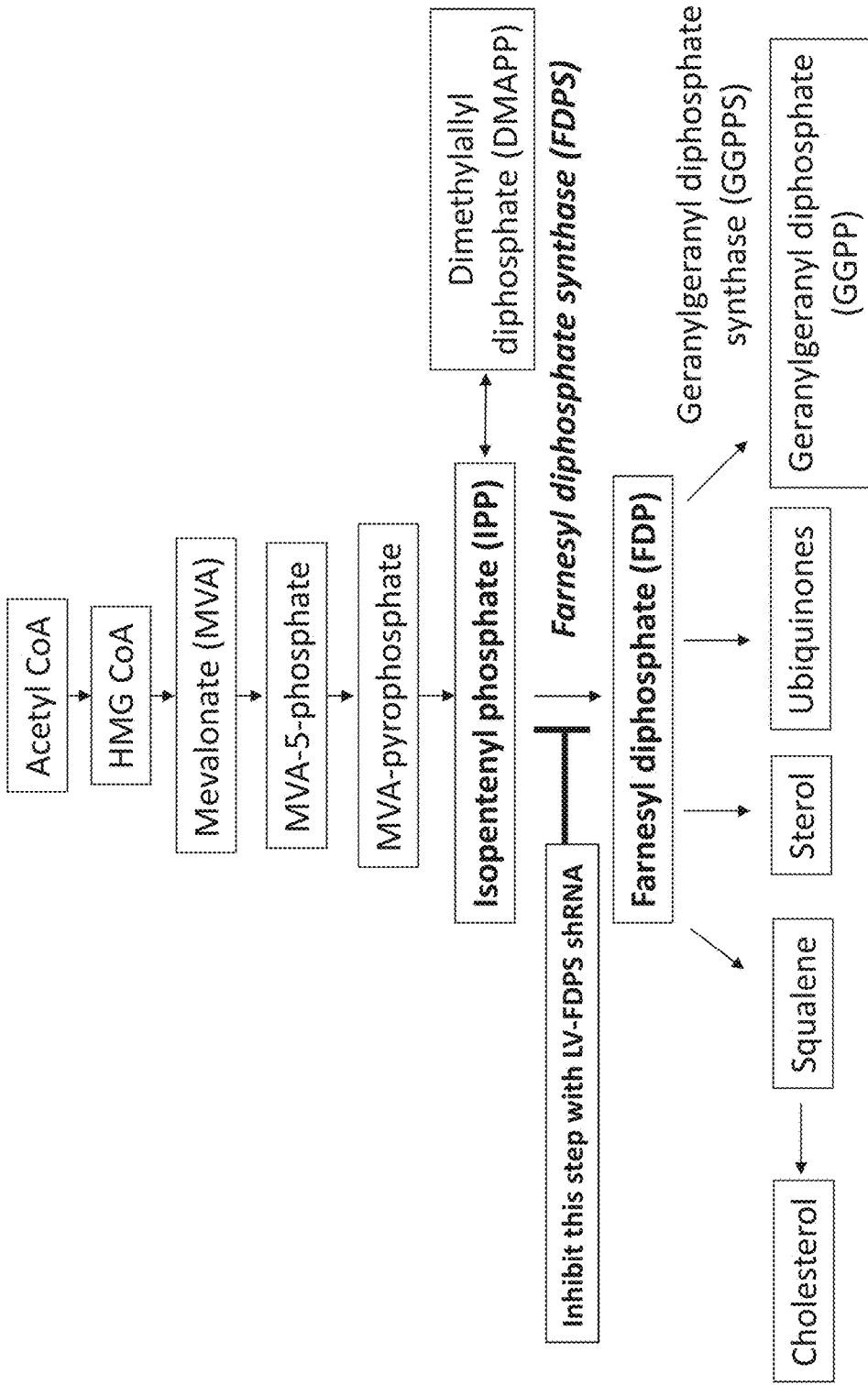
FIG. 1 depicts an overview of the major steps in the mevalonate pathway for biosynthesis of steroids and isoprenoids.

The present disclosure relates to gene therapy constructs and delivery of the same to cells, resulting in suppression of Farnesyl diphosphate synthase ("FDPS"), which is necessary to convert isopentenyl phosphate (IPP) to farnesyl diphosphate (FDP), as shown, for example, in FIG. 1. In embodiments, one or more viral vectors are provided with microRNAs or short hairpin RNAs (shRNA) that target FDPS, thereby reducing expression levels of this enzyme. The viral vectors include lentiviral vectors and AAV vectors. A consequence of modulating expression of FDPS is to increase the accumulation of IPP, which is a stimulator of GD T cell proliferation and differentiation. Accordingly, the constructs provided herein are used to activate GD T cells, and are used to treat cancers and infectious diseases.

Definitions and Interpretation

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. Generally, nomenclature used in connection with, and techniques of, cell and tissue culture, molecular biology, immunology, microbiology, genetics and protein and nucleic acid chemistry and hybridization described herein are those well-known and commonly used in the art. The methods and techniques of the present disclosure are generally performed according to conventional methods well-known in the art and as described in various general and more specific references that are cited and discussed throughout the present specification unless otherwise indicated. See, e.g.: Sambrook J. & Russell D. Molecular Cloning: A Laboratory Manual, 3rd ed., Cold Spring Harbor Laboratory Press, Cold Spring Harbor, N.Y. (2000); Ausubel et al., Short Protocols in Molecular Biology: A Compendium of Methods from Current Protocols in Molecular Biology, Wiley, John & Sons, Inc. (2002); Harlow and Lane Using Antibodies: A Laboratory Manual; Cold Spring Harbor Laboratory Press, Cold Spring Harbor, N.Y. (1998); and Coligan et al., Short Protocols in Protein Science, Wiley, John & Sons, Inc. (2003). Any enzymatic reactions or purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well-known and commonly used in the art.

As used in the description and the appended claims, the singular forms "a", "an" and "the" are used interchangeably and intended to include the plural forms as well and fall within each meaning, unless the context clearly indicates otherwise. Also, as used herein, "and/or" refers to and encompasses any and all possible combinations of one or more of the listed items, as well as the lack of combinations when interpreted in the alternative ("or").

All numerical designations, e.g., pH, temperature, time, concentration, and molecular weight, including ranges, are approximations which are varied (+) or (−) by increments of 0.1. It is to be understood, although not always explicitly stated, that all numerical designations are preceded by the term "about". The term "about" also includes the exact value "X" in addition to minor increments of "X" such as "X+0.1" or "X−0.1." It also is to be understood, although not always explicitly stated, that the reagents described herein are merely exemplary and that equivalents of such are known in the art.

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

As used herein, the terms "administration of" or "administering" refer to providing an active agent to a subject in need of treatment in a form that can be introduced into that individual's body in a therapeutically useful form and therapeutically effective amount.

As used herein, the terms "bisphosphonates" and "bisphosphonate drugs" refer to therapeutic agents of various embodiments, and encompass any of aminobisphosphonates, diphosphonates, biphosphonic acids, and diphosphonic acids, as well as pharmaceutically acceptable salts and derivatives thereof. The use of a specific nomenclature in referring to bisphosphonates is not meant to limit the scope of the present invention, unless specifically indicated.

As used herein, the terms "co-administration" or "combined administration" or "combined use" or "combination therapy" or the like as utilized herein refer to administration of a therapeutic vector or a lentiviral particle and a bisphosphonate drug or a therapeutic vector or a lentiviral particle and an antibody or a therapeutic vector or a lentiviral particle and a bisphosphonate drug and an antibody to a single subject in need thereof (e.g., a patient), and are intended to include treatment regimens in which the agents are not necessarily administered by the same route of administration and/or at the same time.

As used herein, the term "fixed combination," refers to two or more active ingredients or components, including any of their respective compositions, formulations or drug forms, e.g., a therapeutic vector or a lentiviral particle and a bisphosphonate drug or any combination of these, that are administered essentially in combination to a patient, for example essentially simultaneously, in the form of a single entity or dosage or combined entities or dosages, e.g., in one tablet or in one capsule or in combined tablets or capsules or combined liquid forms.

As used herein, the term "non-fixed combination," refers to two or more active ingredients or components, including any of their respective compositions, formulations or drug forms, e.g., a therapeutic vector or a lentiviral particle and a bisphosphonate drug or any combination of these, that are administered in combination to a patient as separate entities either simultaneously, concurrently or sequentially with no specific time limits, wherein such administration provides therapeutically effective levels of the active components in the patient. The non-fixed combination can be dosed independently of each other or by use of different fixed combinations e.g., simultaneously or at different time points. The active components may be administered as separate pharmaceutical dosage forms or pharmaceutical formulations that may be, for example, sold independently of each other, with or without label instructions concerning the possibility of a combined use. Such instructions may be provided in the package equipment, e.g., leaflet or the like, or in other information, e.g., provided to physicians and medical staff. A non-fixed combination, its respective active ingredients or components, including any of their respective compositions, formulations or drug forms, or the parts thereof, can be administered simultaneously or chronologically staggered, e.g., at different time points and with equal or different time intervals for any part of the administration. Such time intervals may be chosen such that the effect on the treated disease, when treated in combination, is more effective than would be obtained by use of only any one of the active components.

As used herein, the terms "combination," "in combination" and "combination therapies," may refer generally to any or both of the "fixed combination" and "non-fixed combination" definitions and embodiments described above.

As used herein, the transitional term "comprising," when used to define compositions and methods, means that the compositions and methods include the recited elements, but does not exclude others. As used herein, "consisting essentially of," when used to define compositions and methods, means that the composition and methods include additional elements, but only if those additional elements do not materially affect the basic and novel characteristics of the composition or methods. As used herein, "consisting of," when used to define compositions and methods, means that the compositions and methods exclude more than trace elements of other ingredients for compositions and substantial method steps. Embodiments defined by each of these transitional terms are within the scope of this disclosure. For example, it is intended that the methods and compositions can include additional steps and components (comprising) or alternatively including steps and compositions of no significance (consisting essentially of) or alternatively, intending only the stated method steps or compositions (consisting of).

As used herein, the terms "expression," "expressed," or "encodes" refer to a process by which polynucleotides are transcribed into mRNA and/or the process by which the transcribed mRNA is subsequently being translated into peptides, polypeptides, or proteins. Expression may include splicing of the mRNA in a eukaryotic cell or other forms of post-transcriptional modification or post-translational modification.

As used herein, the term "farnesyl diphosphate synthase" may also be referred to herein as FDPS, and may also be referred to herein as farnesyl pyrophosphate synthase or FPPS.

As used herein, the term "gamma delta T cell" may also be referred to herein as a γδ T cell, or further as a GD T cell. The term "gamma delta T cell activation" refers to any measurable biological phenomenon associated with a gamma delta T cell that is representative of such T cell being activated. Non-limiting examples of such a biological phenomenon include an increase of cytokine production, changes in the qualitative or quantitative composition of cell surface proteins, an increase in T cell proliferation, and/or an increase in T cell effector function, such killing or a target cell or assisting another effector cell to kill a target cell.

As used herein, the terms "individual," "subject," and "patient" are used interchangeably herein, and refer to any individual mammal subject, e.g., bovine, canine, feline, equine, and/or human.

As used herein, the term "miRNA" refers to a microRNA, and also may be referred to herein as "miR".

The term "packaging cell line" refers to any cell line that can be used to express a lentiviral particle.

As used herein, the term "homology" refers to the percentage number of amino acids, nucleic acids, or analogs thereof, that are identical or constitute conservative substitutions. Homology may be determined using sequence comparison programs such as GAP (Deveraux et al., 1984, Nucleic Acids Research 12, 387-395). In this way sequences of a similar or substantially different length to those cited herein could be compared by insertion of gaps into the alignment, such gaps being determined, for example, by the comparison algorithm used by GAP.

As used herein, the term "sequence identity," which also may appear in the non-limiting context of "a sequence 50% identical to," and "having at least 80%, or at least 85%, or at least 90%, or at least 95% identity with" a given sequence, as similar pharasings, as used herein, refers to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., Nucl. Acids Res. 25:3389, 1997.

As used here, the term "percent identity," which may be used interchangeably with the term "sequence identity", in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the "percent identity" can exist over a region of the sequence being compared, e.g., over a functional domain, or, alternatively, exist over the full length of the two sequences to be compared. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

Suitable algorithms for determining percent sequence identity include the BLAST algorithm, which is described in Altschul et al., J. Mol. Biol. 215:403-410 (1990). Software for performing BLAST analyses is publicly available through the National Center for Biotechnology Information web site.

The percent identity between two nucleotide sequences can be determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present disclosure can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, word length=12 to obtain nucleotide sequences homologous to the nucleic acid molecules provided in the disclosure. BLAST protein searches can be performed with the XBLAST program, score=50, word-length=3 to obtain amino acid sequences homologous to the protein molecules of the disclosure. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See http://www.ncbi.nlm.nih.gov.

As used herein, the term "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

As used herein, the term "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt (see, e.g., Berge et al. (1977) *J. Pharm Sci* 66:1-19).

As used herein, the term "pharmaceutically acceptable salt" refers to derivatives of compounds or other active ingredients, wherein the parent compound or active ingredient is modified by converting an existing acid or base moiety to its salt form. Non-limiting examples of pharmaceutically acceptable salts include, but are not limited to, mineral or organic acid salts of basic residues such as amines; alkali or organic salts of acidic residues such as carboxylic acids; alkali metal, alkaline metal, ammonium, and mono-, di, tri-, or tetra-C1-C30-alkyl-substituted ammonium; and the like. The pharmaceutically acceptable salts of various embodiments include the conventional non-toxic salts of the compound or active ingredient formed, for example, from nontoxic inorganic or organic acids. Suitable organic acids are, e.g., carboxylic acids or sulfonic acids, such as acetic acid, succinic acid, fumaric acid or methanesulfonic acid. The pharmaceutically acceptable salts herein can be synthesized from the parent compound or active ingredient which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "SEQ ID NO" is synonymous with the term "Sequence ID No."

As used herein, the term "small RNA" refers to non-coding RNA that are generally less than about 200 nucleotides or less in length and possess a silencing or interference function. In embodiments, the small RNA is about 175 nucleotides or less, about 150 nucleotides or less, about 125 nucleotides or less, about 100 nucleotides or less, or about 75 nucleotides or less in length. Such RNAs include micro-RNA (miRNA), small interfering RNA (siRNA), double stranded RNA (dsRNA), and short hairpin RNA (shRNA). In embodiments, "small RNA" are capable of inhibiting or knocking-down gene expression of a target gene, generally through pathways that result in the inhibitions or destruction of the target gene mRNA.

As used herein, the term "therapeutically effective amount" refers to a sufficient quantity of the active agents of the present disclosure, in a suitable composition, and in a suitable dosage form to treat or prevent the symptoms, progression, or onset of the complications seen in patients suffering from a given ailment, injury, disease, or condition. The therapeutically effective amount will vary depending on the state of the patient's condition or its severity, and the age, weight, etc., of the subject to be treated. A therapeutically effective amount can vary, depending on any of a number of factors, including, e.g., the route of administration, the condition of the subject, as well as other factors understood by those in the art.

As used herein, the term "therapeutic vector" includes, without limitation, reference to a lentiviral vector or an AAV vector.

As used herein, the terms "treatment" and "treating" refer to the intended targeting of a disease state and combatting of it, i.e., ameliorating or preventing the disease state. A particular treatment thus will depend on the disease state to be targeted and the current or future state of medicinal therapies and therapeutic approaches. A treatment may have associated toxicities.

Desirable effects include, but are not limited to, preventing occurrence or recurrence of disease, alleviating symptoms, suppressing, diminishing or inhibiting any direct or indirect pathological consequences of the disease, ameliorating or palliating the disease state, and causing remission or improved prognosis.

Description of Aspects of the Disclosure

In one aspect, a method of activating a GDT cell is provided. The method includes infecting, in the presence of the GD T cell, a target cell with a viral delivery system encoding at least one genetic element. In embodiments, the at least one encoded genetic element includes a small RNA capable of inhibiting production of an enzyme involved in the mevalonate pathway. In embodiments, the enzyme is FDPS. In embodiments, when the enzyme is inhibited in the target cell, the target cell activates the GD T cell. In embodiments, the target cell is a cancer cell or a cell that has been infected with an infectious agent. In embodiments, the at least one encoded genetic element includes a microRNA or a shRNA.

In embodiments, the at least one encoded genetic element includes a shRNA having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with GTCCTGGAGTACAATGC-CATTCTCGAGAATGGCATTGTACTCCAGGACTTTTT (SEQ ID NO: 1); GCAGGATTTCGTTCAGCACTTCTC-GAGAAGTGCTGAACGAA ATCCTGCTTTTT (SEQ ID NO: 2); GCCATGTACATGGCAGGAATTCTCGAGAA TTCCTGCCATGTACATGGCTTTTT (SEQ ID NO: 3); or GCAGAAGGAGGCTGA GAAAGTCTCGA-GACTTTCTCAGCCTCCTTCTGCTTTTT (SEQ ID NO: 4). In a preferred embodiment, the shRNA includes GTC-CTGGAGTACAATGCCATTCTCGAG AATGGCATTG-TACTCCAGGACTTTTT (SEQ ID NO: 1); GCAG-GATTTCGTTCA GCACTTCTCGAGAAGTGCTGAACGAAATCCT-GCTTTTT (SEQ ID NO: 2); GCCA TGTACATGGCAG-GAATTCTCGAGAATTCCTGCCATGTACATG-GCTTTTT (SEQ ID NO: 3); or GCAGAAGGAGGCTGAGAAAGTCTCGA-GACTTTCTCAGCCTCCTT CTGCTTTTT (SEQ ID NO: 4).

In another aspect, the at least one encoded genetic element includes a microRNA having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with AAGGTATATTGCTGT-TGACAGTGAGCGACACTTTCTCAGCCTCCTTCT-GCGTGAAGC CACAGATGGCAGAAGGAGGCT-GAGAAAGTGCTGCCTACTGCCTCGGACTTCAAGGG GCT (SEQ ID NO: 5); AAGGTATATTGCTGTTGACAGT-GAGCGACACT TTCTCAGCCTCCTTCTGCGT-GAAGCCACAGATGGCAGAAGGGCTGAGAAAGT-GCTGC CTACTGCCTCGGACTTCAAGGGGCT (SEQ ID NO: 6); TGCTGTTGACAGTG AGCGACTTTCTCA-GCCTCCTTCTGCGTGAAGCCACAGATGGCA-GAAGGAGGCTGAG AAAGTTGCCTACTGCCTCGGA (SEQ ID NO: 7); CCTGGAGGCTTGCTGAAG GCTG-TATGCTGACTTTCTCAGCCTCCTTCTGCTTTTGGC-CACTGACTGAGCAGAAGGG CTGAGAAAGTCAG-GACACAAGGCCTGTTACTAGCACTCA (SEQ ID NO: 8); CATCTCCATGGCTGTACCACCTT-GTCGGGACTTTCTCAGCCTCCTTCTGCCTGTTGAA TCTCATGGCAGAAGGAGGCGAGAAAGTCT-GACATTTTGGTATCTTTCATCTGACCA (SEQ ID NO: 9); or GGGCCTGGCTCGAGCAGGGGGCGAGGGA-TACTTTCT CAGCCTCCTTCTGCTGGTCCCCTC-CCCGCAGAAGGAGGCTGAGAAAGTCCTTCCCTC CCAATGACCGCGTCTTCGTCG (SEQ ID NO: 10). In a preferred embodiment, the microRNA includes AAGGTAT-ATTGCTGTTGACAGTGAGCGACACTTTCTCAGCCT CCTTCTGCGTGAAGCCACAGATGGCAGAAGGAG-GCTGAGAAAGTGCTGCCTACTGC CTCGGACT-TCAAGGGGCT (SEQ ID NO: 5); AAGGTATATTGCTGT-TGACAGT GAGCGACACTTTCTCAGCCTCCTTCTGCGTGAAGC-CACAGATGGCAGAAGGGCTGA GAAAGTGCTGC-CTACTGCCTCGGACTTCAAGGGGCT (SEQ ID NO: 6); TGCTG TTGACAGTGAGCGACTTTCTCAGCCTCCT-TCTGCGTGAAGCCACAGATGGCAGAAGG AGGCT-GAGAAAGTTGCCTACTGCCTCGGA (SEQ ID NO: 7); CCTGGAGGCT TGCTGAAGGCTGTATGCT-GACTTTCTCAGCCTCCTTCTGCTTTTGGCCACT-GACTGAG CAGAAGGGCTGAGAAAGTCAGGACA-CAAGGCCTGTTACTAGCACTCA (SEQ ID NO: 8); CATCTCCATGGCTGTACCACCTT-GTCGGGACTTTCTCAGCCTCCTT CTGCCTGTT-GAATCTCATGGCAGAAGGAGGCGAGAAAGTCT-GACATTTTGGTATCTT TCATCTGACCA (SEQ ID NO: 9); or GGGCCTGGCTCGAGCAGGGGGCGAGGG ATACTTTCTCAGCCTCCTTCTGCTGGTCCCCTC-CCCGCAGAAGGAGGCTGAGAAAGT CCTTCCCTC-CCAATGACCGCGTCTTCGTCG (SEQ ID NO: 10).

In another aspect, the target cell is also contacted with a bisphosphonate drug. In a preferred embodiment, the bisphosphonate drug is zoledronic acid. The bisphosphonate drug may be a pharmaceutically acceptable salt, hydrate or a solvate thereof.

In another aspect, a method of treating cancer in a subject is provided. The method includes administering to the subject a therapeutically-effective amount of a viral delivery system encoding at least one genetic element. In embodiments, the at least one encoded genetic element includes a small RNA capable of inhibiting production of an enzyme involved in the mevalonate pathway. In further embodiments, when the enzyme is inhibited in a cancer cell in the presence of a GD T cell, the cancer cell activates the GD T cell, to thereby treat the cancer. In embodiments, the enzyme is FDPS. In embodiments, the at least one encoded genetic element includes a microRNA or a shRNA.

In another aspect, a method of treating an infectious disease in a subject is provided. The method includes administering to the subject a therapeutically-effective amount of a viral delivery system encoding at least one genetic element. In embodiments, the at least one encoded genetic element includes a small RNA capable of inhibiting production of an enzyme involved in the mevalonate pathway. In further embodiments, when the enzyme is inhibited in a cell that is infected with an infectious agent and is in the presence of a GD T cell, the infected cell activates the GD T cell, to thereby treat the infected cell, and the infectious disease. In embodiments, the enzyme is FDPS. In embodiments, the at least one encoded genetic element includes a microRNA or a shRNA.

In embodiments, the at least one encoded genetic element includes a shRNA having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with SEQ ID NO: 1; SEQ ID NO: 2; SEQ ID NO: 3; or SEQ ID NO: 4. In a preferred embodiment, the shRNA includes SEQ ID NO: 1; SEQ ID NO: 2; SEQ ID NO: 3; or SEQ ID NO: 4.

In other embodiments, the at least one encoded genetic element includes a microRNA having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with SEQ ID NO: 5; SEQ ID NO: 6; SEQ ID NO: 7; SEQ ID NO: 8; SEQ ID NO: 9; or SEQ ID NO: 10. In a preferred embodiment, the microRNA includes SEQ ID NO: 5; SEQ ID NO: 6; SEQ ID NO: 7; SEQ ID NO: 8; SEQ ID NO: 9; or SEQ ID NO: 10.

In another aspect, a viral vector comprising at least one encoded genetic element is provided. The at least one encoded genetic element includes a small RNA capable of inhibiting production of an enzyme involved in the mevalonate pathway. In embodiments, the enzyme involved in the mevalonate pathway is farnesyl diphosphate synthase (FDPS). In embodiments, the at least one encoded genetic element includes a microRNA or a shRNA.

In another aspect, the at least one encoded genetic element includes a shRNA having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with SEQ ID NO: 1; SEQ ID NO: 2; SEQ ID NO: 3; or SEQ ID NO: 4. In a preferred embodiment, the shRNA includes SEQ ID NO: 1; SEQ ID NO: 2; SEQ ID NO: 3; or SEQ ID NO: 4.

In another aspect, the at least one encoded genetic element includes a microRNA having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with SEQ ID NO: 5; SEQ ID NO: 6; SEQ ID NO: 7; SEQ ID NO: 8; SEQ ID NO: 9; or SEQ ID NO: 10. In a preferred embodiment, the microRNA includes SEQ ID NO: 5; SEQ ID NO: 6; SEQ ID NO: 7; SEQ ID NO: 8; SEQ ID NO: 9; or SEQ ID NO: 10.

In embodiments, the viral vector includes any vector that can effectively transduce the small RNA. In embodiments, the viral vector is a lentiviral vector. In other embodiments, the viral vector is an adeno-associated virus (AAV) vector.

In another aspect, the viral vector includes a second encoded genetic element. In embodiments, the second genetic element includes at least one cytokine or chemokine. In embodiments, the at least one cytokine is selected from the group consisting of: IL-18, TNF-α, interferon-γ, IL-1, IL-2, IL-15, IL-17, and IL-12. In embodiments, the at least one chemokine is a CC chemokine, CXC chemokine, a CX3 chemokine or a XC chemokine. In a further embodiment, the at least one chemokine is the CC chemokine, RANTES.

In another aspect, a lentiviral vector system for expressing a lentiviral particle is provided. The system includes a lentiviral vector, at least one envelope plasmid for expressing an envelope protein optimized for infecting a cell; and at least one helper plasmid for expressing gag, pol, and rev genes. When the lentiviral vector, the at least one envelope plasmid, and the at least one helper plasmid are transfected into a packaging cell, a lentiviral particle is produced by the packaging cell. In embodiments, the lentiviral particle is capable of infecting a targeting cell, and inhibiting an enzyme involved in the mevalonate pathway within the target cell. In embodiments, the enzyme involved in the mevalonate pathway is FDPS. In embodiments, the lentiviral vector system includes a first helper plasmid for expressing the gag and pol genes, and a second helper plasmid for expressing the rev gene. In embodiments, the envelope protein is preferably optimized for infecting a target cell. In embodiments, the target cell is a cancer cell. In other embodiments, the target cell is a cell that is infected with an infectious disease.

In another aspect a pharmaceutical combination is disclosed which includes a bisphosphonate compound; and a lentiviral particle produced by a packaging cell and capable of infecting a target cell. The lentiviral particle comprises an envelope protein capable of infecting the target cell, and: at least one encoded shRNA capable of inhibiting production of an enzyme of the mevalonate pathway, wherein the at least one encoded shRNA comprises a sequence having at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98% or at least 99% percent identity with SEQ ID NO: 1; SEQ ID NO: 2; SEQ ID NO: 3; or SEQ ID NO: 4; or at least one encoded microRNA capable of inhibiting production of an enzyme of the mevalonate pathway, wherein the at least one encoded microRNA comprises a sequence having at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98% or at least 99% percent identity with SEQ ID NO: 5; SEQ ID NO: 6; SEQ ID NO: 7; SEQ ID NO: 8; SEQ ID NO: 9; or SEQ ID NO: 10, wherein the pharmaceutical combination is at least one of fixed and non-fixed. In embodiments, the at least one encoded shRNA comprises SEQ ID NO: 1; SEQ ID NO: 2; SEQ ID NO: 3; or SEQ ID NO: 4 or the at least one encoded microRNA comprises SEQ ID NO: 5; SEQ ID NO: 6; SEQ ID NO: 7; SEQ ID NO: 8; SEQ ID NO: 9; or SEQ ID NO: 10. In embodiments, the pharmaceutical composition comprises a fixed combination. In embodiments, the pharmaceutical composition comprises a non-fixed combination. In embodiments, the bisphosphonate drug comprises zoledronic acid. In embodiments, the bisphosphonate drug and the lentiviral particle are present in synergistically effective amounts. In embodiments, the target cell is one or more cancer cells that are present in a cancer selected from one or more of a carcinoma, a leukemia, a lymphoma, a sarcoma, a myeloma, a mesothelioma, a mixed type, or mixtures thereof. In embodiments, the target cell is one or more cancer cells that are present in a hepatocellular carcinoma. In embodiments, the target cell is capable of activating a gamma delta T cell following infection with the lentiviral particle. In embodiments, the enzyme is FDPS.

In another aspect, a method of treating a cancer in a subject using an immunotherapy-based composition is disclosed. The method includes administering a therapeutically-effective amount of a bisphosphonate drug to the subject; and administering a therapeutically-effective amount of the immunotherapy-based composition to the subject, wherein the immunotherapy-based composition comprises a lentiviral particle. The lentiviral particle comprises an envelope protein capable of infecting one or more cancer cells, and at least one encoded shRNA capable of inhibiting production of an enzyme of the mevalonate pathway, wherein the at least one encoded shRNA comprises a sequence having at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98% or at least 99% percent identity with SEQ ID NO: 1; SEQ ID NO: 2; SEQ ID NO: 3; or SEQ ID NO: 4 or at least one encoded microRNA capable of inhibiting production of an enzyme of the mevalonate pathway, wherein the at least one encoded microRNA comprises a sequence having at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98% or at least 99% percent identity with SEQ ID NO: 5; SEQ ID NO: 6; SEQ ID NO: 7; SEQ ID NO: 8; SEQ ID NO: 9; or SEQ ID NO: 10. In embodiments, the at least one encoded shRNA comprises SEQ ID NO: 1; SEQ ID NO: 2; SEQ ID NO: 3; or SEQ ID NO: 4. In embodiments, the at least one encoded microRNA comprises SEQ ID NO: 5; SEQ ID NO: 6; SEQ ID NO: 7; SEQ ID NO: 8; SEQ ID NO: 9; or SEQ ID NO: 10. In embodiments, the one or more cancer cells are present in a cancer selected from one or more of a carcinoma, a leukemia, a lymphoma, a sarcoma, a myeloma, a mesothelioma, a mixed type, or mixtures thereof. In embodiments, the bisphosphonate drug comprises zoledronic acid. In embodiments, the bisphosphonate drug and the immunotherapy-based composition are administered in a fixed combination. In embodiments, the bisphosphonate drug and the immunotherapy-based composition are administered in a non-fixed combination. In embodiments, the bisphosphonate drug and the immunotherapy-based composition are administered simultaneously. In embodiments, the bisphosphonate drug and the immunotherapy-based composition are administered sequentially. In embodiments, the bisphosphonate drug and the immunotherapy-based composition are administered in synergistically effective amounts. In embodiments, the bisphosphonate drug and the immunotherapy-based composition are administered at a synergistically effective time interval. In embodiments, the one or more cancer cells are capable of activating a gamma delta T cell resident in the subject following infection of the one or more cancer cells with the immunotherapy-based composition. In embodiments, activating the gamma delta T cell comprises increasing tumor necrosis factor (TNF)-α expression by the gamma delta T cell. In embodiments, the enzyme of the mevalonate pathway is farnesyl diphosphate synthase (FDPS).

Cancer

The compositions and methods provided herein are used to treat cancer. A cell, tissue, or target may be a cancer cell, a cancerous tissue, harbor cancerous tissue, or be a subject or patient diagnosed or at risk of developing a disease or condition. In certain aspects, a cell may be an epithelial, an endothelial, a mesothelial, a glial, a stromal, or a mucosal cell. The cancer cell population can include, but is not limited to a brain, a neuronal, a blood, an endometrial, a meninges, an esophageal, a lung, a cardiovascular, a liver, a lymphoid, a breast, a bone, a connective tissue, a fat, a retinal, a thyroid, a glandular, an adrenal, a pancreatic, a stomach, an intestinal, a kidney, a bladder, a colon, a prostate, a uterine, an ovarian, a cervical, a testicular, a splenic, a skin, a smooth muscle, a cardiac muscle, or a striated muscle cell, and can also include a cancer cell population from any of the foregoing, and can be associated with one or more of carcinomas, sarcomas, myelomas, leukemias, lymphomas, mixed types or mixtures of the foregoing. In still a further aspect cancer includes, but is not limited to astrocytoma, acute myeloid leukemia, anaplastic large cell lymphoma, acute lymphoblastic leukemia, angiosarcoma, B-cell lymphoma, Burkitt's lymphoma, breast carcinoma, bladder carcinoma, carcinoma of the head and neck, cervical carcinoma, chronic lymphoblastic leukemia, chronic myeloid leukemia, colorectal carcinoma, endometrial carcinoma, esophageal squamous cell carcinoma, Ewing's sarcoma, fibrosarcoma, glioma, glioblastoma, gastrinoma, gastric carcinoma, hepatoblastoma, hepatocellular carcinoma, Kaposi's sarcoma, Hodgkin lymphoma, laryngeal squamous cell carcinoma, larynx carcinoma, leukemia, leiomyosarcoma, lipoma, liposarcoma, melanoma, mantle cell lymphoma, medulloblastoma, mesothelioma, myxofibrosarcoma, myeloid leukemia, mucosa-associated lymphoid tissue B cell lymphoma, multiple myeloma, high-risk myelodysplastic syndrome, nasopharyngeal carcinoma, neuroblastoma, neurofibroma, high-grade non-Hodgkin lymphoma, non-Hodgkin lymphoma, lung carcinoma, non-small cell lung carcinoma, ovarian carcinoma, esophageal carcinoma, osteosarcoma, pancreatic carcinoma, pheochromocytoma, prostate carcinoma, renal cell carcinoma, retinoblastoma, rhabdomyosarcoma, salivary gland tumor, schwannoma, small cell lung cancer, squamous cell carcinoma of the head and neck, testicular tumor, thyroid carcinoma, urothelial carcinoma, and Wilms tumor.

The compositions and methods provided herein are also used to treat NSCLC (non-small cell lung cancer), pediatric malignancies, cervical and other tumors caused or promoted by human papilloma virus (HPV), melanoma, Barrett's esophagus (pre-malignant syndrome), adrenal and skin cancers and auto immune, neoplastic cutaneous diseases.

Infectious Diseases

The compositions and methods disclosed herein can be used to treat infectious diseases. The term "infectious disease" includes any disease that is caused by an infectious agent. An "infectious agent" includes any exogenous pathogen including, without limitation, bacteria, fungi, viruses, mycoplasma, and parasites. Infectious agents that may be treated with compositions provided for in this disclosure include any art-recognized infectious organisms that cause pathogenesis in an animal, including such organisms as bacteria that are gram-negative or gram-positive cocci or bacilli, DNA and RNA viruses, including, but not limited to, DNA viruses such as papilloma viruses, parvoviruses, adenoviruses, herpesviruses and vaccinia viruses, and RNA viruses, such as arenaviruses, coronaviruses, rhinoviruses, respiratory syncytial viruses, influenza viruses, picomaviruses, paramyxoviruses, reoviruses, retroviruses, and rhabdoviruses. Examples of fungi that may be treated with the compositions and methods of the disclosure include fungi that grow as molds or are yeast-like, including, for example, fungi that cause diseases such as ringworm, histoplasmosis, blastomycosis, aspergillosis, cryptococcosis, sporotrichosis, coccidioidomycosis, paracoccidio-idomycosis, and candidiasis. Compositions and methods provided for herein may be utilized to treat parasitic infections including, but not limited to, infections caused by somatic tapeworms, blood flukes, tissue roundworms, ameba, and *Plasmodium, Trypanosoma, Leishmania*, and *Toxoplasma* species.

Methods of GD T Cell Activation

Provided herein are compositions and methods for activating GD T cells in an individual, as well as methods for treating tumors and infectious diseases. For instance, in embodiments, the compositions and methods provided herein can be used in methods to treat all known cancers because activated GD T cells comprise a natural mechanism for immune surveillance of tumors (See for e.g.: Pauza et al. 2014 *Frontiers in Immunol.* 5:687). Likewise, in embodiments, the compositions and methods provided herein can be used to treat infectious diseases, including but not limited to flavivirus, influenza virus, human retrovirus, mycobacteria, plasmodia and a variety of other viral, fungal and bacterial infections. (See for e.g.: Pauza and Cairo, 2015 *Cell Immunol.* 296(1).

In general, a vector system is administered to an individual to transfect or transduce a target cell population with the disclosed constructs for decreasing expression of FDPS and, in other embodiments, increasing expression of chemokines or cytokines. Administration and transfection/transduction can occur in vivo or ex vivo, with the transfected cells later administered back into the subject in the latter scenario.

Administration of the disclosed vectors and transfection or transduction of the disclosed constructs into a subject's cells result in decreased expression of FDPS, increased expression of cytokines or chemokines, accumulation of IPP and in many cases, reduced growth rates for genetically modified tumor cells. All of these features work together to activate and co-localize GD T cells to the site of a tumor or infection.

The disclosed methods can also increase the capacity of NK cells to recognize and destroy tumor cells and/or infected cells. Crosstalk between GD T cells and NK cells is an important aspect of regulating the immune and inflammatory responses. Further, GD T cells are known to trigger dendritic cell maturation, recruit B cells and macrophages, and participate in a variety of cytolytic activities, such as secretion of interferon-γ and TNF-α.

In embodiments, the disclosed compositions and methods provided herein comprise a form of gene therapy for activating GD T cells at the site of tumor or infectious disease pathology. In an aspect, the compositions and methods provided herein activate GD T cells and support their proliferation, differentiation, and functional capacities by promoting the production of specific cytokines needed for cytolytic activity capable of killing cancer cells or treating infectious diseases.

In embodiments the gene therapy sequences (e.g., FDPS shRNAs) are carried by therapeutic vectors, including but not limited to viral vectors such as lentiviruses or adeno-associated viruses, although other viral vectors can also be suitable. Gene therapy constructs may also be delivered in the form of DNA or RNA, including but not limited to plasmid forms. In embodiments, the disclosed gene therapy constructs may also be delivered in the form of protein-nucleic acid complexes or lipid nucleic acid complexes and mixtures of these formulations. For instance, a protein-nucleic acid complex can comprise nucleic acids of interest in a complex with cationic peptides such as lysine and arginine. Lipid-nucleic acids complexes can comprise lipid emulsions, micelles, liposomes, and/or mixtures of neutral and cationic lipids such as DOTMA, DOSPA, DOTAP, and DMRIE.

In embodiments, therapeutic vectors may comprise a single construct or at least two, at least three, at least four, or at least five different constructs. When more than one construct is present in a vector the constructs may be identical, or they may be different. For instance, the constructs may vary in terms of their promoters, the presence or absence of integrating elements, and/or their sequences. In some embodiments, a therapeutic vector will comprise at least one construct that encodes a small RNA capable of knocking down the expression of FDPS. In embodiments, the therapeutic vector will also encode a specific cytokine(s) and/or chemokine(s), including but not limited to TNF-α, interferon-γ, IL-1, IL-2, IL-15, IL-17, IL-18 or IL-12. In some embodiments, a single construct may encode both small RNAs capable of knocking down the expression of FDPS and specific cytokines or chemokines, including but not limited to TNF-α, interferon-γ, IL-1, IL-2, IL-15, IL-17, IL-18 or IL-12.

In embodiments, viral vectors may introduce nucleic acid constructs that become integrated into the host chromosome. Alternately, transient delivery vectors may be used to prevent chromosomal integration and limit the lifespan of gene therapy constructs.

In embodiments, the disclosed constructs and vectors comprise short hairpin RNA ("shRNA"), micro RNA ("miRNA"), or siRNA capable of reducing or knocking down expression of FDPS and/or geranyl pyrophosphate synthase ("GPPS") and/or farnesyl transferase ("FT") genes. By down regulating these genes, which control steroid and isoprenoid synthesis, isopentenyl pyrophosphate ("IPP") levels are elevated. Elevation and accumulation of IPP is a known mechanism for increasing GD T cells activation. Further, down regulation of these pyrophosphate synthase genes removes an important negative regulator of inflammasome function that in turn results in increased expression of cytokines that are important for GD T cell activation and effector cell function.

In embodiments, the disclosed constructs are regulated by specific promoters that are capable of producing interleukin-2 and/or interleukin-15 to sustain GD T cell proliferation. In addition, the disclosed constructs may be regulated by specific promoters that are capable of producing interleukin-1 beta and/or interleukin-18 and/or interferon-gamma required for GD T cell differentiation and acquisition of all effector cell function. Desirable effector cell functions include the capacity for direct cytotoxic cell killing of tumors and/or infected cells, secretion of beneficial cytokines and/or chemokines, increased expression of NK receptors required to recognize cancerous or infected cells, and increased expression of Fc receptors needed to bind targeting antibodies in order to co-localize GD T cells with cancerous or infected cell targets.

In embodiments, the disclosed methods activate GD T cells, resulting in the indirect effect of increasing the capacity for NK cells to attack and destroy cancerous cells, tumors, or infected cells. The activation of NK cells requires GD T cells that are stimulated to proliferate and differentiate, and to express 4-1BBL costimulatory ligand needed to engage the 4-1BB costimulatory receptor on NK cells. This form of crosstalk is known as an important mechanism for activating NK cells and is achieved here through the action of the disclosed methods and compositions.

In another aspect, crosstalk between GD T cells and NK cells is an important mechanism for eliminating inflammatory dendritic cells that accumulate in diseased tissues. Alone, neither GD T cells nor NK cells are capable of destroying dendritic cells, but once the aforementioned crosstalk interactions have occurred, NK cells are altered to become cytotoxic against inflammatory dendritic cells. This immuno-regulatory mechanism depends on strong activation and proliferation of GD T cells.

In embodiments, the disclosed methods for activation of GD T cells further comprise a step of suppressing pathologic inflammatory responses that may include cellular proliferation leading to atherosclerosis, chronic immune activation that stimulates tumor growth, autoimmune diseases including psoriasis and other presentations in the epidermis, inflammatory diseases of the central nervous system, and arthritis and other diseases of unregulated immune responses.

In embodiments, therapeutic vectors are administered in combination with bisphosphonate drugs. In various embodiments, such combinations achieve synergistic, positive or heightened activation of gamma delta T cells. Such positive activation may allow alternate, modified or reduced doses of bisphosphonates and may decrease adverse reactions to bisphosphonates including acute inflammatory responses and chronic diseases. Combinations of therapeutic vectors with bisphosphonates may be together or separate, with or without instructions for combined use or to combination products. The therapeutic vectors and/or bisphosphonates may be administered entirely separately and may be formulated in entirely distinct pharmaceutical dosage forms. The therapeutic vectors and/or bisphosphonates may be sold independently of each other, with or without label instructions concerning the possibility of a combined use. Such instructions also may be provided in the package equipment, e.g., leaflet or the like, or in other information, e.g., provided to physicians and medical staff (e.g., oral communications, communications in writing or the like). Such labels or other instructions can refer to either a fixed combination in one dosage unit form, or a non-fixed combination as a kit of parts for the combined administration where the therapeutic vector may be administered independently of the bisphosphonate drug, at the same time, or separately within time intervals. In various embodiments, the combination exhibits a cooperative or joint effect, or a decrease in toxicity or complications of treatment. In one embodiment the effect of the combination is synergistic. A synergistic effect is achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together, albeit subject to potential variances in timing as detailed herein.

The combinations herein may be manufactured and/or formulated by the same or different manufacturers. The active ingredients may be brought together into a combination therapy: (i) prior to release of the combination product to physicians (e.g., in the case of a kit comprising the compound of the disclosure and the other therapeutic agent); (ii) by the treating physician (or under the guidance of a physician) shortly before administration; (iii) in the actual patient, e.g., during sequential administration of the active ingredients disclosed herein.

In embodiments, a therapeutically effective amount of each of the combinations may be administered simultaneously or sequentially and in any order, and the components may be administered together or separate. For example, the method of treating a proliferative disease according to the disclosure may comprise (i) administration of a first agent such as a therapeutic vector that forms part of a lentiviral particle, and (ii) administration of a second agent such as a bisphosphonate drug in free or pharmaceutically acceptable salt form, simultaneously or sequentially in any order, in jointly therapeutically effective amounts, preferably in cooperative, jointly effective, and/or synergistically effective, amounts, e.g., in daily or intermittent dosages corresponding to the amounts described herein. The combinations may be administered separately at different times during the course of therapy or concurrently in divided or single drug forms. Furthermore, the term "administering" also encompasses the use of a pro-drug of a combination partner that converts in vivo to the combination partner as such. The instant disclosure is therefore to be understood as embracing all such regimens of simultaneous or alternating treatment and the term "administering" is to be interpreted accordingly.

In embodiments, agents (i) and (ii) can be administered using any pharmaceutically acceptable method, such as intranasal, buccal, sublingual, oral, rectal, ocular, parenteral (intravenously, intradermally, intramuscularly, subcutaneously, intraperitoneally), pulmonary, intravaginal, locally administered, topically administered, topically administered after scarification, mucosally administered, via an aerosol, in semi-solid media such as agarose or gelatin, or via a buccal or nasal spray formulation, and/or in solid media such as granules or powders including inert excipients. For example, a therapeutic vector and/or bisphosphonate drug may be administered intravenously. Further, agents (i) and (ii) can be formulated into any pharmaceutically acceptable dosage form, such as a solid dosage form, tablet, pill, lozenge, capsule, liquid dispersion, gel, aerosol, pulmonary aerosol, nasal aerosol, ointment, cream, semi-solid dosage form, a solution, an emulsion, and a suspension. For example, a bisphosphonate drug may be formulated into a tablet and administered orally.

A combination therapy according to the disclosure can besides or in addition be administered especially for cancer therapy in combination with chemotherapy, radiotherapy, immunotherapy, surgical intervention, or a combination of these. Long-term therapy is equally possible as is adjuvant therapy in the context of other treatment strategies, as described above. In embodiments, a combination therapy can also include immune adjuvants (e.g., Toll-like receptor ligands), immune stimulating toxins, or stimulatory protozoans or stimulatory bacilli (e.g., *bacille Calmette-Guerin*), cancer therapeutic drugs, cell-based therapies (gamma delta T cell or other cell types known to be in use or under evaluation for tumor therapy and may also include natural or genetically-engineered cells and cells cultured under) ionizing radiation or surgery. Other possible treatments are therapy to maintain the patient's status after tumor regression, or even chemo-preventive therapy, for example in patients at risk.

Constructs for GD T Cell Activation

Inhibition of FDPS results in IPP accumulation, resulting in activation of Vδ2+ GD T cells and expression of IL-18, which is also important in activating GD T cells. Inhibition of farnesyl transferase results in decreased prenylation of proteins. The disclosed constructs can be transfected or transduced into specific target cells, like tumor cells or infected cells, where they can express RNA sequences (i.e., siRNA, shRNA or microRNA) that will inhibit translation of FDPS as well as encode and express cytotoxic cytokines or chemokines.

Disclosed herein are constructs for decreasing expression of FDPS and/or FT, increasing expression of cytokines, and increasing expression of chemokines including RANTES. For instance, in some embodiments the constructs may encode for interferon-gamma, IL-1, IL-2, IL-15, IL-17, IL-18 or IL-12.

Expression of cytokines and chemokines, like those listed above, will result in localized cytotoxic destruction of tumor cells or cells infected with pathogenic organisms. Accordingly, expression of such constructs by a tumor cell or an infected cell will result in the unwanted cells assisting in its own destruction.

Likewise, if the disclosed constructs are expressed in a tumor cell or infected cell, decreasing the expression of FDPS and FT will result in activation and recruitment of GD T cells to the tumor site of site of cell infection. Increasing expression of RANTES will further attract GD T cells to intended tissue location. Because GD T cells can kill a broad range of tumors of epithelial origin as well as many leukemias and lymphomas, and are further able to produce high levels of the anti-tumor cytokine, IFNγ, recruitment of GD T cells to the site of a tumor can be a particularly effective means of inducing anti-tumor immunity.

Decreased expression of FDPS can be achieved via shRNA, microRNA, siRNA, or other means known in the art. For instance, shRNAs according to SEQ ID NOS: 1, 2, 3, or 4, or variants thereof can be used in the disclosed constructs and methods, although this example is not limiting. The coding regions for RNAs to decrease expression of FDPS and FT and the coding regions of cytokine and chemokines may be in the same construct or on different constructs.

The classical approach for the production of recombinant polypeptides or gene regulatory molecules including small RNA is the use of stable expression constructs. These constructs are based upon chromosomal integration of a transduced expression plasmid (or at least a portion thereof) into the genome of the host cell, short-duration plasmid transfection, or non-integrating viral vectors also with limited half-life. The sites of gene integration are generally random, and the number and ratio of genes integrating at any particular site are often unpredictable; likewise, non-integrating plasmids or viral vectors also generate nuclear DNA but these species usually lack sequences required for DNA replication and continuous maintenance. Thus, constructs that rely on chromosomal integration result in permanent maintenance of the recombinant gene that may exceed the therapeutic interval.

An alternative to stable expression constructs for gene expression are transient expression constructs. The expression of the latter gene expression construct is based on non-integrated plasmids, and hence the expression is typically lost as the cell undergoes division or the plasmid vectors are destroyed by endogenous nucleases.

The disclosed constructs are preferably episomal constructs that are transiently expressed. Episomal constructs are degraded or diluted over time such that they do not make permanent changes to a subject's genome, nor are they incorporated into the chromosome of a target cell. The process of episomal replication typically incorporates both host cell replication machinery and viral trans-acting factors.

Avoiding chromosomal integration reduces certain barriers to in vivo gene delivery. However, even integration-defective constructs can have a background frequency of integration, and any DNA molecule can find rare homologies to recombine with host sequences; but these rates of integration are exceptionally rare and generally not clinically significant.

Thus, in some embodiments, the disclosed vectors support active gene and/or small RNA delivery over a period of about 1, about 2, about 3, about 4, about 5, about 6, about 7, about 8, about 9, about 10, about 11, or about 12 weeks. In some embodiments, the disclosed vectors support active gene and/or small RNA delivery over a period of about 1 month, 2 months, 3 months, 4 months, 5 months, 6 months, 7 months, 8 months, 9 months, 10 months, 11 months, 12 months, or longer. Any combination of these time periods can also be used in the methods of the invention, e.g., 1 month and 1 week, or 3 months and 2 weeks.

However, in some embodiments, the constructs comprise integrating elements that depend on a retroviral integrase gene, such that the construct becomes integrated into the subject's chromosome. Retrotransposition and transposition are additional examples of mechanisms whereby mobile genetic elements become integrated or inserted into the chromosome. Plasmids may become integrated into the chromosome by recombination, and gene editing technologies including CRISPR and TALEN utilize guide RNA sequences and alter chromosomal loci by gene conversion mechanisms.

Constructs may comprise specific promoters for expressing cytokines involved in the maintenance of GD T cells (i.e., IL-2, IL-7, IL-17, and IL-15). For example, promoters that may be incorporated into the disclosed constructs include but are not limited to TATA-box promoters, CpG-box promoters, CCAAT-box promoters, TTGACA-box promoters, BRE-box promoters, INR-box promoters, AT-based promoters, CG-based promoters, ATCG-compact promoters, ATCG-balanced promoters, ATCG-middle promoters, ATCG-less promoters, AT-less promoters, CG-less promoters, AT-spike promoters, and CG-spike promoters. See Gagniuc and Ionescu-Tirgoviste, *Eukaryotic genomes may exhibit up to* 10 *generic classes of gene promoters*, BMC GENOMICS 13:512 (2012).

Therapeutic Vectors

The construct can be delivered via known transfection and/or transduction vectors, including but not limited to lentiviral vectors, gamma-retroviruses, adeno-associated virus, poxvirus, herpesvirus vectors, protein and/or lipid complexes, liposomes, micelles, and the like.

Viral vectors can be preferentially targeted to cell types that are useful for the disclosed methods (i.e., tumor cells or myeloid cells). Viral vectors can be used to transduce genes into target cells owing to specific virus envelope-host cell receptor interactions and viral mechanisms for gene expression. As a result, viral vectors have been used as vehicles for the transfer of genes into many different cell types including whole embryos, fertilized eggs, isolated tissue samples, tissue targets in situ, and cultured cell lines. The ability to introduce and express foreign genes in a cell is useful for the study of gene expression, and the elucidation of cell lineages as well as providing the potential for therapeutic interventions such as gene therapy, somatic cell reprogramming of induced pluripotent stem cells, and various types of immunotherapy. Viral components from viruses like Papovaviridae (e.g. bovine papillomavirus or BPV) or Herpesviridae (e.g. Epstein Barr Virus or EBV) or Hepadnaviridae (e.g. Hepatitis B Virus or HBV) or pox vectors including vaccinia may be used in the disclosed vectors.

Lentiviral vectors are a preferred type of vector for the disclosed compositions and methods, although the disclosure is not specifically limited to lentiviral vectors. Lentivirus is a genus of viruses that can deliver a significant amount of viral nucleic acid into a host cell. Lentiviruses are characterized as having a unique ability to infect/transduce non-dividing cells, and following transduction, lentiviruses integrate their nucleic acid into the host cell's chromosomes.

Infectious lentiviruses have three main genes coding for the virulence proteins gag, pol, and env, and two regulatory genes including tat and rev. Depending on the specific serotype and virus, there may be additional accessory genes that code for proteins involved in regulation, synthesis, and/or processing viral nucleic acids and other replicative functions.

Moreover, lentiviruses contain long terminal repeat (LTR) regions, which may be approximately 600 nt long. LTRs may be segmented into U3, R, and U5 regions. LTRs can mediate integration of retroviral DNA into the host chromosome via the action of integrase. Alternatively, without functioning integrase, the LTRs may be used to circularize the viral nucleic acid.

Viral proteins involved in early stages of lentivirus replication include reverse transcriptase and integrase. Reverse transcriptase is the virally encoded, RNA-dependent DNA polymerase. The enzyme uses a viral RNA genome as a template for the synthesis of a complementary DNA copy. Reverse transcriptase also has RNaseH activity for destruction of the RNA-template. Integrase binds both the viral cDNA generated by reverse transcriptase and the host DNA. Integrase processes the LTR before inserting the viral genome into the host DNA. Tat acts as a trans-activator during transcription to enhance initiation and elongation. The rev responsive element acts post-transcriptionally, regulating mRNA splicing and transport to the cytoplasm.

Viral vectors, in general, comprise glycoproteins and the various glycoproteins may provide specific affinities. For instance, VSV-G peptides can increase transfection into myeloid cells. Alternatively, viral vectors can also have targeting moieties, such as antibodies, attached to their shell peptides. Targeting antibodies can be specific for antigens that are overexpressed on a tumor, for instance, like HER-2, PSA, CEA, M2-PK, and CA19-9.

Other viral vector specificities are also known in the art and can be used to target particular populations of cells. For example, poxvirus vectors target to macrophages and dendritic cells.

Lentiviral Vector System

A lentiviral virion (particle) is expressed by a vector system encoding the necessary viral proteins to produce a virion (viral particle). There is at least one vector containing a nucleic acid sequence encoding the lentiviral pol proteins necessary for reverse transcription and integration, operably linked to a promoter. In another embodiment, the pol proteins are expressed by multiple vectors. There is also a vector containing a nucleic acid sequence encoding the lentiviral gag proteins necessary for forming a viral capsid operably linked to a promoter. In an embodiment, this gag nucleic acid sequence is on a separate vector than at least some of the pol nucleic acid sequence. In another embodiment, the gag nucleic acid is on a separate vector from all the pol nucleic acid sequences that encode pol proteins.

Numerous modifications can be made to the vectors, which are used to create the particles to further minimize the chance of obtaining wild type revertants. These include, but are not limited to deletions of the U3 region of the LTR, tat deletions and matrix (MA) deletions.

The gag, pol and env vector(s) do not contain nucleotides from the lentiviral genome that package lentiviral RNA, referred to as the lentiviral packaging sequence.

The vector(s) forming the particle preferably do not contain a nucleic acid sequence from the lentiviral genome that expresses an envelope protein. Preferably, a separate vector that contains a nucleic acid sequence encoding an envelope protein operably linked to a promoter is used. This env vector also does not contain a lentiviral packaging sequence. In one embodiment the env nucleic acid sequence encodes a lentiviral envelope protein.

In another embodiment the envelope protein is not from the lentivirus, but from a different virus. The resultant particle is referred to as a pseudotyped particle. By appropriate selection of envelopes one can "infect" virtually any cell. For example, one can use an env gene that encodes an envelope protein that targets an endocytic compartment such as that of the influenza virus, VSV-G, alpha viruses (Semliki forest virus, Sindbis virus), arenaviruses (lymphocytic choriomeningitis virus), flaviviruses (tick-borne encephalitis virus, Dengue virus, hepatitis C virus, GB virus), rhabdoviruses (vesicular stomatitis virus, rabies virus), paramyxoviruses (mumps or measles) and orthomyxoviruses (influenza virus). Other envelopes that can preferably be used include those from Moloney Leukemia Virus such as MLV-E, MLV-A and GALV. These latter envelopes are particularly preferred where the host cell is a primary cell. Other envelope proteins can be selected depending upon the desired host cell. For example, targeting specific receptors such as a dopamine receptor can be used for brain delivery. Another target can be vascular endothelium. These cells can be targeted using a filovirus envelope. For example, the GP of Ebola, which by post-transcriptional modification become the GP, and $GP_2$ glycoproteins. In another embodiment, one can use different lentiviral capsids with a pseudotyped envelope (for example, FIV or SHIV [U.S. Pat. No. 5,654, 195]). A SHIV pseudotyped vector can readily be used in animal models such as monkeys.

As detailed herein, a lentiviral vector system typically includes at least one helper plasmid comprising at least one of a gag, pol, or rev gene. Each of the gag, pol and rev genes may be provided on individual plasmids, or one or more genes may be provided together on the same plasmid. In one embodiment, the gag, pol, and rev genes are provided on the same plasmid (e.g., FIG. 2). In another embodiment, the gag and pol genes are provided on a first plasmid and the rev gene is provided on a second plasmid (e.g., FIG. 3). Accordingly, both 3-vector and 4-vector systems can be used to produce a lentivirus as described in the Examples section and elsewhere herein. The therapeutic vector, the envelope plasmid and at least one helper plasmid are transfected into a packaging cell line. A non-limiting example of a packaging cell line is the 293T/17 HEK cell line. When the therapeutic vector, the envelope plasmid, and at least one helper plasmid are transfected into the packaging cell line, a lentiviral particle is ultimately produced.

In another aspect, a lentiviral vector system for expressing a lentiviral particle is disclosed. The system includes a lentiviral vector as described herein; an envelope plasmid for expressing an envelope protein optimized for infecting a cell; and at least one helper plasmid for expressing gag, pol, and rev genes, wherein when the lentiviral vector, the envelope plasmid, and the at least one helper plasmid are transfected into a packaging cell line, a lentiviral particle is produced by the packaging cell line, wherein the lentiviral particle is capable of inhibiting production of chemokine receptor CCR5 or targeting an HIV RNA sequence.

Figure 2:
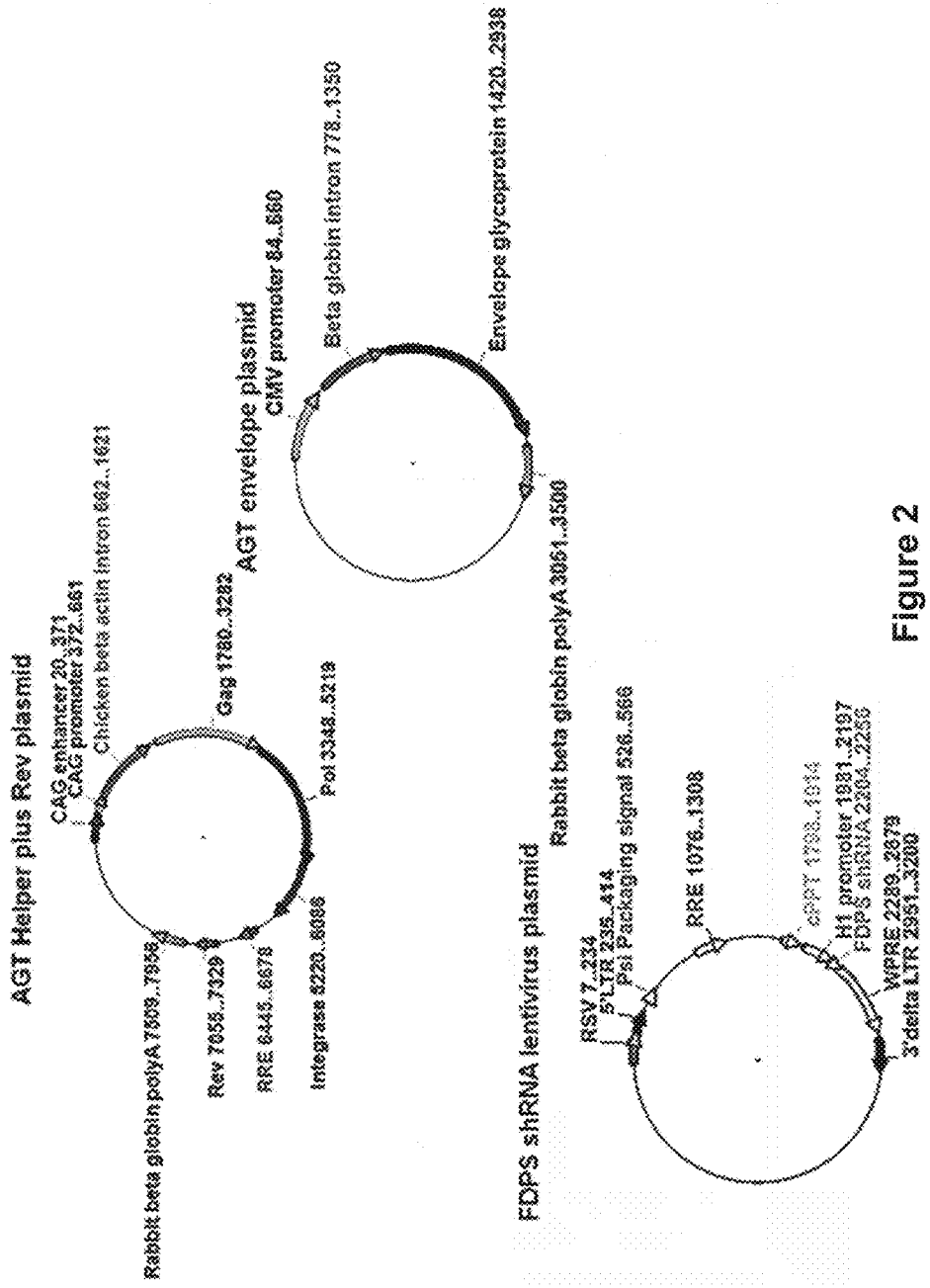
FIG. 2 depicts an exemplary 3-vector lentiviral vector system in a circularized form.

In another aspect, and as detailed in FIG. 2, the lentiviral vector, which is also referred to herein as a therapeutic vector, can include the following elements: hybrid 5' long terminal repeat (RSV/5' LTR) (SEQ ID NOS: 11-12), Psi sequence (RNA packaging site) (SEQ ID NO: 13), RRE (Rev-response element) (SEQ ID NO: 14), cPPT (polypurine tract) (SEQ ID NO: 15), H1 promoter (SEQ ID NO: 16), FDPS shRNA (SEQ ID NOS: 1, 2, 3, 4), Woodchuck Post-Transcriptional Regulatory Element (WPRE) (SEQ ID NO: 17), and 3' Delta LTR (SEQ ID NO: 18). In another aspect, sequence variation, by way of substitution, deletion, addition, or mutation can be used to modify the sequences references herein.

In another aspect, and as detailed herein, a helper plasmid has been designed to include the following elements: CAG promoter (SEQ ID NO: 19); HIV component gag (SEQ ID NO: 20); HIV component pol (SEQ ID NO: 21); HIV Int (SEQ ID NO: 22); HIV RRE (SEQ ID NO: 23); and HIV Rev (SEQ ID NO: 24). In another aspect, the helper plasmid may be modified to include a first helper plasmid for expressing the gag and pol genes, and a second and separate plasmid for expressing the rev gene. In another aspect, sequence variation, by way of substitution, deletion, addition, or mutation can be used to modify the sequences references herein.

In another aspect, and as detailed herein, an envelope plasmid has been designed to include the following elements being from left to right: RNA polymerase II promoter (CMV) (SEQ ID NO: 25) and vesicular stomatitis virus G glycoprotein (VSV-G) (SEQ ID NO: 26). In another aspect, sequence variation, by way of substitution, deletion, addition, or mutation can be used to modify the sequences references herein.

In another aspect, the plasmids used for lentiviral packaging can be modified with similar elements and the intron sequences could potentially be removed without loss of vector function. For example, the following elements can replace similar elements in the plasmids that comprise the packaging system: Elongation Factor-1 (EF-1), phosphoglycerate kinase (PGK), and ubiquitin C (UbC) promoters can replace the CMV or CAG promoter. SV40 poly A and bGH poly A can replace the rabbit beta globin poly A. The HIV sequences in the helper plasmid can be constructed from different HIV strains or clades. The VSV-G glycoprotein can be substituted with membrane glycoproteins from feline endogenous virus (RD114), gibbon ape leukemia virus (GALV), Rabies (FUG), lymphocytic choriomeningitis virus (LCMV), influenza A fowl plague virus (FPV), Ross River alphavirus (RRV), murine leukemia virus 10A1 (MLV), or Ebola virus (EboV).

Of note, lentiviral packaging systems can be acquired commercially (e.g., Lenti-vpak packaging kit from OriGene Technologies, Inc., Rockville, Md.), and can also be designed as described herein. Moreover, it is within the skill of a person skilled in the art to substitute or modify aspects of a lentiviral packaging system to improve any number of relevant factors, including the production efficiency of a lentiviral particle.

Doses and Dosage Forms

The disclosed vectors allow for short, medium, or long-term expression of genes or sequences of interest and episomal maintenance of the disclosed vectors. Accordingly, dosing regimens may vary based upon the condition being treated and the method of administration.

In one embodiment, transduction vectors may be administered to a subject in need in varying doses. Specifically, a subject may be administered about $\geq 10^6$ infectious doses (where 1 dose is needed on average to transduce 1 target cell). More specifically, a subject may be administered about $\geq 10^7$, about $\geq 10^8$, about $\geq 10^9$, or about $\geq 10^{10}$ infectious doses, or any number of doses in-between these values. Upper limits of transduction vector dosing will be determined for each disease indication and will depend on toxicity/safety profiles for each individual product or product lot.

Additionally, a vector of the present disclosure may be administered periodically, such as once or twice a day, or any other suitable time period. For example, vectors may be administered to a subject in need once a week, once every other week, once every three weeks, once a month, every other month, every three months, every six months, every nine months, once a year, every eighteen months, every two years, every thirty months, or every three years.

In one embodiment, the disclosed vectors are administered as a pharmaceutical composition. In some embodiments, the pharmaceutical composition comprising the disclosed vectors can be formulated in a wide variety of dosage forms, including but not limited to nasal, pulmonary, oral, topical, or parenteral dosage forms for clinical application. Each of the dosage forms can comprise various solubilizing agents, disintegrating agents, surfactants, fillers, thickeners, binders, diluents such as wetting agents or other pharmaceutically acceptable excipients. The pharmaceutical composition comprising a vector can also be formulated for injection, insufflation, infusion, or intradermal exposure. For instance, an injectable formulation may comprise the disclosed vectors in an aqueous or non-aqueous solution at a suitable pH and tonicity.

The disclosed vectors may be administered to a subject via direct injection into a tumor site or at a site of infection. In some embodiments, the vectors can be administered systemically. In some embodiments, the vectors can be administered via guided cannulation to tissues immediately surrounding the sites of tumor or infection.

The disclosed vector compositions can be administered using any pharmaceutically acceptable method, such as intranasal, buccal, sublingual, oral, rectal, ocular, parenteral (intravenously, intradermally, intramuscularly, subcutaneously, intraperitoneally), pulmonary, intravaginal, locally administered, topically administered, topically administered after scarification, mucosally administered, via an aerosol, in semi-solid media such as agarose or gelatin, or via a buccal or nasal spray formulation.

Further, the disclosed vector compositions can be formulated into any pharmaceutically acceptable dosage form, such as a solid dosage form, tablet, pill, lozenge, capsule, liquid dispersion, gel, aerosol, pulmonary aerosol, nasal aerosol, ointment, cream, semi-solid dosage form, a solution, an emulsion, and a suspension. Further, the composition may be a controlled release formulation, sustained release formulation, immediate release formulation, or any combination thereof. Further, the composition may be a transdermal delivery system.

In some embodiments, the pharmaceutical composition comprising a vector can be formulated in a solid dosage form for oral administration, and the solid dosage form can be powders, granules, capsules, tablets or pills. In some embodiments, the solid dosage form can include one or more excipients such as calcium carbonate, starch, sucrose, lactose, microcrystalline cellulose or gelatin. In addition, the solid dosage form can include, in addition to the excipients, a lubricant such as talc or magnesium stearate. In some embodiments, the oral dosage form can be immediate release, or a modified release form. Modified release dosage forms include controlled or extended release, enteric release, and the like. The excipients used in the modified release dosage forms are commonly known to a person of ordinary skill in the art.

In a further embodiment, the pharmaceutical composition comprising a vector can be formulated as a sublingual or buccal dosage form. Such dosage forms comprise sublingual tablets or solution compositions that are administered under the tongue and buccal tablets that are placed between the cheek and gum.

In some embodiments, the pharmaceutical composition comprising a vector can be formulated as a nasal dosage form. Such dosage forms of the present invention comprise solution, suspension, and gel compositions for nasal delivery.

In some embodiments, the pharmaceutical composition comprising a vector can be formulated in a liquid dosage form for oral administration, such as suspensions, emulsions or syrups. In some embodiments, the liquid dosage form can include, in addition to commonly used simple diluents such as water and liquid paraffin, various excipients such as humectants, sweeteners, aromatics or preservatives. In particular embodiments, the composition comprising vectors can be formulated to be suitable for administration to a pediatric patient.

In some embodiment, the pharmaceutical composition can be formulated in a dosage form for parenteral administration, such as sterile aqueous solutions, suspensions, emulsions, non-aqueous solutions or suppositories. In some embodiments, the solutions or suspensions can include propylene glycol, polyethylene glycol, vegetable oils such as olive oil or injectable esters such as ethyl oleate.

The dosage of the pharmaceutical composition can vary depending on the patient's weight, age, gender, administration time and mode, excretion rate, and the severity of disease.

In some embodiments, the treatment of cancer is accomplished by guided direct injection of the disclosed vector constructs into tumors, using needle, or intravascular cannulation. In some embodiments, the disclosed vectors are administered into the cerebrospinal fluid, blood or lymphatic circulation by venous or arterial cannulation or injection, intradermal delivery, intramuscular delivery or injection into a draining organ near the site of disease.

The following examples are given to illustrate the present invention. It should be understood, however, that the invention is not to be limited to the specific conditions or details described in these examples. All printed publications referenced herein are specifically incorporated by reference.

EXAMPLES

Example 1: Development of a Lentiviral Vector System

Figure 4:
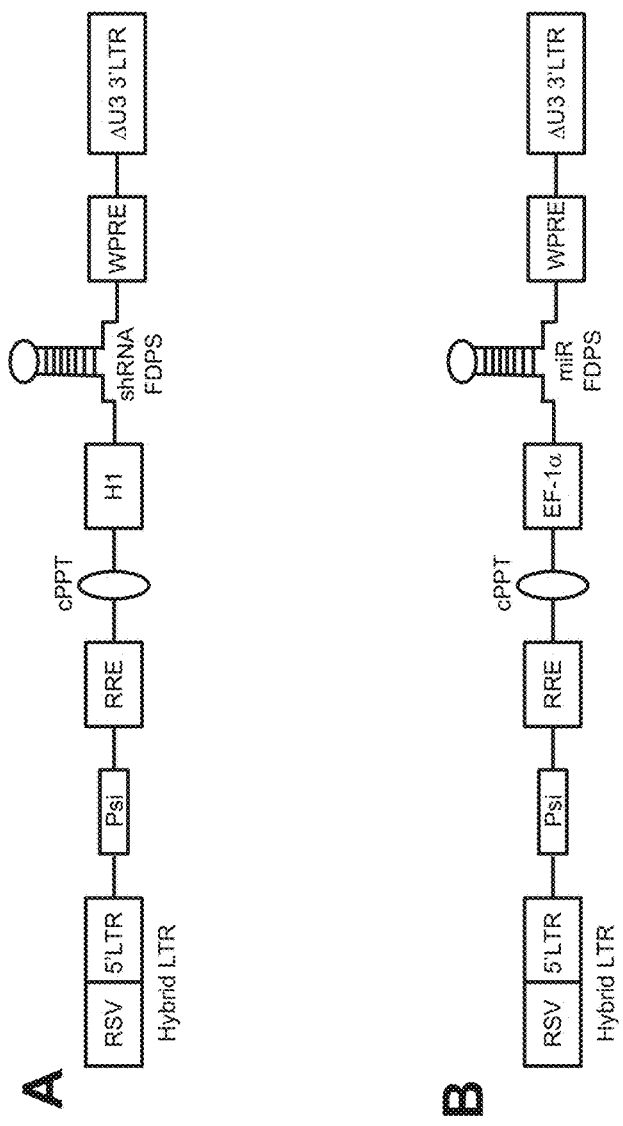
FIG. 4 depicts: (A) a linear map of a lentiviral vector expressing a FDPS shRNA targeting sequence; and (B) a linear map of a lentiviral vector expressing a synthetic microRNA with a FDPS targeting sequence.

A lentiviral vector system was developed as summarized in FIG. 4 (circularized form). Lentiviral particles were produced in 293T/17 HEK cells (purchased from American Type Culture Collection, Manassas, Va.) following transfection with the therapeutic vector, the envelope plasmid, and the helper plasmid. The transfection of 293T/17 HEK cells, which produced functional viral particles, employed the reagent Poly(ethylenimine) (PEI) to increase the efficiency of plasmid DNA uptake. The plasmids and DNA were initially added separately in culture medium without serum in a ratio of 3:1 (mass ratio of PEI to DNA). After 2-3 days, cell medium was collected and lentiviral particles were purified by high-speed centrifugation and/or filtration followed by anion-exchange chromatography. The concentration of lentiviral particles can be expressed in terms of transducing units/ml (TU/ml). The determination of TU was accomplished by measuring HIV p24 levels in culture fluids (p24 protein is incorporated into lentiviral particles), measuring the number of viral DNA copies per cell by quantitative PCR, or by infecting cells and using light (if the vectors encode luciferase or fluorescent protein markers).

As mentioned above, a 3-vector system (i.e., a 2-vector lentiviral packaging system) was designed for the production of lentiviral particles. A schematic of the 3-vector system is shown in FIG. 2. Briefly, and with reference to FIG. 2, the top-most vector is a helper plasmid, which, in this case, includes Rev. The vector appearing in the middle of FIG. 2 is the envelope plasmid. The bottom-most vector is the therapeutic vector, as described herein.

Referring more specifically to FIG. 2, the Helper plus Rev plasmid includes a CAG enhancer (SEQ ID NO: 27); a CAG promoter (SEQ ID NO: 19); a chicken beta actin intron (SEQ ID NO: 28); a HIV gag (SEQ ID NO: 20); a HIV Pol (SEQ ID NO: 21); a HIV Int (SEQ ID NO: 22); a HIV RRE (SEQ ID NO: 23); a HIV Rev (SEQ ID NO: 24); and a rabbit beta globin poly A (SEQ ID NO: 29).

The Envelope plasmid includes a CMV promoter (SEQ ID NO: 25); a beta globin intron (SEQ ID NO: 30); a VSV-G (SEQ ID NO: 28); and a rabbit beta globin poly A (SEQ ID NO: 31).

Synthesis of a 2-Vector Lentiviral Packaging System Including Helper (Plus Rev) and Envelope Plasmids.

Materials and Methods:

Construction of the helper plasmid: The helper plasmid was constructed by initial PCR amplification of a DNA fragment from the pNL4-3 HIV plasmid (NIH Aids Reagent Program) containing Gag, Pol, and Integrase genes. Primers were designed to amplify the fragment with EcoRI and NotI restriction sites which could be used to insert at the same sites in the pCDNA3 plasmid (Invitrogen). The forward primer was (5'-TAAGCAGAATTC ATGAATTTGCCAG-GAAGAT-3') (SEQ ID NO: 32) and reverse primer was (5'-CCATACAATGAATGGACACTAGGCGGCCGCAC-GAAT-3') (SEQ ID NO: 33).

The sequence for the Gag, Pol, Integrase fragment was as follows:

```
                                    (SEQ ID NO: 34)
GAATTCATGAATTTGCCAGGAAGATGGAAACCAAAAATGATAGGGGGAAT

TGGAGGTTTTATCAAAGTAAGACAGTATGATCAGATACTCATAGAAATCT

GCGGACATAAAGCTATAGGTACAGTATTAGTAGGACCTACACCTGTCAAC

ATAATTGGAAGAAATCTGTTGACTCAGATTGGCTGCACTTTAAATTTTCC

CATTAGTCCTATTGAGACTGTACCAGTAAAATTAAAGCCAGGAATGGATG

GCCCAAAAGTTAAACAATGGCCATTGACAGAAGAAAAAATAAAAGCATTA
```

-continued

GTAGAAATTTGTACAGAAATGGAAAAGGAAGGAAAAATTTCAAAAATTGG

GCCTGAAAATCCATACAATACTCCAGTATTTGCCATAAAGAAAAAAGACA

GTACTAAATGGAGAAAATTAGTAGATTTCAGAGAACTTAATAAGAGAACT

CAAGATTTCTGGGAAGTTCAATTAGGAATACCACATCCTGCAGGGTTAAA

ACAGAAAAAATCAGTAACAGTACTGGATGTGGGCGATGCATATTTTCAG

TTCCCTTAGATAAAGACTTCAGGAAGTATACTGCATTTACCATACCTAGT

ATAAACAATGAGACACCAGGGATTAGATATCAGTACAATGTGCTTCCACA

GGGATGGAAAGGATCACCAGCAATATTCCAGTGTAGCATGACAAAAATCT

TAGAGCCTTTTAGAAAACAAAATCCAGACATAGTCATCTATCAATACATG

GATGATTTGTATGTAGGATCTGACTTAGAAATAGGGCAGCATAGAACAAA

AATAGAGGAACTGAGACAACATCTGTTGAGGTGGGGATTTACCACACCAG

ACAAAAAACATCAGAAAGAACCTCCATTCCTTTGGATGGGTTATGAACTC

CATCCTGATAAATGGACAGTACAGCCTATAGTGCTGCCAGAAAAGGACAG

CTGGACTGTCAATGACATACAGAAATTAGTGGGAAAATTGAATTGGGCAA

GTCAGATTTATGCAGGGATTAAAGTAAGGCAATTATGTAAACTTCTTAGG

GGAACCAAAGCACTAACAGAAGTAGTACCACTAACAGAAGAAGCAGAGCT

AGAACTGGCAGAAAACAGGGAGATTCTAAAAGAACCGGTACATGGAGTGT

ATTATGACCCATCAAAAGACTTAATAGCAGAAATACAGAAGCAGGGGCAA

GGCCAATGGACATATCAAATTTATCAAGAGCCATTTAAAAATCTGAAAAC

AGGAAAGTATGCAAGAATGAAGGGTGCCCACACTAATGATGTGAAACAAT

TAACAGAGGCAGTACAAAAAATAGCCACAGAAAGCATAGTAATATGGGGA

AAGACTCCTAAATTTAAATTACCCATACAAAAGGAAACATGGGAAGCATG

GTGGACAGAGTATTGGCAAGCCACCTGGATTCCTGAGTGGGAGTTTGTCA

ATACCCCTCCCTTAGTGAAGTTATGGTACCAGTTAGAGAAAGAACCCATA

ATAGGAGCAGAAACTTTCTATGTAGATGGGGCAGCCAATAGGGAAACTAA

ATTAGGAAAAGCAGGATATGTAACTGACAGAGGAAGACAAAAAGTTGTCC

CCCTAACGGACACAACAAATCAGAAGACTGAGTTACAAGCAATTCATCTA

GCTTTGCAGGATTCGGGATTAGAAGTAAACATAGTGACAGACTCACAATA

TGCATTGGGAATCATTCAAGCACAACCAGATAAGAGTGAATCAGAGTTAG

TCAGTCAAATAATAGAGCAGTTAATAAAAAAGGAAAAAGTCTACCTGGCA

TGGGTACCAGCACACAAAGGAATTGGAGGAAATGAACAAGTAGATAAATT

GGTCAGTGCTGGAATCAGGAAAGTACTATTTTTAGATGGAATAGATAAGG

CCCAAGAAGAACATGAGAAATATCACAGTAATTGGAGAGCAATGGCTAGT

GATTTTAACCTACCACCTGTAGTAGCAAAAGAAATAGTAGCCAGCTGTGA

TAAATGTCAGCTAAAAGGGAAGCCATGCATGGACAAGTAGACTGTAGCC

CAGGAATATGGCAGCTAGATTGTACACATTTAGAAGGAAAAGTTATCTTG

GTAGCAGTTCATGTAGCCAGTGGATATATAGAAGCAGAAGTAATTCCAGC

AGAGACAGGGCAAGAAACAGCATACTTCCTCTTAAAATTAGCAGGAAGAT

GGCCAGTAAAAACAGTACATACAGACAATGGCAGCAATTTCACCAGTACT

ACAGTTAAGGCCGCCTGTTGGTGGGCGGGGATCAAGCAGGAATTTGGCAT

TCCCTACAATCCCCAAAGTCAAGGAGTAATAGAATCTATGAATAAAGAAT

TAAAGAAAATTATAGGACAGGTAAGAGATCAGGCTGAACATCTTAAGACA

GCAGTACAAATGGCAGTATTCATCCACAATTTTAAAAGAAAAGGGGGGAT

TGGGGGGTACAGTGCAGGGGAAAGAATAGTAGACATAATAGCAACAGACA

TACAAACTAAAGAATTACAAAAACAAATTACAAAAATTCAAAATTTTCGG

GTTTATTACAGGGACAGCAGAGATCCAGTTTGGAAAGGACCAGCAAAGCT

CCTCTGGAAAGGTGAAGGGGCAGTAGTAATACAAGATAATAGTGACATAA

AAGTAGTGCCAAGAAGAAAAGCAAAGATCATCAGGGATTATGGAAAACAG

ATGGCAGGTGATGATTGTGTGGCAAGTAGACAGGATGAGGATTAA

Next, a DNA fragment containing the Rev, RRE, and rabbit beta globin poly A sequence with XbaI and XmaI flanking restriction sites was synthesized by MWG Operon. The DNA fragment was then inserted into the plasmid at the XbaI and XmaI restriction sites The DNA sequence was as follows:

(SEQ ID NO: 35)
TCTAGAATGGCAGGAAGAAGCGGAGACAGCGACGAAGAGCTCATCAGAAC

AGTCAGACTCATCAAGCTTCTCTATCAAAGCAACCCACCTCCCAATCCCG

AGGGGACCCGACAGGCCCGAAGGAATAGAAGAAGAAGGTGGAGAGAGAGA

CAGAGACAGATCCATTCGATTAGTGAACGGATCCTTGGCACTTATCTGGG

ACGATCTGCGGAGCCTGTGCCTCTTCAGCTACCACCGCTTGAGAGACTTA

CTCTTGATTGTAACGAGGATTGTGGAACTTCTGGGACGCAGGGGGTGGGA

AGCCCTCAAATATTGGTGGAATCTCCTACAATATTGGAGTCAGGAGCTAA

AGAATAGAGGAGCTTTGTTCCTTGGGTTCTTGGGAGCAGCAGGAAGCACT

ATGGGCGCAGCGTCAATGACGCTGACGGTACAGGCCAGACAATTATTGTC

TGGTATAGTGCAGCAGCAGAACAATTTGCTGAGGGCTATTGAGGCGCAAC

AGCATCTGTTGCAACTCACAGTCTGGGGCATCAAGCAGCTCCAGGCAAGA

ATCCTGGCTGTGGAAAGATACCTAAAGGATCAACAGCTCCTAGATCTTTT

TCCCTCTGCCAAAAATTATGGGGACATCATGAAGCCCCTTGAGCATCTGA

CTTCTGGCTAATAAAGGAAATTTATTTTCATTGCAATAGTGTGTTGGAAT

TTTTTGTGTCTCTCACTCGGAAGGACATATGGGAGGGCAAATCATTTAAA

ACATCAGAATGAGTATTTGGTTTAGAGTTTGGCAACATATGCCATATGCT

GGCTGCCATGAACAAAGGTGGCTATAAAGAGGTCATCAGTATATGAAACA

GCCCCCTGCTGTCCATTCCTTATTCCATAGAAAAGCCTTGACTTGAGGTT

AGATTTTTTTATATTTTGTTTTGTGTTATTTTTTTCTTTAACATCCCTA

AAATTTTCCTTACATGTTTTACTAGCCAGATTTTTCCTCCTCTCCTGACT

ACTCCCAGTCATAGCTGTCCCTCTTCTCTTATGAAGATCCCTCGACCTGC

AGCCCAAGCTTGGCGTAATCATGGTCATAGCTGTTTCCTGTGTGAAATTG

TTATCCGCTCACAATTCCACACAACATACGAGCCGGAAGCATAAAGTGTA

AAGCCTGGGGTGCCTAATGAGTGAGCTAACTCACATTAATTGCGTTGCGC

TCACTGCCCGCTTTCCAGTCGGGAAACCTGTCGTGCCAGCGGATCCGCAT

CTCAATTAGTCAGCAACCATAGTCCCGCCCCTAACTCCGCCCATCCCGCC

```
CCTAACTCCGCCCAGTTCCGCCCATTCTCCGCCCCATGGCTGACTAATTT

TTTTTATTTATGCAGAGGCCGAGGCCGCCTCGGCCTCTGAGCTATTCCAG

AAGTAGTGAGGAGGCTTTTTTGGAGGCCTAGGCTTTTGCAAAAAGCTAAC

TTGTTTATTGCAGCTTATAATGGTTACAAATAAAGCAATAGCATCACAAA

TTTCACAAATAAAGCATTTTTTTCACTGCATTCTAGTTGTGGTTTGTCCA

AACTCATCAATGTATCTTATCAGCGGCCGCCCCGGG
```

Finally, the CMV promoter of pCDNA3.1 was replaced with the CAG enhancer/promoter plus a chicken beta actin intron sequence. A DNA fragment containing the CAG enhancer/promoter/intron sequence with MluI and EcoRI flanking restriction sites was synthesized by MWG Operon. The DNA fragment was then inserted into the plasmid at the MluI and EcoRI restriction sites. The DNA sequence was as follows:

```
                                             (SEQ ID NO: 36)
ACGCGTTAGTTATTAATAGTAATCAATTACGGGGTCATTAGTTCATAGCC

CATATATGGAGTTCCGCGTTACATAACTTACGGTAAATGGCCCGCCTGGC

TGACCGCCCAACGACCCCCGCCCATTGACGTCAATAATGACGTATGTTCC

CATAGTAACGCCAATAGGGACTTTCCATTGACGTCAATGGGTGGACTATT

TACGGTAAACTGCCCACTTGGCAGTACATCAAGTGTATCATATGCCAAGT

ACGCCCCCTATTGACGTCAATGACGGTAAATGGCCCGCCTGGCATTATGC

CCAGTACATGACCTTATGGGACTTTCCTACTTGGCAGTACATCTACGTAT

TAGTCATCGCTATTACCATGGGTCGAGGTGAGCCCCACGTTCTGCTTCAC

TCTCCCCATCTCCCCCCCCTCCCCACCCCCAATTTTGTATTTATTTATTT

TTTAATTATTTTGTGCAGCGATGGGGGCGGGGGGGGGGGGGCGCGCGCC

AGGCGGGGCGGGGCGGGGCGAGGGCGGGGCGGGGCGAGGCGGAGAGGTG

CGGCGGCAGCCAATCAGAGCGGCGCGCTCCGAAAGTTTCCTTTTATGGCG

AGGCGGCGGCGGCGGCGGCCCTATAAAAAGCGAAGCGCGCGGCGGGCGGG

AGTCGCTGCGTTGCCTTCGCCCCGTGCCCCGCTCCGCGCCGCCTCGCGCC

GCCCGCCCCGGCTCTGACTGACCGCGTTACTCCCACAGGTGAGCGGGCGG

GACGGCCCTTCTCCTCCGGGCTGTAATTAGCGCTTGGTTTAATGACGGCT

CGTTTCTTTTCTGTGGCTGCGTGAAAGCCTTAAAGGGCTCCGGGAGGGCC

CTTTGTGCGGGGGGAGCGGCTCGGGGGGTGCGTGCGTGTGTGTGCGT

GGGGAGCGCCGCGTGCGGCCCGCGCTGCCCGGCGGCTGTGAGCGCTGCGG

GCGCGGCGCGGGGCTTTGTGCGCTCCGCGTGTGCGCGAGGGGAGCGCGGC

CGGGGGCGGTGCCCCGCGGTGCGGGGGGGCTGCGAGGGGAACAAAGGCTG

CGTGCGGGGTGTGTGCGTGGGGGGGTGAGCAGGGGTGTGGGCGCGGCGG

TCGGGCTGTAACCCCCCCCTGCACCCCCCTCCCCGAGTTGCTGAGCACGG

CCCGGCTTCGGGTGCGGGCTCCGTGCGGGCGTGGCGCGGGGCTCGCCG

TGCCGGGCGGGGGTGGCGGCAGGTGGGGGTGCCGGGCGGGGCGGGCCG

CCTCGGGCCGGGGAGGGCTCGGGGAGGGGCGCGGCGGCCCCGGAGCGCC

GGCGGCTGTCGAGGCGCGGCGAGCCGCAGCCATTGCCTTTTATGGTAATC

GTGCGAGAGGGCGCAGGGACTTCCTTTGTCCCAAATCTGGCGGAGCCGAA
```

Construction of the VSV-G Envelope Plasmid:

The vesicular stomatitis Indiana virus glycoprotein (VSV-G) sequence was synthesized by MWG Operon with flanking EcoRI restriction sites. The DNA fragment was then inserted into the pCDNA3.1 plasmid (Invitrogen) at the EcoRI restriction site and the correct orientation was determined by sequencing using a CMV specific primer. The DNA sequence was as follows:

```
ATCTGGGAGGCGCCGCCGCACCCCCTCTAGCGGGCGCGGGCGAAGCGGTG

CGGCGCCGGCAGGAAGGAAATGGGCGGGGAGGGCCTTCGTGCGTCGCCGC

GCCGCCGTCCCCTTCTCCATCTCCAGCCTCGGGGCTGCCGCAGGGGACG

GCTGCCTTCGGGGGGGACGGGGCAGGGCGGGGTTCGGCTTCTGGCGTGTG

ACCGGCGGGAATTC
```

```
                                            (SEQ ID NO: 37)
GAATTCATGAAGTGCCTTTTGTACTTAGCCTTTTTATTCATTGGGGTGAA

TTGCAAGTTCACCATAGTTTTTCCACACAACCAAAAAGGAAACTGGAAAA

ATGTTCCTTCTAATTACCATTATTGCCCGTCAAGCTCAGATTTAAATTGG

CATAATGACTTAATAGGCACAGCCTTACAAGTCAAAATGCCCAAGAGTCA

CAAGGCTATTCAAGCAGACGGTTGGATGTGTCATGCTTCCAAATGGGTCA

CTACTTGTGATTTCCGCTGGTATGGACCGAAGTATATAACACATTCCATC

CGATCCTTCACTCCATCTGTAGAACAATGCAAGGAAAGCATTGAACAAAC

GAAACAAGGAACTTGGCTGAATCCAGGCTTCCCTCCTCAAAGTTGTGGAT

ATGCAACTGTGACGGATGCCGAAGCAGTGATTGTCCAGGTGACTCCTCAC

CATGTGCTGGTTGATGAATACACAGGAGAATGGGTTGATTCACAGTTCAT

CAACGGAAAATGCAGCAATTACATATGCCCCACTGTCCATAACTCTACAA

CCTGGCATTCTGACTATAAGGTCAAAGGGCTATGTGATTCTAACCTCATT

TCCATGGACATCACCTTCTTCTCAGAGGACGGAGAGCTATCATCCCTGGG

AAAGGAGGGCACAGGGTTCAGAAGTAACTACTTTGCTTATGAAACTGGAG

GCAAGGCCTGCAAAATGCAATACTGCAAGCATTGGGGAGTCAGACTCCCA

TCAGGTGTCTGGTTCGAGATGGCTGATAAGGATCTCTTTGCTGCAGCCAG

ATTCCCTGAATGCCCAGAAGGGTCAAGTATCTCTGCTCCATCTCAGACCT

CAGTGGATGTAAGTCTAATTCAGGACGTTGAGAGGATCTTGGATTATTCC

CTCTGCCAAGAAACCTGGAGCAAAATCAGAGCGGGTCTTCCAATCTCTCC

AGTGGATCTCAGCTATCTTGCTCCTAAAAACCCAGGAACCGGTCCTGCTT

TCACCATAATCAATGGTACCCTAAAATACTTTGAGACCAGATACATCAGA

GTCGATATTGCTGCTCCAATCCTCTCAAGAATGGTCGGAATGATCAGTGG

AACTACCACAGAAAGGGAACTGTGGGATGACTGGGCACCATATGAAGACG

TGGAAATTGGACCCAATGGAGTTCTGAGGACCAGTTCAGGATATAAGTTT

CCTTTATACATGATTGGACATGGTATGTTGGACTCCGATCTTCATCTTAG

CTCAAAGGCTCAGGTGTTCGAACATCCTCACATTCAAGACGCTGCTTCGC

AACTTCCTGATGATGAGAGTTTATTTTTTGGTGATACTGGGCTATCCAAA

AATCCAATCGAGCTTGTAGAAGGTTGGTTCAGTAGTTGGAAAAGCTCTAT

TGCCTCTTTTTTCTTTATCATAGGGTTAATCATTGGACTATTCTTGGTTC
```

-continued
TCCGAGTTGGTATCCATCTTTGCATTAAATTAAAGCACACCAAGAAAAGA

CAGATTTATACAGACATAGAGATGAGAATTC

Figure 3:
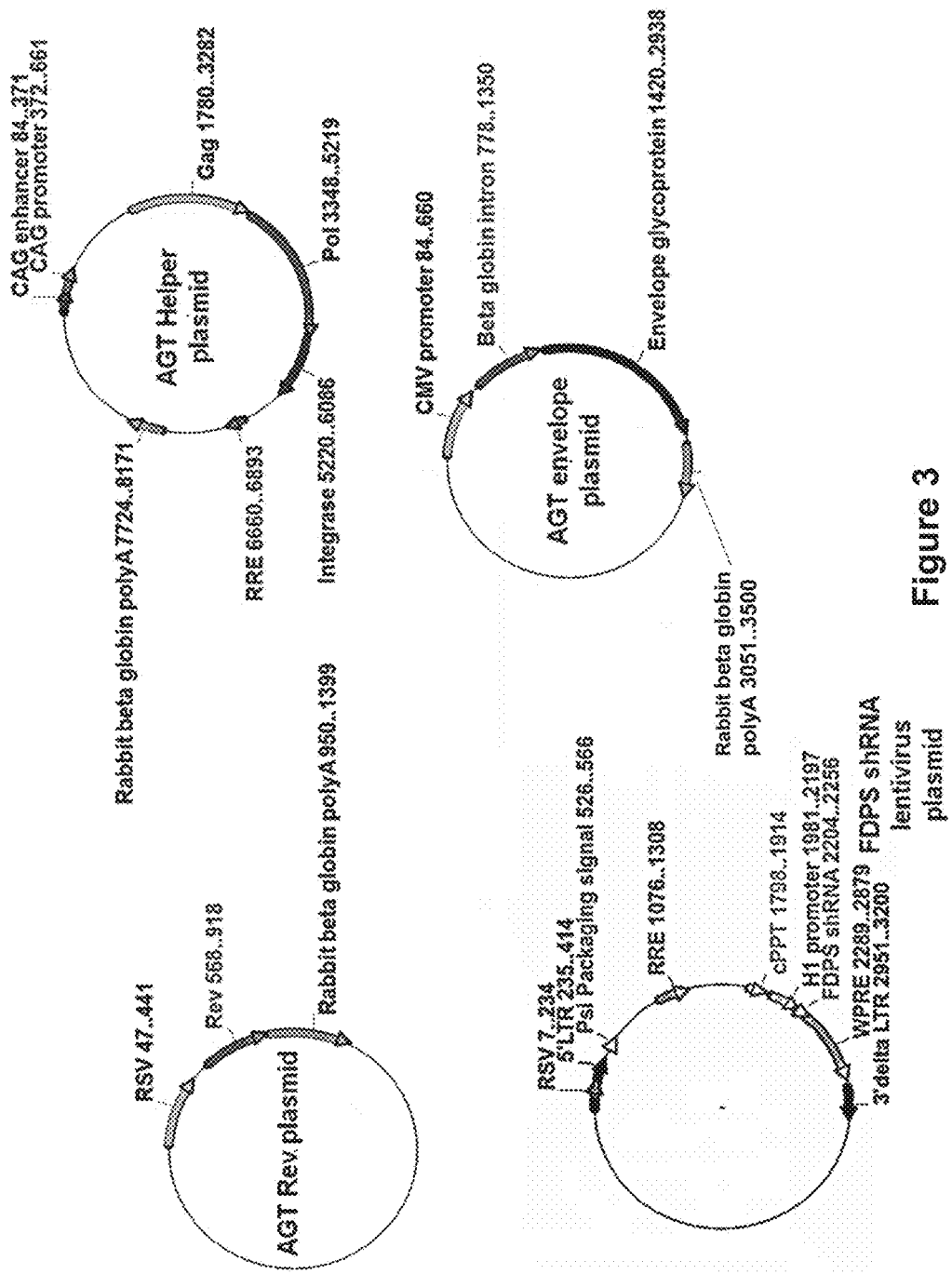
FIG. 3 depicts an exemplary 4-vector lentiviral vector system in a circularized form.

A 4-vector system (i.e., a 3-vector lentiviral packaging system) has also been designed and produced using the methods and materials described herein. A schematic of the 4-vector system is shown in FIG. 3. Briefly, and with reference to FIG. 3, the top-most vector is a helper plasmid, which, in this case, does not include Rev. The vector second from the top is a separate Rev plasmid. The vector second from the bottom is the envelope plasmid. The bottom-most vector is the previously described therapeutic vector.

Referring, in part, to FIG. 2, the Helper plasmid includes a CAG enhancer (SEQ ID NO: 27); a CAG promoter (SEQ ID NO: 19); a chicken beta actin intron (SEQ ID NO: 28); a HIV gag (SEQ ID NO: 20); a HIV Pol (SEQ ID NO: 21); a HIV Int (SEQ ID NO: 22); a HIV RRE (SEQ ID NO: 23); and a rabbit beta globin poly A (SEQ ID NO: 29).

The Rev plasmid includes a RSV promoter and a HIV Rev (SEQ ID NO: 38); and a rabbit beta globin poly A (SEQ ID NO: 29).

The Envelope plasmid includes a CMV promoter (SEQ ID NO: 25); a beta globin intron (SEQ ID NO: 30); a VSV-G (SEQ ID NO: 28); and a rabbit beta globin poly A (SEQ ID NO: 29).

Synthesis of a 3-Vector Lentiviral Packaging System including Helper, Rev, and Envelope Plasmids.

Materials and Methods:
Construction of the Helper Plasmid without Rev:
The Helper plasmid without Rev was constructed by inserting a DNA fragment containing the RRE and rabbit beta globin poly A sequence. This sequence was synthesized by MWG Operon with flanking XbaI and XmaI restriction sites. The RRE/rabbit poly A beta globin sequence was then inserted into the Helper plasmid at the XbaI and XmaI restriction sites. The DNA sequence is as follows:

(SEQ ID NO: 65)
TCTAGAAGGAGCTTTGTTCCTTGGGTTCTTGGGAGCAGCAGGAAGCACTA

TGGGCGCAGCGTCAATGACGCTGACGGTACAGGCCAGACAATTATTGTCT

GGTATAGTGCAGCAGCAGAACAATTTGCTGAGGGCTATTGAGGCGCAACA

GCATCTGTTGCAACTCACAGTCTGGGGCATCAAGCAGCTCCAGGCAAGAA

TCCTGGCTGTGGAAAGATACCTAAAGGATCAACAGCTCCTAGATCTTTTT

CCCTCTGCCAAAAATTATGGGGACATCATGAAGCCCCTTGAGCATCTGAC

TTCTGGCTAATAAAGGAAATTTATTTTCATTGCAATAGTGTGTTGGAATT

TTTTGTGTCTCTCACTCGGAAGGACATATGGGAGGGCAAATCATTTAAAA

CATCAGAATGAGTATTTGGTTTAGAGTTTGGCAACATATGCCATATGCTG

GCTGCCATGAACAAAGGTGGCTATAAAGAGGTCATCAGTATATGAAACAG

CCCCCTGCTGTCCATTCCTTATTCCATAGAAAAGCCTTGACTTGAGGTTA

GATTTTTTTATATTTTGTTTGTGTTATTTTTTCTTTAACATCCCTAA

AATTTTCCTTACATGTTTTACTAGCCAGATTTTTCCTCCTCTCCTGACTA

CTCCCAGTCATAGCTGTCCCTCTTCTCTTATGAAGATCCCTCGACCTGCA

GCCCAAGCTTGGCGTAATCATGGTCATAGCTGTTTCCTGTGTGAAATTGT

TATCCGCTCACAATTCCACACAACATACGAGCCGGAAGCATAAAGTGTAA

-continued
AGCCTGGGGTGCCTAATGAGTGAGCTAACTCACATTAATTGCGTTGCGCT

CACTGCCCGCTTTCCAGTCGGGAAACCTGTCGTGCCAGCGGATCCGCATC

TCAATTAGTCAGCAACCATAGTCCCGCCCCTAACTCCGCCCATCCCGCCC

CTAACTCCGCCCAGTTCCGCCCATTCTCCGCCCCATGGCTGACTAATTTT

TTTTATTTATGCAGAGGCCGAGGCCGCCTCGGCCTCTGAGCTATTCCAGA

AGTAGTGAGGAGGCTTTTTTGGAGGCCTAGGCTTTTGCAAAAAGCTAACT

TGTTTATTGCAGCTTATAATGGTTACAAATAAAGCAATAGCATCACAAAT

TTCACAAATAAAGCATTTTTTTCACTGCATTCTAGTTGTGGTTTGTCCAA

ACTCATCAATGTATCTTATCACCCGGG

Construction of the Rev Plasmid:
The RSV promoter and HIV Rev sequence was synthesized as a single DNA fragment by MWG Operon with flanking MfeI and XbaI restriction sites. The DNA fragment was then inserted into the pCDNA3.1 plasmid (Invitrogen) at the MfeI and XbaI restriction sites in which the CMV promoter is replaced with the RSV promoter. The DNA sequence was as follows:

(SEQ ID NO: 38)
CAATTGCGATGTACGGGCCAGATATACGCGTATCTGAGGGGACTAGGGTG

TGTTTAGGCGAAAAGCGGGGCTTCGGTTGTACGCGGTTAGGAGTCCCCTC

AGGATATAGTAGTTTCGCTTTTGCATAGGGAGGGGGAAATGTAGTCTTAT

GCAATACACTTGTAGTCTTGCAACATGGTAACGATGAGTTAGCAACATGC

CTTACAAGGAGAGAAAAGCACCGTGCATGCCGATTGGTGGAAGTAAGGT

GGTACGATCGTGCCTTATTAGGAAGGCAACAGACAGGTCTGACATGGATT

GGACGAACCACTGAATTCCGCATTGCAGAGATAATTGTATTTAAGTGCCT

AGCTCGATACAATAAACGCCATTTGACCATTCACCACATTGGTGTGCACC

TCCAAGCTCGAGCTCGTTTAGTGAACCGTCAGATCGCCTGGAGACGCCAT

CCACGCTGTTTTGACCTCCATAGAAGACACCGGGACCGATCCAGCCTCCC

CTCGAAGCTAGCGATTAGGCATCTCCTATGGCAGGAAGAAGCGGAGACAG

CGACGAAGAACTCCTCAAGGCAGTCAGACTCATCAAGTTTCTCTATCAAA

GCAACCCACCTCCCAATCCCGAGGGGACCCGACAGGCCCGAAGGAATAGA

AGAAGAAGGTGGAGAGAGAGACAGAGACAGATCCATTCGATTAGTGAACG

GATCCTTAGCACTTATCTGGGACGATCTGCGGAGCCTGTGCCTCTTCAGC

TACCACCGCTTGAGAGACTTACTCTTGATTGTAACGAGGATTGTGGAACT

TCTGGGACGCAGGGGGTGGGAAGCCCTCAAATATTGGTGGAATCTCCTAC

AATATTGGAGTCAGGAGCTAAAGAATAGTCTAGA

The plasmids for the 2-vector and 3-vector packaging systems could be modified with similar elements and the intron sequences could potentially be removed without loss of vector function. For example, the following elements could replace similar elements in the 2-vector and 3-vector packaging system:

Promoters: Elongation Factor-1 (EF-1) (SEQ ID NO: 39), phosphoglycerate kinase (PGK) (SEQ ID NO: 40), and ubiquitin C (UbC) (SEQ ID NO: 41) can replace the CMV (SEQ ID NO: 25) or CAG promoter (SEQ ID NO: 19). These sequences can also be further varied by addition, substitution, deletion or mutation.

Poly A sequences: SV40 poly A (SEQ ID NO: 42) and bGH poly A (SEQ ID NO: 43) can replace the rabbit beta globin poly A (SEQ ID NO: 29). These sequences can also be further varied by addition, substitution, deletion or mutation.

HIV Gag, Pol, and Integrase sequences: The HIV sequences in the Helper plasmid can be constructed from different HIV strains or clades. For example, HIV Gag (SEQ ID NO: 20); HIV Pol (SEQ ID NO: 21); and HIV Int (SEQ ID NO: 22) from the Bal strain can be interchanged with the gag, pol, and int sequences contained in the helper/helper plus Rev plasmids as outlined herein. These sequences can also be further varied by addition, substitution, deletion or mutation.

Envelope: The VSV-G glycoprotein can be substituted with membrane glycoproteins from feline endogenous virus (RD114) (SEQ ID NO: 44), gibbon ape leukemia virus (GALV) (SEQ ID NO: 45), Rabies (FUG) (SEQ ID NO: 46), lymphocytic choriomeningitis virus (LCMV) (SEQ ID NO: 47), influenza A fowl plague virus (FPV) (SEQ ID NO: 48), Ross River alphavirus (RRV) (SEQ ID NO: 49), murine leukemia virus 10A1 (MLV) (SEQ ID NO: 50), or Ebola virus (EboV) (SEQ ID NO: 51). Sequences for these envelopes are identified in the sequence portion herein. Further, these sequences can also be further varied by addition, substitution, deletion or mutation.

In summary, the 3-vector versus 4-vector systems can be compared and contrasted, in part, as follows. The 3-vector lentiviral vector system contains: 1. Helper plasmid: HIV Gag, Pol, Integrase, and Rev/Tat; 2. Envelope plasmid: VSV-G/FUG envelope; and 3. Therapeutic vector: RSV 5'LTR, Psi Packaging Signal, Gag fragment, RRE, Env fragment, cPPT, WPRE, and 3'δ LTR. The 4-vector lentiviral vector system contains: 1. Helper plasmid: HIV Gag, Pol, and Integrase; 2. Rev plasmid: Rev; 3. Envelope plasmid: VSV-G/FUG envelope; and 4. Therapeutic vector: RSV 5'LTR, Psi Packaging Signal, Gag fragment, RRE, Env fragment, cPPT, WPRE, and 3' delta LTR. Sequences corresponding with the above elements are identified in the sequence listings portion herein.

Example 2: Development of a Lentiviral Vector that Expresses FDPS

The purpose of this Example was to develop an FDPS lentivirus vector.

Inhibitory RNA Design:

The sequence of Homo sapiens Farnesyl diphosphate synthase (FDPS) (NM_002004.3) mRNA was used to search for potential siRNA or shRNA candidates to knockdown FDPS levels in human cells. Potential RNA interference sequences were chosen from candidates selected by siRNA or shRNA design programs such as from GPP Web Portal hosted by the Broad Institute (http://portals.broadinstitute.org/gpp/public/) or the BLOCK-iT RNAi Designer from Thermo Scientific (https://rnaidesigner.thermofisher.com/rnaiexpress/). Individual selected shRNA sequences were inserted into a lentiviral vector immediately 3 prime to a RNA polymerase III promoter such as H1 (SEQ ID NO: 16), U6 (SEQ ID NO: 52), or 7SK (SEQ ID NO: 53) to regulate shRNA expression. These lentivirus shRNA constructs were used to transduce cells and measure the change in specific mRNA levels. The shRNA most potent for reducing mRNA levels were embedded individually within a microRNA backbone to allow for expression by either the EF-1alpha or CMV RNA polymerase II promoters. The microRNA backbone was selected from mirbase.org. RNA sequences were also synthesized as synthetic siRNA oligonucleotides and introduced directly into cells without using a lentiviral vector.

Vector Construction:

For FDPS shRNA, oligonucleotide sequences containing BamHI and EcoRI restriction sites were synthesized by Eurofins MWG Operon. Overlapping sense and antisense oligonucleotide sequences were mixed and annealed during cooling from 70 degrees Celsius to room temperature. The lentiviral vector was digested with the restriction enzymes BamHI and EcoRI for one hour at 37 degrees Celsius. The digested lentiviral vector was purified by agarose gel electrophoresis and extracted from the gel using a DNA gel extraction kit from Thermo Scientific. The DNA concentrations were determined and vector to oligo (3:1 ratio) were mixed, allowed to anneal, and ligated. The ligation reaction was performed with T4 DNA ligase for 30 minutes at room temperature. 2.5 microliters of the ligation mix were added to 25 microliters of STBL3 competent bacterial cells. Transformation was achieved after heat-shock at 42 degrees Celsius. Bacterial cells were spread on agar plates containing ampicillin and drug-resistant colonies (indicating the presence of ampicillin-resistance plasmids) were recovered and expanded in LB broth. To check for insertion of the oligo sequences, plasmid DNA was extracted from harvested bacteria cultures with the Thermo Scientific DNA mini prep kit. Insertion of shRNA sequences in the lentiviral vector was verified by DNA sequencing using a specific primer for the promoter used to regulate shRNA expression. Using the following target sequences, exemplary shRNA sequences were determined to knock-down FDPS:

```
        (FDPS target sequence #1; SEQ ID NO: 54)
GTCCTGGAGTACAATGCCATT;

(FDPS shRNA sequence #1; SEQ ID NO: 1)
GTCCTGGAGTACAATGCCATTCTCGAGAATGGCATTGTACTCCAGGACTT
TTT;

(FDPS target sequence #2; SEQ ID NO: 55)
GCAGGATTTCGTTCAGCACTT;

(FDPS shRNA sequence #2; SEQ ID NO: 2)
GCAGGATTTCGTTCAGCACTTCTCGAGAAGTGCTGAACGAAATCCTGCTT
TTT;

(FDPS target sequence #3; SEQ ID NO: 56)
GCCATGTACATGGCAGGAATT;

(FDPS shRNA sequence #3; SEQ ID NO: 3)
GCCATGTACATGGCAGGAATTCTCGAGAATTCCTGCCATGTACATGGCTT
TTT;

(FDPS target sequence #4; SEQ ID NO: 57)
GCAGAAGGAGGCTGAGAAAGT;
and (FDPS shRNA sequence #4; SEQ ID NO: 4)
GCAGAAGGAGGCTGAGAAAGTCTCGAGACTTTCTCAGCCTCCTTCTGCTT
TTT.
``` shRNA sequences were then assembled into a synthetic microRNA (miR) under control of the EF-1 alpha promoter. Briefly, a miR hairpin sequences, such as miR30, miR21, or miR185 as detailed below, was obtained from mirbase.org. The 19-22mer shRNA target sequence was used to construct the synthetic miR sequence. The miR sequence was arranged as an anti-sense-target-sequence-hairpin loop sequence (specific for each microRNA)-sense target sequence.

The following miR sequences were developed:

```
            (miR30 FDPS sequence #1; SEQ ID NO: 5)
AAGGTATATTGCTGTTGACAGTGAGCGACACTTTCTCAGCCTCCTTCTGC
GTGAAGCCACAGATGGCAGAAGGAGGCTGAGAAAGTGCTGCCTACTGCCT
CGGACTTCAAGGGGCT (miR30 FDPS sequence #2; SEQ ID NO: 6)
AAGGTATATTGCTGTTGACAGTGAGCGACACTTTCTCAGCCTCCTTCTGC
GTGAAGCCACAGATGGCAGAAGGGCTGAGAAAGTGCTGCCTACTGCCTCG
GACTTCAAGGGGCT (miR30 FDPS sequence #3; SEQ ID NO: 7)
TGCTGTTGACAGTGAGCGACTTTCTCAGCCTCCTTCTGCGTGAAGCCACA
GATGGCAGAAGGAGGCTGAGAAAGTTGCCTACTGCCTCGGA (miR155 FDPS sequence #1; SEQ ID NO: 8)
CCTGGAGGCTTGCTGAAGGCTGTATGCTGACTTTCTCAGCCTCCTTCTGC
TTTTGGCCACTGACTGAGCAGAAGGGCTGAGAAAGTCAGGACACAAGGCC
TGTTACTAGCACTCA (miR21 FDPS sequence #1; SEQ ID NO: 9)
CATCTCCATGGCTGTACCACCTTGTCGGGACTTTCTCAGCCTCCTTCTGC
CTGTTGAATCTCATGGCAGAAGGAGGCGAGAAAGTCTGACATTTTGGTAT
CTTTCATCTGACCA (miR185 FDPS sequence #1; SEQ ID NO: 10)
GGGCCTGGCTCGAGCAGGGGGCGAGGGATACTTTCTCAGCCTCCTTCTGC
TGGTCCCCTCCCCGCAGAAGGAGGCTGAGAAAGTCCTTCCCTCCCAATGA
CCGCGTCTTCGTCG
```

Example 3—Knock-Down of FDPS for 3 Days in
THP1 Monocytic Leukemia by shRNA #4

Figure 5:
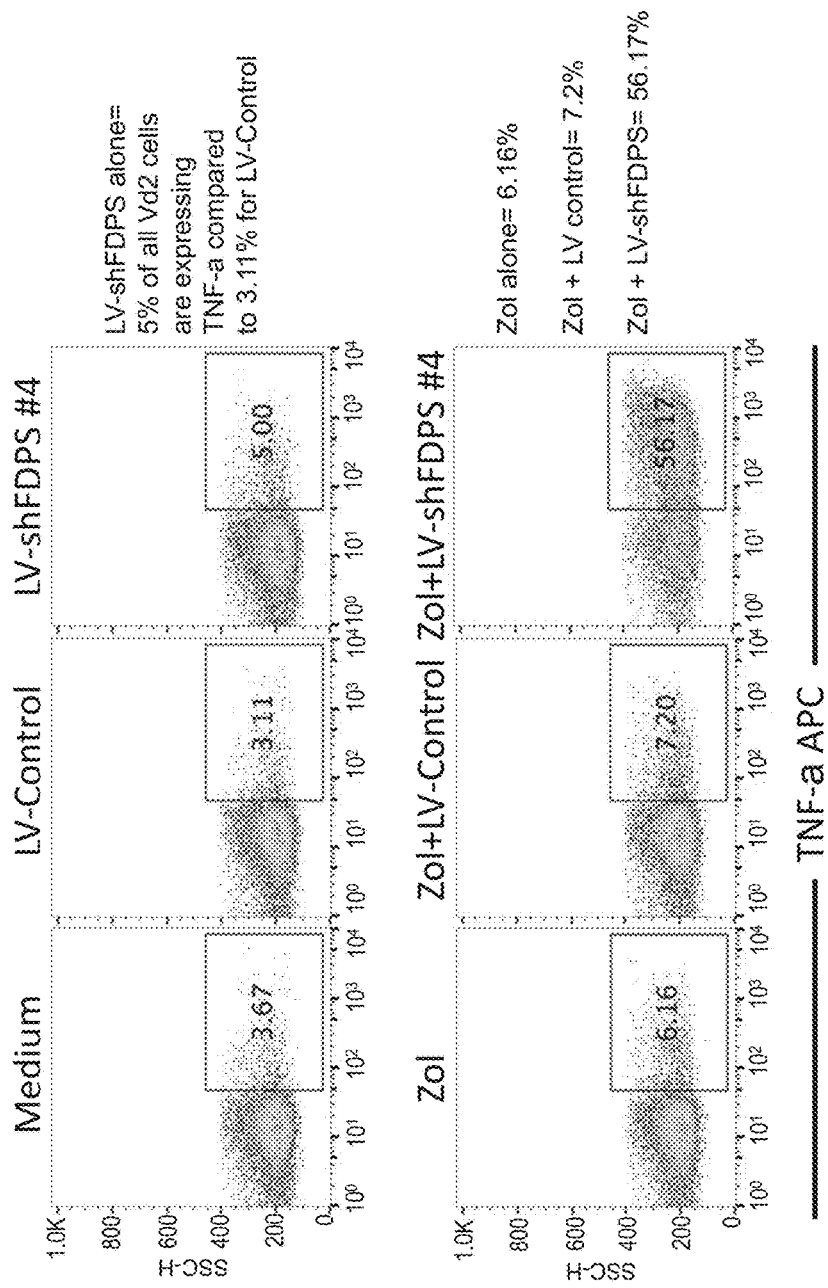
FIG. 5 depicts data demonstrating activation of Vδ2+ T cells THP-1 leukemia cells with a lentivirus expressing FDPS shRNA #4 (SEQ ID NO: 4), as described herein.

This Example illustrates that knock-down of FDPS in THP1 monocytic leukemia cells by lentiviral (LV)-expressing FDPS shRNA #4 stimulates TNF-α expression in gamma delta T cells, as shown in FIG. 5.

THP1 cells ($1\times10^5$ cells) were transduced with LV-control or LV-FDPS shRNA #4 for 3 days. Two days after transduction, cells were treated with or without 1 μM zoledronic acid. After 24 hours, the transduced THP-1 cells were co-cultured with $5\times10^5$ PBMC cells and IL-2 in a round bottom 96 well plate for 4 hours. The PBMC cells were pre-stimulated with zoledronic acid and IL-2 for 11 days to expand Vγ9Vδ2 T cells. After staining for Vγ9Vδ2 and TNF-α using fluorophore-conjugated anti TCR-Vδ2 and anti-TNF-α antibody, cells were analyzed via flow cytometry. Live cells were gated, and Vδ2+ and TNF-α+ cells were selected on a dot blot. The activated cytotoxic Vγ9Vδ2 T cells appeared in the upper right quadrant of flow cytograms. Without zoledronic acid, LV-control stimulated 3.1% of TNF-α expressing Vγ9Vδ2 T cells and LV-FDPS shRNA #4 stimulated 5%. With zoledronic acid treatment, LV-control stimulated 7.2% of TNF-α expressing Vγ9Vδ2 T cells and LV-FDPS shRNA #4 stimulated 56.2%.

Example 4—Knock-down of FDPS for 14 Days in
THP1 Leukemia Cells by shRNA #4

Figure 6:
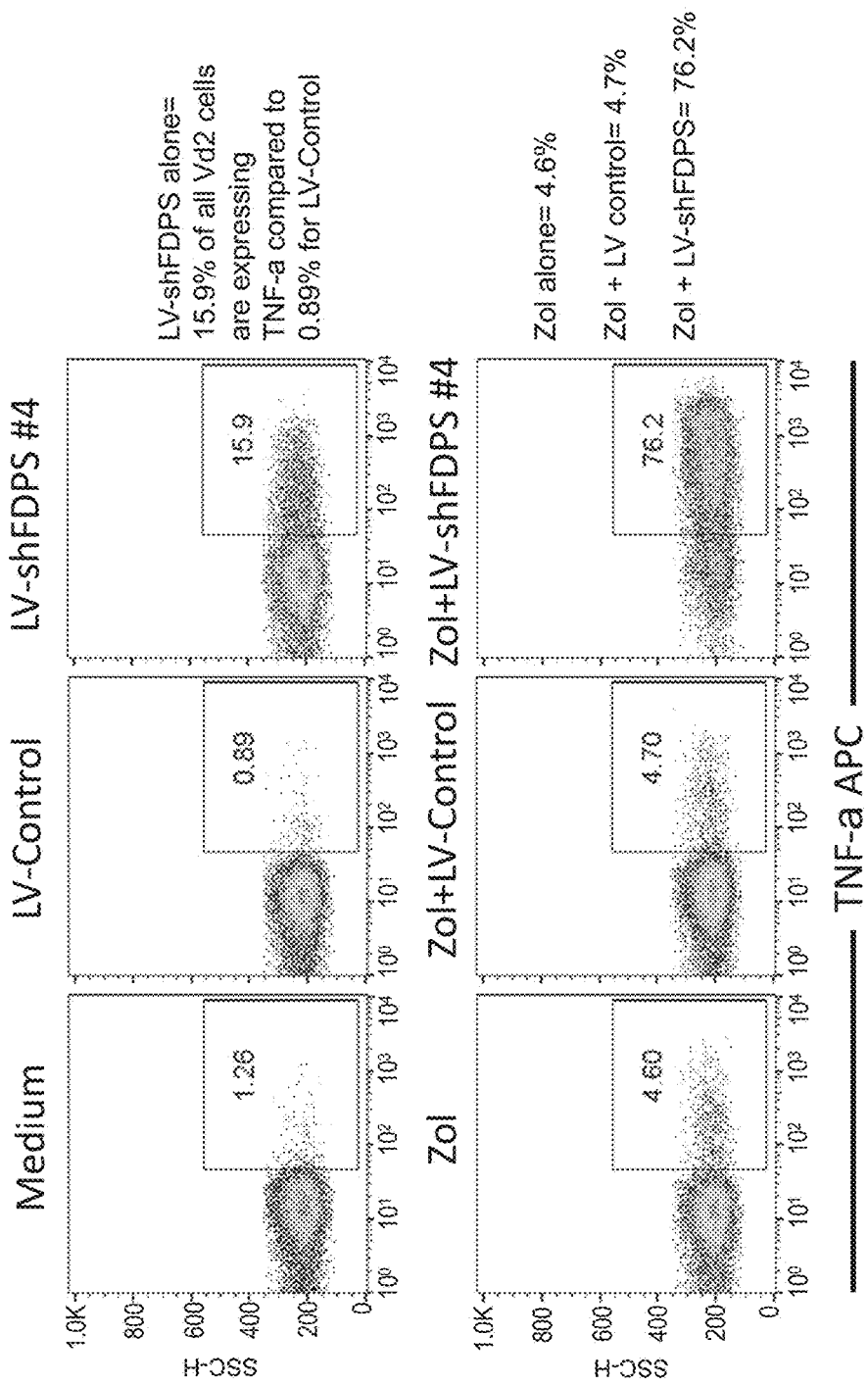
FIG. 6 depicts data demonstrating activation of Vδ2+ T cells by THP-1 leukemia cells with a lentivirus expressing FDPS shRNA #4 (SEQ ID NO: 4), as described herein.

This Example illustrates that Knock-down of FDPS for 14 days in THP1 leukemia cells by lentiviral (LV)-expressing FDPS shRNA #4 stimulates TNF-α expression in GD T cells, as shown in FIG. 6.

THP1 cells ($1\times10^5$ cells) were transduced with LV-control or LV-FDPS shRNA #4 for 14 days. Two days after transduction, cells were treated with or without 1 μM zoledronic acid. After 24 hours, the transduced THP-1 cells were co-cultured with $5\times10^5$ PBMC cells and IL-2 in a round bottom 96 well plate for 4 hours. The PBMC cells were pre-stimulated with zoledronic acid and IL-2 for 11 days to expand Vγ9Vδ2 T cells. After staining for Vγ9Vδ2 and TNF-α using fluorophore-conjugated anti TCR-Vδ2 and anti-TNF-α antibody, cells were analyzed via flow cytometry. Live cells were gated, and Vδ2+ and TNF-α+ cells were selected on a dot blot. The activated cytotoxic Vγ9Vδ2 T cells appeared in the upper right quadrant of flow cytograms. Without zoledronic acid, LV-control stimulated 0.9% of TNF-α expressing Vγ9Vδ2 T cells and LV-FDPS shRNA #4 (SEQ ID NO: 4) stimulated 15.9%. With zoledronic acid treatment, LV-control stimulated 4.7% of TNF-α expressing Vγ9Vδ2 T cells and LV-FDPS shRNA #4 (SEQ ID NO: 4) stimulated 76.2%.

Example 5—Knock-down of FDPS for 3 Days in
PC3 Prostate Carcinoma Cells by shRNA #1

Figure 7:
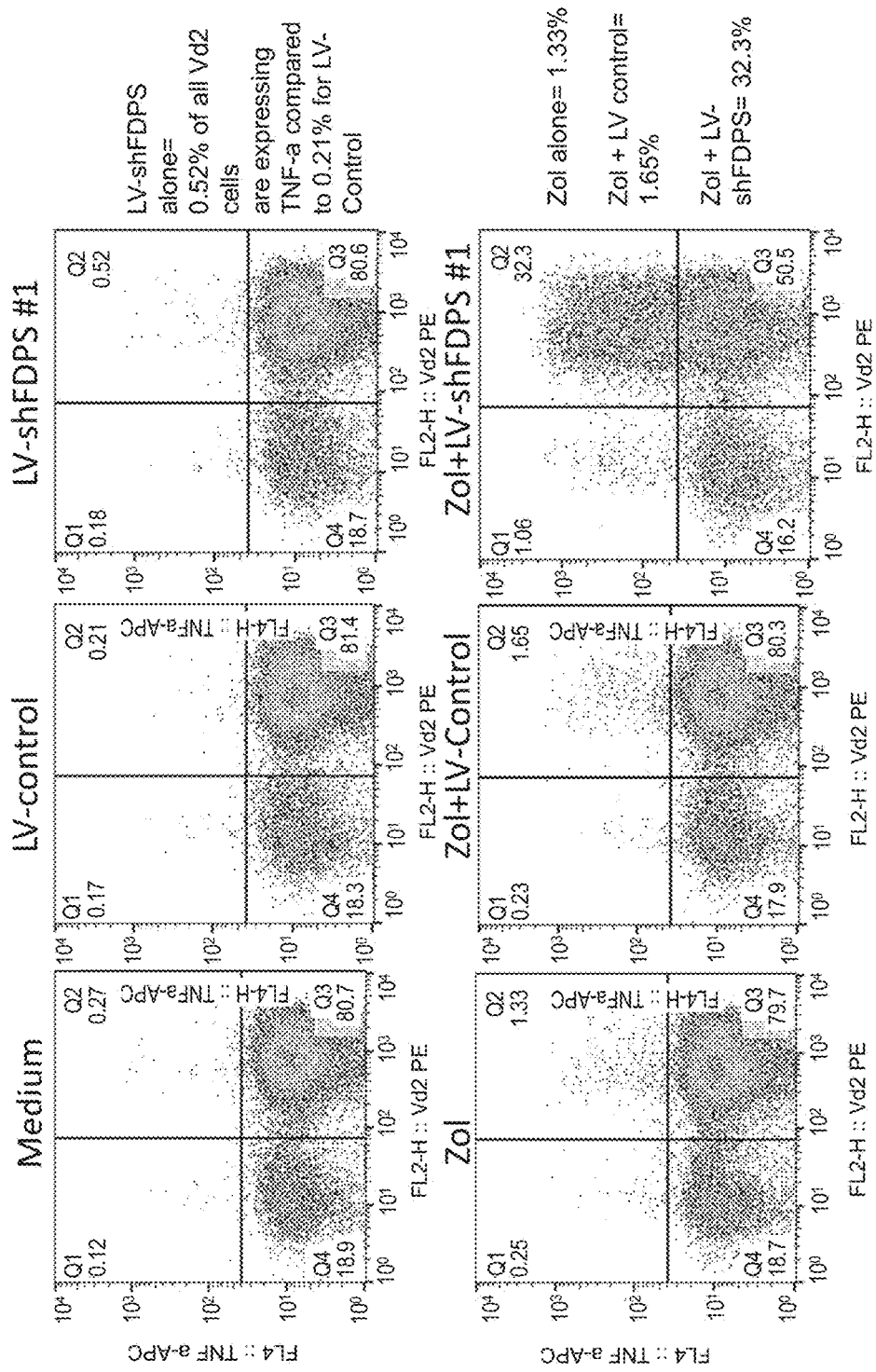
FIG. 7 depicts data demonstrating activation of Vδ2+ T cells by PC3 prostate carcinoma cells with a lentivirus expressing FDPS shRNA #1 (SEQ ID NO: 1), as described herein.

This Example illustrates that knock-down of FDPS for 3 days in PC3 prostate carcinoma cells by lentiviral (LV)-expressing FDPS shRNA #1 stimulates TNF-α expression in GD T cells, as shown in FIG. 7.

PC3 cells were transduced with LV-control or LV-FDPS shRNA #1 (SEQ ID NO: 1) for 3 days. Two days after transduction, cells were treated with or without 1 μM zoledronic acid. After 24 hours, the transduced PC3 cells were co-cultured with $5\times10^5$ PBMC cells and IL-2 in a round bottom 96 well plate for 4 hours. The PBMC cells were pre-stimulated with zoledronic acid and IL-2 for 11 days to expand Vγ9Vδ2 T cells. After staining for Vγ9Vδ2 and TNF-α using fluorophore-conjugated anti TCR-Vδ2 and anti-TNF-α antibody, cells were analyzed via flow cytometry. Live cells were gated, and Vδ2+ and TNF-α+ cells were selected on a dot blot. The activated cytotoxic Vγ9Vδ2 T cells appeared in the upper right quadrant of flow cytograms. Without zoledronic acid, LV-control stimulated 0.2% of TNF-α expressing Vγ9Vδ2 T cells and LV-FDPS shRNA #1 stimulated 0.5%. With zoledronic acid treatment, LV-control stimulated 1.7% of TNF-α expressing Vγ9Vδ2 T cells and LV-FDPS shRNA #1 (SEQ ID NO: 1) stimulated 32.2%.

Example 6—Knock-Down of FDPS for 3 Days in
PC3 Prostate Carcinoma Cells by shRNA #4

Figure 8:
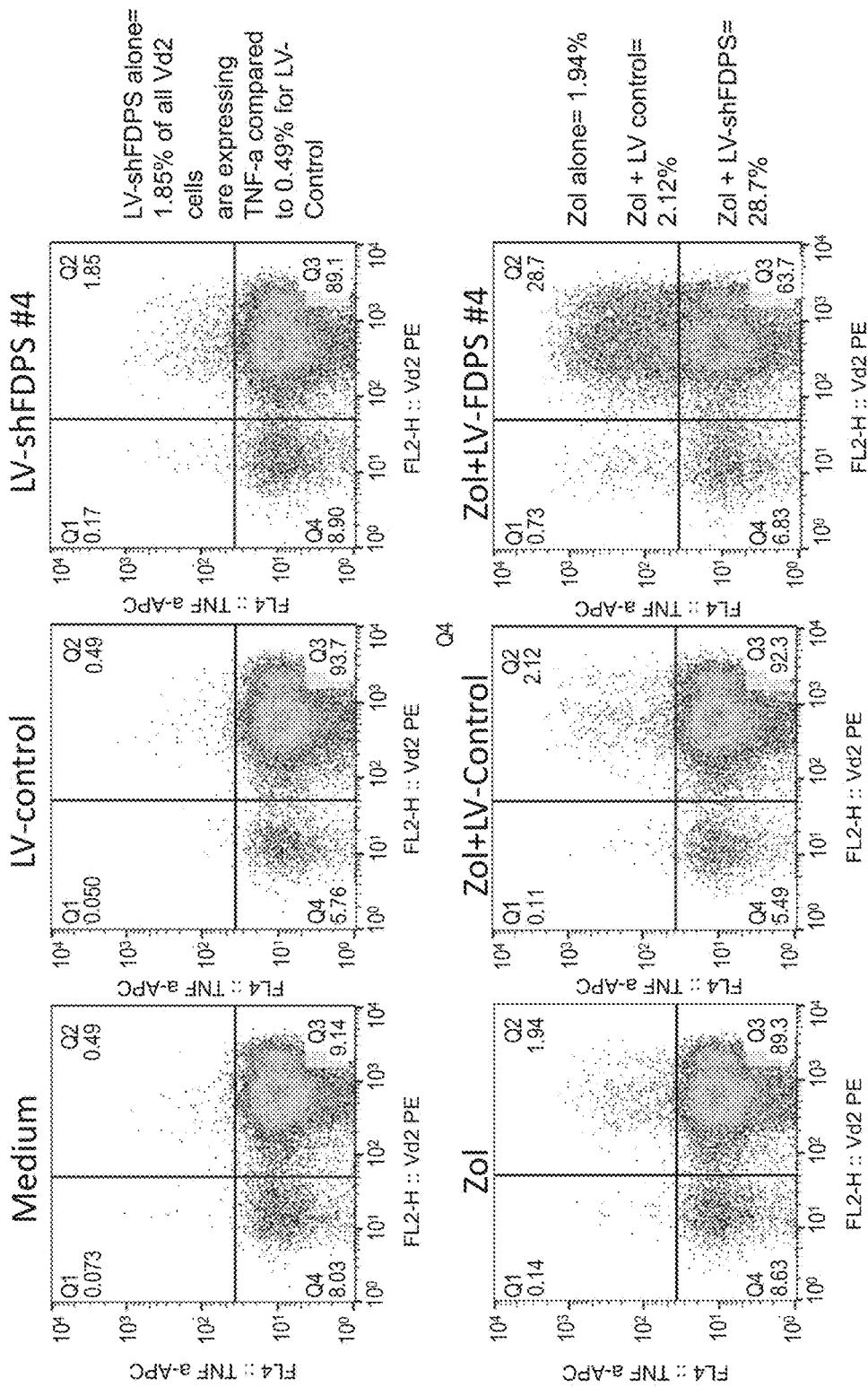
FIG. 8 depicts data demonstrating activation of Vδ2+ T cells by PC3 prostate carcinoma cells with a lentivirus expressing FDPS shRNA #4 (SEQ ID NO: 4), as described herein.

This Example illustrates that Knock-down of FDPS for 3 days in PC3 prostate carcinoma cells by lentiviral (LV)-expressing FDPS shRNA #4 stimulates TNF-α expression in GD T cells, as shown in FIG. 8.

PC3 cells were transduced with LV-control or LV-FDPS shRNA #4 (SEQ ID NO: 4) for 3 days. Two days after transduction, cells were treated with or without 1 μM zoledronic acid. After 24 hours, the transduced PC3 cells were co-cultured with $5\times10^5$ PBMC cells and IL-2 in a round bottom 96 well plate for 4 hours. The PBMC cells were pre-stimulated with zoledronic acid and IL-2 for 11 days to expand Vγ9Vδ2 T cells. After staining for Vγ9Vδ2 and TNF-α using fluorophore-conjugated anti TCR-Vδ2 and anti-TNF-α antibody, cells were analyzed via flow cytometry. Live cells were gated, and Vδ2+ and TNF-α+ cells were selected on a dot blot. The activated cytotoxic Vγ9Vδ2 T cells appeared in the upper right quadrant of flow cytograms. Without zoledronic acid, LV-control stimulated 0.5% of TNF-α expressing Vγ9Vδ2 T cells and LV-FDPS shRNA #4 (SEQ ID NO: 4) stimulated 1.9%. With zoledronic acid treatment, LV-control stimulated 2.1% of TNF-α expressing Vγ9Vδ2 T cells and LV-FDPS shRNA #4 stimulated 28.7%.

Example 7—Knock-Down of FDPS for 3 Days in HepG2 Liver Carcinoma Cells by shRNA #1 and #4

Figure 9:
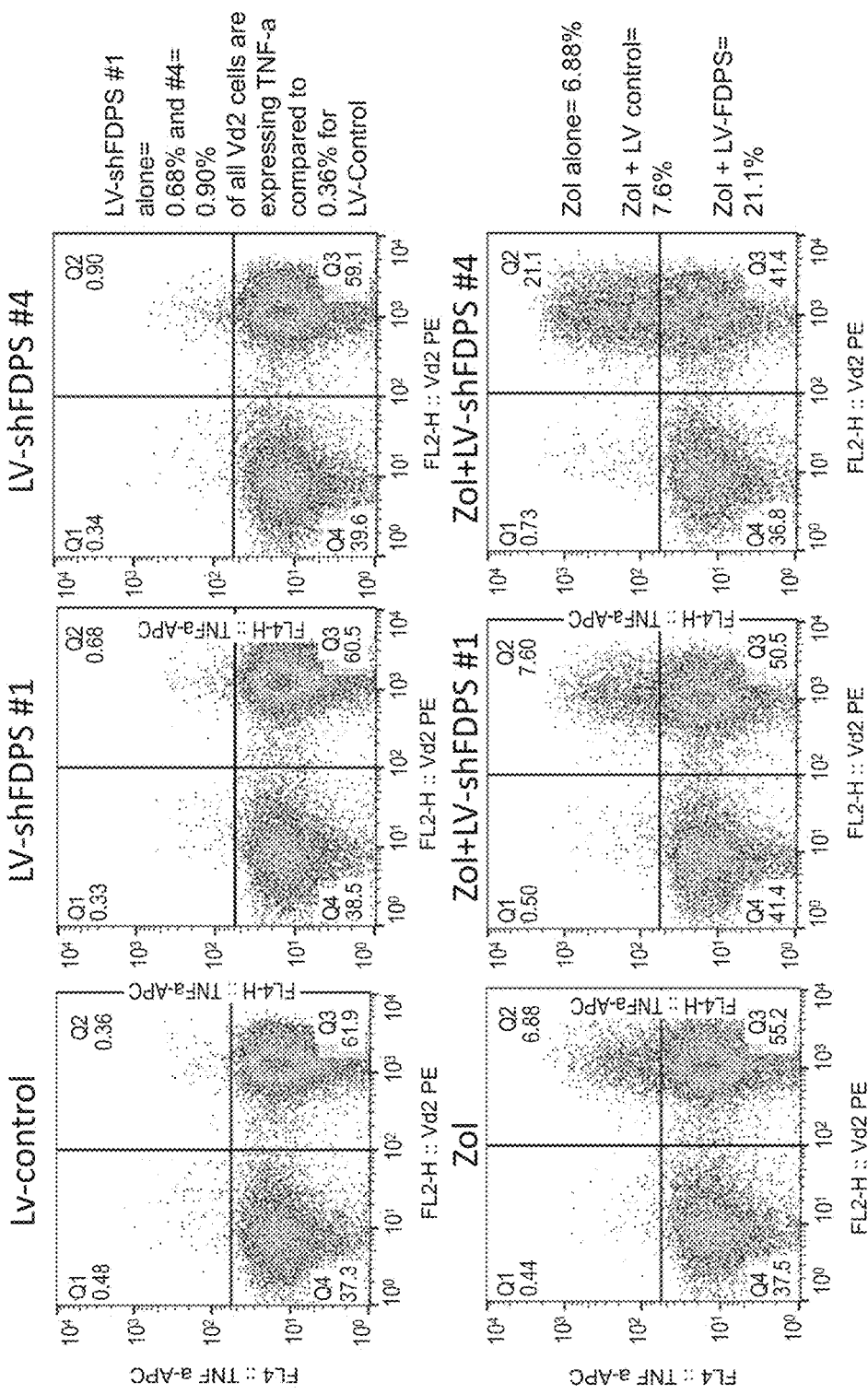
FIG. 9 depicts data demonstrating activation of Vδ2+ T cells by HepG2 carcinoma cells with a lentivirus expressing FDPS shRNA #1 (SEQ ID NO: 1) or FDPS shRNA #4 (SEQ ID NO: 4), as described herein.

This Example illustrates that Knock-down of FDPS for 3 days in HepG2 liver carcinoma cells by lentiviral (LV)-expressing FDPS shRNA #1 (SEQ ID NO: 1) and shRNA#4 (SEQ ID NO: 4) stimulates TNF-α expression in GD T cells, as shown in FIG. 9.

HepG2 cells were transduced with LV-control, LV-FDPS shRNA #1 (SEQ ID NO: 1), or LV-FDPS shRNA #4 (SEQ ID NO: 4) for 3 days. Two days after transduction, cells were treated with or without 1 µM zoledronic acid. After 24 hours, the transduced HepG2 cells were co-cultured with $5\times10^5$ PBMC cells and IL-2 in a round bottom 96 well plate for 4 hours. The PBMC cells were pre-stimulated with zoledronic acid and IL-2 for 11 days to expand Vγ9Vδ2 T cells. After staining for Vγ9Vδ2 and TNF-α using fluorophore-conjugated anti TCR-Vδ2 and anti-TNF-α antibody, cells were analyzed via flow cytometry. Live cells were gated, and Vδ2+ and TNF-α+ cells were selected on a dot blot. The activated cytotoxic Vγ9Vδ2 T cells appeared in the upper right quadrant of flow cytograms. Without zoledronic acid, LV-control stimulated 0.4% of TNF-α expressing Vγ9Vδ2 T cells and LV-FDPS shRNA #1 (SEQ ID NO: 1) and #4 (SEQ ID NO: 4) stimulated 0.7% and 0.9%, respectively. With zoledronic acid treatment, LV-control stimulated 6.9% of TNF-α expressing Vγ9Vδ2 T cells and LV-FDPS shRNA #1 and #4 stimulated 7.6% and 21.1%, respectively.

Example 8—Knock-down of FDPS for 3 Days in THP1 Leukemia by MicroRNA-30

Figure 10:
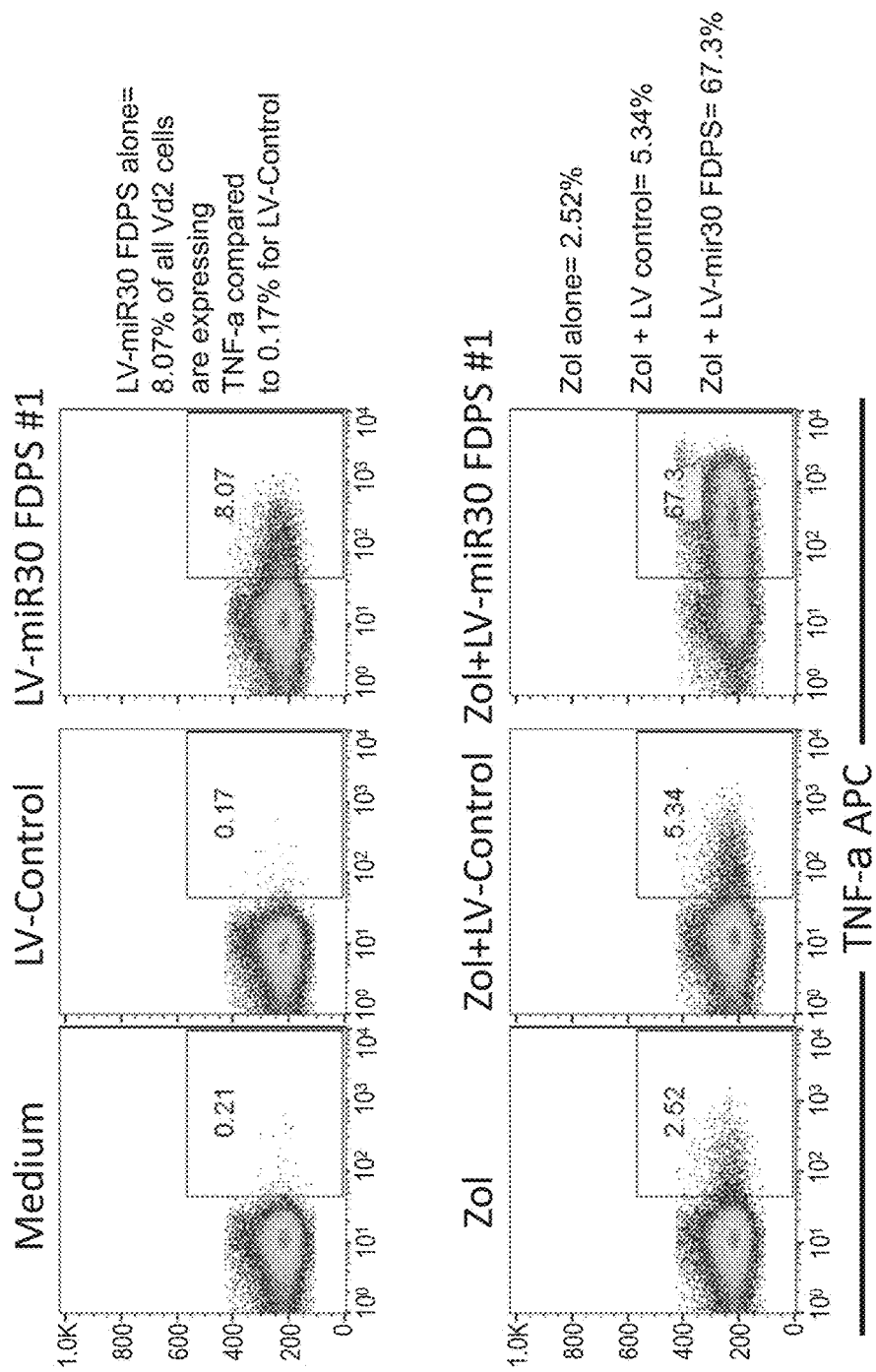
FIG. 10 depicts data demonstrating activation of Vδ2+ T cells by THP-1 leukemia cells with a lentivirus expressing miR30 FDPS #1 (SEQ ID NO: 5), as described herein.

This Example illustrates that Knock-down of FDPS for 3 days in THP1 leukemia cells by lentiviral (LV)-expressing FDPS-targeted synthetic microRNA-30 stimulates TNF-α expression in gamma delta T cells, as shown in FIG. 10.

THP1 cells ($1\times10^5$ cells) were transduced with LV-control or LV-miR30 FDPS #1 (SEQ ID NO: 5) for 3 days. Two days after transduction, cells were treated with or without 1 µM zoledronic acid. After 24 hours, the transduced THP-1 cells were co-cultured with $5\times10^5$ PBMC cells and IL-2 in a round bottom 96 well plate for 4 hours. The PBMC cells were pre-stimulated with zoledronic acid and IL-2 for 11 days to expand Vγ9Vδ2 T cells. After staining for Vγ9Vδ2 and TNF-α using fluorophore-conjugated anti TCR-Vδ2 and anti-TNF-α antibody, cells were analyzed via flow cytometry. Live cells were gated, and Vδ2+ and TNF-α+ cells were selected on a dot blot. The activated cytotoxic Vγ9Vδ2 T cells appeared in the upper right quadrant of flow cytograms. Without zoledronic acid, LV-control stimulated 0.2% of TNF-α expressing Vγ9Vδ2 T cells and LV-miR30 FDPS stimulated 8.1%. With zoledronic acid treatment, LV-control stimulated 5.3% of TNF-α expressing Vγ9Vδ2 T cells and LV-miR30 FDPS #1 (SEQ ID NO: 5) stimulated 67.3%.

Example 9: E:T Ratios Resulting from Mixture of THP-1 Cells, Cultured Human GD T Cells, and/or Zometa (Zol)

Figure 11:
FIG. 11 depicts data demonstrating the percent of specific lysis versus an E:T ratio for a variety of experimental conditions, as described herein.

This Example demonstrates results from mixing treated THP-1 monocytoid tumor cells with cultured human GD T cells, as shown in FIG. 11.

The monocytoid cell line THP-1 was treated with control lentivirus vector (LV), LV suppressing farnesyl diphosphate synthase gene expression (LV-FDPS), zoledronic acid (Zol) or combinations. The legend, as shown in FIG. 11, was: lentiviral control vectors (LV-Control), lentiviral vectors expressing microRNA to down regulate FDPS (LV-FPPS), Zometa (Zol), Zometa plus lentiviral control (Zol+LV-Control), or Zometa plus lentiviral vectors expressing microRNA to down regulate FPPS (Zol+LV-FPPS).

Human GD T cells were cultured from an anonymous donor and added to treated THP-1 cells in 4:1, 2:1 or 1:1 ratios (GD T:THP-1) for 4 hours. Cell killing was measured by a fluorescence assay. When THP-1 cells were treated with a combination of LV-FDPS and Zol, cytotoxic T cell killing by GD T cells was increased greatly compared to either treatment alone. When LV-FDPS treatment alone was compared to Zol treatment alone, the LV-FDPS lead to greater killing but was >3-fold below tumor cell killing after combination treatment. The combined LV-FDPS plus Zol treatment caused nearly 70% tumor cell killing with 4:1 ratio; this was more than 3-fold higher than the second best treatment (LV-FDPS alone).

Figure 12:
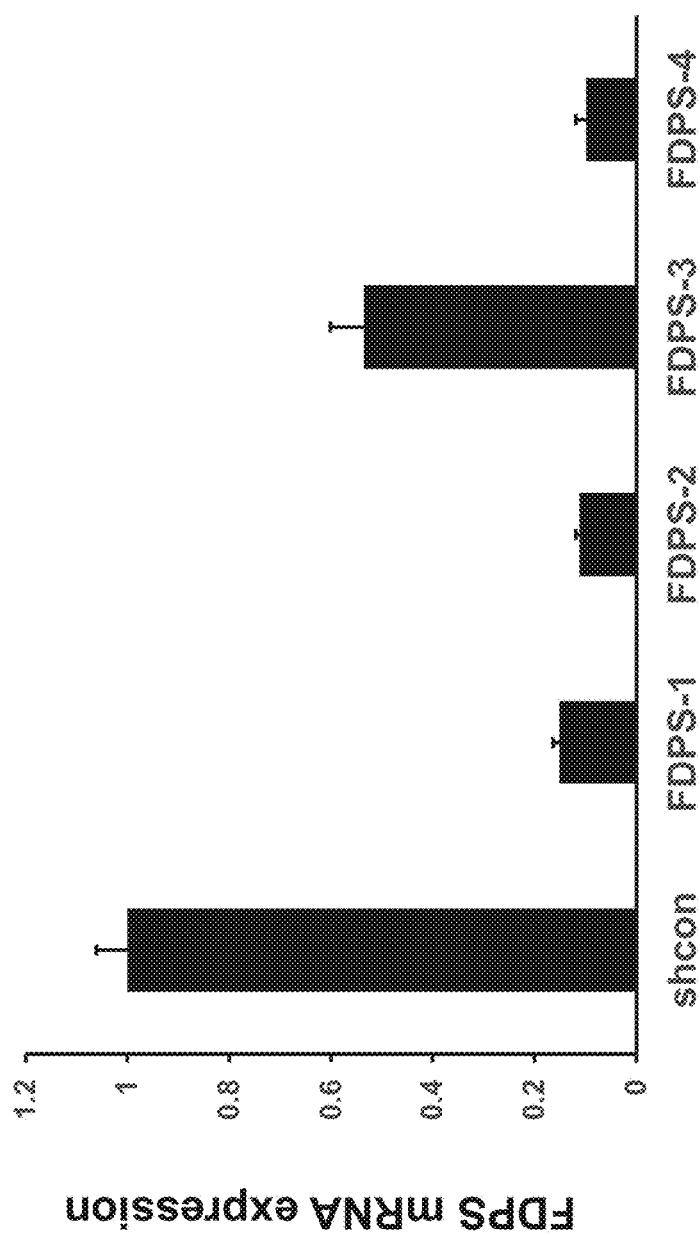
FIG. 12 depicts data demonstrating lentiviral-delivered shRNA-based RNA interference targeting the human FDPS gene.

Example 10—Lentiviral-delivered shRNA-based RNA Interference Targeting the Human Farnesyl Diphosphate Synthase (FDPS) Gene HepG2 human hepatocellular carcinoma cells were infected with lentiviral vectors containing the H1 promoter and either a non-targeting or four different FDPS shRNA sequences, as shown in FIG. 12. After 48 hours, RNA was extracted from the cells and converted to cDNA. Expression of FDPS cDNA was determined by quantitative PCR using SYBR Green and FDPS primers. FDPS expression was normalized to actin levels for each sample.

```
FDPS-targeting lentiviral vectors containing the
H1 promoter and either a non-targeting sequence
                                   (SEQ ID NO: 58)
(5'-GCCGCTTTGTAGGATAGAGCTCGAGCTCTATCCTACAAAGCGGCTT
TTT-3')
or one of four different FDPS shRNA sequences
           (FDPS shRNA sequence #1; SEQ ID NO: 1)
GTCCTGGAGTACAATGCCATTCTCGAGAATGGCATTGTACTCCAGGACTT
TTT;

(FDPS shRNA sequence #2; SEQ ID NO: 2)
GCAGGATTTCGTTCAGCACTTCTCGAGAAGTGCTGAACGAAATCCTGCTT
TTT;

(FDPS shRNA sequence #3; SEQ ID NO: 3)
GCCATGTACATGGCAGGAATTCTCGAGAATTCCTGCCATGTACATGGCTT
TTT;
and (FDPS shRNA sequence #4; SEQ ID NO: 4)
GCAGAAGGAGGCTGAGAAAGTCTCGAGACTTTCTCAGCCTCCTTCTGCTT
TTT
were produced in 293 T cells.
```

HepG2 human hepatocellular carcinoma cells were then infected with lentiviral vectors to determine the efficacy of FDPS knock-down. After 48 hours, RNA was extracted from the cells using the RNeasy RNA isolation kit (Qiagen) and converted to cDNA with the SuperScript VILO cDNA synthesis kit (Thermo Scientific). Expression of FDPS cDNA was determined by quantitative PCR on an Applied Biosystems StepOne qPCR machine using a SYBR Green PCR mix (Thermo Scientific) and FDPS primers (Forward primer: 5'-AGGAATTGATGGCGAGAAGG-3' (SEQ ID NO: 59) and Reverse primer: 5'-CCCAAAGAGGTCAAGGTAATCA-3' (SEQ ID NO: 60)). FDPS expression was normalized to actin levels for each sample using the actin primers (Forward primer: 5'-AGCGCGGCTACAGCT-TCA-3' (SEQ ID NO: 61) and Reverse primer: 5'-GGC-GACGTAGCACAGCTTCT-3' (SEQ ID NO: 62). The relative FDPS RNA expression of the shCon sample is set at 100%. There was an 85% (FDPS sequence #1), 89% (FDPS sequence #2), 46% (FDPS sequence #3), and 98% (FDPS sequence #4) decrease in FDPS expression.

Figure 13:
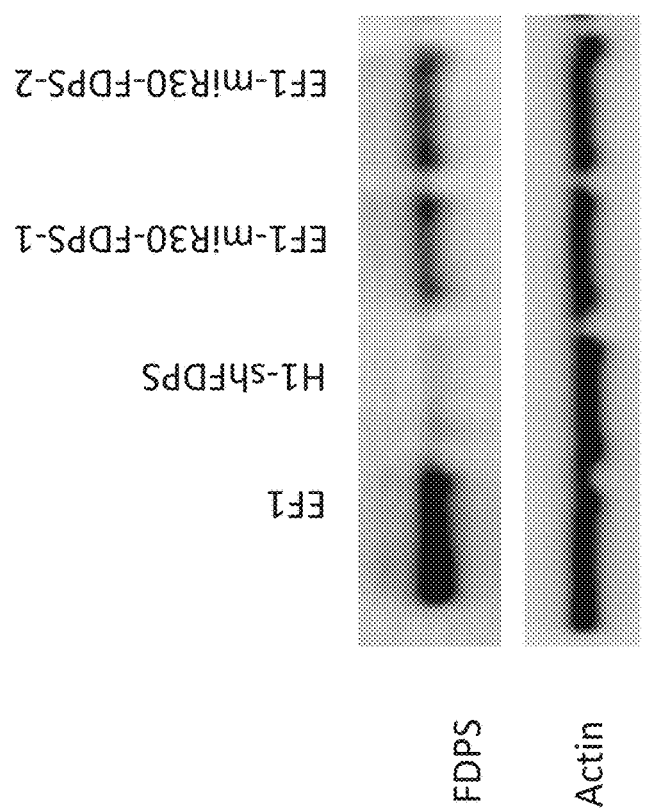
FIG. 13 depicts data demonstrating lentiviral-delivered miR-based RNA interference targeting the human FDPS gene.

Example 11—Lentiviral-delivered miR-based RNA Interference Targeting the Human Farnesyl Diphosphate Synthase (FDPS) Gene As shown in FIG. 13, HepG2 human hepatocellular carcinoma cells were infected with lentiviral vectors containing either the H1 promoter (SEQ ID NO: 16) the FDPS shRNA #4 (SEQ ID NO: 4) sequence or the EF-1α promoter (SEQ ID NO: 40) and miR30-based FDPS sequences. After 48 hours, cells were lysed and an immunoblot was performed using an anti-FDPS (Thermo Scientific) and an anti-actin (Sigma) antibody as a protein loading control.

More specifically, HepG2 human hepatocellular carcinoma cells were infected with lentiviral vectors containing either the H1 promoter (SEQ ID NO: 16) and the FDPS shRNA sequence GCAGAAGGAGGCTGAGAAAGTCTCGA-GACTTTCTCAGCCTCCTTCTGCTTTTT (FDPS shRNA sequence #4; SEQ ID NO: 4) or the EF-1alpha promoter (SEQ ID NO: 39) and miR30-based FDPS sequences AAGGTATATTGCTGTTGACAGTGAGCGA-CACTTTCTCAGCCTCCTTCTGCGTGAAGC CACA-GATGGCAGAAGGAGGCTGAGAAAGTGCTGC-CTACTGCCTCGGACTTCAAGGG GCT (miR30 FDPS sequence #1; SEQ ID NO: 5) and AAGGTATATTGCTGTTGACAGTGAGCGA-CACTTTCTCAGCCTCCTTCTGCGTGAAGC CACA-GATGGCAGAAGGGCTGAGAAAGTGCTGCCTACT-GCCTCGGACTTCAAGGGGC T (miR30 FDPS sequence #2; SEQ ID NO: 6).

After 48 hours, cells were lysed with NP-40 lysis buffer and protein was quantified with the Bio-Rad protein assay reagent. Protein samples at 50 micrograms were electrophoresed on 4-12% Bis-Tris gels (Thermo Scientific and transferred to PVDF membranes (EMD Millipore). An immunoblot was performed using an anti-FDPS (Thermo Scientific) and an anti-actin (Sigma) antibody as a protein loading control. Antibodies were bound with HRP-conjugated secondary antibodies and detected with a Licor c-DiGit Blot scanner using the Immobilon Western ECL reagent (EMD Millipore). The densitometry of the immunoblot bands were quantified with the NIH image software. The LV control with the EF-1 promoter was set at 100%. There was a 68% (LV-shFDPS #4), 43% (LV-miR FDPS #1), and 38% (LV-miR FDPS #3) reduction of FDPS protein expression.

Example 12—Knock-down of FDPS for 3 Days in HepG2 Liver Carcinoma Cells by Adeno-associated Virus (AAV)-expressing FDPS shRNA #4

Figure 14:
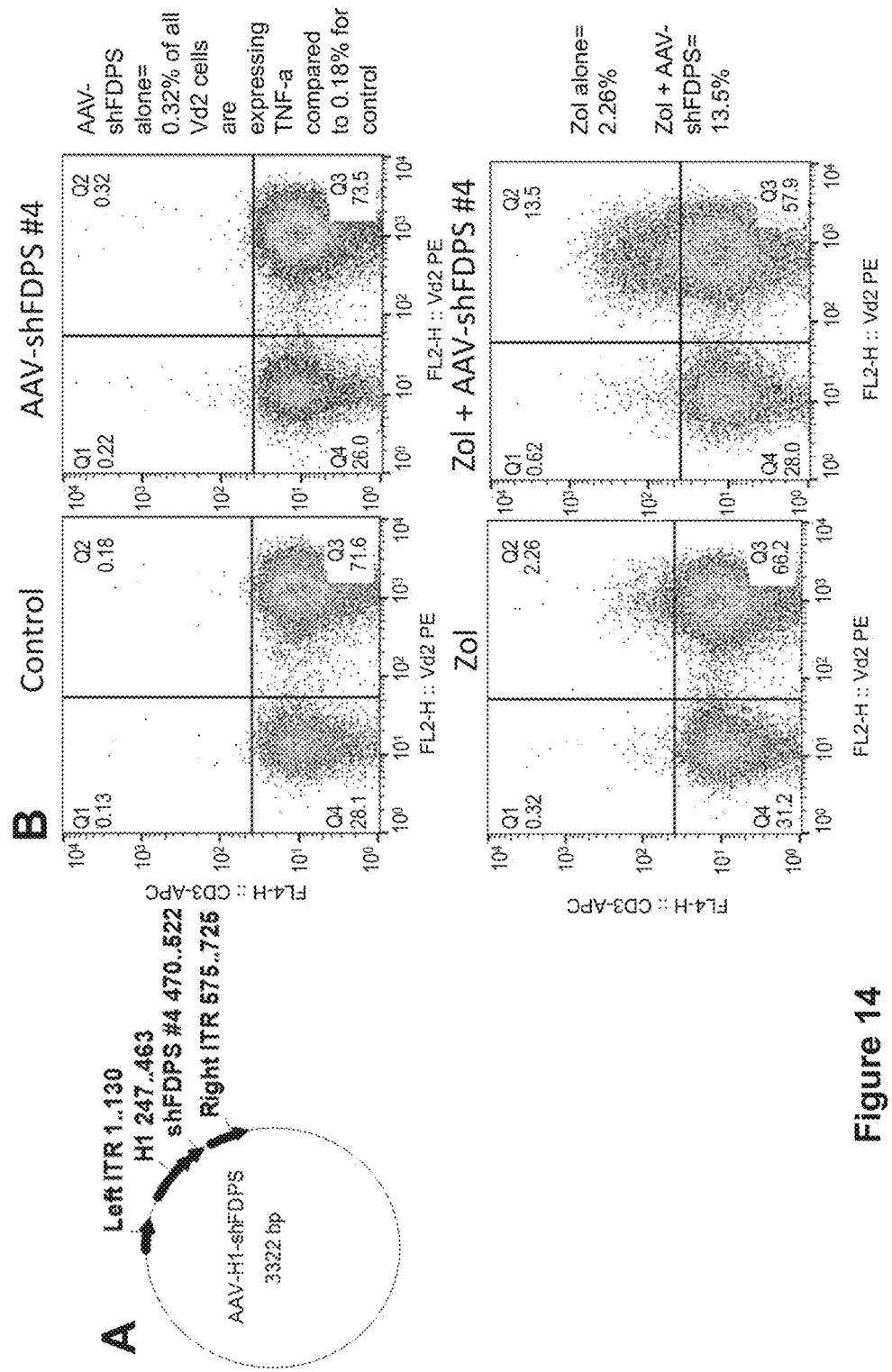
FIG. 14 depicts data demonstrating activation of Vδ2+ T cells by HepG2 carcinoma cells with an adeno-associated virus expressing FDPS shRNA #4 (SEQ ID NO: 4), as described herein.

This Example illustrates that knock-down of FDPS for 3 days in HepG2 liver carcinoma cells by adeno-associated virus (AAV)-expressing FDPS shRNA #4 (SEQ ID NO: 4) stimulates TNF-α expression in GD T cells (FIG. 14, Panel B).

HepG2 cells were transduced with control or AAV-FDPS shRNA #4 (SEQ ID NO: 8) for 3 days. Two days after transduction, cells were treated with or without 1 μM zoledronic acid. After 24 hours, the transduced HepG2 cells were co-cultured with 5×10$^5$ PBMC cells and IL-2 in a round bottom 96 well plate for 4 hours. The PBMC cells were pre-stimulated with zoledronic acid and IL-2 for 11 days to expand Vγ9Vδ2 T cells. After staining for Vγ9Vδ2 and TNF-α using fluorophore-conjugated anti TCR-Vδ2 and anti-TNF-α antibody, cells were analyzed via flow cytometry. Live cells were gated, and Vδ2+ and TNF-α+ cells were selected on a dot blot. The activated cytotoxic Vγ9Vδ2 T cells appeared in the upper right quadrant of flow cytograms (FIG. 14, Panel B).

AAV Vector Construction.

FDPS shRNA sequence #4 (SEQ ID NO: 4) was inserted into the pAAV plasmid (Cell Biolabs). FDPS oligonucleotide sequences containing BamHI and EcoRI restriction sites were synthesized by Eurofins MWG Operon. Overlapping sense and antisense oligonucleotide sequences were mixed and annealed during cooling from 70 degrees Celsius to room temperature. The pAAV was digested with the restriction enzymes BamHI and EcoRI for one hour at 37 degrees Celsius. The digested pAAV plasmid was purified by agarose gel electrophoresis and extracted from the gel using a DNA gel extraction kit from Thermo Scientific. The DNA concentrations were determined and vector to oligo (3:1 ratio) were mixed, allowed to anneal, and ligated. The ligation reaction was performed with T4 DNA ligase for 30 minutes at room temperature. 2.5 microliters of the ligation mix were added to 25 microliters of STBL3 competent bacterial cells. Transformation was achieved after heat-shock at 42 degrees Celsius. Bacterial cells were spread on agar plates containing ampicillin and drug-resistant colonies (indicating the presence of ampicillin-resistance plasmids) were recovered and expanded in LB broth. To check for insertion of the oligo sequences, plasmid DNA was extracted from harvested bacteria cultures with the Thermo Scientific DNA mini prep kit. Insertion of shRNA sequences in the pAAV plasmid was verified by DNA sequencing using a specific primer for the promoter used to regulate shRNA expression. An exemplary AAV vector with a H1 promoter (SEQ ID NO: 16), shFDPS sequence (e.g., SEQ ID NO: 4), Left Inverted Terminal Repeat (Left ITR; SEQ ID NO: 63), and Right Inverted Terminal Repeat (Right ITR; SEQ ID NO: 64) can be found in FIG. 14, Panel A).

Production of AAV Particles.

The AAV-FDPS shRNA plasmid was combined with the plasmids pAAV-RC2 (Cell Biolabs) and pHelper (Cell Biolabs). The pAAV-RC2 plasmid contains the Rep and AAV2 capsid genes and pHelper contains the adenovirus E2A, E4, and VA genes. To produce AAV particles, these plasmids were transfected in the ratio 1:1:1 (pAAV-shFDPS: pAAV-RC2: pHelper) into 293T cells. For transfection of cells in 150 mm dishes (BD Falcon), 10 micrograms of each plasmid were added together in 1 ml of DMEM. In another tube, 60 microliters of the transfection reagent PEI (1 microgram/ml) (Polysciences) was added to 1 ml of DMEM. The two tubes were mixed together and allowed to incubate for 15 minutes. Then the transfection mixture was added to cells and the cells were collected after 3 days. The cells were lysed by freeze/thaw lysis in dry ice/isopropanol. Benzonase nuclease (Sigma) was added to the cell lysate for 30 minutes at 37 degrees Celsius. Cell debris were then pelleted by centrifugation at 4 degrees Celsius for 15 minutes at 12,000 rpm. The supernatant was collected and then added to target cells.

Example 13—Decreased RAP1 Prenylation in the Cells Transduced with LV-shFDPS and Treated with Zoledronic Acid This Example illustrates that lentiviral-delivered shRNA targeting the human farnesyl diphosphate synthase (FDPS) gene and zoledronic acid synergize to inhibit farnesyl diphosphate production.

Figure 15:
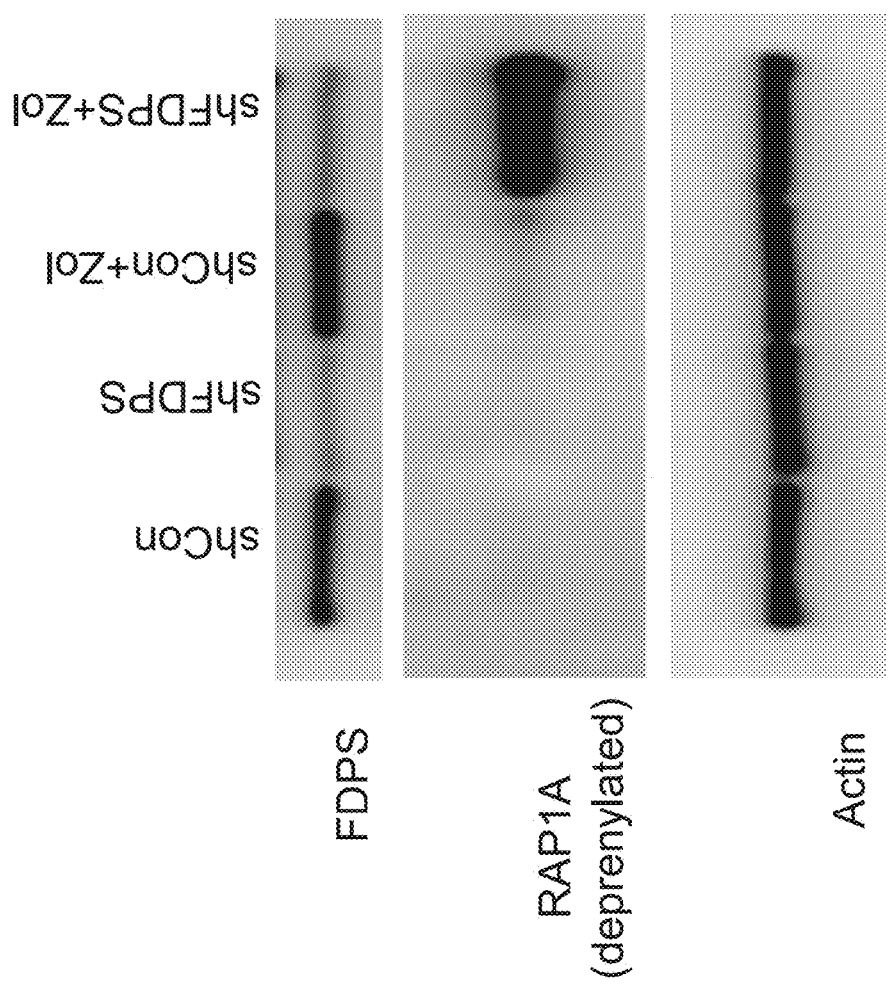
FIG. 15 depicts immunoblot data demonstrating lack of RAP1 prenylation in the cells transduced with LV-shFDPS and treated with zoledronic acid.

FDPS is an enzyme in the isoprenoid synthesis pathway that catalyzes the production of farnesyl diphosphate. Inhibiting the enzyme activity of FDPS by zoledronic acid or reduced protein expression by shRNA-mediated knockdown will result in reduced farnesyl diphosphate levels. Farnesylation of cellular proteins requires farnesyl diphosphate. RAP1A is a protein that is modified by farnesylation, which can be used as a biomarker for levels of cellular farnesyl diphosphate. An antibody that specifically recognizes reduced RAP1A farnesylation was used to measure FDPS activity after transduction with LV-shFDPS alone or in combination with zoledronic acid. HepG2 human hepatocellular carcinoma cells were infected with lentiviral vectors containing FDPS shRNA sequence #4. For the zoledronic acid treated cells, zoledronic acid (Sigma) was added for the last 24 hours. After 48 hours, cells were lysed with NP-40 lysis buffer and protein was quantified with the Bio-Rad protein assay reagent. Protein samples at 50 micrograms were electrophoresed on 4-12% Bis-Tris gels (Thermo Scientific and transferred to PVDF membranes (EMD Millipore). As shown in FIG. 15, an immunoblot was performed using an anti-FDPS (Thermo Scientific), anti-RAP1A (Santa Cruz), and an anti-actin (Sigma) antibody as a protein loading control. Antibodies were bound with HRP-conjugated secondary antibodies and detected with a Licor c-DiGit Blot scanner using the Immobilon Western ECL reagent (EMD Millipore). An increase in the RAP1A band intensity correlates with reduced farnesylation. RAP1A defarnesylation occurred only in the cells transduced with LV-shFDPS and treated with zoledronic acid.

Example 14—Treatment of a Subject with Cancer

LV-FDPS is a Genetic Medicine Delivered by a Lentivirus Vector Via Local Administration to the Site of Late Stage, Non-Resectable Hepatocellular Carcinoma A Phase I clinical trial will test safety and feasibility of delivering LV-FDPS to the site of hepatocellular carcinoma (HCC) using ultrasound guided cannulation of the liver in patients without concomitant radiotherapy or chemotherapy. It is rationally predicted that this study will result in the successful treatment of HCC. The study is an open label, 4×3 dose escalation (4 dose ranges, up to 3 subjects per dose) to identify the maximum tolerable dose of LV-FDPS in patients 18 years or older with Stage III/IV non-resectable HCC.

LV-FDPS is a genetic therapy designed to reduce expression in tumor cells of the enzyme farnesyl diphosphate synthase. Experimental studies show that tumor cells modified by LV-FDPS induce the anti-tumor activity of human gamma delta T cells, including the capacity for tumor killing by cellular cytotoxicity.

Subjects with target lesions ≥1 cm in longest diameter (measured by helical CT) and ≤4.9 cm maximum diameter and meeting inclusion and exclusion criteria detailed below, are enrolled into the next available dosing category. A maximum of 3 subjects are recruited for each dosage group. The dose is number of transducing units of LV-FDPS as described in the product release criteria, delivered via intra-hepatic cannulation in a single bolus with volume not to exceed 25 mL. The minimum dose is $1 \times 10^9$ transducing units and escalation is 10-fold to a next dose of $1 \times 10^{10}$ transducing units, the next dose is $1 \times 10^{11}$ transducing units, and a maximum dose of $1 \times 10^{12}$ transducing units based on reported experience with recombinant adenovirus therapy for HCC (Sangro et al., A phase I clinic trial of thymidine kinase-based gene therapy in advanced hepatocellular carcinoma, 2010, *Cancer Gene Ther.* 17:837-43). Subjects are enrolled, treated and evaluated for 3 months. All safety evaluations are completed for each group prior to enrolling and treating subjects at the next higher dose level. Enrollment and dose escalation continue until a maximum tolerable dose is achieved or the study is terminated.

Cannulation is via the left subclavian artery until tip of catheter is at the proper hepatic artery junction. Cannulation is guided by ultrasonography as described (Lin et al., Clinical effects of intra-arterial infusion chemotherapy with cisplatin, mitomycin C, leucovor and 5-Fluorouracil for unresectable advanced hepatocellular carcinoma, 2004, 1 Chin. Med. Assoc. 67:602-10).

Primary Outcome Measures

Safety: Systemic and locoregional adverse events are graded according to CTCAS and coded according to MedRA. The adverse events data for all subjects at a single dose range will be evaluated prior to dose escalation. The final safety assessment incorporates data from all dose ranges.

Secondary Outcome Measures
- Lesion distribution and retention of LV-FDPS following locoregional administration and subsequent biopsy or necropsy to obtain tissues.
- Objective response rate (ORR) in target and measurable non-local lesions (if present) by physical analysis, medical imaging or biopsy during 3 months after treatment.
- Levels of LV-FDPS in blood stream during 10 minutes, 30 minutes, 1 hour and 1 day after local injection.
- Changes in markers of hepatic function including ALP, ALT, ASAT, total bilirubin and GGT during 3 months after treatment.
- Disease free survival beyond historical control (no LV-FDPS) patients in ad hoc analysis.

Inclusion Criteria
- Greater than 18 years and including both males and females.
- Diagnosis confirmed by histology or cytology or based on currently accepted clinical standards of hepatocellular carcinoma of parenchyma cell origin that is not amenable, at the time of screening, to resection, transplant or other potentially curative therapies.
- Treating physician determines that the lesion is amenable to locoregional targeted delivery.
- Target lesion must represent measurable disease with a unidimensional longest diameter of ≥1.0 cm by computed tomography; the maximum longest diameter is ≤5.0 cm.
- Karnofsky performance score 60-80% of ECOG values.
- Life expectancy ≥12 weeks.
- Hematopoietic function: WBC≥2,500/mm$^3$; ANC≥1000/mm$^3$; Hemoglobin≥8 g/dL; Platelet count≥50,000/mm$^3$; Coagulation INR≤1.3.
- AST and ALT<5 times ULN; ALPS<5 time ULN. Bilirubin≤1.5 times ULV; Creatine≤1.5 times ULN and eGFR≥50.
- Thyroid function: Total T3 or free T3, total T4 or free T4 and THC≤CTCAE Grade 2 abnormality.

Renal, cardiovascular and respiratory function adequate in the opinion of the attending physician.

Immunological function: Circulating Vgamma9Vdelta2+ T cells≥30/mm$^3$; no immunodeficiency disease.

Negative for HIV by serology and viral RNA test.

Written informed consent.

Exclusion Criteria

Target lesion contiguous with, encompasses or infiltrates blood vessel.

Primary HCC amenable to resection, transplantation or other potentially curative therapies.

Hepatic surgery or chemoembolization within the past 4 months.

Hepatic radiation or whole body radiation therapy within past 4 months.

Chemotherapy with 4 weeks or any use of nitrosourea, mitomycin C or cisplatin.

Current or within past 4 weeks receipt of bisphosphonate therapy

Investigational agents within 4 weeks or <5 drug half-lives.

Impaired wound healing due to diabetes.

Significant psychiatric illness, alcohol dependence or illicit drug use.

Unwilling to comply with study protocols and reporting requirements.

Bisphosphonate treatment within past 4 months.

Presence of clinically significant cardiovascular, cerebrovascular (stroke), immunological (except hepatitis B or C virus infection, viral hepatitis or cirrhosis), endocrine or central nervous system disorders; current encephalopathy; variceal bleeding requiring hospitalization or transfusion within past 4 months.

History of HIV or acquired immune deficiency syndrome.

Current or prior treatment with antiretroviral medications.

Pregnant, lactating or refusal to adopt barrier or chemical contraceptive use throughout trial and follow-up interval.

LV-FDPS is a Genetic Medicine Delivered by a Lentivirus Vector Via Local Administration to the Site of Late Stage, Non-Resectable Hepatocellular Carcinoma—Adjunct Administration of Bisphosphonate A Phase I clinical trial will test safety and feasibility of delivering LV-FDPS to the site of hepatocellular carcinoma (HCC) using ultrasound guided cannulation of the liver in patients with concomitant bisphosphonate chemotherapy. It is rationally predicted that this study will result in the successful treatment of HCC. The study is an open label, 4×3 dose escalation (4 dose ranges, up to 3 subjects per dose) to identify the maximum tolerable dose of LV-FDPS in patients 18 years or older with Stage III/IV non-resectable HCC.

LV-FDPS is a genetic therapy designed to reduce expression in tumor cells of the enzyme farnesyl diphosphate synthase. Experimental studies show that tumor cells modified by LV-FDPS induce the anti-tumor activity of human gamma delta T cells, including the capacity for tumor killing by cellular cytotoxicity. Prior experimental studies also showed the potential for positive interactions of LV-FDPS and specific bisphosphonate drugs that may be prescribed in primary or metastatic diseases. For this study, subjects will receive dose escalating amounts of LV-FDPS with continuous standard of care dosing with Aredia® (pamidronate), Zometa® (zoledronic acid) or Actonel® (risedronate) according to physician advice and subject preference.

Subjects with target lesions ≥1 cm in longest diameter (measured by helical CT) and ≤4.9 cm maximum diameter and meeting inclusion and exclusion criteria detailed below, are enrolled and started on bisphosphonate therapy. 30 days later size of the target lesion is re-evaluated to ensure subjects still meet starting criteria for LV-FDPS. Subjects without objective clinical response on bisphosphonate are enrolled into the next available LV-FDPS dosing category. A maximum of 3 subjects are recruited for each dosage group and all continue on bisphosphonate for the study duration unless otherwise advised by the attending physician. The LV-FDPS dose is a number of transducing units of LV-FDPS as described in the product release criteria, delivered via intrahepatic cannulation in a single bolus with volume not to exceed 25 mL. The minimum dose is $1\times10^9$ transducing units and escalation is 10-fold to a next dose of $1\times10^{10}$ transducing units, the next dose is $1\times10^{11}$ transducing units, and a maximum dose of $1\times10^{12}$ transducing units based on reported experience with recombinant adenovirus therapy for HCC (Sangro, et al., A phase I clinic trial of thymidine kinase-based gene therapy in advanced hepatocellular carcinoma, 2010, *Cancer Gene Ther.* 17:837-43). Subjects are enrolled, treated and evaluated for 3 months. All safety evaluations are completed for each group prior to enrolling and treating subjects at the next higher dose level. Enrollment and dose escalation continue until a maximum tolerable dose is achieved or the study is terminated.

Cannulation is via the left subclavian artery until tip of catheter is at the proper hepatic artery junction. Cannulation is guided by ultrasonography as described (Lin et al., Clinical effects of intra-arterial infusion chemotherapy with cisplatin, mitomycin C, leucovor and 5-Fluorouracil for unresectable advanced hepatocellular carcinoma, 2004, *J. Chin. Med. Assoc.* 67:602-10).

Primary Outcome Measures

Safety: Systemic and locoregional adverse events are graded according to CTCAS and coded according to MedRA. The adverse events data for all subjects at a single dose range will be evaluated prior to dose escalation. The final safety assessment incorporates data from all dose ranges.

Secondary Outcome Measures

Lesion distribution and retention of LV-FDPS following locoregional administration and subsequent biopsy or necropsy to obtain tissues.

Objective response rate (ORR) in target and measurable non-local lesions (if present) by physical analysis, medical imaging or biopsy during 3 months after treatment.

Levels of LV-FDPS in blood stream during 10 minutes, 30 minutes, 1 hour and 1 day after local injection.

Changes in markers of hepatic function including ALP, ALT, ASAT, total bilirubin and GGT during 3 months after treatment.

Disease free survival beyond historical control (no LV-FDPS) patients in ad hoc analysis.

Inclusion Criteria

Greater than 18 years and including both males and females.

Diagnosis confirmed by histology or cytology or based on currently accepted clinical standards of hepatocellular carcinoma of parenchyma cell origin that is not amenable, at the time of screening, to resection, transplant or other potentially curative therapies.

Treating physician determines that the lesion is amenable to locoregional targeted delivery.

Target lesion must represent measurable disease with a unidimensional longest diameter of ≥1.0 cm by computed tomography; the maximum longest diameter is ≤5.0 cm.

Karnofsky performance score 60-80% of ECOG values.

Life expectancy ≥12 weeks.

Hematopoietic function: WBC≥2,500/mm$^3$; ANC≥1000/mm$^3$; Hemoglobin≥8 g/dL; Platelet count≥50,000/mm$^3$; Coagulation INR≤1.3.

AST and ALT<5 times ULN; ALPS<5 time ULN. Bilirubin≤1.5 times ULV; Creatine≤1.5 times ULN and eGFR≥50.

Thyroid function: Total T3 or free T3, total T4 or free T4 and THC≤CTCAE Grade 2 abnormality.

Renal, cardiovascular and respiratory function adequate in the opinion of the attending physician.

Immunological function: Circulating Vgamma9Vdelta2+ T cells≥30/mm$^3$; no immunodeficiency disease.

Negative for HIV by serology and viral RNA test.

Written informed consent.

Exclusion Criteria

Intolerant to or unwilling to continue bisphosphonate adjunct therapy.

Objective clinical response after bisphosphonate therapy.

Target lesion contiguous with, encompasses or infiltrates blood vessel.

Primary HCC amenable to resection, transplantation or other potentially curative therapies.

Hepatic surgery or chemoembolization within the past 4 months.

Hepatic radiation or whole body radiation therapy within past 4 months.

Chemotherapy excluding bisphosphonate, within 4 weeks or any use of nitrosourea, mitomycin C or cisplatin.

Investigational agents within 4 weeks or <5 drug half-lives.

Impaired wound healing due to diabetes.

Significant psychiatric illness, alcohol dependence or illicit drug use.

Unwilling to comply with study protocols and reporting requirements.

Presence of clinically significant cardiovascular, cerebrovascular (stroke), immunological (except hepatitis B or C virus infection, viral hepatitis or cirrhosis), endocrine or central nervous system disorders; current encephalopathy; variceal bleeding requiring hospitalization or transfusion within past 4 months.

History of HIV or acquired immune deficiency syndrome.

Current or prior treatment with antiretroviral medications.

Pregnant, lactating or refusal to adopt barrier or chemical contraceptive use throughout trial and follow-up interval.

Example 15—Treatment of a Subject with Chronic Viral Disease(s) of the Liver

LV-FDPS is a Genetic Medicine Delivered by a Lentivirus Vector Via Local Administration to Liver for the Treatment of Hepatitis B Virus, Hepatitis C Virus, HIV or Other Viral Infection of the Liver A Phase I clinical trial will test safety and feasibility of delivering LV-FDPS to virally infected liver using ultrasound guided cannulation. It is rationally predicted that this study will result in the successful treatment of infections of the liver. The study is an open label, 4×3 dose escalation (4 dose ranges, up to 3 subjects per dose) to identify the maximum tolerable dose of LV-FDPS in patients 18 years or older with chronic viral disease of the liver that is resistant to chemotherapy.

LV-FDPS is a genetic therapy designed to reduce expression in tumor cells of the enzyme farnesyl diphosphate synthase. Experimental studies show that tumor cells modified by LV-FDPS induce human gamma delta T cells, including a capacity for cellular cytotoxicity against virally-infected cells.

Subjects with confirmed viral infection of the liver including hepatitis B virus, hepatitis C virus, HIV or other viruses are enrolled into the next available LV-FDPS dosing category. A maximum of 3 subjects are recruited for each dosage group. The LV-FDPS dose is a number of transducing units of LV-FDPS as described in the product release criteria, delivered via intrahepatic cannulation in a single bolus with volume not to exceed 25 mL. The minimum dose is $1\times10^9$ transducing units and escalation is 10-fold to a next dose of $1\times10^{10}$ transducing units, the next dose is $1\times10^{11}$ transducing units, and a maximum dose of $1\times10^{12}$ transducing units based on reported experience with recombinant adenovirus therapy for HCC (Sangro, et al., A phase I clinic trial of thymidine kinase-based gene therapy in advanced hepatocellular carcinoma, 2010, *Cancer Gene Ther.* 17:837-43). Subjects are enrolled, treated and evaluated for 3 months. All safety evaluations are completed for each group prior to enrolling and treating subjects at the next higher dose level. Enrollment and dose escalation continue until a maximum tolerable dose is achieved or the study is terminated.

Cannulation is via the left subclavian artery until tip of catheter is at the proper hepatic artery junction. Cannulation is guided by ultrasonography as described (Lin et al., Clinical effects of intra-arterial infusion chemotherapy with cisplatin, mitomycin C, leucovor and 5-Fluorouracil for unresectable advanced hepatocellular carcinoma, 2004, *J. Chin. Med. Assoc.* 67:602-10).

Primary Outcome Measures

Safety: Systemic and locoregional adverse events are graded according to CTCAS and coded according to MedRA. The adverse events data for all subjects at a single dose range will be evaluated prior to dose escalation. The final safety assessment incorporates data from all dose ranges.

Secondary Outcome Measures

Lesion distribution and retention of LV-FDPS following locoregional administration and subsequent biopsy or necropsy to obtain tissues.

Objective response rate (ORR) measured as a Sustained Viral Response (SVR) within the organ or systemically during 3 months after treatment.

Levels of LV-FDPS in blood stream during 10 minutes, 30 minutes, 1 hour and 1 day after local injection.

Changes in markers of hepatic function including ALP, ALT, ASAT, total bilirubin and GGT during 3 months after treatment.

Disease free survival beyond historical control (no LV-FDPS) patients in ad hoc analysis.

Inclusion Criteria

Greater than 18 years and including both males and females.

Diagnosis confirmed by histology or cytology or based on currently accepted clinical standards of chronic viral infection of the liver that is not amenable, at the time of screening, to resection, transplant or other potentially curative therapies.

Treating physician determines that the lesion is amenable to locoregional targeted delivery.

Karnofsky performance score 60-80% of ECOG values.

Life expectancy ≥12 weeks.

Hematopoietic function: WBC≥2,500/mm³; ANC≥1000/mm³; Hemoglobin≥8 g/dL; Platelet count≥50,000/mm³; Coagulation INR≤1.3.

AST and ALT<5 times ULN; ALPS<5 time ULN. Bilirubin≤1.5 times ULV; Creatine≤1.5 times ULN and eGFR≥50.

Thyroid function: Total T3 or free T3, total T4 or free T4 and THC≤CTCAE Grade 2 abnormality.

Renal, cardiovascular and respiratory function adequate in the opinion of the attending physician.

Immunological function: Circulating Vgamma9Vdelta2+ T cells≥30/mm³; no immunodeficiency disease.

Negative for HIV by serology and viral RNA test.

Written informed consent.

Exclusion Criteria

Chronic viral disease amenable to resection, transplantation or other potentially curative therapies.

Hepatic surgery or chemoembolization within the past 4 months.

Hepatic radiation or whole body radiation therapy within past 4 months.

Investigational agents within 4 weeks or <5 drug half-lives.

Current (within past 4 weeks) or ongoing receipt of bisphosphonate therapy.

Impaired wound healing due to diabetes.

Significant psychiatric illness, alcohol dependence or illicit drug use.

Unwilling to comply with study protocols and reporting requirements.

Presence of clinically significant cardiovascular, cerebrovascular (stroke), immunological (except virus infection, viral hepatitis or cirrhosis), endocrine or central nervous system disorders; current encephalopathy; variceal bleeding requiring hospitalization or transfusion within past 4 months.

Pregnant, lactating or refusal to adopt barrier or chemical contraceptive use throughout trial and follow-up interval.

LV-FDPS is a Genetic Medicine Delivered by a Lentivirus Vector Via Local Administration to Liver for the Treatment of Hepatitis B Virus, Hepatitis C Virus, HIV or other Viral Infection of the Liver—Concomitant Adjunct Bisphosphonate Therapy A Phase I clinical trial will test safety and feasibility of delivering LV-FDPS to virally infected liver using ultrasound guided cannulation. It is rationally predicted that this study will result in the successful treatment of infections of the liver. The study is an open label, 4×3 dose escalation (4 dose ranges, up to 3 subjects per dose) to identify the maximum tolerable dose of LV-FDPS in patients 18 years or older with chronic viral disease of the liver that is resistant to chemotherapy.

LV-FDPS is a genetic therapy designed to reduce expression in tumor cells of the enzyme farnesyl diphosphate synthase. Experimental studies show that tumor cells modified by LV-FDPS induce human gamma delta T cells, including a capacity for cellular cytotoxicity against virally-infected cells. Prior experimental studies also showed the potential for positive interactions of LV-FDPS and specific bisphosphonate drugs that may be prescribed during infectious disease. For this study, subjects will receive dose escalating amounts of LV-FDPS with continuous standard of care dosing with Aredia® (pamidronate), Zometa® (zoledronic acid) or Actonel® (risedronate) according to physician advice and subject preference.

Subjects with confirmed viral infection of the liver including hepatitis B virus, hepatitis C virus, HIV or other viruses will initiate bisphosphonate therapy for 45 days before re-screening to meet enrollment criteria for LV-FDPS treatment of infectious disease. Eligible subjects are enrolled into the next available LV-FDPS dosing category. A maximum of 3 subjects are recruited for each dosage group. The LV-FDPS dose is a number of transducing units of LV-FDPS as described in the product release criteria, delivered via intrahepatic cannulation in a single bolus with volume not to exceed 25 mL. The minimum dose is $1 \times 10^9$ transducing units and escalation is 10-fold to a next dose of $1 \times 10^{10}$ transducing units, the next dose is $1 \times 10^{11}$ transducing units, and a maximum dose of $1 \times 10^{12}$ transducing units based on reported experience with recombinant adenovirus therapy for HCC (Sangro, et al., A phase I clinic trial of thymidine kinase-based gene therapy in advanced hepatocellular carcinoma, 2010, *Cancer Gene Ther.* 17:837-43). Subjects are enrolled, treated and evaluated for 3 months. All safety evaluations are completed for each group prior to enrolling and treating subjects at the next higher dose level. Enrollment and dose escalation continue until a maximum tolerable dose is achieved or the study is terminated.

Cannulation is via the left subclavian artery until tip of catheter is at the proper hepatic artery junction. Cannulation is guided by ultrasonography as described (Lin et al., Clinical effects of intra-arterial infusion chemotherapy with cisplatin, mitomycin C, leucovor and 5-Fluorouracil for unresectable advanced hepatocellular carcinoma, 2004, *J. Chin. Med. Assoc.* 67:602-10).

Primary Outcome Measures

Safety: Systemic and locoregional adverse events are graded according to CTCAS and coded according to MedRA. The adverse events data for all subjects at a single dose range will be evaluated prior to dose escalation. The final safety assessment incorporates data from all dose ranges.

Secondary Outcome Measures

Lesion distribution and retention of LV-FDPS following locoregional administration and subsequent biopsy or necropsy to obtain tissues.

Objective response rate (ORR) measured as a Sustained Viral Response (SVR) within the organ or systemically during 3 months after treatment.

Levels of LV-FDPS in blood stream during 10 minutes, 30 minutes, 1 hour and 1 day after local injection.

Changes in markers of hepatic function including ALP, ALT, ASAT, total bilirubin and GGT during 3 months after treatment.

Disease free survival beyond historical control (no LV-FDPS) patients in ad hoc analysis.

Inclusion Criteria

Greater than 18 years and including both males and females.

Diagnosis confirmed by histology or cytology or based on currently accepted clinical standards of chronic viral infection of the liver that is not amenable, at the time of screening, to resection, transplant or other potentially curative therapies.

Treating physician determines that the lesion is amenable to locoregional targeted delivery.

Karnofsky performance score 60-80% of ECOG values.

Life expectancy≥12 weeks.

Hematopoietic function: WBC≥2,500/mm³; ANC≥1000/mm³; Hemoglobin≥8 g/dL; Platelet count≥50,000/mm³; Coagulation INR≤1.3.

AST and ALT<5 times ULN; ALPS<5 time ULN. Bilirubin≤1.5 times ULV; Creatine≤1.5 times ULN and eGFR≥50.

Thyroid function: Total T3 or free T3, total T4 or free T4 and THC≤CTCAE Grade 2 abnormality.

Renal, cardiovascular and respiratory function adequate in the opinion of the attending physician.

Immunological function: Circulating Vgamma9Vdelta2+ T cells≥30/mm³; no immunodeficiency disease.

Negative for HIV by serology and viral RNA test.

Written informed consent.

Exclusion Criteria

Chronic viral disease amenable to resection, transplantation or other potentially curative therapies.

Hepatic surgery or chemoembolization within the past 4 months.

Hepatic radiation or whole body radiation therapy within past 4 months.

Investigational agents within 4 weeks or <5 drug half-lives.

Impaired wound healing due to diabetes.

Significant psychiatric illness, alcohol dependence or illicit drug use.

Unwilling to comply with study protocols and reporting requirements.

Presence of clinically significant cardiovascular, cerebrovascular (stroke), immunological (except virus infection, viral hepatitis or cirrhosis), endocrine or central nervous system disorders; current encephalopathy; variceal bleeding requiring hospitalization or transfusion within past 4 months.

Pregnant, lactating or refusal to adopt barrier or chemical contraceptive use throughout trial and follow-up interval Sequences The following sequences are referred to herein:

| SEQ ID NO: | Description | Sequence |
|---|---|---|
| 1 | FDPS shRNA sequence #1 | GTCCTGGAGTACAATGCCATTCTCGAGAATGGCATTGTACTCCAGGACTTTTT |
| 2 | FDPS shRNA sequence #2 | GCAGGATTTCGTTCAGCACTTCTCGAGAAGTGCTGAACGAAATCCTGCTTTTT |
| 3 | FDPS shRNA sequence #3 | GCCATGTACATGGCAGGAATTCTCGAGAATTCCTGCCATGTACATGGCTTTTT |
| 4 | FDPS shRNA sequence #4 | GCAGAAGGAGGCTGAGAAAGTCTCGAGACTTTCTCAGCCTCCTTCTGCTTTTT |
| 5 | miR30 FDPS sequence #1 | AAGGTATATTGCTGTTGACAGTGAGCGACACTTTCTCAGCCTCCTTCTGCGTGAAGCCACAGATGGCAGAAGGAGGCTGAGAAAGTGCTGCCTACTGCCTCGGACTTCAAGGGGCT |
| 6 | miR30 FDPS sequence #2 | AAGGTATATTGCTGTTGACAGTGAGCGACACTTTCTCAGCCTCCTTCTGCGTGAAGCCACAGATGGCAGAAGGGCTGAGAAAGTGCTGCCTACTGCCTCGGACTTCAAGGGGCT |
| 7 | miR30 FDPS sequence #3 | TGCTGTTGACAGTGAGCGACTTTCTCAGCCTCCTTCTGCGTGAAGCCACAGATGGCAGAAGGAGGCTGAGAAAGTTGCCTACTGCCTCGGA |
| 8 | miR155 FDPS sequence #1 | CCTGGAGGCTTGCTGAAGGCTGTATGCTGACTTTCTCAGCCTCCTTCTGCTTTTGGCCACTGACTGAGCAGAAGGGCTGAGAAAGTCAGGACACAAGGCCTGTTACTAGCACTCA |
| 9 | miR21 FDPS sequence #1 | CATCTCCATGGCTGTACCACCTTGTCGGGACTTTCTCAGCCTCCTTCTGCCTGTTGAATCTCATGGCAGAAGGAGGCGAGAAAGTCTGACATTTTGGTATCTTTCATCTGACCA |
| 10 | miR185 FDPS sequence #1 | GGGCCTGGCTCGAGCAGGGGCGAGGGATACTTTCTCAGCCTCCTTCTGCTGGTCCCCTCCCCGCAGAAGGAGGCTGAGAAAGTCCTTCCCTCCCAATGACCGCGTCTTCGTCG |
| 11 | Rous Sarcoma virus (RSV) promoter | GTAGTCTTATGCAATACTCTTGTAGTCTTGCAACATGGTAACGATGAGTTAGCAACATGCCTTACAAGGAGAGAAAAGCACCGTGCATGCCGATTGGTGGAAGTAAGGTGGTACGATCGTGCCTTATTAGGAAGGCAACAGACGGGTCTGACATGGATTGGACGAACCACTGAATTGCCGCATTGCAGAGATATTGTATTTAAGTGCCTAGCTCGATACAATAAACG |
| 12 | 5' Long terminal repeat (LTR) | GGTCTCTCTGGTTAGACCAGATCTGAGCCTGGGAGCTCTCTGGCTAACTAGGGAACCCACTGCTTAAGCCTCAATAAAGCTTGCCTTGAGTGCTTCAAGTAGTGTGTGCCCGTCTGTTGTGTGACTCTGGTAACTAGAGATCCCTCAGACCCTTTTAGTCAGTGTGGAAAATCTCTAGCA |
| 13 | Psi Packaging signal | TACGCCAAAAATTTTGACTAGCGGAGGCTAGAAGGAGAGAG |

-continued

| SEQ ID NO: | Description | Sequence |
|---|---|---|
| 14 | Rev response element (RRE) | AGGAGCTTTGTTCCTTGGGTTCTTGGGAGCAGCAGGAAG<br>CACTATGGGCGCAGCCTCAATGACGCTGACGGTACAGGC<br>CAGACAATTATTGTCTGGTATAGTGCAGCAGCAGAACAA<br>TTTGCTGAGGGCTATTGAGGCGCAACAGCATCTGTTGCA<br>ACTCACAGTCTGGGGCATCAAGCAGCTCCAGGCAAGAAT<br>CCTGGCTGTGGAAAGATACCTAAAGGATCAACAGCTCC |
| 15 | Central polypurine tract (cPPT) | TTTTAAAAGAAAAGGGGGGATTGGGGGGTACAGTGCAG<br>GGGAAAGAATAGTAGACATAATAGCAACAGACATACAA<br>ACTAAAGAATTACAAAAACAAATTACAAAATTCAAAATT<br>TTA |
| 16 | Polymerase III shRNA promoters; H1 promoter | GAACGCTGACGTCATCAACCCGCTCCAAGGAATCGCGGG<br>CCCAGTGTCACTAGGCGGGAACACCCAGCGCGCGTGCGC<br>CCTGGCAGGAAGATGGCTGTGAGGGACAGGGGAGTGGC<br>GCCCTGCAATATTTGCATGTCGCTATGTGTTCTGGGAAAT<br>CACCATAAACGTGAAATGTCTTTGGATTTGGGAATCTTA<br>TAAGTTCTGTATGAGACCACTT |
| 17 | Long WPRE sequence | AATCAACCTCTGATTACAAAATTTGTGAAAGATTGACTG<br>GTATTCTTAACTATGTTGCTCCTTTTACGCTATGTGGATA<br>CGCTGCTTTAATGCCTTTGTATCATGCTATTGCTTCCCGT<br>ATGGCTTTCATTTTCTCCTCCTTGTATAAATCCTGGTTGC<br>TGTCTCTTTATGAGGAGTTGTGGCCCGTTGTCAGGCAAC<br>GTGGCGTGGTGTGCACTGTGTTTGCTGACGCAACCCCCA<br>CTGGTTGGGGCATTGCCACCACCTGTCAGCTCCTTTCCGG<br>GACTTTCGCTTTCCCCCTCCCTATTGCCACGGCGGAACTC<br>ATCGCCGCCTGCCTTGCCCGCTGCTGGACAGGGGCTCGG<br>CTGTTGGGCACTGACAATTCCGTGGTGTTGTCGGGGAAA<br>TCATCGTCCTTTCCTTGGCTGCTCGCCTGTGTTGCCACCT<br>GGATTCTGCGCGGGACGTCCTTCTGCTACGTCCCTTCGGC<br>CCTCAATCCAGCGGACCTTCCTTCCCGCGGCCTGCTGCC<br>GGCTCTGCGGCCTCTTCCGCGTCTTCGCCTTCGCCCTCAG<br>ACGAGTCGGATCTCCCTTTGGGCCGCCTCCCCGCCT |
| 18 | 3' delta LTR | TGGAAGGGCTAATTCACTCCCAACGAAGATAAGATCTGC<br>TTTTTGCTTGTACTGGGTCTCTCTGGTTAGACCAGATCTG<br>AGCCTGGGAGCTCTCTGGCTAACTAGGGAACCCACTGCT<br>TAAGCCTCAATAAAGCTTGCCTTGAGTGCTTCAAGTAGT<br>GTGTGCCCGTCTGTTGTGTGACTCTGGTAACTAGAGATC<br>CCTCAGACCCTTTTAGTCAGTGTGGAAAATCTCTAGCAG<br>TAGTAGTTCATGTCA |
| 19 | Helper/Rev; Chicken beta actin (CAG) promoter; Transcription | GCTATTACCATGGGTCGAGGTGAGCCCCACGTTCTGCTT<br>CACTCTCCCCATCTCCCCCCCCTCCCCACCCCCAATTTTG<br>TATTTATTTATTTTTTAATTATTTTGTGCAGCGATGGGGG<br>CGGGGGGGGGGGGGCGCGCGCCAGGCGGGGCGGGGC<br>GGGGCGAGGGGCGGGGCGGGGCGAGGCGGAGAGGTGC<br>GGCGGCAGCCAATCAGAGCGGCGCGCTCCGAAAGTTTCC<br>TTTTATGGCGAGGCGGCGGCGGCGGCGGCCCTATAAAAA<br>GCGAAGCGCGCGGCGGGCG |
| 20 | Helper/Rev; HIV Gag; Viral capsid | ATGGGTGCGAGAGCGTCAGTATTAAGCGGGGGAGAATT<br>AGATCGATGGGAAAAAATTCGGTTAAGGCCAGGGGGAA<br>AGAAAAAATATAAATTAAAACATATAGTATGGGCAAGC<br>AGGGAGCTAGAACGATTCGCAGTTAATCCTGGCCTGTTA<br>GAAACATCAGAAGGCTGTAGACAAATACTGGGACAGCT<br>ACAACCATCCCTTCAGACAGGATCAGAAGAACTTAGATC<br>ATTATATAATACAGTAGCAACCCTCTATTGTGTGCATCA<br>AAGGATAGAGATAAAAGACACCAAGGAAGCTTTAGACA<br>AGATAGAGGAAGAGCAAAACAAAAGTAAGAAAAAAGC<br>ACAGCAAGCAGCAGCTGACACAGGACACAGCAATCAGG<br>TCAGCCAAAATTACCCTATAGTGCAGAACATCCAGGGGC<br>AAATGGTACATCAGGCCATATCACCTAGAACTTTAAATG<br>CATGGGTAAAAGTAGTAGAAGAGAAGGCTTTCAGCCCA<br>GAAGTGATACCCATGTTTTCAGCATTATCAGAAGGAGCC<br>ACCCCACAAGATTTAAACACCATGCTAAACACAGTGGGG<br>GGACATCAAGCAGCCATGCAAATGTTAAAAGAGACCAT<br>CAATGAGGAAGCTGCAGAATGGGATAGAGTGCATCCAG<br>TGCATGCAGGGCCTATTGCACCAGGCCAGATGAGAGAA<br>CCAAGGGGAAGTGACATAGCAGGAACTACTAGTACCCTT<br>CAGGAACAAATAGGATGGATGACACATAATCCACCTATC<br>CCAGTAGGAGAAATCTATAAAAGATGGATAATCCTGGG<br>ATTAAATAAAATAGTAAGAATGTATAGCCCTACCAGCAT<br>TCTGGACATAAGACAAGGACCAAAGGAACCCTTTAGAG<br>ACTATGTAGACCGATTCTATAAAACTCTAAGAGCCGAGC |

| SEQ ID NO: | Description | Sequence |
|---|---|---|
| | | AAGCTTCACAAGAGGTAAAAAATTGGATGACAGAAACC<br>TTGTTGGTCCAAAATGCGAACCCAGATTGTAAGACTATT<br>TTAAAAGCATTGGGACCAGGAGCGACACTAGAAGAAAT<br>GATGACAGCATGTCAGGGAGTGGGGGGACCCGGCCATA<br>AAGCAAGAGTTTTGGCTGAAGCAATGAGCCAAGTAACA<br>AATCCAGCTACCATAATGATACAGAAAGGCAATTTTAGG<br>AACCAAAGAAAGACTGTTAAGTGTTTCAATTGTGGCAAA<br>GAAGGGCACATAGCCAAAAATTGCAGGGCCCCTAGGAA<br>AAAGGGCTGTTGGAAATGTGGAAAGGAAGGACACCAAA<br>TGAAAGATTGTACTGAGAGACAGGCTAATTTTTTAGGGA<br>AGATCTGGCCTTCCCACAAGGGAAGGCCAGGGAATTTTC<br>TTCAGAGCAGACCAGAGCCAACAGCCCCACCAGAAGAG<br>AGCTTCAGGTTTGGGGAAGAGACAACAACTCCCTCTCAG<br>AAGCAGGAGCCGATAGACAAGGAACTGTATCCTTTAGCT<br>TCCCTCAGATCACTCTTTGGCAGCGACCCCTCGTCACAAT<br>AA |
| 21 | Helper/Rev; HIV Pol; Protease and reverse transcriptase | ATGAATTTGCCAGGAAGATGGAAACCAAAAATGATAGG<br>GGGAATTGGAGGTTTTATCAAAGTAGGACAGTATGATCA<br>GATACTCATAGAAATCTGCGGACATAAAGCTATAGGTAC<br>AGTATTAGTAGGACCTACACCTGTCAACATAATTGGAAG<br>AAATCTGTTGACTCAGATTGGCTGCACTTTAAATTTTCCC<br>ATTAGTCCTATTGAGACTGTACCAGTAAAATTAAAGCCA<br>GGAATGGATGGCCCAAAAGTTAAACAATGGCCATTGAC<br>AGAAGAAAAAATAAAAGCATTAGTAGAAATTTGTACAG<br>AAATGGAAAAGGAAGGAAAAATTTCAAAAATTGGGCCT<br>GAAAATCCATACAATACTCCAGTATTTGCCATAAAGAAA<br>AAAGACAGTACTAAATGGAGAAAATTAGTAGATTTCAG<br>AGAACTTAATAAGAGAACTCAAGATTTCTGGGAAGTTCA<br>ATTAGGAATACCACATCCTGCAGGGTTAAAACAGAAAA<br>AATCAGTAACAGTACTGGATGTGGGCGATGCATATTTTT<br>CAGTTCCCTTAGATAAAGACTTCAGGAAGTATACTGCAT<br>TTACCATACCTAGTATAAACAATGAGACACCAGGGATTA<br>GATATCAGTACAATGTGCTTCCACAGGGATGGAAAGGAT<br>CACCAGCAATATTCCAGTGTAGCATGACAAAAATCTTAG<br>AGCCTTTTAGAAAACAAAATCCAGACATAGTCATCTATC<br>AATACATGGATGATTTGTATGTAGGATCTGACTTAGAAA<br>TAGGGCAGCATAGAACAAAAATAGAGGAACTGAGACAA<br>CATCTGTTGAGGTGGGGATTTACCACACCAGACAAAAAA<br>CATCAGAAAGAACCTCCATTCCTTTGGATGGGTTATGAA<br>CTCCATCCTGATAAATGGACAGTACAGCCTATAGTGCTG<br>CCAGAAAAGGACAGCTGGACTGTCAATGACATACAGAA<br>ATTAGTGGGAAAATTGAATTGGGCAAGTCAGATTTATGC<br>AGGGATTAAAGTAAGGCAATTATGTAAACTTCTTAGGGG<br>AACCAAAGCACTAACAGAAGTAGTACCACTAACAGAAG<br>AAGCAGAGCTAGAACTGGCAGAAAACAGGGAGATTCTA<br>AAAGAACCGGTACATGGAGTGTATTATGACCCATCAAAA<br>GACTTAATAGCAGAAATACAGAAGCAGGGGCAAGGCCA<br>ATGGACATATCAAATTTATCAAGAGCCATTTAAAAATCT<br>GAAAACAGGAAAATATGCAAGAATGAAGGGTGCCCACA<br>CTAATGATGTGAAACAATTAACAGAGGCAGTACAAAAA<br>ATAGCCACAGAAAGCATAGTAATATGGGGAAAGACTCC<br>TAAATTTAAATTACCCATACAAAAGGAAACATGGGAAG<br>CATGGTGGACAGAGTATTGGCAAGCCACCTGGATTCCTG<br>AGTGGGAGTTTGTCAATACCCCTCCCTTAGTGAAGTTAT<br>GGTACCAGTTAGAGAAAGAACCCATAATAGGAGCAGAA<br>ACTTTCTATGTAGATGGGGCAGCCAATAGGGAAACTAAA<br>TTAGGAAAAGCAGGATATGTAACTGACAGAGGAAGACA<br>AAAAGTTGTCCCCCTAACGGACACAACAAATCAGAAGA<br>CTGAGTTACAAGCAATTCATCTAGCTTTGCAGGATTCGG<br>GATTAGAAGTAAACATAGTGACAGACTCACAATATGCAT<br>TGGGAATCATTCAAGCACAACCAGATAAGAGTGAATCA<br>GAGTTAGTCAGTCAAATAATAGAGCAGTTAATAAAAAA<br>GGAAAAAGTCTACCTGGCATGGGTACCAGCACACAAAG<br>GAATTGGAGGAAATGAACAAGTAGATGGGTTGGTCAGT<br>GCTGGAATCAGGAAAGTACTA |
| 22 | Helper Rev; HIV Integrase; Integration of viral RNA | TTTTTAGATGGAATAGATAAGGCCCAAGAAGAACATGA<br>GAAATATCACAGTAATTGGAGAGCAATGGCTAGTGATTT<br>TAACCTACCACCTGTAGTAGCAAAAGAAATAGTAGCCAG<br>CTGTGATAAATGTCAGCTAAAAGGGGAAGCCATGCATG<br>GACAAGTAGACTGTAGCCCAGGAATATGGCAGCTAGATT<br>GTACACATTTAGAAGGAAAAGTTATCTTGGTAGCAGTTC<br>ATGTAGCCAGTGGATATATAGAAGCAGAAGTAATTCCAG<br>CAGAGACAGGGCAAGAAACAGCATACTTCCTCTTAAAAT<br>TAGCAGGAAGATGGCCAGTAAAAACAGTACATACAGAC |

-continued

| SEQ ID NO: | Description | Sequence |
|---|---|---|
| | | AATGGCAGCAATTTCACCAGTACTACAGTTAAGGCCGCC
TGTTGGTGGGCGGGGATCAAGCAGGAATTTGGCATTCCC
TACAATCCCCAAAGTCAAGGAGTAATAGAATCTATGAAT
AAAGAATTAAAGAAAATTATAGGACAGGTAAGAGATCA
GGCTGAACATCTTAAGACAGCAGTACAAATGGCAGTATT
CATCCACAATTTTAAAAGAAAAGGGGGGATTGGGGGGT
ACAGTGCAGGGGAAAGAATAGTAGACATAATAGCAACA
GACATACAAACTAAAGAATTACAAAAACAAATTACAAA
AATTCAAAATTTTCGGGTTTATTACAGGGACAGCAGAGA
TCCAGTTTGGAAAGGACCAGCAAAGCTCCTCTGGAAAGG
TGAAGGGGCAGTAGTAATACAAGATAATAGTGACATAA
AAGTAGTGCCAAGAAGAAAAGCAAAGATCATCAGGGAT
TATGGAAAACAGATGGCAGGTGATGATTGTGTGGCAAGT
AGACAGGATGAGGATTAA |
| 23 | Helper/Rev; HIV RRE; Binds Rev element | AGGAGCTTTGTTCCTTGGGTTCTTGGGAGCAGCAGGAAG
CACTATGGGCGCAGCGTCAATGACGCTGACGGTACAGGC
CAGACAATTATTGTCTGGTATAGTGCAGCAGCAGAACAA
TTTGCTGAGGGCTATTGAGGCGCAACAGCATCTGTTGCA
ACTCACAGTCTGGGGCATCAAGCAGCTCCAGGCAAGAAT
CCTGGCTGTGGAAAGATACCTAAAGGATCAACAGCTCCT |
| 24 | Helper/Rev; HIV Rev; Nuclear export and stabilize viral mRNA | ATGGCAGGAAGAAGCGGAGACAGCGACGAAGAACTCCT
CAAGGCAGTCAGACTCATCAAGTTTCTCTATCAAAGCAA
CCCACCTCCCAATCCCGAGGGGACCCGACAGGCCCGAA
GGAATAGAAGAAGAAGGTGGAGAGAGAGACAGAGACA
GATCCATTCGATTAGTGAACGGATCCTTAGCACTTATCT
GGGACGATCTGCGGAGCCTGTGCCTCTTCAGCTACCACC
GCTTGAGAGACTTACTCTTGATTGTAACGAGGATTGTGG
AACTTCTGGGACGCAGGGGTGGGAAGCCCTCAAATATT
GGTGGAATCCTACAATATTGGAGTCAGGAGCTAAAGA
ATAG |
| 25 | Envelope; CMV promoter; Transcription | ACATTGATTATTGACTAGTTATTAATAGTAATCAATTACG
GGGTCATTAGTTCATAGCCCATATATGGAGTTCCGCGTT
ACATAACTTACGGTAAATGGCCCGCCTGGCTGACCGCCC
AACGACCCCCGCCCATTGACGTCAATAATGACGTATGTT
CCCATAGTAACGCCAATAGGGACTTTCCATTGACGTCAA
TGGGTGGAGTATTTACGGTAAACTGCCCACTTGGCAGTA
CATCAAGTGTATCATATGCCAAGTACGCCCCCTATTGAC
GTCAATGACGGTAAATGGCCCGCCTGGCATTATGCCCAG
TACATGACCTTATGGGACTTTCCTACTTGGCAGTACATCT
ACGTATTAGTCATCGCTATTACCATGGTGATGCGGTTTTG
GCAGTACATCAATGGGCGTGGATAGCGGTTTGACTCACG
GGGATTTCCAAGTCTCCACCCCATTGACGTCAATGGGAG
TTTGTTTTGGCACCAAAATCAACGGGACTTTCCAAAATG
TCGTAACAACTCCGCCCCATTGACGCAAATGGGCGGTAG
GCGTGTACGGTGGGAGGTCTATATAAGC |
| 26 | Envelope; VSV-G; Glycoprotein envelope-cell entry | ATGAAGTGCCTTTTGTACTTAGCCTTTTTATTCATTGGGG
TGAATTGCAAGTTCACCATAGTTTTTCCACACAACCAAA
AAGGAAACTGGAAAAATGTTCCTTCTAATTACCATTATT
GCCCGTCAAGCTCAGATTTAAATTGGCATAATGACTTAA
TAGGCACAGCCTTACAAGTCAAATGCCCAAGAGTCACA
AGGCTATTCAAGCAGACGGTTGGATGTGTCATGCTTCCA
AATGGGTCACTACTTGTGATTTCCGCTGGTATGGACCGA
AGTATATAACACATTCCATCCGATCCTTCACTCCATCTGT
AGAACAATGCAAGGAAAGCATTGAACAAACGAAACAAG
GAACTTGGCTGAATCCAGGCTTCCCTCCTCAAAGTTGTG
GATATGCAACTGTGACGGATGCCGAAGCAGTGATTGTCC
AGGTGACTCCTCACCATGTGCTGGTTGATGAATACACAG
GAGAATGGGTTGATTCACAGTTCATCAACGGAAAATGCA
GCAATTACATATGCCCCACTGTCCATAACTCTACAACCT
GGCATTCTGACTATAAGGTCAAAGGGCTATGTGATTCTA
ACCTCATTTCCATGGACATCACCTTCTTCTCAGAGGACG
GAGAGCTATCATCCCTGGGAAAGGAGGGCACAGGGTTC
AGAAGTAACTACTTTGCTTATGAAACTGGAGGCAAGGCC
TGCAAAATGCAATACTGCAAGCATTGGGGAGTCAGACTC
CCATCAGGTGTCTGGTTCGAGATGGCTGATAAGGATCTC
TTTGCTGCAGCCAGATTCCCTGAATGCCCAGAAGGGTCA
AGTATCTCTGCTCCATCTCAGACCTCAGTGGATGTAAGT
CTAATTCAGGACGTTGAGAGGATCTTGGATTATTCCCTCT
GCCAAGAAACCTGGAGCAAAATCAGAGCGGGTCTTCCA
ATCTCTCCAGTGGATCTCAGCTATCTTGCTCCTAAAAACC
CAGGAACCGGTCCTGCTTTCACCATAATCAATGGTACCC
TAAAATACTTTGAGACCAGATACATCAGAGTCGATATTG |

| SEQ ID NO: | Description | Sequence |
|---|---|---|
|  |  | CTGCTCCAATCCTCTCAAGAATGGTCGGAATGATCAGTG GAACTACCACAGAAAGGGAACTGTGGGATGACTGGGCA CCATATGAAGACGTGGAAATTGGACCCAATGGAGTTCTG AGGACCAGTTCAGGATATAAGTTTCCTTTATACATGATT GGACATGGTATGTTGGACTCCGATCTTCATCTTAGCTCA AAGGCTCAGGTGTTCGAACATCCTCACATTCAAGACGCT GCTTCGCAACTTCCTGATGATGAGAGTTTATTTTTTGGTG ATACTGGGCTATCCAAAAATCCAATCGAGCTTGTAGAAG GTTGGTTCAGTAGTTGGAAAAGCTCTATTGCCTCTTTTTT CTTTTATCATAGGGTTAATCATTGGACTATTCTTGGTTCTC CGAGTTGGTATCCATCTTTGCATTAAATTAAAGCACACC AAGAAAAGACAGATTTATACAGACATAGAGATGA |
| 27 | Helper/Rev; CMV early (CAG) enhancer; Enhance Transcription | TAGTTATTAATAGTAATCAATTACGGGGTCATTAGTTCAT AGCCCATATATGGAGTTCCGCGTTACATAACTTACGGTA AATGGCCCGCCTGGCTGACCGCCCAACGACCCCCGCCCA TTGACGTCAATAATGACGTATGTTCCCATAGTAACGCCA ATAGGGACTTTCCATTGACGTCAATGGGTGGACTATTTA CGGTAAACTGCCCACTTGGCAGTACATCAAGTGTATCAT ATGCCAAGTACGCCCCCTATTGACGTCAATGACGGTAAA TGGCCCGCCTGGCATTATGCCCAGTACATGACCTTATGG GACTTTCCTACTTGGCAGTACATCTACGTATTAGTCATC |
| 28 | Helper/Rev; Chicken beta actin intron; Enhance gene expression | GGAGTCGCTGCGTTGCCTTCGCCCCGTGCCCCGCTCCGC GCCGCCTCGCGCCGCCCGCCCCGGCTCTGACTGACCGCG TTACTCCCACAGGTGAGCGGGCGGGACGGCCCTTCTCCT CCGGGCTGTAATTAGCGCTTGGTTTAATGACGGCTCGTTT CTTTTCTGTGGCTGCGTGAAAGCCTTAAAGGGCTCCGGG AGGGCCCTTTGTGCGGGGGGGAGCGGCTCGGGGGGTGC GTGCGTGTGTGTGCGTGGGGAGCGCCGCGTGCGGCCC GCGCTGCCCGGCGGCTGTGAGCGCTGCGGGCGCGGCGC GGGGCTTTGTGCGCTCCGCGTGTGCGCGAGGGGAGCGCG GCCGGGGGCGGTGCCCCGCGGTGCGGGGGGGCTGCGAG GGGAACAAAGGCTGCGTGCGGGGTGTGTGCGTGGGGGG GTGAGCAGGGGGTGTGGGCGCGGCGGTCGGGCTGTAAC CCCCCCCTGCACCCCCCTCCCCGAGTTGCTGAGCACGGC CCGGCTTCGGGTGCGGGGCTCCGTGCGGGGCGTGGCGCG GGGCTCGCCGTGCCGGGCGGGGGGTGGCGGCAGGTGGG GGTGCCGGGCGGGGCGGGGCCGCCTCGGGCCGGGGAGG GCTCGGGGAGGGGCGCGGCGGCCCCCGGAGCGCCGGCG GCTGTCGAGGCGCGGCGAGCCGCAGCCATTGCCTTTTAT GGTAATCGTGCGAGAGGGCGCAGGGACTTCCTTTGTCCC AAATCTGGCGGAGCCGAAATCTGGGAGGCGCCGCCGCA CCCCCTCTAGCGGGCGCGGGGCGAAGCGGTGCGGCGCCG GCAGGAAGGAAATGGGCGGGGAGGGCCTTCGTGCGTCG CCGCGCCGCCGTCCCCTTCTCCATCTCCAGCCTCGGGGCT GCCGCAGGGGGACGGCTGCCTTCGGGGGGGACGGGGCA GGGCGGGGTTCGGCTTCTGGCGTGTGACCGGCGG |
| 29 | Helper/Rev; Rabbit beta globin poly A; RNA stability | AGATCTTTTTCCCTCTGCCAAAAATTATGGGGACATCAT GAAGCCCCTTGAGCATCTGACTTCTGGCTAATAAAGGAA ATTTATTTTCATTGCAATAGTGTGTTGGAATTTTTTGTGT CTCTCACTCGGAAGGACATATGGGAGGGCAAATCATTTA AAACATCAGAATGAGTATTTGGTTTAGAGTTTGGCAACA TATGCCATATGCTGGCTGCCATGAACAAAGGTGGCTATA AAGAGGTCATCAGTATATGAAACAGCCCCCTGCTGTCCA TTCCTTATTCCATAGAAAAGCCTTGACTTGAGGTTAGATT TTTTTTATATTTTGTTTTGTGTTATTTTTTCTTTAACATCC CTAAAATTTTCCTTACATGTTTTACTAGCCAGATTTTTCC TCCTCTCCTGACTACTCCCAGTCATAGCTGTCCCTCTTCT CTTATGAAGATC |
| 30 | Envelope; Beta globin intron; Enhance gene expression | GTGAGTTTGGGGACCCTTGATTGTTCTTTCTTTTTCGCTA TTGTAAAATTCATGTTATATGGAGGGGGCAAAGTTTTCA GGGTGTTGTTTAGAATGGGAAGATGTCCCTTGTATCACC ATGGACCCTCATGATAATTTTGTTCTTTCACTTTCTACT CTGTTGACAACCATTGTCTCCTCTTATTTTCTTTTCATTTT CTGTAACTTTTTCGTTAAACTTTAGCTTGCATTTGTAACG AATTTTTAAATTCACTTTTGTTTATTTGTCAGATTGTAAG TACTTTCTCTAATCACTTTTTTTTCAAGGCAATCAGGGTA TATTATATTGTACTTCAGCACAGTTTTAGAGAACAATTGT TATAATTAAATGATAAGGTAGAATATTTCTGCATATAAA TTCTGGCTGGCGTGGAAATATTCTTATTGGTAGAAACAA CTACACCCTGGTCATCATCCTGCCTTTCTCTTTATGGTTA CAATGATATACACTGTTTGAGATGAGGATAAAATACTCT GAGTCCAAACCGGGCCCCTCTGCTAACCATGTTCATGCC |

-continued

| SEQ ID NO: | Description | Sequence |
|---|---|---|
| | | TTCTTCTCTTTCCTACAG |
| 31 | Envelope; Rabbit beta globin poly A; RNA stability | AGATCTTTTTCCCTCTGCCAAAAATTATGGGGACATCAT GAAGCCCCTTGAGCATCTGACTTCTGGCTAATAAAGGAA ATTTATTTTCATTGCAATAGTGTGTTGGAATTTTTTGTGT CTCTCACTCGGAAGGACATATGGGAGGGCAAATCATTTA AAACATCAGAATGAGTATTTGGTTTAGAGTTTGGCAACA TATGCCCATATGCTGGCTGCCATGAACAAAGGTTGGCTA TAAAGAGGTCATCAGTATATGAAACAGCCCCCTGCTGTC CATTCCTTATTCCATAGAAAAGCCTTGACTTGAGGTTAG ATTTTTTTTATATTTTGTTTTGTGTTATTTTTTTCTTTAACA TCCCTAAAATTTTCCTTACATGTTTTACTAGCCAGATTTT TCCTCCTCTCCTGACTACTCCCAGTCATAGCTGTCCCTCT TCTCTTATGGAGATC |
| 32 | Primer | TAAGCAGAATTCATGAATTTGCCAGGAAGAT |
| 33 | Primer | CCATACAATGAATGGACACTAGGCGGCCGCACGAAT |
| 34 | Gag, Pol, Integrase fragment | GAATTCATGAATTTGCCAGGAAGATGGAAACCAAAAAT GATAGGGGGAATTGGAGGTTTTATCAAAGTAAGACAGT ATGATCAGATACTCATAGAAATCTGCGGACATAAAGCTA TAGGTACAGTATTAGTAGGACCTACACCTGTCAACATAA TTGGAAGAAATCTGTTGACTCAGATTGGCTGCACTTTAA ATTTTCCCATTAGTCCTATTGAGACTGTACCAGTAAAATT AAAGCCAGGAATGGATGGCCCAAAAGTTAAACAATGGC CATTGACAGAAGAAAAAATAAAAGCATTAGTAGAAATT TGTACAGAAATGGAAAAGGAAGGAAAAATTTCAAAAAT TGGGCCTGAAAATCCATACAATACTCCAGTATTTGCCAT AAAGAAAAAAGACAGTACTAAATGGAGAAAATTAGTAG ATTTCAGAGAACTTAATAAGAGAACTCAAGATTTCTGGG AAGTTCAATTAGGAATACCACATCCTGCAGGGTTAAAAC AGAAAAAATCAGTAACAGTACTGGATGTGGGCGATGCA TATTTTTCAGTTCCCTTAGATAAAGACTTCAGGAAGTATA CTGCATTTACCATACCTAGTATAAACAATGAGACACCAG GGATTAGATATCAGTACAATGTGCTTCCACAGGGATGGA AAGGATCACCAGCAATATTCCAGTGTAGCATGACAAAA ATCTTAGAGCCTTTTAGAAAACAAAATCCAGACATAGTC ATCTATCAATACATGGATGATTTGTATGTAGGATCTGAC TTAGAAATAGGGCAGCATAGAACAAAAATAGAGGAACT GAGACAACATCTGTTGAGGTGGGGATTTACCACACCAGA CAAAAAACATCAGAAAGAACCTCCATTCCTTTGGATGGG TTATGAACTCCATCCTGATAAATGGACAGTACAGCCTAT AGTGCTGCCAGAAAAGGACAGCTGGACTGTCAATGACA TACAGAAATTAGTGGGAAAATTGAATTGGGCAAGTCAG ATTTATGCAGGGATTAAAGTAAGGCAATTATGTAAACTT CTTAGGGGAACCAAAGCACTAACAGAAGTAGTACCACT AACAGAAGAAGCAGAGCTAGAACTGGCAGAAAACAGGG AGATTCTAAAAGAACCGGTACATGGAGTGTATTATGACC CATCAAAAGACTTAATAGCAGAAATACAGAAGCAGGGG CAAGGCCAATGGACATATCAAATTTATCAAGAGCCATTT AAAAATCTGAAAACAGGAAAGTATGCAAGAATGAAGGG TGCCCACACTAATGATGTGAAACAATTAACAGAGGCAGT ACAAAAAATAGCCACAGAAAGCATAGTAATATGGGGAA AGACTCCTAAATTTAAATTACCCATACAAAAGGAAACAT GGGAAGCATGGTGGACAGAGTATTGGCAAGCCACCTGG ATTCCTGAGTGGGAGTTTGTCAATACCCCTCCCTTAGTGA AGTTATGGTACCAGTTAGAGAAAGAACCCATAATAGGA GCAGAAACTTTCTATGTAGATGGGGCAGCCAATAGGGA AACTAAATTAGGAAAAGCAGGATATGTAACTGACAGAG GAAGACAAAAAGTTGTCCCCCTAACGGACACAACAAAT CAGAAGACTGAGTTACAAGCAATTCATCTAGCTTTGCAG GATTCGGGATTAGAAGTAAACATAGTGACAGACTCACA ATATGCATTGGGAATCATTCAAGCACAACCAGATAAGAG TGAATCAGAGTTAGTCAGTCAAATAATAGAGCAGTTAAT AAAAAAGGAAAAGTCTACCTGGCATGGGTACCAGCAC ACAAAGGAATTGGAGGAAATGAACAAGTAGATAAATTG GTCAGTGCTGGAATCAGGAAAGTACTATTTTTAGATGGA ATAGATAAGGCCCAAGAAGAACATGAGAAATATCACAG TAATTGGAGAGCAATGGCTAGTGATTTTAACCTACCACC TGTAGTAGCAAAAGAAATAGTAGCCAGCTGTGATAAAT GTCAGCTAAAAGGGGAAGCCATGCATGGACAAGTAGAC TGTAGCCCAGGAATATGGCAGCTAGATTGTACACATTTA GAAGGAAAAGTTATCTTGGTAGCAGTTCATGTAGCCAGT GGATATATAGAAGCAGAAGTAATTCCAGCAGAGACAGG GCAAGAAACAGCATACTTCCTCTTAAAATTAGCAGGAAG |

| SEQ ID NO: | Description | Sequence |
|---|---|---|
| | | ATGGCCAGTAAAAACAGTACATACAGACAATGGCAGCA<br>ATTTCACCAGTACTACAGTTAAGGCCGCCTGTTGGTGGG<br>CGGGGATCAAGCAGGAATTTGGCATTCCCTACAATCCCC<br>AAAGTCAAGGAGTAATAGAATCTATGAATAAAGAATTA<br>AAGAAAATTATAGGACAGGTAAGAGATCAGGCTGAACA<br>TCTTAAGACAGCAGTACAAATGGCAGTATTCATCCACAA<br>TTTTAAAAGAAAAGGGGGGATTGGGGGGTACAGTGCAG<br>GGGAAAGAATAGTAGACATAATAGCAACAGACATACAA<br>ACTAAAGAATTACAAAAACAAATTACAAAAATTCAAAA<br>TTTTCGGGTTTATTACAGGGACAGCAGAGATCCAGTTTG<br>GAAAGGACCAGCAAAGCTCCTCTGGAAAGGTGAAGGGG<br>CAGTAGTAATACAAGATAATAGTGACATAAAAGTAGTG<br>CCAAGAAGAAAAGCAAAGATCATCAGGGATTATGGAAA<br>ACAGATGGCAGGTGATGATTGTGTGGCAAGTAGACAGG<br>ATGAGGATTAA |
| 35 | DNA Fragment containing Rev, RRE and rabbit beta globin poly A | TCTAGAATGGCAGGAAGAAGCGGAGACAGCGACGAAGA<br>GCTCATCAGAACAGTCAGACTCATCAAGCTTCTCTATCA<br>AAGCAACCCACCTCCCAATCCCGAGGGGACCCGACAGG<br>CCCGAAGGAATAGAAGAAGAAGGTGGAGAGAGAGACA<br>GAGACAGATCCATTCGATTAGTGAACGGATCCTTGGCAC<br>TTATCTGGGACGATCTGCGGAGCCTGTGCCTCTTCAGCT<br>ACCACCGCTTGAGAGACTTACTCTTGATTGTAACGAGGA<br>TTGTGGAACTTCTGGGACGCAGGGGGTGGGAAGCCCTCA<br>AATATTGGTGGAATCTCCTACAATATTGGAGTCAGGAGC<br>TAAAGAATAGAGGAGCTTTGTTCCTTGGGTTCTTGGGAG<br>CAGCAGGAAGCACTATGGGCGCAGCGTCAATGACGCTG<br>ACGGTACAGGCCAGACAATTATTGTCTGGTATAGTGCAG<br>CAGCAGAACAATTTGCTGAGGGCTATTGAGGCGCAACA<br>GCATCTGTTGCAACTCACAGTCTGGGCATCAAGCAGCT<br>CCAGGCAAGAATCCTGGCTGTGGAAAGATACCTAAAGG<br>ATCAACAGCTCCTAGATCTTTTTCCCTCTGCCAAAAATTA<br>TGGGGACATCATGAAGCCCCTTGAGCATCTGACTTCTGG<br>CTAATAAAGGAAATTTATTTTCATTGCAATAGTGTGTTG<br>GAATTTTTTGTGTCTCTCACTCGGAAGGACATATGGGAG<br>GGCAAATCATTTAAAACATCAGAATGAGTATTTGGTTTA<br>GAGTTTGGCAACATATGCCATATGCTGGCTGCCATGAAC<br>AAAGGTGGCTATAAAGAGGTCATCAGTATATGAAACAG<br>CCCCCTGCTGTCCATTCCTTATTCCATAGAAAAGCCTTGA<br>CTTGAGGTTAGATTTTTTTTATATTTTGTTTTGTGTTATTT<br>TTTTCTTTAACATCCCTAAAATTTTCCTTACATGTTTTACT<br>AGCCAGATTTTTCCTCCTCTCCTGACTACTCCCAGTCATA<br>GCTGTCCCTCTTCTCTTATGAAGATCCCTCGACCTGCAGC<br>CCAAGCTTGGCGTAATCATGGTCATAGCTGTTTCCTGTGT<br>GAAATTGTTATCCGCTCACAATTCCACACAACATACGAG<br>CCGGAAGCATAAAGTGTAAAGCCTGGGGTGCCTAATGA<br>GTGAGCTAACTCACATTAATTGCGTTGCGCTCACTGCCC<br>GCTTTCCAGTCGGGAAACCTGTCGTGCCAGCGGATCGC<br>ATCTCAATTAGTCAGCAACCATAGTCCCGCCCCTAACTC<br>CGCCCATCCCGCCCCTAACTCCGCCCAGTTCCGCCCATTC<br>TCCGCCCCATGGCTGACTAATTTTTTTTATTTATGCAGAG<br>GCCGAGGCCGCCTCGGCCTCTGAGCTATTCCAGAAGTAG<br>TGAGGAGGCTTTTTTGGAGGCCTAGGCTTTTGCAAAAAG<br>CTAACTTGTTTATTGCAGCTTATAATGGTTACAAATAAA<br>GCAATAGCATCACAAATTTCACAAATAAAGCATTTTTTT<br>CACTGCATTCTAGTTGTGGTTTGTCCAAACTCATCAATGT<br>ATCTTATCAGCGGCCGCCCCGGG |
| 36 | DNA fragment containing the CAG enhancer/promoter/ intron sequence | ACGCGTTAGTTATTAATAGTAATCAATTACGGGGTCATT<br>AGTTCATAGCCCATATATGGAGTTCCGCGTTACATAACT<br>TACGGTAAATGGCCCGCCTGGCTGACCGCCCAACGACCC<br>CCGCCCATTGACGTCAATAATGACGTATGTTCCCATAGT<br>AACGCCAATAGGGACTTTCCATTGACGTCAATGGGTGGA<br>CTATTTACGGTAAACTGCCCACTTGGCAGTACATCAAGT<br>GTATCATATGCCAAGTACGCCCCCTATTGACGTCAATGA<br>CGGTAAATGGCCCGCCTGGCATTATGCCCAGTACATGAC<br>CTTATGGGACTTTCCTACTTGGCAGTACATCTACGTATTA<br>GTCATCGCTATTACCATGGGTCGAGGTGAGCCCCACGTT<br>CTGCTTCACTCTCCCCATCTCCCCCCCCTCCCCACCCCCA<br>ATTTTGTATTTATTTATTTTTTAATTATTTTGTGCAGCGAT<br>GGGGGCGGGGGGGGGGGGGCGCGCGCCAGGCGGGGC<br>GGGGCGGGGCGAGGGGCGGGGCGGGGCGAGGCGGAGA<br>GGTGCGGCGGCAGCCAATCAGAGCGGCGCGCTCCGAAA<br>GTTTCCTTTTATGGCGAGGCGGCGGCGGCGGCGGCCCTA<br>TAAAAAGCGAAGCGCGCGGCGGGCGGGAGTCGCTGCGT<br>TGCCTTCGCCCCGTGCCCCGCTCCGCGCCGCCTCGCGCC |

| SEQ ID NO: | Description | Sequence |
|---|---|---|
|  |  | GCCCGCCCCGGCTCTGACTGACCGCGTTACTCCCACAGG<br>TGAGCGGGCGGGACGGCCCTTCTCCTCCGGGCTGTAATT<br>AGCGCTTGGTTTAATGACGGCTCGTTTCTTTTCTGTGGCT<br>GCGTGAAAGCCTTAAAGGGCTCCGGGAGGGCCCTTTGTG<br>CGGGGGGGAGCGGCTCGGGGGGTGCGTGCGTGTGTGTG<br>TGCGTGGGGAGCGCCGCGTGCGGCCCGCGCTGCCCGGCG<br>GCTGTGAGCGCTGCGGGCGCGGCGCGGGGCTTTGTGCGC<br>TCCGCGTGTGCGCGAGGGGAGCGCGGCCGGGGGCGGTG<br>CCCCGCGGTGCGGGGGGCTGCGAGGGGAACAAAGGCT<br>GCGTGCGGGGTGTGTGCGTGGGGGGGTGAGCAGGGGGT<br>GTGGGCGCGGCGGTCGGGCTGTAACCCCCCCCTGCACCC<br>CCCTCCCCGAGTTGCTGAGCACGGCCCGGCTTCGGGTGC<br>GGGGCTCCGTGCGGGGCGTGGCGCGGGGCTCGCCGTGCC<br>GGGCGGGGGTGGCGGCAGGTGGGGGTGCCGGGCGGGG<br>CGGGGCCGCCTCGGGCGGGGAGGGCTCGGGGGAGGGG<br>CGCGGCGGCCCCGGAGCGCCGGCGGCTGTCGAGGCGCG<br>GCGAGCCGCAGCCATTGCCTTTTATGGTAATCGTGCGAG<br>AGGGCGCAGGGACTTCCTTTGTCCCAAATCTGGCGGAGC<br>CGAAATCTGGGAGGCGCCGCCGCACCCCCTCTAGCGGGC<br>GCGGGCGAAGCGGTGCGGCGCCGGCAGGAAGGAAATGG<br>GCGGGGAGGGCCTTCGTGCGTCGCCGCGCCGCCGTCCCC<br>TTCTCCATCTCCAGCCTCGGGGCTGCCGCAGGGGACGG<br>CTGCCTTCGGGGGGACGGGGCAGGGCGGGGTTCGGCTT<br>CTGGCGTGTGACCGGCGGGAATTC |
| 37 | DNA fragment containing VSV-G | GAATTCATGAAGTGCCTTTTGTACTTAGCCTTTTTATTCA<br>TTGGGGTGAATTGCAAGTTCACCATAGTTTTTCCACACA<br>ACCAAAAAGGAAACTGGAAAAATGTTCCTTCTAATTACC<br>ATTATTGCCCGTCAAGCTCAGATTTAAATTGGCATAATG<br>ACTTAATAGGCACAGCCTTACAAGTCAAAATGCCCAAGA<br>GTCACAAGGCTATTCAAGCAGACGGTTGGATGTGTCATG<br>CTTCCAAATGGGTCACTACTTGTGATTTCCGCTGGTATGG<br>ACCGAAGTATATAACACATTCCATCCGATCCTTCACTCC<br>ATCTGTAGAACAATGCAAGGAAAGCATTGAACAAACGA<br>AACAAGGAACTTGGCTGAATCAGGCTTCCCTCCTCAAA<br>GTTGTGGATATGCAACTGTGACGGATGCCGAAGCAGTGA<br>TTGTCCAGGTGACTCCTCACCATGTGCTGGTTGATGAAT<br>ACACAGGAGAATGGGTTGATTCACAGTTCATCAACGGAA<br>AATGCAGCAATTACATATGCCCCACTGTCCATAACTCTA<br>CAACCTGGCATTCTGACTATAAGGTCAAAGGGCTATGTG<br>ATTCTAACCTCATTTCCATGGACATCACCTTCTTCTCAGA<br>GGACGGAGAGCTATCATCCCTGGGAAAGGAGGGCACAG<br>GGTTCAGAAGTAACTACTTTGCTTATGAAACTGGAGGCA<br>AGGCCTGCAAAATGCAATACTGCAAGCATTGGGGAGTC<br>AGACTCCCATCAGGTGTCTGGTTCGAGATGGCTGATAAG<br>GATCTCTTTGCTGCAGCCAGATTCCCTGAATGCCCAGAA<br>GGGTCAAGTATCTCTGCTCCATCTCAGACCTCAGTGGAT<br>GTAAGTCTAATTCAGGACGTTGAGAGGATCTTGGATTAT<br>TCCCTCTGCCAAGAAACCTGGAGCAAAATCAGAGCGGGT<br>CTTCCAATCTCTCCAGTGGATCTCAGCTATCTTGCTCCTA<br>AAAACCCAGGAACCGGTCCTGCTTTCACCATAATCAATG<br>GTACCCTAAAATACTTTGAGACCAGATACATCAGAGTCG<br>ATATTGCTGCTCCAATCCTCTCAAGAATGGTCGGAATGA<br>TCAGTGGAACTACCACAGAAAGGGAACTGTGGGATGAC<br>TGGGCACCATATGAAGACGTGGAAATTGGACCCAATGG<br>AGTTCTGAGGACCAGTTCAGGATATAAGTTTCCTTTATA<br>CATGATTGGACATGGTATGTTGGACTCCGATCTTCATCTT<br>AGCTCAAAGGCTCAGGTGTTCGAACATCCTCACATTCAA<br>GACGCTGCTTCGCAACTTCCTGATGATGAGAGTTTATTTT<br>TTGGTGATACTGGGCTATCCAAAAATCCAATCGAGCTTG<br>TAGAAGGTTGGTTCAGTAGTTGGAAAAGCTCTATTGCCT<br>CTTTTTTCTTTATCATAGGGTTAATCATTGGACTATTCTT<br>GGTTCTCCGAGTTGGTATCCATCTTTGCATTAAATTAAAG<br>CACACCAAGAAAAGACAGATTTATACAGACATAGAGAT<br>GAGAATTC |
| 38 | RSV promoter and HIV Rev | CAATTGCGATGTACGGGCCAGATATACGCGTATCTGAGG<br>GGACTAGGGTGTGTTTAGGCGAAAAGCGGGGCTTCGGTT<br>GTACGCGGTTAGGAGTCCCCTCAGGATATAGTAGTTTCG<br>CTTTTGCATAGGGAGGGGGAAATGTAGTCTTATGCAATA<br>CACTTGTAGTCTTGCAACATGGTAACGATGAGTTAGCAA<br>CATGCCTTACAAGGAGAGAAAAAGCACCGTGCATGCCG<br>ATTGGTGGAAGTAAGGTGGTACGATCGTGCCTTATTAGG<br>AAGGCAACAGACAGGTCTGACATGGATTGGACGAACCA<br>CTGAATTCCGCATTGCAGAGATAATTGTATTTAAGTGCC<br>TAGCTCGATACAATAAACGCCATTTGACCATTCACCACA |

| SEQ ID NO: | Description | Sequence |
|---|---|---|
| | | TTGGTGTGCACCTCCAAGCTCGAGCTCGTTTAGTGAACC
GTCAGATCGCCTGGAGACGCCATCCACGCTGTTTTGACC
TCCATAGAAGACACCGGGACCGATCCAGCCTCCCCTCGA
AGCTAGCGATTAGGCATCTCCTATGGCAGGAAGAAGCG
GAGACAGCGACGAAGAACTCCTCAAGGCAGTCAGACTC
ATCAAGTTTCTCTATCAAAGCAACCCACCTCCCAATCCC
GAGGGGACCCGACAGGCCCGAAGGAATAGAAGAAGAA
GGTGGAGAGAGAGACAGAGACAGATCCATTCGATTAGT
GAACGGATCCTTAGCACTTATCTGGGACGATCTGCGGAG
CCTGTGCCTCTTCAGCTACCACCGCTTGAGAGACTTACTC
TTGATTGTAACGAGGATTGTGGAACTTCTGGGACGCAGG
GGGTGGGAAGCCCTCAAATATTGGTGGAATCTCCTACAA
TATTGGAGTCAGGAGCTAAAGAATAGTCTAGA |
| 39 | Elongation Factor-1 alpha (EF1-alpha) promoter | CCGGTGCCTAGAGAAGGTGGCGCGGGGTAAACTGGGAA
AGTGATGTCGTGTACTGGCTCCGCCTTTTTCCCGAGGGTG
GGGGAGAACCGTATATAAGTGCAGTAGTCGCCGTGAAC
GTTCTTTTTCGCAACGGGTTTGCCGCCAGAACACAGGTA
AGTGCCGTGTGTGGTTCCCGCGGGCCTGGCCTCTTTACG
GGTTATGGCCCTTGCGTGCCTTGAATTACTTCCACGCCCC
TGGCTGCAGTACGTGATTCTTGATCCCGAGCTTCGGGTT
GGAAGTGGGTGGGAGAGTTCGAGGCCTTGCGCTTAAGG
AGCCCCTTCGCCTCGTGCTTGAGTTGAGGCCTGGCCTGG
GCGCTGGGGCCGCCGCGTGCGAATCTGGTGGCACCTTCG
CGCCTGTCTCGCTGCTTTCGATAAGTCTCTAGCCATTTAA
AATTTTTGATGACCTGCTGCGACGCTTTTTTTCTGGCAAG
ATAGTCTTGTAAATGCGGGCCAAGATCTGCACACTGGTA
TTTCGGTTTTTGGGGCCGCGGGCGGCGACGGGGCCCGTG
CGTCCCAGCGCACATGTTCGGCGAGGCGGGGCCTGCGAG
CGCGGCCACCGAGAATCGGACGGGGGTAGTCTCAAGCT
GGCCGGCCTGCTCTGGTGCCTGGCCTCGCGCCGCCGTGT
ATCGCCCCGCCCTGGGCGGCAAGGCTGGCCCGGTCGGCA
CCAGTTGCGTGAGCGGAAAGATGGCCGCTTCCCGGCCCT
GCTGCAGGGAGCTCAAAATGGAGGACGCGGCGCTCGGG
AGAGCGGGCGGGTGAGTCACCCACACAAAGGAAAAGGG
CCTTTCCGTCCTCAGCCGTCGCTTCATGTGACTCCACGGA
GTACCGGGCGCCGTCCAGGCACCTCGATTAGTTCTCGAG
CTTTTGGAGTACGTCGTCTTTAGGTTGGGGGGAGGGGTT
TTATGCGATGGAGTTTCCCCACACTGAGTGGGTGGAGAC
TGAAGTTAGGCCAGCTTGGCACTTGATGTAATTCTCCTTG
GAATTTGCCCTTTTTGAGTTTGGATCTTGGTTCATTCTCA
AGCCTCAGACAGTGGTTCAAAGTTTTTTTCTTCCATTTCA
GGTGTCGTGA |
| 40 | Promoter; PGK | GGGGTTGGGGTTGCGCCTTTTCCAAGGCAGCCCTGGGTT
TGCGCAGGGACGCGGCTGCTCTGGGCGTGGTTCCGGGAA
ACGCAGCGGCGCCGACCCTGGGTCTCGCACATTCTTCAC
GTCCGTTCGCAGCGTCACCCGGATCTTCGCCGCTACCCTT
GTGGGCCCCCCGGCGACGCTTCCTGCTCCGCCCCTAAGT
CGGGAAGGTTCCTTGCGGTTCGCGGCGTGCCGGACGTGA
CAAACGGAAGCCGCACGTCTCACTAGTACCCTCGCAGAC
GGACAGCGCCAGGGAGCAATGGCAGCGCGCCGACCGCG
ATGGGCTGTGGCCAATAGCGGCTGCTCAGCAGGGCGCGC
CGAGAGCAGCGGCCGGGAAGGGGCGGTGCGGGAGGCGG
GGTGTGGGCGGTAGTGTGGGCCCTGTTCCTGCCCGCGC
GGTGTTCCGCATTCTGCAAGCCTCCGGAGCGCACGTCGG
CAGTCGGCTCCCTCGTTGACCGAATCACCGACCTCTCTCC
CCAG |
| 41 | Promoter; UbC | GCGCCGGGTTTTGGCGCCTCCCGCGGGCGCCCCCCTCCT
CACGGCGAGCGCTGCCACGTCAGACGAAGGGCGCAGGA
GCGTTCCTGATCCTTCCGCCCGGACGCTCAGGACAGCGG
CCCGCTGCTCATAAGACTCGGCCTTAGAACCCCAGTATC
AGCAGAAGGACATTTTAGGACGGGACTTGGGTGACTCTA
GGGCACTGGTTTTCTTTCCAGAGAGCGGAACAGGCGAGG
AAAAGTAGTCCCTTCTCGGCGATTCTGCGGAGGGATCTC
CGTGGGCGGTGAACGCCGATGATTATATAAGGACGCG
CCGGGTGTGGCACAGCTAGTTCCGTCGCAGCCGGGATTT
GGGTCGCGGTTCTTGTTTGTGGATCGCTGTGATCGTCACT
TGGTGAGTTGCGGGCTGCTGGGCTGGCCGGGGCTTTCGT
GGCCGCCGGGCCGCTCGGTGGGACGGAAGCGTGTGGAG
AGACCGCCAAGGGCTGTAGTCTGGGTCCGCGAGCAAGG
TTGCCCTGAACTGGGGGTTGGGGGGAGCGCACAAAATG
GCGGCTGTTCCCGAGTCTTGAATGAAGACGCTTGTAAG
GCGGGCTGTGAGGTCGTTGAAACAAGGTGGGGGGCATG
GTGGGCGGCAAGAACCCAAGGTCTTGAGGCCTTCGCTAA |

| SEQ ID NO: | Description | Sequence |
|---|---|---|
| | | TGCGGGAAAGCTCTTATTCGGGTGAGATGGGCTGGGGCA<br>CCATCTGGGGACCCTGACGTGAAGTTTGTCACTGACTGG<br>AGAACTCGGGTTTGTCGTCTGGTTGCGGGGGCGGCAGTT<br>ATGCGGTGCCGTTGGGCAGTGCACCCGTACCTTTGGGAG<br>CGCGCGCCTCGTCGTGTCGTGACGTCACCCGTTCTGTTGG<br>CTTATAATGCAGGGTGGGGCCACCTGCCGGTAGGTGTGC<br>GGTAGGCTTTTCTCCGTCGCAGGACGCAGGGTTCGGGCC<br>TAGGGTAGGCTCTCCTGAATCGACAGGCGCCGGACCTCT<br>GGTGAGGGGAGGGATAAGTGAGGCGTCAGTTTCTTTGGT<br>CGGTTTTATGTACCTATCTTCTTAAGTAGCTGAAGCTCCG<br>GTTTTGAACTATGCGCTCGGGGTTGGCGAGTGTGTTTTGT<br>GAAGTTTTTTAGGCACCTTTTGAAATGTAATCATTTGGGT<br>CAATATGTAATTTTCAGTGTTAGACTAGTAAA |
| 42 | Poly A; SV40 | GTTTATTGCAGCTTATAATGGTTACAAATAAAGCAATAG<br>CATCACAAATTTCACAAATAAAGCATTTTTTTCACTGCAT<br>TCTAGTTGTGGTTTGTCCAAACTCATCAATGTATCTTATC<br>A |
| 43 | Poly A; bGH | GACTGTGCCTTCTAGTTGCCAGCCATCTGTTGTTTGCCCC<br>TCCCCCGTGCCTTCCTTGACCCTGGAAGGTGCCACTCCCA<br>CTGTCCTTTCCTAATAAAATGAGGAAATTGCATCGCATT<br>GTCTGAGTAGGTGTCATTCTATTCTGGGGGGTGGGGTGG<br>GGCAGGACAGCAAGGGGGAGGATTGGGAAGACAATAGC<br>AGGCATGCTGGGGATGCGGTGGGCTCTATGG |
| 44 | Envelope; RD114 | ATGAAACTCCCAACAGGAATGGTCATTTTATGTAGCCTA<br>ATAATAGTTCGGGCAGGGTTTGACGACCCCCGCAAGGCT<br>ATCGCATTAGTACAAAAACAACATGGTAAACCATGCGA<br>ATGCAGCGGAGGGCAGGTATCCGAGGCCCCACCGAACT<br>CCATCCAACAGGTAACTTGCCCAGGCAAGACGGCCTACT<br>TAATGACCAACCAAAAATGGAAATGCAGAGTCACTCCA<br>AAAAATCTCACCCCTAGCGGGGGAGAACTCCAGAACTG<br>CCCCTGTAACACTTTCCAGGACTCGATGCACAGTTCTTGT<br>TATACTGAATACCGGCAATGCAGGGCGAATAATAAGAC<br>ATACTACACGGCCACCTTGCTTAAAATACGGTCTGGGAG<br>CCTCAACGAGGTACAGATATTACAAAACCCCAATCAGCT<br>CCTACAGTCCCCTTGTAGGGGCTCTATAAATCAGCCCGT<br>TTGCTGGAGTGCCACAGCCCCCATCCATATCTCCGATGG<br>TGGAGGACCCCTCGATACTAAGAGAGTGTGGACAGTCCA<br>AAAAAGGCTAGAACAAATTCATAAGGCTATGCATCCTGA<br>ACTTCAATACCACCCCTTAGCCCTGCCCAAAGTCAGAGA<br>TGACCTTAGCCTTGATGCACGGACTTTTGATATCCTGAAT<br>ACCACTTTTAGGTTACTCCAGATGTCCAATTTTAGCCTTG<br>CCCAAGATTGTTGGCTCTGTTTAAAACTAGGTACCCCTA<br>CCCCTCTTGCGATACCCACTCCCTCTTTAACCTACTCCCT<br>AGCAGACTCCCTAGCGAATGCCTCCTGTCAGATTATACC<br>TCCCCTCTTGGTTCAACCGATGCAGTTCTCCAACTCGTCC<br>TGTTTATCTTCCCCTTTCATTAACGATACGGAACAAATAG<br>ACTTAGGTGCAGTCACCTTTACTAACTGCACCTCTGTAGC<br>CAATGTCAGTAGTCCTTTATGTGCCCTAAACGGGTCAGT<br>CTTCCTCTGTGGAAATAACATGGCATACACCTATTTACCC<br>CAAAACTGGACAGGACTTTGCGTCCAAGCCTCCCTCCTC<br>CCCGACATTGACATCATCCCGGGGGATGAGCCAGTCCCC<br>ATTCCTGCCATTGATCATTATATACATAGACCTAAACGA<br>GCTGTACAGTTCATCCCTTTACTAGCTGGACTGGGAATC<br>ACCGCAGCATTCACCACCGGAGCTACAGGCCTAGGTGTC<br>TCCGTCACCCAGTATACAAAATTATCCCATCAGTTAATA<br>TCTGATGTCCAAGTCTTATCCGGTACCATACAAGATTTAC<br>AAGACCAGGTAGACTCGTTAGCTGAAGTAGTTCTCCAAA<br>ATAGGAGGGACTGGACCTACTAACGGCAGAACAAGGA<br>GGAATTTGTTTAGCCTTACAAGAAAAATGCTGTTTTTATG<br>CTAACAAGTCAGGAATTGTGAGAAACAAAATAAGAACC<br>CTACAAGAAGAATTACAAAAACGCAGGGAAAGCCTGGC<br>ATCCAACCCTCTCTGGACCGGGCTGCAGGGCTTTCTTCC<br>GTACCTCCTACCTCTCCTGGGACCCCTACTCACCCTCCTA<br>CTCATACTAACCATTGGGCCATGCGTTTTCAATCGATTGG<br>TCCAATTTGTTAAAGACAGGATCTCAGTGGTCCAGGCTC<br>TGGTTTTGACTCAGCAATATCACCAGCTAAAACCCATAG<br>AGTACGAGCCATGA |
| 45 | Envelope; GALV | ATGCTTCTCACCTCAAGCCCGCACCACCTTCGGCACCAG<br>ATGAGTCCTGGGAGCTGGAAAAGACTGATCATCCTCTTA<br>AGCTGCGTATTCGGAGACGGCAAAACGAGTCTGCAGAA<br>TAAGAACCCCCACCAGCCTGTGACCCTCACCTGGCAGGT<br>ACTGTCCCAAACTGGGGACGTTGTCTGGGACAAAAAGGC |

| SEQ ID NO: | Description | Sequence |
|---|---|---|
| | | AGTCCAGCCCCTTTGGACTTGGTGGCCCTCTCTTACACCT<br>GATGTATGTGCCCTGGCGGCCGGTCTTGAGTCCTGGGAT<br>ATCCCGGGATCCGATGTATCGTCCTCTAAAAGAGTTAGA<br>CCTCCTGATTCAGACTATACTGCCGCTTATAAGCAAATC<br>ACCTGGGGAGCCATAGGGTGCAGCTACCCTCGGGCTAGG<br>ACCAGGATGGCAAATTCCCCCTTCTACGTGTGTCCCCGA<br>GCTGGCCGAACCCATTCAGAAGCTAGGAGGTGTGGGGG<br>GCTAGAATCCCTATACTGTAAAGAATGGAGTTGTGAGAC<br>CACGGGTACCGTTTATTGGCAACCCAAGTCCTCATGGGA<br>CCTCATAACTGTAAAATGGGACCAAATGTGAAATGGG<br>AGCAAAAATTTCAAAAGTGTGAACAAACCGGCTGGTGT<br>AACCCCCTCAAGATAGACTTCACAGAAAAGGAAAACT<br>CTCCAGAGATTGGATAACGGAAAAAACCTGGGAATTAA<br>GGTTCTATGTATATGGACACCCAGGCATACAGTTGACTA<br>TCCGCTTAGAGGTCACTAACATGCCGGTTGTGGCAGTGG<br>GCCCAGACCCTGTCCTTGCGGAACAGGGACCTCCTAGCA<br>AGCCCCTCACTCTCCCTCTCTCCCCACGGAAAGCGCCGC<br>CCACCCCTCTACCCCCGGCGGCTAGTGAGCAAACCCCTG<br>CGGTGCATGGAGAAACTGTTACCCTAAACTCTCCGCCTC<br>CCACCAGTGGCGACCGACTCTTTGGCCTTGTGCAGGGGG<br>CCTTCCTAACCTTGAATGCTACCAACCCAGGGGCCACTA<br>AGTCTTGCTGGCTCTGTTTGGGCATGAGCCCCCCTTATTA<br>TGAAGGGATAGCCTCTTCAGGAGAGGTCGCTTATACCTC<br>CAACCATACCCGATGCCACTGGGGGGCCCAAGGAAAGC<br>TTACCCTCACTGAGGTCTCCGGACTCGGGTCATGCATAG<br>GGAAGGTGCCTCTTACCCATCAACATCTTTGCAACCAGA<br>CCTTACCCATCAATTCCTCTAAAAACCATCAGTATCTGCT<br>CCCCTCAAACCATAGCTGGTGGGCCTGCAGCACTGGCCT<br>CACCCCCTGCCTCTCCACCTCAGTTTTTAATCAGTCTAAA<br>GACTTCTGTGTCCAGGTCCAGCTGATCCCCCGCATCTATT<br>ACCATTCTGAAGAAACCTTGTTACAAGCCTATGACAAAT<br>CACCCCCCAGGTTTAAAAGAGAGCCTGCCTCACTTACCC<br>TAGCTGTCTTCCTGGGGTTAGGGATTGCGGCAGGTATAG<br>GTACTGGCTCAACCGCCCTAATTAAAGGGCCCATAGACC<br>TCCAGCAAGGCCTAACCAGCCTCCAAATCGCCATTGACG<br>CTGACCTCCGGGCCCTTCAGGACTCAATCAGCAAGCTAG<br>AGGACTCACTGACTTCCCTATCTGAGGTAGTACTCCAAA<br>ATAGGAGAGGCCTTGACTTACTATTCCTTAAAGAAGGAG<br>GCCTCTGCGCGGCCCTAAAAGAAGAGTGCTGTTTTTATG<br>TAGACCACTCAGGTGCAGTACGAGACTCCATGAAAAAA<br>CTTAAAGAAAGACTAGATAAAAGACAGTTAGAGCGCCA<br>GAAAAACCAAAACTGGTATGAAGGGTGGTTCAATAACT<br>CCCCTTGGTTTACTACCCTACTATCAACCATCGCTGGGCC<br>CCTATTGCTCCTCCTTTTGTTACTCACTCTTGGGCCCTGC<br>ATCATCAATAAATTAATCCAATTCATCAATGATAGGATA<br>AGTGCAGTCAAAATTTTAGTCCTTAGACAGAAATATCAG<br>ACCCTAGATAACGAGGAAAACCTTTAA |
| 46 | Envelope; FUG | ATGGTTCCGCAGGTTCTTTTGTTTGTACTCCTTCTGGGTT<br>TTTCGTTGTGTTTCGGGAAGTTCCCCATTTACACGATACC<br>AGACGAACTTGGTCCCTGGAGCCCTATTGACATACACCA<br>TCTCAGCTGTCCAAATAACCTGGTTGTGGAGGATGAAGG<br>ATGTACCAACCTGTCCGAGTTCTCCTACATGGAACTCAA<br>AGTGGGATACATCTCAGCCATCAAAGTGAACGGGTTCAC<br>TTGCACAGGTGTTGTGACAGAGGCAGAGACCTACACCAA<br>CTTTGTTGGTTATGTCACAACCACATTCAAGAGAAAGCA<br>TTTCCGCCCCACCCCAGACGCATGTAGAGCCGCGTATAA<br>CTGGAAGATGGCCGGTGACCCCAGATATGAAGAGTCCCT<br>ACACAATCCATACCCCGACTACCACTGGCTTCGAACTGT<br>AAGAACCACCAAAGAGTCCCTCATTATCATATCCCCAAG<br>TGTGACAGATTTGGACCCATATGACAAATCCCTTCACTC<br>AAGGGTCTTCCCTGGCGGAAAGTGCTCAGGAATAACGGT<br>GTCCTCTACCTACTGCTCAACTAACCATGATTACACCATT<br>TGGATGCCCGAGAATCCGAGACCAAGGACACCTTGTGAC<br>ATTTTTACCAATAGCAGAGGGAAGAGAGCATCCAACGG<br>GAACAAGACTTGCGGCTTTGTGGATGAAAGAGGCCTGTA<br>TAAGTCTCTAAAAGGAGCATGCAGGCTCAAGTTATGTGG<br>AGTTCTTGGACTTAGACTTATGGATGGAACATGGGTCGC<br>GATGCAAACATCAGATGAGACCAAATGGTGCCCTCCAG<br>ATCAGTTGGTGAATTTGCACGACTTTCGCTCAGACGAGA<br>TCGAGCATCTCGTTGTGGAGGAGTTAGTTAAGAAAAGAG<br>AGGAATGTCTGGATGCATTAGAGTCCATCATGACCACCA<br>AGTCAGTAAGTTTCAGACGTCTCAGTCACCTGAGAAAAC<br>TTGTCCCAGGGTTTGGAAAAGCATATACCATATTCAACA<br>AAACCTTGATGGAGGCTGATGCTCACTACAAGTCAGTCC<br>GGACCTGGAATGAGATCATCCCCTCAAAAGGGTGTTTGA |

| SEQ ID NO: | Description | Sequence |
| --- | --- | --- |
|  |  | AAGTTGGAGGAAGGTGCCATCCTCATGTGAACGGGGTGT<br>TTTTCAATGGTATAATATTAGGGCCTGACGACCATGTCCT<br>AATCCCAGAGATGCAATCATCCCTCCTCCAGCAACATAT<br>GGAGTTGTTGGAATCTTCAGTTATCCCCCTGATGCACCCC<br>CTGGCAGACCCTTCTACAGTTTTCAAAGAAGGTGATGAG<br>GCTGAGGATTTTGTTGAAGTTCACCTCCCCGATGTGTAC<br>AAACAGATCTCAGGGGTTGACCTGGGTCTCCCGAACTGG<br>GGAAAGTATGTATTGATGACTGCAGGGGCCATGATTGGC<br>CTGGTGTTGATATTTTCCCTAATGACATGGTGCAGAGTTG<br>GTATCCATCTTTGCATTAAATTAAAGCACACCAAGAAAA<br>GACAGATTTATACAGACATAGAGATGAACCGACTTGGA<br>AAGTAA |
| 47 | Envelope; LCMV | ATGGGTCAGATTGTGACAATGTTTGAGGCTCTGCCTCAC<br>ATCATCGATGAGGTGATCAACATTGTCATTATTGTGCTTA<br>TCGTGATCACGGGTATCAAGGCTGTCTACAATTTTGCCA<br>CCTGTGGGATATTCGCATTGATCAGTTTCCTACTTCTGGC<br>TGGCAGGTCCTGTGGCATGTACGGTCTTAAGGGACCCGA<br>CATTTACAAAGGAGTTTACCAATTTAAGTCAGTGGAGTT<br>TGATATGTCACATCTGAACCTGACCATGCCCAACGCATG<br>TTCAGCCAACAACTCCCACCATTACATCAGTATGGGGAC<br>TTCTGGACTAGAATTGACCTTCACCAATGATTCCATCATC<br>AGTCACAACTTTTGCAATCTGACCTCTGCCTTCAACAAA<br>AAGACCTTTGACCACACACTCATGAGTATAGTTTCGAGC<br>CTACACCTCAGTATCAGAGGGAACTCCAACTATAAGGCA<br>GTATCCTGCGACTTCAACAATGGCATAACCATCCAATAC<br>AACTTGACATTCTCAGATCGACAAAGTGCTCAGAGCCAG<br>TGTAGAACCTTCAGAGGTAGAGTCCTAGATATGTTTAGA<br>ACTGCCTTCGGGGGAAATACATGAGGAGTGGCTGGGG<br>CTGGACAGGCTCAGATGGCAAGACCACCTGGTGTAGCCA<br>GACGAGTTACCAATACCTGATTATACAAAATAGAACCTG<br>GGAAAACCACTGCACATATGCAGGTCCTTTTGGGATGTC<br>CAGGATTCTCCTTTCCCAAGAGAAGACTAAGTTCTTCAC<br>TAGGAGACTAGCGGCACATTCACCTGGACTTTGTCAGA<br>CTCTTCAGGGGTGGAGAATCCAGGTGGTTATTGCCTGAC<br>CAAATGGATGATTCTTGCTGCAGAGCTTAAGTGTTTCGG<br>GAACACAGCAGTTGCGAAATGCAATGTAAATCATGATGC<br>CGAATTCTGTGACATGCTGCGACTAATTGACTACAACAA<br>GGCTGCTTTGAGTAAGTTCAAAGAGGACGTAGAATCTGC<br>CTTGCACTTATTCAAAACAACAGTGAATTCTTTGATTTCA<br>GATCAACTACTGATGAGGAACCACTTGAGAGATCTGATG<br>GGGGTGCCATATTGCAATTACTCAAAGTTTTGGTACCTA<br>GAACATGCAAAGACCGGCGAAACTAGTGTCCCCAAGTG<br>CTGGCTTGTCACCAATGGTTCTTACTTAAATGAGACCCA<br>CTTCAGTGATCAAATCGAACAGGAAGCCGATAACATGAT<br>TACAGAGATGTTGAGGAAGGATTACATAAAGAGGCAGG<br>GGAGTACCCCCCTAGCATTGATGGACCTTCTGATGTTTTC<br>CACATCTGCATATCTAGTCAGCATCTTCCTGCACCTTGTC<br>AAAATACCAACACACAGGCACATAAAAGGTGGCTCATG<br>TCCAAAGCCACACCGATTAACCAACAAAGGAATTTGTAG<br>TTGTGGTGCATTTAAGGTGCCTGGTGTAAAAACCGTCTG<br>GAAAAGACGCTGA |
| 48 | Envelope; FPV | ATGAACACTCAAATCCTGGTTTTCGCCCTTGTGGCAGTC<br>ATCCCCACAAATGCAGACAAAATTTGTCTTGGACATCAT<br>GCTGTATCAAATGGCACCAAAGTAAACACACTCACTGAG<br>AGAGGAGTAGAAGTTGTCAATGCAACGGAAACAGTGGA<br>GCGGACAAACATCCCCAAAATTTGCTCAAAAGGGAAA<br>GAACCACTGATCTTGGCCAATGCGGACTGTTAGGGACCA<br>TTACCGGACCACCTCAATGCGACCAATTTCTAGAATTTTC<br>AGCTGATCTAATAATCGAGAGACGAGAAGGAAATGATG<br>TTTGTTACCCGGGGAAGTTTGTTAATGAAGAGGCATTGC<br>GACAAATCCTCAGAGGATCAGGTGGGATTGACAAAGAA<br>ACAATGGGATTCACATATAGTGGAATAAGGACCAACGG<br>AACAACTAGTGCATGTAGAAGATCAGGGTCTTCATTCTA<br>TGCAGAAATGGAGTGGCTCCTGTCAAATACAGACAATGC<br>TGCTTTCCCACAAATGACAAAATCATACAAAAACACAAG<br>GAGAGAATCAGCTCTGATAGTCTGGGGAATCCACCATTC<br>AGGATCAACCACCGAACAGACCAAACTATATGGGAGTG<br>GAAATAAACTGATAACAGTCGGGAGTTCCAAATATCATC<br>AATCTTTTGTGCCGAGTCCAGGAACACGACCGCAGATAA<br>ATGGCCAGTCCGGACGGATTGATTTTCATTGGTTGATCTT<br>GGATCCCAATGATCAGTTACTTTTAGTTTCAATGGGGC<br>TTTCATAGCTCCAAATCGTGCCAGCTTCTTGAGGGGAAA<br>GTCCATGGGGATCCAGAGCGATGTGCAGGTTGATGCCAA<br>TTGCGAAGGGGAATGCTACCACAGTGGAGGGACTATAA |

| SEQ ID NO: | Description | Sequence |
|---|---|---|
| | | CAAGCAGATTGCCTTTTCAAAACATCAATAGCAGAGCAG<br>TTGGCAAATGCCCAAGATATGTAAAACAGGAAAGTTTAT<br>TATTGGCAACTGGGATGAAGAACGTTCCCGAACCTTCCA<br>AAAAAAGGAAAAAAAGAGGCCTGTTTGGCGCTATAGCA<br>GGGTTTATTGAAAATGGTTGGGAAGGTCTGGTCGACGGG<br>TGGTACGGTTTCAGGCATCAGAATGCACAAGGAGAAGG<br>AACTGCAGCAGACTACAAAAGCACCCAATCGGCAATTG<br>ATCAGATAACCGGAAAGTTAAATAGACTCATTGAGAAA<br>ACCAACCAGCAATTTGAGCTAATAGATAATGAATTCACT<br>GAGGTGGAAAAGCAGATTGGCAATTTAATTAACTGGACC<br>AAAGACTCCATCACAGAAGTATGGTCTTACAATGCTGAA<br>CTTCTTGTGGCAATGGAAAACCAGCACACTATTGATTTG<br>GCTGATTCAGAGATGAACAAGCTGTATGAGCGAGTGAG<br>GAAACAATTAAGGGAAAATGCTGAAGAGGATGGCACTG<br>GTTGCTTTGAAATTTTTCATAAATGTGACGATGATTGTAT<br>GGCTAGTATAAGGAACAATACTTATGATCACAGCAAATA<br>CAGAGAAGAAGCGATGCAAAATAGAATACAAATTGACC<br>CAGTCAAATTGAGTAGTGGCTACAAAGATGTGATACTTT<br>GGTTTAGCTTCGGGGCATCATGCTTTTTGCTTCTTGCCAT<br>TGCAATGGGCCTTGTTTTCATATGTGTGAAGAACGGAAA<br>CATGCGGTGCACTATTTGTATATAA |
| 49 | Envelope; RRV | AGTGTAACAGAGCACTTTAATGTGTATAAGGCTACTAGA<br>CCATACCTAGCACATTGCGCCGATTGCGGGGACGGGTAC<br>TTCTGCTATAGCCCAGTTGCTATCGAGGAGATCCGAGAT<br>GAGGCGTCTGATGGCATGCTTAAGATCCAAGTCTCCGCC<br>CAAATAGGTCTGGACAAGGCAGGCACCCACGCCCACAC<br>GAAGCTCCGATATATGGCTGGTCATGATGTTCAGGAATC<br>TAAGAGAGATTCCTTGAGGGTGTACACGTCCGCAGCGTG<br>CTCCATACATGGGACGATGGGACACTTCATCGTCGCACA<br>CTGTCCACCAGGCGACTACCTCAAGGTTTCGTTCGAGGA<br>CGCAGATTCGCACGTGAAGGCATGTAAGGTCCAATACAA<br>GCACAATCCATTGCCGGTGGGTAGAGAGAAGTTCGTGGT<br>TAGACCACACTTTGGCGTAGAGCTGCCATGCACCTCATA<br>CCAGCTGACAACGGCTCCCACCGACGAGGAGATTGACAT<br>GCATACACCGCCAGATATACCGGATCGCACCCTGCTATC<br>ACAGACGGCGGGCAACGTCAAAATAACAGCAGGCGGCA<br>GGACTATCAGGTACAACTGTACCTGCGGCCGTGACAACG<br>TAGGCACTACCAGTACTGACAAGACCATCAACACATGCA<br>AGATTGACCAATGCCATGCTGCCGTCACCAGCCATGACA<br>AATGGCAATTTACCTCTCCATTTGTTCCCAGGGCTGATCA<br>GACAGCTAGGAAAGGCAAGGTACACGTTCCGTTCCCTCT<br>GACTAACGTCACCTGCCGAGTGCCGTTGGCTCGAGCGCC<br>GGATGCCACCTATGGTAAGAAGGAGGTGACCCTGAGATT<br>ACACCCAGATCATCCGACGCTCTTCTCCTATAGGAGTTT<br>AGGAGCCGAACCGCACCCGTACGAGGAATGGGTTGACA<br>AGTTCTCTGAGCGCATCATCCCAGTGACGGAAGAAGGGA<br>TTGAGTACCAGTGGGGCAACAACCCGCCGGTCTGCCTGT<br>GGGCGCAACTGACGACCGAGGGCAAACCCCATGGCTGG<br>CCACATGAAATCATTCAGTACTATTATGGACTATACCCC<br>GCCGCCACTATTGCCGCAGTATCCGGGGCGAGTCTGATG<br>GCCCTCCTAACTCTGGCGGCCACATGCTGCATGCTGGCC<br>ACCGCGAGGAGAAAGTGCCTAACACCGTACGCCCTGAC<br>GCCAGGAGCGGTGGTACCGTTGACACTGGGGCTGCTTTG<br>CTGCGCACCGAGGGCGAATGCA |
| 50 | Envelope; MLV 10A1 | ATGGAAGGTCCAGCGTTCTCAAAACCCCTTAAAGATAAG<br>ATTAACCCGTGGAAGTCCTTAATGGTCATGGGGGTCTAT<br>TTAAGAGTAGGGATGGCAGAGAGCCCCCATCAGGTCTTT<br>AATGTAACCTGGAGAGTCACCAACCTGATGACTGGGCGT<br>ACCGCCAATGCCACCTCCCTTTTAGGAACTGTACAAGAT<br>GCCTTCCCAAGATTATATTTTGATCTATGTGATCTGGTCG<br>GAGAAGAGTGGGACCCTTCAGACCAGGAACCATATGTC<br>GGGTATGGCTGCAAATACCCCGGAGGGAGAAAGCGGAC<br>CCGGACTTTTGACTTTTACGTGTGCCCTGGGCATACCGTA<br>AAATCGGGGTGTGGGGGGCCAAGAGAGGGCTACTGTGG<br>TGAATGGGGTTGTGAAACCACCGGACAGGCTTACTGGAA<br>GCCCACATCATCATGGGACCTAATCTCCCTTAAGCGCGG<br>TAACACCCCTGGGACACGGGATGCTCCAAAATGGCTTG<br>TGGCCCCTGCTACGACCTCTCCAAAGTATCCAATTCCTTC<br>CAAGGGGCTACTCGAGGGGCAGATGCAACCCTCTAGTC<br>CTAGAATTCACTGATGCAGGAAAAAAGGCTAATTGGGA<br>CGGGCCCAAATCGTGGGGACTGAGACTGTACCGGACAG<br>GAACAGATCCTATTACCATGTTCTCCCTGACCCGCCAGG<br>TCCTCAATATAGGGCCCCGCATCCCCATTGGGCCTAATC<br>CCGTGATCACTGGTCAACTACCCCCCTCCCGACCCGTGC |

| SEQ ID NO: | Description | Sequence |
|---|---|---|
| | | AGATCAGGCTCCCCAGGCCTCCTCAGCCTCCTCCTACAG<br>GCGCAGCCTCTATAGTCCCTGAGACTGCCCCACCTTCTC<br>AACAACCTGGGACGGGAGACAGGCTGCTAAACCTGGTA<br>GAAGGAGCCTATCAGGCGCTTAACCTCACCAATCCCGAC<br>AAGACCCAAGAATGTTGGCTGTGCTTAGTGTCGGACCT<br>CCTTATTACGAAGGAGTAGCGGTCGTGGGCACTTATACC<br>AATCATTCTACCGCCCCGGCCAGCTGTACGGCCACTTCC<br>CAACATAAGCTTACCCTATCTGAAGTGACAGGACAGGGC<br>CTATGCATGGGAGCACTACCTAAAACTCACCAGGCCTTA<br>TGTAACACCACCCAAAGTGCCGGCTCAGGATCCTACTAC<br>CTTGCAGCACCCGCTGGAACAATGTGGGCTTGTAGCACT<br>GGATTGACTCCCTGCTTGTCCACCACGATGCTCAATCTA<br>ACCACAGACTATTGTGTATTAGTTGAGCTCTGGCCCAGA<br>ATAATTTACCACTCCCCCGATTATATGTATGGTCAGCTTG<br>AACAGCGTACCAAATATAAGAGGGAGCCAGTATCGTTG<br>ACCCTGGCCCTTCTGCTAGGAGGATTAACCATGGGAGGG<br>ATTGCAGCTGGAATAGGGACGGGGACCACTGCCCTAATC<br>AAAACCCAGCAGTTTGAGCAGCTTCACGCCGCTATCCAG<br>ACAGACCTCAACGAAGTCGAAAAATCAATTACCAACCTA<br>GAAAAGTCACTGACCTCGTTGTCTGAAGTAGTCCTACAG<br>AACCGAAGAGGCCTAGATTTGCTCTTCCTAAAAGAGGGA<br>GGTCTCTGCGCAGCCCTAAAAGAAGAATGTTGTTTTTAT<br>GCAGACCACACGGGACTAGTGAGAGACAGCATGGCCAA<br>ACTAAGGGAAAGGCTTAATCAGAGACAAAAACTATTTG<br>AGTCAGGCCAAGGTTGGTTCGAAGGGCAGTTTAATAGAT<br>CCCCCTGGTTTACCACCTTAATCTCCACCATCATGGGACC<br>TCTAATAGTACTCTTACTGATCTTACTCTTTGGACCCTGC<br>ATTCTCAATCGATTGGTCCAATTTGTTAAAGACAGGATC<br>TCAGTGGTCCAGGCTCTGGTTTTGACTCAACAATATCAC<br>CAGCTAAAACCTATAGAGTACGAGCCATGA |
| 51 | Envelope; Ebola | ATGGGTGTTACAGGAATATTGCAGTTACCTCGTGATCGA<br>TTCAAGAGGACATCATTCTTTCTTTGGGTAATTATCCTTT<br>TCCAAAGAACATTTTCCATCCCACTTGGAGTCATCCACA<br>ATAGCACATTACAGGTTAGTGATGTCGACAAACTGGTTT<br>GCCGTGACAAACTGTCATCCACAAATCAATTGAGATCAG<br>TTGGACTGAATCTCGAAGGGAATGGAGTGGCAACTGAC<br>GTGCCATCTGCAACTAAAAGATGGGGCTTCAGGTCCGGT<br>GTCCCACCAAAGGTGGTCAATTATGAAGCTGGTGAATGG<br>GCTGAAAACTGCTACAATCTTGAAATCAAAAAACCTGAC<br>GGGAGTGAGTGTCTACCAGCAGCGCCAGACGGGATTCG<br>GGGCTTCCCCCGGTGCCGGTATGTGCACAAAGTATCAGG<br>AACGGGACCGTGTGCCGGAGACTTTGCCTTCCACAAAGA<br>GGGTGCTTTCTTCCTGTATGACCGACTTGCTTCCACAGTT<br>ATCTACCGAGGAACGACTTTCGCTGAAGGTGTCGTTGCA<br>TTTCTGATACTGCCCCAAGCTAAGAAGGACTTCTTCAGC<br>TCACACCCCTTGAGAGAGCCGGTCAATGCAACGGAGGA<br>CCCGTCTAGTGGCTACTATTCTACCACAATTAGATATCA<br>AGCTACCGGTTTTGGAACCAATGAGACAGAGTATTTGTT<br>CGAGGTTGACAATTTGACCTACGTCCAACTTGAATCAAG<br>ATTCACACCACAGTTTCTGCTCCAGCTGAATGAGACAAT<br>ATATACAAGTGGGAAAAGGAGCAATACCACGGGAAAAC<br>TAATTTGGAAGGTCAACCCCGAAATTGATACAACAATCG<br>GGGAGTGGGCCTTCTGGGAAACTAAAAAAACCTCACTA<br>GAAAAATTCGCAGTGAAGAGTTGTCTTTCACAGCTGTAT<br>CAAACAGAGCCAAAAACATCAGTGGTCAGAGTCCGGCG<br>CGAACTTCTTCCGACCCAGGGACCAACACAACAACTGAA<br>GACCACAAAATCATGGCTTCAGAAAATTCCTCTGCAATG<br>GTTCAAGTGCACAGTCAAGGAAGGGAAGCTGCAGTGTC<br>GCATCTGACAACCCTTGCCACAATCTCCACGAGTCCTCA<br>ACCCCCACAACCAAACCAGGTCCGGACAACAGCACCC<br>ACAATACACCCGTGTATAAACTTGACATCTCTGAGGCAA<br>CTCAAGTTGAACAACATCACCGCAGAACAGACAACGAC<br>AGCACAGCCTCCGACACTCCCCCCGCCACGACCGCAGCC<br>GGACCCCTAAAAGCAGAGAACACCAACACGAGCAAGGG<br>TACCGACCTCCTGGACCCCGCCACCACAACAAGTCCCCA<br>AAACCACAGCGAGACCGCTGGCAACAACAACACTCATC<br>ACCAAGATACCGGAGAAGAGAGTGCCAGCAGCGGGAAG<br>CTAGGCTTAATTACCAATACTATTGCTGGAGTCGCAGGA<br>CTGATCACAGGCGGGAGGAGAGCTCGAAGAGAAGCAAT<br>TGTCAATGCTCAACCCAAATGCAACCCTAATTTACATTA<br>CTGGACTACTCAGGATGAAGGTGCTGCAATCGGACTGGC<br>CTGGATACCATATTTCGGGCCAGCAGCCGAGGGAATTTA<br>CATAGAGGGGCTGATGCACAATCAAGATGGTTTAATCTG<br>TGGGTTGAGACAGCTGGCCAACGAGACGACTCAAGCTCT<br>TCAACTGTTCCTGAGAGCCACAACCGAGCTACGCACCTT |

| SEQ ID NO: | Description | Sequence |
|---|---|---|
| | | TTCAATCCTCAACCGTAAGGCAATTGATTTCTTGCTGCAG<br>CGATGGGGCGGCACATGCCACATTTTGGGACCGGACTGC<br>TGTATCGAACCACATGATTGGACCAAGAACATAACAGAC<br>AAAATTGATCAGATTATTCATGATTTTGTTGATAAAACC<br>CTTCCGGACCAGGGGGACAATGACAATTGGTGGACAGG<br>ATGGAGACAATGGATACCGGCAGGTATTGGAGTTACAG<br>GCGTTATAATTGCAGTTATCGCTTTATTCTGTATATGCAA<br>ATTTGTCTTTTAG |
| 52 | Polymerase III shRNA promoters; U6 promoter | TTTCCCATGATTCCTTCATATTTGCATATACGATACAAGG<br>CTGTTAGAGAGATAATTGGAATTAATTTGACTGTAAACA<br>CAAAGATATTAGTACAAAATACGTGACGTAGAAAGTAA<br>TAATTTCTTGGGTAGTTTGCAGTTTTAAAATTATGTTTTA<br>AAATGGACTATCATATGCTTACCGTAACTTGAAAGTATT<br>TCGATTTCTTGGCTTTATATATCTTGTGGAAAGGACGAA<br>AC |
| 53 | Polymerase III shRNA promoters; 7SK promoter | CTGCAGTATTTAGCATGCCCCACCCATCTGCAAGGCATT<br>CTGGATAGTGTCAAAACAGCCGGAAATCAAGTCCGTTTA<br>TCTCAAACTTTAGCATTTTGGGAATAAATGATATTTGCTA<br>TGCTGGTTAAATTAGATTTTAGTTAAATTTCCTGCTGAAG<br>CTCTAGTACGATAAGCAACTTGACCTAAGTGTAAAGTTG<br>AGATTTCCTTCAGGTTTATATAGCTTGTGCGCCGCCTGGC<br>TACCTC |
| 54 | FDPS target sequence #1 | GTCCTGGAGTACAATGCCATT |
| 55 | FDPS target sequence #2 | GCAGGATTTCGTTCAGCACTT |
| 56 | FDPS target sequence #3 | GCCATGTACATGGCAGGAATT |
| 57 | FDPS target sequence #4 | GCAGAAGGAGGCTGAGAAAGT |
| 58 | Non-targeting sequence | GCCGCTTTGTAGGATAGAGCTCGAGCTCTATCCTACAAA<br>GCGGCTTTTT |
| 59 | Forward primer | AGGAATTGATGGCGAGAAGG |
| 60 | Reverse primer | CCCAAAGAGGTCAAGGTAATCA |
| 61 | Forward primer | AGCGCGGCTACAGCTTCA |
| 62 | Reverse primer | GGCGACGTAGCACAGCTTCT |
| 63 | Left Inverted Terminal Repeat (Left ITR) | CCTGCAGGCAGCTGCGCGCTCGCTCGCTCACTGAGGCCG<br>CCCGGGCGTCGGGCGACCTTTGGTCGCCCGGCCTCAGTG<br>AGCGAGCGAGCGCGCAGAGAGGGAGTGGCCAACTCCAT<br>CACTAGGGGTTCCT |
| 64 | Right Inverted Terminal Repeat (Right ITR) | GAGCGGCCGCAGGAACCCCTAGTGATGGAGTTGGCCACT<br>CCCTCTCTGCGCGCTCGCTCGCTCACTGAGGCCGGGCGA<br>CCAAAGGTCGCCCGACGCCCGGGCTTTGCCCGGGCGGCC<br>TCAGTGAGCGAGCGAGCGCGCAGCTGCCTGCAGG |
| 65 | RRE/rabbit poly A beta globin | TCTAGAAGGAGCTTTGTTCCTTGGGTTCTTGGGAGCAGC<br>AGGAAGCACTATGGGCGCAGCGTCAATGACGCTGACGG<br>TACAGGCCAGACAATTATTGTCTGGTATAGTGCAGCAGC<br>AGAACAATTTGCTGAGGGCTATTGAGGCGCAACAGCATC<br>TGTTGCAACTCACAGTCTGGGGCATCAAGCAGCTCCAGG<br>CAAGAATCCTGGCTGTGGAAAGATACCTAAAGGATCAA<br>CAGCTCCTAGATCTTTTTCCCTCTGCCAAAAATTATGGGG<br>ACATCATGAAGCCCCTTGAGCATCTGACTTCTGGCTAAT<br>AAAGGAAATTTATTTTCATTGCAATAGTGTGTTGGAATTT<br>TTTGTGTCTCTCACTCGGAAGGACATATGGGAGGGCAAA<br>TCATTTAAAACATCAGAATGAGTATTTGGTTTAGAGTTT<br>GGCAACATATGCCATATGCTGGCTGCCATGAACAAAGGT<br>GGCTATAAAGAGGTCATCAGTATATGAAACAGCCCCCTG<br>CTGTCCATTCCTTATTCCATAGAAAAGCCTTGACTTGAGG<br>TTAGATTTTTTTTATATTTGTTTTGTGTTATTTTTTTCTTT<br>AACATCCCTAAAATTTTCCTTACATGTTTTACTAGCCAGA<br>TTTTTCCTCCTCTCCTGACTACTCCCAGTCATAGCTGTCC<br>CTCTTCTCTTATGAAGATCCCTCGACCTGCAGCCCAAGCT |

| SEQ ID NO: | Description | Sequence |
|---|---|---|
| | | TGGCGTAATCATGGTCATAGCTGTTTCCTGTGTGAAATTG<br>TTATCCGCTCACAATTCCACACAACATACGAGCCGGAAG<br>CATAAAGTGTAAAGCCTGGGGTGCCTAATGAGTGAGCTA<br>ACTCACATTAATTGCGTTGCGCTCACTGCCCGCTTTCCAG<br>TCGGGAAACCTGTCGTGCCAGCGGATCCGCATCTCAATT<br>AGTCAGCAACCATAGTCCCGCCCCTAACTCCGCCCATCC<br>CGCCCCTAACTCCGCCCAGTTCCGCCCATTCTCCGCCCCA<br>TGGCTGACTAATTTTTTTTATTTATGCAGAGGCCGAGGCC<br>GCCTCGGCCTCTGAGCTATTCCAGAAGTAGTGAGGAGGC<br>TTTTTTGGAGGCCTAGGCTTTTGCAAAAAGCTAACTTGTT<br>TATTGCAGCTTATAATGGTTACAAATAAAGCAATAGCAT<br>CACAAATTTCACAAATAAAGCATTTTTTTCACTGCATTCT<br>AGTTGTGGTTTGTCCAAACTCATCAATGTATCTTATCACC<br>CGGG |

While certain of the preferred embodiments of the present invention have been described and specifically exemplified above, it is not intended that the invention be limited to such embodiments. Various modifications may be made thereto without departing from the scope and spirit of the present invention.

What is claimed is:

1. A pharmaceutical combination, comprising:
(a) a bisphosphonate drug; and
(b) a lentiviral particle comprising an envelope protein and:
(i) at least one encoded shRNA capable of inhibiting production of farnesyl diphosphate synthase, or
(ii) at least one encoded microRNA capable of inhibiting production of farnesyl diphosphate synthase.

2. The pharmaceutical combination of claim 1, wherein the pharmaceutical combination comprises a fixed combination.

3. The pharmaceutical combination of claim 1, wherein the pharmaceutical combination comprises a non-fixed combination.

4. The pharmaceutical combination of claim 1, wherein the bisphosphonate compound comprises zoledronic acid.

5. The pharmaceutical combination of claim 1, wherein the shRNA comprises a sequence having at least 80% identity with SEQ ID NO: 1, SEQ ID NO: 2, SEQ ID NO: 3, or SEQ ID NO: 4.

6. The pharmaceutical combination of claim 1, wherein the microRNA comprises a sequence having at least 80% identity with SEQ ID NO: 5, SEQ ID NO: 6, SEQ ID NO: 7, SEQ ID NO: 8, SEQ ID NO: 9, or SEQ ID NO: 10.

7. A pharmaceutical combination, comprising:
(a) a bisphosphonate drug;
(b) at least one helper plasmid comprising sequences that encode gag, pol, and rev genes;
(c) an envelope plasmid comprising a sequence that encodes an envelope gene; and
(d) a therapeutic vector comprising:
(i) at least one sequence that encodes a shRNA capable of inhibiting production of farnesyl diphosphate synthase, or
(ii) at least one sequence that encodes a microRNA capable of inhibiting production of farnesyl diphosphate synthase.

8. The pharmaceutical combination of claim 7, wherein the at least one helper plasmid comprises a first helper plasmid and a second helper plasmid.

9. The pharmaceutical combination of claim 8, wherein the first helper plasmid comprises sequences that encode the gag and pol genes, wherein the second helper plasmid comprises a sequence that encodes the rev gene.

10. The pharmaceutical combination of claim 7, wherein the bisphosphonate drug comprises zoledronic acid.

11. The pharmaceutical combination of claim 7, wherein the shRNA comprises a sequence having at least 80% identity with SEQ ID NO: 1, SEQ ID NO: 2, SEQ ID NO: 3, or SEQ ID NO: 4.

12. The pharmaceutical combination of claim 7, wherein the microRNA comprises a sequence having at least 80% identity with SEQ ID NO: 5, SEQ ID NO: 6, SEQ ID NO: 7, SEQ ID NO: 8, SEQ ID NO: 9, or SEQ ID NO: 10.

13. A pharmaceutical combination, comprising:
(a) a bisphosphonate drug; and
(b) an immunotherapy-based viral delivery system, comprising:
(i) at least one helper plasmid comprising sequences that encode gag, pol, and rev genes;
(ii) an envelope plasmid comprising a sequence that encodes an env gene; and
(iii) a therapeutic vector comprising:
at least one encoded shRNA capable of inhibiting production of farnesyl diphosphate synthase, or
at least one encoded microRNA capable of inhibiting production of farnesyl diphosphate synthase.

14. The pharmaceutical combination of claim 13, wherein the at least one helper plasmid comprises a first helper plasmid and a second helper plasmid.

15. The pharmaceutical combination of claim 14 wherein the first helper plasmid comprises sequences that encode the gag and pol genes, wherein the second helper plasmid comprises a sequence that encodes the rev gene.

16. The pharmaceutical combination of claim 13, wherein the bisphosphonate drug comprises zoledronic acid.

17. The pharmaceutical combination of claim 13, wherein the shRNA comprises a sequence having at least 80% identity with SEQ ID NO: 1, SEQ ID NO: 2, SEQ ID NO: 3, or SEQ ID NO: 4.

18. The pharmaceutical combination of claim 13, wherein the microRNA comprises a sequence having at least 80% identity with SEQ ID NO: 5, SEQ ID NO: 6, SEQ ID NO: 7, SEQ ID NO: 8, SEQ ID NO: 9, or SEQ ID NO: 10.

19. The pharmaceutical combination of claim 13, wherein the at least one helper plasmid comprises a first helper plasmid and a second helper plasmid.

20. The pharmaceutical combination of claim 19, wherein the first helper plasmid comprises sequences that encode the gag and pol genes, wherein the second helper plasmid comprises a sequence that encodes the rev gene.

* * * * *

SEQUENCE LISTING

<160> NUMBER OF SEQ ID NOS: 65

<210> SEQ ID NO 1
<211> LENGTH: 53
<212> TYPE: DNA
<213> ORGANISM: Artificial Sequence
<220> FEATURE:
<223> OTHER INFORMATION: FDPS shRNA sequence #1

<400> SEQUENCE: 1
gtcctggagt acaatgccat tctcgagaat ggcattgtac tccaggactt ttt            53

<210> SEQ ID NO 2
<211> LENGTH: 53
<212> TYPE: DNA
<213> ORGANISM: Artificial Sequence
<220> FEATURE:
<223> OTHER INFORMATION: FDPS shRNA sequence #2

<400> SEQUENCE: 2
gcaggatttc gttcagcact tctcgagaag tgctgaacga aatcctgctt ttt            53

<210> SEQ ID NO 3
<211> LENGTH: 53
<212> TYPE: DNA
<213> ORGANISM: Artificial Sequence
<220> FEATURE:
<223> OTHER INFORMATION: FDPS shRNA sequence #3

<400> SEQUENCE: 3
gccatgtaca tggcaggaat tctcgagaat tcctgccatg tacatggctt ttt            53

<210> SEQ ID NO 4
<211> LENGTH: 53
<212> TYPE: DNA
<213> ORGANISM: Artificial Sequence
<220> FEATURE:
<223> OTHER INFORMATION: FDPS shRNA sequence #4

<400> SEQUENCE: 4
gcagaaggag gctgagaaag tctcgagact ttctcagcct ccttctgctt ttt            53

<210> SEQ ID NO 5

<210> SEQ ID NO 5
<211> LENGTH: 116
<212> TYPE: DNA
<213> ORGANISM: Artificial Sequence
<220> FEATURE:
<223> OTHER INFORMATION: miR30 FDPS sequence #1

<400> SEQUENCE: 5
aaggtatatt gctgttgaca gtgagcgaca ctttctcagc ctccttctgc gtgaagccac    60
agatggcaga aggaggctga gaaagtgctg cctactgcct cggacttcaa ggggct      116

<210> SEQ ID NO 6
<211> LENGTH: 114
<212> TYPE: DNA
<213> ORGANISM: Artificial Sequence
<220> FEATURE:
<223> OTHER INFORMATION: miR30 FDPS sequence #2

<400> SEQUENCE: 6
aaggtatatt gctgttgaca gtgagcgaca ctttctcagc ctccttctgc gtgaagccac    60
agatggcaga agggctgaga aagtgctgcc tactgcctcg acttcaagg ggct          114

<210> SEQ ID NO 7
<211> LENGTH: 91
<212> TYPE: DNA
<213> ORGANISM: Artificial Sequence
<220> FEATURE:
<223> OTHER INFORMATION: miR30 FDPS sequence #3

<400> SEQUENCE: 7
tgctgttgac agtgagcgac tttctcagcc tccttctgcg tgaagccaca gatggcagaa    60
ggaggctgag aaagttgcct actgcctcgg a                                    91

<210> SEQ ID NO 8
<211> LENGTH: 115
<212> TYPE: DNA
<213> ORGANISM: Artificial Sequence
<220> FEATURE:
<223> OTHER INFORMATION: miR155 FDPS sequence #1

<400> SEQUENCE: 8
cctggaggct tgctgaaggc tgtatgctga ctttctcagc ctccttctgc ttttggccac    60
tgactgagca aagggctga gaaagtcagg acacaaggcc tgttactagc actca         115

<210> SEQ ID NO 9
<211> LENGTH: 114
<212> TYPE: DNA
<213> ORGANISM: Artificial Sequence
<220> FEATURE:
<223> OTHER INFORMATION: miR21 FDPS sequence #1

<400> SEQUENCE: 9
catctccatg gctgtaccac cttgtcggga ctttctcagc ctccttctgc ctgttgaatc    60
tcatggcaga aggaggcgag aaagtctgac attttggtat ctttcatctg acca         114

<210> SEQ ID NO 10
<211> LENGTH: 114
<212> TYPE: DNA
<213> ORGANISM: Artificial Sequence
<220> FEATURE:
<223> OTHER INFORMATION: miR185 FDPS sequence #1

<400> SEQUENCE: 10
gggcctggct cgagcagggg gcgagggata ctttctcagc ctccttctgc tggtcccctc    60

```
cccgcagaag gaggctgaga aagtccttcc ctcccaatga ccgcgtcttc gtcg        114
```

<210> SEQ ID NO 11
<211> LENGTH: 228
<212> TYPE: DNA
<213> ORGANISM: Artificial Sequence
<220> FEATURE:
<223> OTHER INFORMATION: Rous Sarcoma virus (RSV) promoter

<400> SEQUENCE: 11

```
gtagtcttat gcaatactct tgtagtcttg caacatggta acgatgagtt agcaacatgc   60
cttacaagga gagaaaaagc accgtgcatg ccgattggtg gaagtaaggt ggtacgatcg  120
tgccttatta ggaaggcaac agacgggtct gacatggatt ggacgaacca ctgaattgcc  180
gcattgcaga gatattgtat ttaagtgcct agctcgatac aataaacg              228
```

<210> SEQ ID NO 12
<211> LENGTH: 180
<212> TYPE: DNA
<213> ORGANISM: Artificial Sequence
<220> FEATURE:
<223> OTHER INFORMATION: 5' Long terminal repeat (LTR)

<400> SEQUENCE: 12

```
ggtctctctg gttagaccag atctgagcct gggagctctc tggctaacta gggaacccac   60
tgcttaagcc tcaataaagc ttgccttgag tgcttcaagt agtgtgtgcc cgtctgttgt  120
gtgactctgg taactagaga tccctcagac ccttttagtc agtgtggaaa atctctagca  180
```

<210> SEQ ID NO 13
<211> LENGTH: 41
<212> TYPE: DNA
<213> ORGANISM: Artificial Sequence
<220> FEATURE:
<223> OTHER INFORMATION: Psi Packaging signal

<400> SEQUENCE: 13

```
tacgccaaaa attttgacta gcggaggcta aaggagaga g                        41
```

<210> SEQ ID NO 14
<211> LENGTH: 233
<212> TYPE: DNA
<213> ORGANISM: Artificial Sequence
<220> FEATURE:
<223> OTHER INFORMATION: Rev response element (RRE)

<400> SEQUENCE: 14

```
aggagctttg ttccttgggt tcttgggagc agcaggaagc actatgggcg cagcctcaat   60
gacgctgacg gtacaggcca gacaattatt gtctggtata gtgcagcagc agaacaattt  120
gctgagggct attgaggcgc aacagcatct gttgcaactc acagtctggg gcatcaagca  180
gctccaggca agaatcctgg ctgtggaaag atacctaaag gatcaacagc tcc         233
```

<210> SEQ ID NO 15
<211> LENGTH: 118
<212> TYPE: DNA
<213> ORGANISM: Artificial Sequence
<220> FEATURE:
<223> OTHER INFORMATION: Central polypurine tract (cPPT)

<400> SEQUENCE: 15

```
ttttaaaaga aaagggggga ttggggggta cagtgcaggg gaaagaatag tagacataat   60
```
agcaacagac atacaaacta aagaattaca aaaacaaatt acaaaattca aaatttta    118

<210> SEQ ID NO 16
<211> LENGTH: 217
<212> TYPE: DNA
<213> ORGANISM: Artificial Sequence
<220> FEATURE:
<223> OTHER INFORMATION: Polymerase III shRNA promoters; H1 promoter

<400> SEQUENCE: 16
gaacgctgac gtcatcaacc cgctccaagg aatcgcgggc ccagtgtcac taggcgggaa    60
cacccagcgc gcgtgcgccc tggcaggaag atggctgtga gggacagggg agtggcgccc    120
tgcaatattt gcatgtcgct atgtgttctg ggaaatcacc ataaacgtga aatgtctttg    180
gatttgggaa tcttataagt tctgtatgag accactt    217

<210> SEQ ID NO 17
<211> LENGTH: 590
<212> TYPE: DNA
<213> ORGANISM: Artificial Sequence
<220> FEATURE:
<223> OTHER INFORMATION: Long WPRE sequence

<400> SEQUENCE: 17
aatcaacctc tgattacaaa atttgtgaaa gattgactgg tattcttaac tatgttgctc    60
cttttacgct atgtggatac gctgctttaa tgcctttgta tcatgctatt gcttcccgta    120
tggctttcat tttctcctcc ttgtataaat cctggttgct gtctctttat gaggagttgt    180
ggcccgttgt caggcaacgt ggcgtggtgt gcactgtgtt tgctgacgca acccccactg    240
gttggggcat tgccaccacc tgtcagctcc tttccgggac tttcgctttc ccctcccta    300 ttgccacggc ggaactcatc gccgcctgcc ttgcccgctg ctggacaggg gctcggctgt    360
tgggcactga caattccgtg gtgttgtcgg ggaaatcatc gtcctttcct ggctgctcg    420 cctgtgttgc cacctggatt ctgcgcggga cgtccttctg ctacgtccct tcggccctca    480
atccagcgga ccttccttcc gcggcctgc tgccggctct gcggcctctt ccgcgtcttc    540
gccttcgccc tcagacgagt cggatctccc tttgggccgc ctccccgcct    590

<210> SEQ ID NO 18
<211> LENGTH: 250
<212> TYPE: DNA
<213> ORGANISM: Artificial Sequence
<220> FEATURE:
<223> OTHER INFORMATION: 3' delta LTR

<400> SEQUENCE: 18
tggaagggct aattcactcc caacgaagat aagatctgct ttttgcttgt actgggtctc    60
tctggttaga ccagatctga gcctgggagc tctctggcta actagggaac ccactgctta    120
agcctcaata aagcttgcct tgagtgcttc aagtagtgtg tgcccgtctg ttgtgtgact    180
ctggtaacta gagatccctc agaccctttt agtcagtgtg gaaaatctct agcagtagta    240
gttcatgtca    250

<210> SEQ ID NO 19
<211> LENGTH: 290
<212> TYPE: DNA
<213> ORGANISM: Artificial Sequence
<220> FEATURE:
<223> OTHER INFORMATION: Helper/Rev; Chicken beta actin (CAG) promoter;
      Transcription

<400> SEQUENCE: 19

```
gctattacca tgggtcgagg tgagccccac gttctgcttc actctcccca tctcccccc      60
ctccccaccc ccaatttgt atttattat tttttaatta ttttgtgcag cgatgggggc       120
ggggggggg gggcgcgcg ccaggcgggg cgggcgggg cgaggggcgg ggcggggcga        180
ggcggagagg tgcggcggca gccaatcaga gcggcgcgct ccgaaagttt ccttttatgg    240
cgaggcggcg gcggcggcgg ccctataaaa agcgaagcgc gcggcgggcg               290
```

<210> SEQ ID NO 20
<211> LENGTH: 1503
<212> TYPE: DNA
<213> ORGANISM: Artificial Sequence
<220> FEATURE:
<223> OTHER INFORMATION: Helper/Rev; HIV Gag; Viral capsid

<400> SEQUENCE: 20

```
atgggtgcga gagcgtcagt attaagcggg ggagaattag atcgatggga aaaaattcgg     60
ttaaggccag ggggaaagaa aaatataaa ttaaaacata tagtatgggc aagcagggag     120
ctagaacgat tcgcagttaa tcctggcctg ttagaaacat cagaaggctg tagacaaata   180
ctgggacagc tacaaccatc ccttcagaca ggatcagaag aacttagatc attatataat   240
acagtagcaa ccctctattg tgtgcatcaa aggatagaga taaaagacac caaggaagct   300
ttagacaaga tagaggaaga gcaaaacaaa agtaagaaaa agcacagca agcagcagct    360
gacacaggac acagcaatca ggtcagccaa aattacccta tagtgcagaa catccagggg   420
caaatggtac atcaggccat atcacctaga acttttaaatg catgggtaaa agtagtagaa  480
gagaaggctt tcagcccaga agtgatacc atgttttcag cattatcaga aggagccacc    540
ccacaagatt taaacaccat gctaaacaca gtggggggac atcaagcagc catgcaaatg   600
ttaaaagaga ccatcaatga ggaagctgca gaatgggata gagtgcatcc agtgcatgca   660
gggcctattg caccaggcca gatgagagaa ccaaggggaa gtgacatagc aggaactact   720
agtacccttc aggaacaaat aggatggatg acacataatc cacctatccc agtaggagaa   780
atctataaaa gatggataat cctgggatta aataaaatag taagaatgta tagccctacc   840
agcattctgg acataagaca aggaccaaag gaaccctta gagactatgt agaccgattc    900
tataaaactc taagagccga gcaagcttca caagaggtaa aaaattggat gacagaaacc    960
ttgttggtcc aaaatgcgaa cccagattgt aagactattt taaaagcatt gggaccagga  1020
gcgacactag aagaaatgat gacagcatgt caggagtgg ggggacccgg ccataaagca   1080
agagttttgg ctgaagcaat gagccaagta acaaatccag ctaccataat gatacagaaa  1140
ggcaatttta ggaaccaaag aaagactgtt aagtgtttca attgtggcaa agaagggcac   1200
atagccaaaa attgcagggc ccctaggaaa aagggctgtt ggaaatgtgg aaggaagga   1260
caccaaatga aagattgtac tgagagacag gctaatttt tagggaagat ctggccttcc    1320
cacaagggaa ggccagggaa ttttcttcag agcagaccag agccaacagc cccaccagaa   1380
gagagcttca ggtttgggga agacaaca actccctctc agaagcagga gccgatagac    1440
aaggaactgt atcctttagc ttccctcaga tcactctttg gcagcgaccc ctcgtcacaa   1500
taa                                                                  1503
```

<210> SEQ ID NO 21
<211> LENGTH: 1872
<212> TYPE: DNA
<213> ORGANISM: Artificial Sequence
<220> FEATURE:
<223> OTHER INFORMATION: Helper/Rev; HIV Pol; Protease and reverse
      transcriptase

<400> SEQUENCE: 21

```
atgaatttgc caggaagatg gaaaccaaaa atgatagggg gaattggagg ttttatcaaa      60
gtaggacagt atgatcagat actcatagaa atctgcggac ataaagctat aggtacagta     120
ttagtaggac ctacacctgt caacataatt ggaagaaatc tgttgactca gattggctgc     180
actttaaatt ttcccattag tcctattgag actgtaccag taaaattaaa gccaggaatg     240
gatggcccaa agttaaaaca atggccattg acagaagaaa aaataaaagc attagtagaa     300
atttgtacag aaatggaaaa ggaaggaaaa atttcaaaaa ttgggcctga aaatccatac     360
aatactccag tatttgccat aaagaaaaaa gacagtacta atggagaaaa attagtagat     420
ttcagagaac ttaataagag aactcaagat ttctgggaag ttcaattagg aataccacat     480
cctgcagggt taaaacagaa aaaatcagta acagtactgg atgtgggcga tgcatatttt     540
tcagttccct tagataaaga cttcaggaag tatactgcat ttaccatacc tagtataaac     600
aatgagacac cagggattag atatcagtac aatgtgcttc cacagggatg gaaaggatca     660
ccagcaatat tccagtgtag catgacaaaa atcttagagc cttttagaaa acaaaatcca     720
gacatagtca tctatcaata catggatgat ttgtatgtag gatctgactt agaaataggg     780
cagcatagaa caaaaataga ggaactgaga caacatctgt tgaggtgggg atttaccaca     840
ccagacaaaa aacatcagaa agaacctcca ttcctttgga tgggttatga actccatcct     900
gataaatgga cagtacagcc tatagtgctg ccagaaaagg acagctggac tgtcaatgac     960
atacagaaat tagtgggaaa attgaattgg gcaagtcaga tttatgcagg gattaaagta    1020
aggcaattat gtaaacttct taggggaacc aaagcactaa cagaagtagt accactaaca    1080
gaagaagcag agctagaact ggcagaaaac agggagattc taaaagaacc ggtacatgga    1140
gtgtattatg acccatcaaa agacttaata gcagaaatac agaagcaggg gcaaggccaa    1200
tggacatatc aaatttatca agagccattt aaaaatctga aaacaggaaa atatgcaaga    1260
atgaagggtg cccacactaa tgatgtgaaa caattaacag aggcagtaca aaaaatagcc    1320
acagaaagca tagtaatatg gggaaagact cctaaattta aattacccat acaaaaggaa    1380
acatgggaag catggtggac agagtattgg caagccacct ggattcctga gtgggagttt    1440
gtcaataccc ctcccttagt gaagttatgg taccagttag agaaagaacc cataatagga    1500
gcagaaactt tctatgtaga tggggcagcc aatagggaaa ctaaattagg aaaagcagga    1560
tatgtaactg acagaggaag acaaaaagtt gtcccctaa cggacacaac aaatcagaag    1620
actgagttac aagcaattca tctagctttg caggattcgg gattagaagt aaacatagtg    1680
acagactcac aatatgcatt gggaatcatt caagcacaac cagataagag tgaatcagag    1740
ttagtcagtc aaataataga gcagttaata aaaaaggaaa aagtctacct ggcatgggta    1800
ccagcacaca aaggaattgg aggaaatgaa caagtagatg gttggtcag tgctggaatc    1860
aggaaagtac ta                                                       1872
```

<210> SEQ ID NO 22
<211> LENGTH: 867
<212> TYPE: DNA
<213> ORGANISM: Artificial Sequence
<220> FEATURE:
<223> OTHER INFORMATION: Helper Rev; HIV Integrase; Integration of viral
      RNA

<400> SEQUENCE: 22

```
tttttagatg gaatagataa ggcccaagaa gaacatgaga aatatcacag taattggaga      60
gcaatggcta gtgattttaa cctaccacct gtagtagcaa aagaaatagt agccagctgt     120
gataaatgtc agctaaaagg ggaagccatg catggacaag tagactgtag cccaggaata    180
tggcagctag attgtacaca tttagaagga aaagttatct tggtagcagt tcatgtagcc    240
agtggatata tagaagcaga agtaattcca gcagagacag ggcaagaaac agcatacttc    300
ctcttaaaat tagcaggaag atggccagta aaaacagtac atacagacaa tggcagcaat    360
ttcaccagta ctacagttaa ggccgcctgt tggtgggcgg ggatcaagca ggaatttggc    420
attccctaca atccccaaag tcaaggagta atagaatcta tgaataaaga attaaagaaa    480
attataggac aggtaagaga tcaggctgaa catcttaaga cagcagtaca aatggcagta    540
ttcatccaca attttaaaag aaaaggggggg attgggggggt acagtgcagg ggaaagaata    600
gtagacataa tagcaacaga catacaaact aaagaattac aaaaacaaat tacaaaaatt    660
caaaattttc gggtttatta cagggacagc agagatccag tttggaaagg accagcaaag    720
ctcctctgga aaggtgaagg ggcagtagta atacaagata atagtgacat aaaagtagtg    780
ccaagaagaa aagcaaagat catcagggat tatggaaaac agatggcagg tgatgattgt    840
gtggcaagta gacaggatga ggattaa                                         867
```

<210> SEQ ID NO 23
<211> LENGTH: 234
<212> TYPE: DNA
<213> ORGANISM: Artificial Sequence
<220> FEATURE:
<223> OTHER INFORMATION: Helper/Rev; HIV RRE; Binds Rev element

<400> SEQUENCE: 23

```
aggagctttg ttccttgggt tcttgggagc agcaggaagc actatgggcg cagcgtcaat     60
gacgctgacg gtacaggcca gacaattatt gtctggtata gtgcagcagc agaacaattt    120
gctgagggct attgaggcgc aacagcatct gttgcaactc acagtctggg gcatcaagca    180
gctccaggca agaatcctgg ctgtggaaag atacctaaag gatcaacagc tcct           234
```

<210> SEQ ID NO 24
<211> LENGTH: 351
<212> TYPE: DNA
<213> ORGANISM: Artificial Sequence
<220> FEATURE:
<223> OTHER INFORMATION: Helper/Rev; HIV Rev; Nuclear export and
      stabilize viral mRNA

<400> SEQUENCE: 24

```
atggcaggaa gaagcggaga cagcgacgaa gaactcctca aggcagtcag actcatcaag     60
tttctctatc aaagcaaccc acctcccaat cccgagggga cccgacaggc ccgaaggaat    120
agaagaagaa ggtggagaga gagacagaga cagatccatt cgattagtga acggatcctt    180
agcacttatc tgggacgatc tgcggagcct gtgcctcttc agctaccacc gcttgagaga    240
cttactcttg attgtaacga ggattgtgga acttctggga cgcaggggggt gggaagccct    300
caaatattgg tggaatctcc tacaatattg gagtcaggag ctaaagaata g              351
```

<210> SEQ ID NO 25
<211> LENGTH: 577
<212> TYPE: DNA
<213> ORGANISM: Artificial Sequence
<220> FEATURE:

<223> OTHER INFORMATION: Envelope; CMV promoter; Transcription

<400> SEQUENCE: 25

```
acattgatta ttgactagtt attaatagta atcaattacg gggtcattag ttcatagccc      60
atatatggag ttccgcgtta cataacttac ggtaaatggc ccgcctggct gaccgcccaa     120
cgacccccgc ccattgacgt caataatgac gtatgttccc atagtaacgc caatagggac     180
tttccattga cgtcaatggg tggagtattt acggtaaact gcccacttgg cagtacatca     240
agtgtatcat atgccaagta cgccccctat tgacgtcaat gacggtaaat ggcccgcctg     300
gcattatgcc cagtacatga ccttatggga ctttcctact tggcagtaca tctacgtatt     360
agtcatcgct attaccatgg tgatgcggtt ttggcagtac atcaatgggc gtggatagcg     420
gtttgactca cggggatttc caagtctcca ccccattgac gtcaatggga gtttgttttg     480
gcaccaaaat caacgggact ttccaaaatg tcgtaacaac tccgccccat tgacgcaaat     540
gggcggtagg cgtgtacggt gggaggtcta tataagc                             577
```

<210> SEQ ID NO 26
<211> LENGTH: 1519
<212> TYPE: DNA
<213> ORGANISM: Artificial Sequence
<220> FEATURE:
<223> OTHER INFORMATION: Envelope; VSV-G; Glycoprotein envelope-cell entry

<400> SEQUENCE: 26

```
atgaagtgcc ttttgtactt agccttttta ttcattgggg tgaattgcaa gttcaccata      60
gttttccac acaaccaaaa aggaaactgg aaaaatgttc cttctaatta ccattattgc     120
ccgtcaagct cagatttaaa ttggcataat gacttaatag gcacagcctt acaagtcaaa     180
atgcccaaga gtcacaaggc tattcaagca gacggttgga tgtgtcatgc ttccaaatgg     240
gtcactactt gtgatttccg ctggtatgga ccgaagtata aacacattc catccgatcc     300
ttcactccat ctgtagaaca atgcaaggaa agcattgaac aaacgaaaca aggaacttgg     360
ctgaatccag gcttccctcc tcaaagttgt ggatatgcaa ctgtgacgga tgccgaagca     420
gtgattgtcc aggtgactcc tcaccatgtg ctggttgatg aatacacagg agaatgggtt     480
gattcacagt tcatcaacgg aaaatgcagc aattacatat gccccactgt ccataactct     540
acaacctggc attctgacta aaggtcaaa gggctatgtg attctaacct catttccatg     600
gacatcacct tcttctcaga ggacggagag ctatcatccc tgggaaagga gggcacaggg     660
ttcagaagta actactttgc ttatgaaact ggaggcaagg cctgcaaaat gcaatactgc     720
aagcattggg gagtcagact cccatcaggt gtctggttcg agatggctga taaggatctc     780
tttgctgcag ccagattccc tgaatgccca gaagggtcaa gtatctctgc tccatctcag     840
acctcagtgg atgtaagtct aattcaggac gttgagagga tcttggatta ttccctctgc     900
caagaaacct ggagcaaaat cagagcgggt cttccaatct ctccagtgga tctcagctat     960
cttgctccta aaaacccagg aaccggtcct gctttcacca taatcaatgg taccctaaaa    1020
tactttgaga ccagatacat cagagtcgat attgctgctc caatcctctc aagaatggtc    1080
ggaatgatca gtggaactac cacagaaagg gaactgtggg atgactgggc accatatgaa    1140
gacgtggaaa ttggacccaa tggagttctg aggaccagtt caggatataa gtttcctta    1200
tacatgattg acatggtat gttggactcc gatcttcatc ttagctcaaa ggctcaggtg    1260
ttcgaacatc ctcacattca agacgctgct tcgcaacttc ctgatgatga gagtttattt    1320
```

```
tttggtgata ctgggctatc caaaaatcca atcgagcttg tagaaggttg gttcagtagt    1380
tggaaaagct ctattgcctc ttttttcttt atcatagggt taatcattgg actattcttg    1440
gttctccgag ttggtatcca tctttgcatt aaattaaagc acaccaagaa aagacagatt    1500
tatacagaca tagagatga                                                 1519
```

<210> SEQ ID NO 27
<211> LENGTH: 352
<212> TYPE: DNA
<213> ORGANISM: Artificial Sequence
<220> FEATURE:
<223> OTHER INFORMATION: Helper/Rev; CMV early (CAG) enhancer; Enhance
      Transcription

<400> SEQUENCE: 27

```
tagttattaa tagtaatcaa ttacggggtc attagttcat agcccatata tggagttccg     60
cgttacataa cttacggtaa atggcccgcc tggctgaccg cccaacgacc cccgcccatt    120
gacgtcaata atgacgtatg ttcccatagt aacgccaata gggactttcc attgacgtca    180
atgggtggac tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tc            352
```

<210> SEQ ID NO 28
<211> LENGTH: 960
<212> TYPE: DNA
<213> ORGANISM: Artificial Sequence
<220> FEATURE:
<223> OTHER INFORMATION: Helper/Rev; Chicken beta actin intron; Enhance
      gene expression

<400> SEQUENCE: 28

```
ggagtcgctg cgttgccttc gccccgtgcc ccgctccgcg ccgcctcgcg ccgcccgccc     60
cggctctgac tgaccgcgtt actcccacag gtgagcgggc gggacggccc ttctcctccg    120
ggctgtaatt agcgcttggt ttaatgacgg ctcgtttctt ttctgtggct gcgtgaaagc    180
cttaaagggc tccggagggc cctttgtgcg gggggagcg gctcgggggg gtgcgtgcgt    240
gtgtgtgtgc gtggggagcg ccgcgtgcgg cccgcgctgc ccggcggctg tgagcgctgc    300
gggcgcggcg cggggctttg tgcgctccgc gtgtgcgcga ggggagcgcg gccggggggcg    360 gtgccccgcg gtgcgggggg gctgcgaggg gaacaaaggc tgcgtgcggg gtgtgtgcgt    420 ggggggggtga gcaggggtg tgggcgcggc ggtcgggctg taaccccccc ctgcaccccc    480
ctccccgagt tgctgagcac ggcccggctt cgggtgcggg gctccgtgcg gggcgtggcg    540
cggggctcgc cgtgccgggc gggggtggc ggcaggtggg ggtgccgggc ggggcggggc    600
cgcctcgggc cggggagggc tcgggggagg ggcgcggcgg ccccggagcg ccggcggctg    660
tcgaggcgcg gcgagccgca gccattgcct tttatggtaa tcgtgcgaga gggcgcaggg    720
acttcctttg tcccaaatct ggcggagccg aaatctggga ggcgccgccg cacccctct    780 agcgggcgcg ggcgaagcgg tgcggcgccg gcaggaagga aatgggcggg agggccttc    840 gtgcgtcgcc gcgccgccgt ccccttctcc atctccagcc tcggggctgc cgcaggggga    900
cggctgcctt cgggggggac ggggcagggc ggggttcggc ttctggcgtg tgaccggcgg    960
```

<210> SEQ ID NO 29
<211> LENGTH: 448
<212> TYPE: DNA
<213> ORGANISM: Artificial Sequence

```
<220> FEATURE:
<223> OTHER INFORMATION: Helper/Rev; Rabbit beta globin poly A; RNA
      stability

<400> SEQUENCE: 29 agatctttt   ccctctgcca   aaaattatgg   ggacatcatg   aagcccttg    agcatctgac      60 ttctggctaa  taaaggaaat   ttattttcat   tgcaatagtg   tgttggaatt   ttttgtgtct     120
ctcactcgga  aggacatatg   ggagggcaaa   tcatttaaaa   catcagaatg   agtatttggt     180
ttagagtttg  gcaacatatg   ccatatgctg   gctgccatga   acaaaggtgg   ctataaagag     240
gtcatcagta  tatgaaacag   cccctgctg   tccattcctt   attccataga   aaagccttga     300
cttgaggtta  gattttttt    atattttgtt   ttgtgttatt   tttttcttta   acatccctaa     360
aattttcctt  acatgtttta   ctagccagat   ttttcctcct   ctcctgacta   ctcccagtca     420
tagctgtccc  tcttctctta   tgaagatc                                               448

<210> SEQ ID NO 30
<211> LENGTH: 573
<212> TYPE: DNA
<213> ORGANISM: Artificial Sequence
<220> FEATURE:
<223> OTHER INFORMATION: Envelope; Beta globin intron; Enhance gene
      expression

<400> SEQUENCE: 30
gtgagtttgg  ggaccttga   ttgttctttc   tttttcgcta   ttgtaaaatt   catgttatat      60
ggagggggca  aagttttcag   ggtgttgttt   agaatgggaa   gatgtccctt   gtatcaccat     120
ggaccctcat  gataattttg   tttctttcac   tttctactct   gttgacaacc   attgtctcct     180
cttattttct  tttcattttc   tgtaactttt   tcgttaaact   ttagcttgca   tttgtaacga     240
atttttaaat  tcactttgt    ttatttgtca   gattgtaagt   actttctcta   atcacttttt     300
tttcaaggca  atcagggtat   attatattgt   acttcagcac   agttttagag   aacaattgtt     360
ataattaaat  gataaggtag   aatatttctg   catataaatt   ctggctggcg   tggaaatatt     420
cttattggta  gaaacaacta   caccctggtc   atcatcctgc   ctttctcttt   atggttacaa     480
tgatatacac  tgtttgagat   gaggataaaa   tactctgagt   ccaaaccggg   cccctctgct     540
aaccatgttc  atgccttctt   ctctttccta   cag                                      573

<210> SEQ ID NO 31
<211> LENGTH: 450
<212> TYPE: DNA
<213> ORGANISM: Artificial Sequence
<220> FEATURE:
<223> OTHER INFORMATION: Envelope; Rabbit beta globin poly A; RNA
      stability

<400> SEQUENCE: 31 agatctttt   ccctctgcca   aaaattatgg   ggacatcatg   aagcccttg    agcatctgac      60 ttctggctaa  taaaggaaat   ttattttcat   tgcaatagtg   tgttggaatt   ttttgtgtct     120
ctcactcgga  aggacatatg   ggagggcaaa   tcatttaaaa   catcagaatg   agtatttggt     180
ttagagtttg  gcaacatatg   cccatatgct   ggctgccatg   aacaaaggtt   ggctataaag     240
aggtcatcag  tatatgaaac   agcccctgc    tgtccattcc   ttattccata   gaaaagcctt     300
gacttgaggt  tagattttt    ttatattttg   ttttgtgtta   ttttttctt    taacatccct     360 aaaattttcc  ttacatgttt   tactagccag   attttcctc    ctctcctgac   tactcccagt     420
catagctgtc  cctcttctct   tatggagatc                                             450
```

<210> SEQ ID NO 32
<211> LENGTH: 31
<212> TYPE: DNA
<213> ORGANISM: Artificial Sequence
<220> FEATURE:
<223> OTHER INFORMATION: Primer

<400> SEQUENCE: 32

```
taagcagaat tcatgaattt gccaggaaga t                                31
```

<210> SEQ ID NO 33
<211> LENGTH: 36
<212> TYPE: DNA
<213> ORGANISM: Artificial Sequence
<220> FEATURE:
<223> OTHER INFORMATION: Primer

<400> SEQUENCE: 33

```
ccatacaatg aatggacact aggcggccgc acgaat                           36
```

<210> SEQ ID NO 34
<211> LENGTH: 2745
<212> TYPE: DNA
<213> ORGANISM: Artificial Sequence
<220> FEATURE:
<223> OTHER INFORMATION: Gag, Pol, Integrase fragment

<400> SEQUENCE: 34

```
gaattcatga atttgccagg aagatggaaa ccaaaaatga tagggggaat tggaggtttt    60
atcaaagtaa gacagtatga tcagatactc atagaaatct gcggacataa agctataggt   120
acagtattag taggacctac acctgtcaac ataattggaa gaaatctgtt gactcagatt   180
ggctgcactt taaattttcc cattagtcct attgagactg taccagtaaa attaaagcca   240
ggaatggatg gcccaaaagt taaacaatgg ccattgacag aagaaaaaat aaaagcatta   300
gtagaaattt gtacagaaat ggaaaaggaa ggaaaaattt caaaaattgg gcctgaaaat   360
ccatacaata ctccagtatt tgccataaag aaaaaagaca gtactaaatg gagaaaatta   420
gtagatttca gagaacttaa taagagaact caagatttct gggaagttca attaggaata   480
ccacatcctg cagggttaaa acagaaaaaa tcagtaacag tactggatgt gggcgatgca   540
tatttttcag ttcccttaga taaagacttc aggaagtata ctgcatttac catacctagt   600
ataaacaatg agacaccagg gattagatat cagtacaatg tgcttccaca gggatggaaa   660
ggatcaccag caatattcca gtgtagcatg acaaaaatct tagagccttt tagaaaacaa   720
aatccagaca tagtcatcta tcaatacatg gatgatttgt atgtaggatc tgacttagaa   780
atagggcagc atagaacaaa aatagaggaa ctgagacaac atctgttgag gtggggattt   840
accacaccag acaaaaaaca tcagaaagaa cctccattcc tttggatggg ttatgaactc   900
catcctgata aatggacagt acagcctata gtgctgccag aaaaggacag ctggactgtc   960
aatgacatac agaaattagt gggaaaattg aattgggcaa gtcagattta tgcagggatt  1020
aaagtaaggc aattatgtaa actccttagg ggaaccaaag cactaacaga agtagtacca  1080
ctaacagaag aagcagagct agaactggca gaaaacaggg agattctaaa agaaccggta  1140
catggagtgt attatgaccc atcaaaagac ttaatagcag aaatacagaa gcaggggcaa  1200
ggccaatgga catatcaaat ttatcaagag ccatttaaaa atctgaaaac aggaaagtat  1260
gcaagaatga agggtgccca cactaatgat gtgaaacaat taacagaggc agtacaaaaa  1320
```

| | |
|---|---|
| atagccacag aaagcatagt aatatgggga aagactccta aatttaaatt acccatacaa | 1380 |
| aaggaaacat gggaagcatg gtggacagag tattggcaag ccacctggat tcctgagtgg | 1440 |
| gagtttgtca atacccctcc cttagtgaag ttatggtacc agttagagaa agaacccata | 1500 |
| ataggagcag aaactttcta tgtagatggg gcagccaata gggaaactaa attaggaaaa | 1560 |
| gcaggatatg taactgacag aggaagacaa aaagttgtcc ccctaacgga cacaacaaat | 1620 |
| cagaagactg agttacaagc aattcatcta gctttgcagg attcgggatt agaagtaaac | 1680 |
| atagtgacag actcacaata tgcattggga atcattcaag cacaaccaga taagagtgaa | 1740 |
| tcagagttag tcagtcaaat aatagagcag ttaataaaaa aggaaaaagt ctacctggca | 1800 |
| tgggtaccag cacacaaagg aattggagga aatgaacaag tagataaatt ggtcagtgct | 1860 |
| ggaatcagga aagtactatt tttagatgga atagataagg cccaagaaga acatgagaaa | 1920 |
| tatcacagta attggagagc aatggctagt gattttaacc taccacctgt agtagcaaaa | 1980 |
| gaaatagtag ccagctgtga taatgtcag ctaaaagggg aagccatgca tggacaagta | 2040 |
| gactgtagcc caggaatatg gcagctagat tgtacacatt tagaaggaaa agttatcttg | 2100 |
| gtagcagttc atgtagccag tggatatata gaagcagaag taattccagc agagacaggg | 2160 |
| caagaaacag catacttcct cttaaaatta gcaggaagat ggccagtaaa aacagtacat | 2220 |
| acagacaatg gcagcaattt caccagtact acagttaagg ccgcctgttg gtgggcgggg | 2280 |
| atcaagcagg aatttggcat tccctacaat ccccaaagtc aaggagtaat agaatctatg | 2340 |
| aataaagaat taagaaaat tataggacag gtaagagatc aggctgaaca tcttaagaca | 2400 |
| gcagtacaaa tggcagtatt catccacaat tttaaaagaa aaggggggat tggggggtac | 2460 |
| agtgcagggg aaagaatagt agacataata gcaacagaca tacaaactaa agaattacaa | 2520 |
| aaacaaatta caaaaattca aaattttcgg gtttattaca gggacagcag agatccagtt | 2580 |
| tggaaaggac cagcaaagct cctctggaaa ggtgaagggg cagtagtaat acaagataat | 2640 |
| agtgacataa aagtagtgcc aagaagaaaa gcaaagatca tcagggatta tggaaaacag | 2700 |
| atggcaggtg atgattgtgt ggcaagtaga caggatgagg attaa | 2745 |

<210> SEQ ID NO 35
<211> LENGTH: 1586
<212> TYPE: DNA
<213> ORGANISM: Artificial Sequence
<220> FEATURE:
<223> OTHER INFORMATION: DNA Fragment containing Rev, RRE and rabbit
      beta globin poly A

<400> SEQUENCE: 35

| | |
|---|---|
| tctagaatgg caggaagaag cggagacagc gacgaagagc tcatcagaac agtcagactc | 60 |
| atcaagcttc tctatcaaag caacccacct cccaatcccg aggggacccg acaggcccga | 120 |
| aggaatagaa gaagaaggtg gagagagaga cagagacaga tccattcgat tagtgaacgg | 180 |
| atccttggca cttatctggg acgatctgcg gagcctgtgc ctcttcagct accaccgctt | 240 |
| gagagactta ctcttgattg taacgaggat tgtggaactt ctgggacgca ggggtggga | 300 |
| agccctcaaa tattggtgga atctcctaca atattggagt caggagctaa agaatagagg | 360 |
| agctttgttc cttgggttct tgggagcagc aggaagcact atgggcgcag cgtcaatgac | 420 |
| gctgacggta caggccagac aattattgtc tggtatagtg cagcagcaga acaatttgct | 480 |
| gagggctatt gaggcgcaac agcatctgtt gcaactcaca gtctggggca tcaagcagct | 540 |
| ccaggcaaga atcctggctg tggaaagata cctaaaggat caacagctcc tagatctttt | 600 |

-continued

```
tccctctgcc aaaaattatg gggacatcat gaagcccctt gagcatctga cttctggcta      660
ataaaggaaa tttatttca ttgcaatagt gtgttggaat ttttgtgtc tctcactcgg        720 aaggacatat gggagggcaa atcatttaaa acatcagaat gagtatttgg tttagagttt     780
ggcaacatat gccatatgct ggctgccatg aacaaaggtg gctataaaga ggtcatcagt     840
atatgaaaca gccccctgct gtccattcct tattccatag aaaagccttg acttgaggtt     900 agatttttt tatattttgt tttgtgttat ttttttcttt aacatcccta aaattttcct      960
tacatgtttt actagccaga ttttcctcc tctcctgact actcccagtc atagctgtcc     1020
ctcttctctt atgaagatcc ctcgacctgc agcccaagct ggcgtaatc atggtcatag     1080 ctgtttcctg tgtgaaattg ttatccgctc acaattccac acaacatacg agccggaagc    1140
ataaagtgta aagcctgggg tgcctaatga gtgagctaac tcacattaat tgcgttgcgc    1200
tcactgcccg ctttccagtc gggaaacctg tcgtgccagc ggatccgcat ctcaattagt    1260
cagcaaccat agtcccgccc ctaactccgc ccatcccgcc cctaactccg cccagttccg    1320
cccattctcc gccccatggc tgactaattt tttttattta tgcagaggcc gaggccgcct    1380
cggcctctga gctattccag aagtagtgag gaggctttt tggaggccta ggcttttgca    1440
aaaagctaac ttgtttattg cagcttataa tggttacaaa taaagcaata gcatcacaaa    1500
tttcacaaat aaagcatttt tttcactgca ttctagttgt ggtttgtcca aactcatcaa    1560
tgtatcttat cagcggccgc ccggg                                          1586
```

<210> SEQ ID NO 36
<211> LENGTH: 1614
<212> TYPE: DNA
<213> ORGANISM: Artificial Sequence
<220> FEATURE:
<223> OTHER INFORMATION: DNA fragment containing the CAG enhancer/promoter/intron sequence

<400> SEQUENCE: 36

```
acgcgttagt tattaatagt aatcaattac ggggtcatta gttcatagcc catatatgga      60
gttccgcgtt acataactta cggtaaatgg cccgcctggc tgaccgccca acgacccccg     120
cccattgacg tcaataatga cgtatgttcc catagtaacg ccaatagggga ctttccattg   180 acgtcaatgg gtggactatt tacggtaaac tgcccacttg gcagtacatc aagtgtatca    240
tatgccaagt acgccccta ttgacgtcaa tgacggtaaa tggcccgcct ggcattatgc     300
ccagtacatg accttatggg actttcctac ttggcagtac atctacgtat tagtcatcgc    360
tattaccatg gtcgaggtg agccccacgt tctgcttcac tctccccatc tccccccct     420 ccccacccc aattttgtat ttatttattt tttaattatt ttgtgcagcg atggggggcgg    480 ggggggggg ggcgcgcgcc aggcggggcg gggcggggcg aggggcgggg cggggcgagg    540
cggagaggtg cggcggcagc caatcagagc ggcgcgctcc gaaagtttcc ttttatggcg    600
aggcggcggc ggcggcggcc ctataaaaag cgaagcgcgc ggcgggcggg agtcgctgcg    660
ttgccttcgc cccgtgcccc gctccgcgcc gcctcgcgcc gcccgccccg gctctgactg    720
accgcgttac tcccacaggt gagcggggcgg gacggcccct tctcctccggg ctgtaattag  780 cgcttggttt aatgacggct cgtttctttt ctgtggctgc gtgaaagcct taaagggctc    840
cgggagggcc ctttgtgcgg gggggagcgg ctcgggggt gcgtgcgtgt gtgtgtgcgt     900
ggggagcgcc gcgtgcggcc cgcgctgccc ggcggctgtg agcgctgcgg gcgcggcgcg    960
gggctttgtg cgctccgcgt gtgcgcgagg ggagcgcggc cggggcggt gccccgcggt    1020
```

-continued

```
gcggggggc tgcgagggga acaaaggctg cgtgcggggt gtgtgcgtgg gggggtgagc   1080
agggggtgtg ggcgcggcgg tcgggctgta acccccccct gcaccccccct ccccgagttg   1140 ctgagcacgg cccggcttcg ggtgcggggc tccgtgcggg gcgtggcgcg gggctcgccg   1200
tgccgggcgg ggggtggcgg caggtggggg tgccgggcgg ggcggggccg cctcgggccg   1260
gggagggctc gggggagggg cgcggcggcc ccggagcgcc ggcggctgtc gaggcgcggc   1320
gagccgcagc cattgccttt tatggtaatc gtgcgagagg gcgcagggac ttcctttgtc   1380
ccaaatctgg cggagccgaa atctgggagg cgccgccgca ccccctctag cgggcgcggg   1440
cgaagcggtg cggcgccggc aggaaggaaa tgggcgggga gggccttcgt gcgtcgccgc   1500
gccgccgtcc ccttctccat ctccagcctc ggggctgccg cagggggacg gctgccttcg   1560 gggggacgg ggcagggcgg ggttcggctt ctggcgtgtg accggcggga attc          1614
```

```
<210> SEQ ID NO 37
<211> LENGTH: 1531
<212> TYPE: DNA
<213> ORGANISM: Artificial Sequence
<220> FEATURE:
<223> OTHER INFORMATION: DNA fragment containing VSV-G

<400> SEQUENCE: 37
gaattcatga agtgcctttt gtacttagcc tttttattca ttggggtgaa ttgcaagttc     60
accatagttt ttccacacaa ccaaaaagga aactggaaaa atgttccttc taattaccat    120
tattgcccgt caagctcaga tttaaattgg cataatgact taataggcac agccttacaa    180
gtcaaaatgc ccaagagtca caaggctatt caagcagacg gttggatgtg tcatgcttcc    240
aaatgggtca ctacttgtga tttccgctgg tatggaccga agtatataac acattccatc    300
cgatccttca ctccatctgt agaacaatgc aaggaaagca ttgaacaaac gaaacaagga    360
acttggctga atccaggctt ccctcctcaa agttgtggat atgcaactgt gacggatgcc    420
gaagcagtga ttgtccaggt gactcctcac catgtgctgg ttgatgaata cacaggagaa    480
tgggttgatt cacagttcat caacggaaaa tgcagcaatt acatatgccc cactgtccat    540
aactctacaa cctggcattc tgactataag gtcaaagggc tatgtgattc taacctcatt    600
tccatggaca tcaccttctt ctcagaggac ggagagctat catccctggg aaaggagggc    660
acagggttca gaagtaacta ctttgcttat gaaactggag gcaaggcctg caaaatgcaa    720
tactgcaagc attggggagt cagactccca tcaggtgtct ggttcgagat ggctgataag    780
gatctctttg ctgcagccag attccctgaa tgcccagaag ggtcaagtat ctctgctcca    840
tctcagacct cagtggatgt aagtctaatt caggacgttg agaggatctt ggattattcc    900
ctctgccaag aaacctggag caaaatcaga gcgggtcttc caatctctcc agtggatctc    960
agctatcttg ctcctaaaaa cccaggaacc ggtcctgctt tcaccataat caatggtacc   1020
ctaaaatact ttgagaccag atacatcaga gtcgatattg ctgctccaat cctctcaaga   1080
atggtcggaa tgatcagtgg aactaccaca gaaagggaac tgtgggatga ctgggcacca   1140
tatgaagacg tggaaattgg acccaatgga gttctgagga ccagttcagg atataagttt   1200
cctttataca tgattggaca tggtatgttg gactccgatc ttcatcttag ctcaaaggct   1260
caggtgttcg aacatcctca cattcaagac gctgcttcgc aacttcctga tgatgagagt   1320
ttattttttg gtgatactgg gctatccaaa aatccaatcg agcttgtaga aggttggttc   1380
agtagttgga aagctctat tgcctctttt ttctttatca tagggttaat cattggacta    1440
ttcttggttc tccgagttgg tatccatctt tgcattaaat taaagcacac caagaaaaga   1500
```
cagatttata cagacataga gatgagaatt c                              1531

<210> SEQ ID NO 38
<211> LENGTH: 884
<212> TYPE: DNA
<213> ORGANISM: Artificial Sequence
<220> FEATURE:
<223> OTHER INFORMATION: RSV promoter and HIV Rev

<400> SEQUENCE: 38
caattgcgat gtacgggcca gatatacgcg tatctgaggg gactagggtg tgtttaggcg      60
aaaagcgggg cttcggttgt acgcggttag gagtcccctc aggatatagt agtttcgctt     120
ttgcataggg aggggaaat gtagtcttat gcaatacact tgtagtcttg caacatggta     180
acgatgagtt agcaacatgc cttacaagga gagaaaaagc accgtgcatg ccgattggtg     240
gaagtaaggt ggtacgatcg tgccttatta ggaaggcaac agacaggtct gacatggatt     300
ggacgaacca ctgaattccg cattgcagag ataattgtat ttaagtgcct agctcgatac     360
aataaacgcc atttgaccat tcaccacatt ggtgtgcacc tccaagctcg agctcgttta     420
gtgaaccgtc agatcgcctg gagacgccat ccacgctgtt ttgacctcca tagaagacac     480
cgggaccgat ccagcctccc ctcgaagcta gcgattaggc atctcctatg caggaagaa     540
gcggagacag cgacgaagaa ctcctcaagg cagtcagact catcaagttt ctctatcaaa     600
gcaacccacc tcccaatccc gaggggaccc gacaggcccg aaggaataga agaagaaggt     660
ggagagagag acagagacag atccattcga ttagtgaacg gatccttagc acttatctgg     720
gacgatctgc ggagcctgtg cctcttcagc taccaccgct tgagagactt actcttgatt     780
gtaacgagga ttgtggaact tctgggacgc aggggtggg aagccctcaa atattggtgg     840
aatctcctac aatattggag tcaggagcta agaatagtc taga                       884

<210> SEQ ID NO 39
<211> LENGTH: 1104
<212> TYPE: DNA
<213> ORGANISM: Artificial Sequence
<220> FEATURE:
<223> OTHER INFORMATION: Elongation Factor-1 alpha (EF1-alpha) promoter

<400> SEQUENCE: 39
ccggtgccta gagaaggtgg cgcggggtaa actgggaaag tgatgtcgtg tactggctcc      60
gcctttttcc cgagggtggg ggagaaccgt atataagtgc agtagtcgcc gtgaacgttc     120
tttttcgcaa cgggtttgcc gccagaacac aggtaagtgc cgtgtgtggt tcccgcgggc     180
ctggcctctt tacgggttat ggcccttgcg tgccttgaat tacttccacg cccctggctg     240
cagtacgtga ttcttgatcc cgagcttcgg gttggaagtg ggtgggagag ttcgaggcct     300
tgcgcttaag gagccccttc gcctcgtgct tgagttgagg cctggcctgg gcgctgggc     360
cgccgcgtgc gaatctggtg gcaccttcgc gcctgtctcg ctgctttcga taagtctcta     420
gccatttaaa attttttgatg acctgctgcg acgctttttt tctggcaaga tagtcttgta     480
aatgcgggcc aagatctgca cactggtatt tcggtttttg gggccgcggg cggcgacggg     540
gcccgtgcgt cccagcgcac atgttcggcg aaggcggggcc tgcgagcgcg ccaccgaga     600
atcggacggg ggtagtctca agctggccgg cctgctctgg tgcctggcct cgcgccgccg     660
tgtatcgccc cgccctgggc ggcaaggctg gcccggtcgg caccagttgc gtgagcggaa     720
agatggccgc ttcccggccc tgctgcaggg agctcaaaat ggaggacgcg gcgctcggga     780

| | |
|---|---|
| gagcgggcgg gtgagtcacc cacacaaagg aaaagggcct ttccgtcctc agccgtcgct | 840 |
| tcatgtgact ccacggagta ccgggcgccg tccaggcacc tcgattagtt ctcgagcttt | 900 |
| tggagtacgt cgtctttagg ttgggggggag gggttttatg cgatggagtt tccccacact | 960 |
| gagtgggtgg agactgaagt taggccagct tggcacttga tgtaattctc cttggaattt | 1020 |
| gcccttttg agtttggatc ttggttcatt ctcaagcctc agacagtggt tcaaagtttt | 1080 |
| tttcttccat ttcaggtgtc gtga | 1104 |

```
<210> SEQ ID NO 40
<211> LENGTH: 511
<212> TYPE: DNA
<213> ORGANISM: Artificial Sequence
<220> FEATURE:
<223> OTHER INFORMATION: Promoter; PGK

<400> SEQUENCE: 40
```

| | |
|---|---|
| ggggttgggg ttgcgccttt tccaaggcag ccctgggttt gcgcagggac gcggctgctc | 60 |
| tgggcgtggt tccgggaaac gcagcggcgc cgaccctggg tctcgcacat tcttcacgtc | 120 |
| cgttcgcagc gtcacccgga tcttcgccgc taccctgtg ggccccccgg cgacgcttcc | 180 |
| tgctccgccc ctaagtcggg aaggttcctt gcggttcgcg gcgtgccgga cgtgacaaac | 240 |
| ggaagccgca cgtctcacta gtaccctcgc agacggacag cgccagggag caatggcagc | 300 |
| gcgccgaccg cgatgggctg tggccaatag cggctgctca gcaggcgcg ccgagagcag | 360 |
| cggccgggaa ggggcggtgc gggaggcggg gtgtggggcg gtagtgtggg ccctgttcct | 420 |
| gcccgcgcg tgttccgcat tctgcaagcc tccgagcgc acgtcggcag tcggctccct | 480 |
| cgttgaccga atcaccgacc tctctcccca g | 511 |

```
<210> SEQ ID NO 41
<211> LENGTH: 1162
<212> TYPE: DNA
<213> ORGANISM: Artificial Sequence
<220> FEATURE:
<223> OTHER INFORMATION: Promoter; UbC

<400> SEQUENCE: 41
```

| | |
|---|---|
| gcgccgggtt ttggcgcctc ccgcgggcgc ccccctcctc acggcgagcg ctgccacgtc | 60 |
| agacgaaggg cgcaggagcg ttcctgatcc ttccgcccgg acgctcagga cagcggcccg | 120 |
| ctgctcataa gactcggcct tagaaccccca gtatcagcag aaggacatt taggacggga | 180 |
| cttgggtgac tctagggcac tggttttctt tccagagagc ggaacaggcg aggaaaagta | 240 |
| gtcccttctc ggcgattctg cggagggatc tccgtgggc ggtgaacgcc gatgattata | 300 |
| taaggacgcg ccgggtgtgg cacagctagt tccgtcgcag ccgggattg gtcgcggtt | 360 |
| cttgtttgtg gatcgctgtg atcgtcactt ggtgagttgc gggctgctgg gctggccggg | 420 |
| gctttcgtgg ccgccgggcc gctcggtggg acggaagcgt gtggagagac cgccaagggc | 480 |
| tgtagtctgg gtccgcgagc aaggttgccc tgaactgggg gttgggggga gcgcacaaaa | 540 |
| tggcggctgt tcccgagtct tgaatggaag acgcttgtaa ggcgggctgt gaggtcgttg | 600 |
| aaacaaggtg gggggcatgg tgggcggcaa gaacccaagg tcttgaggcc ttcgctaatg | 660 |
| cgggaaagct cttattcggg tgagatgggc tggggcacca tctgggacc ctgacgtgaa | 720 |
| gtttgtcact gactggagaa ctcgggttg tcgtctggtt gcggggggcgg cagttatgcg | 780 |
| gtgccgttgg gcagtgcacc cgtacctttg ggagcgcgcg cctcgtcgtg tcgtgacgtc | 840 |
| acccgttctg ttggcttata atgcaggggtg gggccacctg ccggtaggtg tgcggtaggc | 900 |

```
tttctccgt cgcaggacgc agggttcggg cctagggtag gctctcctga atcgacaggc    960
gccggacctc tggtgagggg agggataagt gaggcgtcag tttctttggt cggttttatg   1020
tacctatctt cttaagtagc tgaagctccg gttttgaact atgcgctcgg ggttggcgag   1080
tgtgttttgt gaagtttttt aggcaccttt tgaaatgtaa tcatttgggt caatatgtaa   1140
ttttcagtgt tagactagta aa                                            1162

<210> SEQ ID NO 42
<211> LENGTH: 120
<212> TYPE: DNA
<213> ORGANISM: Artificial Sequence
<220> FEATURE:
<223> OTHER INFORMATION: Poly A; SV40

<400> SEQUENCE: 42
gtttattgca gcttataatg gttacaaata aagcaatagc atcacaaatt tcacaaataa     60 agcattttt tcactgcatt ctagttgtgg tttgtccaaa ctcatcaatg tatcttatca    120

<210> SEQ ID NO 43
<211> LENGTH: 227
<212> TYPE: DNA
<213> ORGANISM: Artificial Sequence
<220> FEATURE:
<223> OTHER INFORMATION: Poly A; bGH

<400> SEQUENCE: 43
gactgtgcct tctagttgcc agccatctgt tgtttgcccc tcccccgtgc cttccttgac     60
cctggaaggt gccactccca ctgtcctttc ctaataaaat gaggaaattg catcgcattg    120
tctgagtagg tgtcattcta ttctgggggg tggggtgggg caggacagca agggggagga    180
ttgggaagac aatagcaggc atgctgggga tgcggtgggc tctatgg                 227

<210> SEQ ID NO 44
<211> LENGTH: 1695
<212> TYPE: DNA
<213> ORGANISM: Artificial Sequence
<220> FEATURE:
<223> OTHER INFORMATION: Envelope; RD114

<400> SEQUENCE: 44
atgaaactcc caacaggaat ggtcattta tgtagcctaa taatagttcg ggcagggttt     60
gacgaccccc gcaaggctat cgcattagta caaaacaac atggtaaacc atgcgaatgc    120
agcggagggc aggtatccga ggccccaccg aactccatcc aacaggtaac ttgcccaggc    180
aagacggcct acttaatgac caaccaaaaa tggaaatgca gagtcactcc aaaaaatctc    240
acccctagcg ggggagaact ccagaactgc cctgtaaca ctttccagga ctcgatgcac    300
agttcttgtt atactgaata ccggcaatgc agggcgaata taagacata ctacacggcc    360 accttgctta aaatcggtc tgggagcctc aacgaggtac agatattaca aaaccccaat    420
cagctcctac agtccccttg tagggctct ataaatcagc ccgtttgctg gagtgccaca    480
gcccccatcc atatctccga tggtggagga cccctcgata ctaagagagt gtggacagtc    540
caaaaaaggc tagaacaaat tcataaggct atgcatcctg aacttcaata ccacccctta    600
gccctgccca agtcagaga tgaccttagc cttgatgcac ggacttttga tatcctgaat    660 accacttta ggttactcca gatgtccaat tttagccttg cccaagattg ttggctctgt    720
ttaaaactag gtaccctac ccctcttgcg atacccactc cctctttaac ctactcccta    780
```

```
gcagactccc tagcgaatgc ctcctgtcag attatacctc ccctcttggt tcaaccgatg      840
cagttctcca actcgtcctg tttatcttcc cctttcatta acgatacgga acaaatagac      900
ttaggtgcag tcacctttac taactgcacc tctgtagcca atgtcagtag tcctttatgt      960
gccctaaacg ggtcagtctt cctctgtgga aataacatgg catacaccta tttaccccaa     1020
aactggacag gactttgcgt ccaagcctcc ctcctcccg acattgacat catcccgggg     1080
gatgagccag tccccattcc tgccattgat cattatatac atagacctaa acgagctgta     1140
cagttcatcc ctttactagc tggactggga atcaccgcag cattcaccac cggagctaca     1200
ggcctaggtg tctccgtcac ccagtataca aaattatccc atcagttaat atctgatgtc     1260
caagtcttat ccggtaccat acaagattta caagaccagg tagactcgtt agctgaagta     1320
gttctccaaa ataggagggg actggaccta ctaacggcag aacaaggagg aatttgttta     1380
gccttacaag aaaaatgctg tttttatgct aacaagtcag gaattgtgag aaacaaaata     1440
agaaccctac aagaagaatt acaaaaacgc agggaaagcc tggcatccaa ccctctctgg     1500
accgggctgc agggctttct tccgtacctc ctacctctcc tgggaccct actcaccctc      1560 ctactcatac taaccattgg gccatgcgtt ttcaatcgat tggtccaatt tgttaaagac     1620
aggatctcag tggtccaggc tctggttttg actcagcaat atcaccagct aaaacccata     1680
gagtacgagc catga                                                      1695
```

<210> SEQ ID NO 45
<211> LENGTH: 2013
<212> TYPE: DNA
<213> ORGANISM: Artificial Sequence
<220> FEATURE:
<223> OTHER INFORMATION: Envelope; GALV

<400> SEQUENCE: 45

```
atgcttctca cctcaagccc gcaccacctt cggcaccaga tgagtcctgg gagctggaaa       60
agactgatca tcctcttaag ctgcgtattc ggagacggca aaacgagtct gcagaataag      120
aacccccacc agcctgtgac cctcacctgg caggtactgt cccaaactgg gacgttgtc      180 tgggacaaaa aggcagtcca gccccttttgg acttggtggc cctctcttac acctgatgta     240
tgtgccctgg cggccggtct tgagtcctgg gatatcccgg gatccgatgt atcgtcctct     300
aaaagagtta gacctcctga ttcagactat actgccgctt ataagcaaat cacctgggga     360
gccataggtg tcagctaccc tcgggctagg accaggatgg caaattcccc cttctacgtg     420
tgtccccgag ctggccgaac ccattcagaa gctaggaggt gtgggggct agaatcccta     480 tactgtaaag aatggagttg tgagaccacg ggtaccgttt attggcaacc caagtcctca     540
tgggacctca taactgtaaa atgggaccaa aatgtgaaat gggagcaaaa atttcaaaag     600
tgtgaacaaa ccggctggtg taaccccctc aagatagact tcacagaaaa aggaaaactc     660
tccagagatt ggataacgga aaaaacctgg gaattaaggt tctatgtata tggcacccca     720
ggcatacagt tgactatccg cttagaggtc actaacatgc cggttgtggc agtgggccca     780
gaccctgtcc ttgcggaaca gggacctcct agcaagcccc tcactctccc tctctcccca     840
cggaaagcgc cgcccacccc tctacccccg gcggctagtg agcaaacccc tgcggtgcat     900
ggagaaactg ttaccctaaa ctctccgcct cccaccagtg gcgaccgact cttggccctt     960 gtgcagggg ccttcctaac cttgaatgct accaacccag gggccactaa gtcttgctgg     1020
ctctgttttg gcatgagccc cccttattat gaagggatag cctcttcagg agaggtcgct     1080
tatacctcca accataccc gatgccactgg ggggcccaag gaaagcttac cctcactgag     1140
```

```
gtctccggac tcgggtcatg catagggaag gtgcctctta cccatcaaca tctttgcaac     1200
cagaccttac ccatcaattc ctctaaaaac catcagtatc tgctcccctc aaaccatagc     1260
tggtgggcct gcagcactgg cctcaccccc tgcctctcca cctcagtttt taatcagtct     1320
aaagacttct gtgtccaggt ccagctgatc ccccgcatct attaccattc tgaagaaacc     1380
ttgttacaag cctatgacaa atcaccccc aggtttaaaa gagagcctgc ctcacttacc     1440
ctagctgtct tcctggggtt agggattgcg gcaggtatag gtactggctc aaccgcccta     1500
attaaagggc ccatagacct ccagcaaggc ctaaccagcc tccaaatcgc cattgacgct     1560
gacctccggg cccttcagga ctcaatcagc aagctagagg actcactgac ttccctatct     1620
gaggtagtac tccaaaatag gagaggcctt gacttactat tccttaaaga aggaggcctc     1680
tgcgcggccc taaaagaaga gtgctgtttt tatgtagacc actcaggtgc agtacgagac     1740
tccatgaaaa aacttaaaga aagactagat aaaagacagt tagagcgcca gaaaaaccaa     1800
aactggtatg aagggtggtt caataactcc ccttggttta ctaccctact atcaaccatc     1860
gctgggcccc tattgctcct ccttttgtta ctcactcttg ggccctgcat catcaataaa     1920
ttaatccaat tcatcaatga taggataagt gcagtcaaaa ttttagtcct tagacagaaa     1980
tatcagaccc tagataacga ggaaaacctt taa                                  2013

<210> SEQ ID NO 46
<211> LENGTH: 1530
<212> TYPE: DNA
<213> ORGANISM: Artificial Sequence
<220> FEATURE:
<223> OTHER INFORMATION: Envelope; FUG

<400> SEQUENCE: 46
atggttccgc aggttctttt gtttgtactc cttctgggtt tttcgttgtg tttcgggaag       60
ttccccattt acacgatacc agacgaactt ggtccctgga gcctattga catacaccat      120 ctcagctgtc caaataacct ggttgtggag gatgaaggat gtaccaacct gtccgagttc      180
tcctacatgg aactcaaagt gggatacatc tcagccatca agtgaacgg gttcacttgc      240 acaggtgttg tgacagaggc agagacctac accaactttg ttggttatgt cacaaccaca      300
ttcaagagaa agcatttccg ccccacccca gacgcatgta gagccgcgta taactggaag      360
atggccggtg accccagata tgaagagtcc ctacacaatc cataccccga ctaccactgg      420
cttcgaactg taagaaccac caaagagtcc ctcattatca tatccccaag tgtgacagat      480
ttggacccat atgacaaatc ccttcactca agggtcttcc ctggcggaaa gtgctcagga      540
ataacggtgt cctctaccta ctgctcaact aaccatgatt acaccatttg gatgcccgag      600
aatccgagac caaggacacc ttgtgacatt tttaccaata gcagagggaa gagagcatcc      660
aacgggaaca gacttgcgg ctttgtggat gaaagaggcc tgtataagtc tctaaaagga      720
gcatgcaggc tcaagttatg tggagttctt ggacttagac ttatggatgg aacatgggtc      780
gcgatgcaaa catcagatga gaccaaatgg tgccctccag atcagttggt gaatttgcac      840
gactttcgct cagacgagat cgagcatctc gttgtggagg agttagttaa gaaaagagag      900
gaatgtctgg atgcattaga gtccatcatg accaccaagt cagtaagttt cagacgtctc      960
agtcacctga aaaacttgt cccagggttt ggaaaagcat ataccatatt caacaaaacc     1020
ttgatggagg ctgatgctca ctacaagtca gtccggacct ggaatgagat catcccctca     1080
aaagggtgtt tgaaagttgg aggaaggtgc catcctcatg tgaacggggt gttttcaat      1140
```

```
ggtataatat tagggcctga cgaccatgtc ctaatcccag agatgcaatc atccctcctc   1200
cagcaacata tggagttgtt ggaatcttca gttatccccc tgatgcaccc cctggcagac   1260
ccttctacag ttttcaaaga aggtgatgag gctgaggatt tgttgaagt tcacctcccc    1320 gatgtgtaca acagatctc aggggttgac ctgggtctcc cgaactgggg aaagtatgta    1380
ttgatgactg caggggccat gattggcctg tgttgatat tttccctaat gacatggtgc    1440
agagttggta tccatctttg cattaaatta aagcacacca agaaaagaca gatttataca   1500
gacatagaga tgaaccgact tggaaagtaa                                    1530
```

<210> SEQ ID NO 47
<211> LENGTH: 1497
<212> TYPE: DNA
<213> ORGANISM: Artificial Sequence
<220> FEATURE:
<223> OTHER INFORMATION: Envelope; LCMV

<400> SEQUENCE: 47

```
atgggtcaga ttgtgacaat gtttgaggct ctgcctcaca tcatcgatga ggtgatcaac     60
attgtcatta ttgtgcttat cgtgatcacg ggtatcaagg ctgtctacaa ttttgccacc    120
tgtgggatat tcgcattgat cagtttccta cttctggctg caggtcctg tggcatgtac     180 ggtcttaagg gacccgacat ttacaaagga gtttaccaat taagtcagt ggagtttgat     240 atgtcacatc tgaacctgac catgcccaac gcatgttcag ccaacaactc ccaccattac    300
atcagtatgg ggacttctgg actagaattg accttcacca tgattccat catcagtcac     360 aacttttgca atctgacctc tgccttcaac aaaaagacct tgaccacac actcatgagt     420 atagtttcga gcctacacct cagtatcaga gggaactcca actataaggc agtatcctgc    480
gacttcaaca atggcataac catccaatac aacttgacat tctcagatcg acaaagtgct   540
cagagccagt gtagaacctt cagaggtaga gtcctagata tgtttagaac tgccttcggg    600
gggaaataca tgaggagtgg ctggggctgg acaggctcag atggcaagac cacctggtgt    660
agccagacga gttaccaata cctgattata caaaatagaa cctgggaaaa ccactgcaca    720
tatgcaggtc cttttgggat gtccaggatt ctccttttcc aagagaagac taagttcttc    780
actaggagac tagcgggcac attcacctgg actttgtcag actcttcagg ggtggagaat    840
ccaggtggtt attgcctgac caaatggatg attcttgctg cagagcttaa gtgtttcggg    900
aacacagcag ttgcgaaatg caatgtaaat catgatgccg aattctgtga catgctgcga    960
ctaattgact acaacaaggc tgctttgagt aagttcaaag aggacgtaga atctgccttg    1020
cacttattca aaacaacagt gaattctttg atttcagatc aactactgat gaggaaccac    1080
ttgagagatc tgatggggt gccatattgc aattactcaa agttttggta cctagaacat    1140
gcaaagaccg gcgaaactag tgtccccaag tgctggcttg tcaccaatgg ttcttactta    1200
aatgagaccc acttcagtga tcaaatcgaa caggaagccg ataacatgat tacagagatg    1260
ttgaggaagg attacataaa gaggcagggg agtaccccc tagcattgat ggaccttctg    1320
atgttttcca catctgcata tctagtcagc atcttcctgc accttgtcaa ataccaaca    1380 cacaggcaca taaaggtgg ctcatgtcca agccacacc gattaaccaa caagggaatt    1440
tgtagttgtg gtgcatttaa ggtgcctggt gtaaaaaccg tctggaaaag acgctga      1497
```

<210> SEQ ID NO 48
<211> LENGTH: 1692
<212> TYPE: DNA
<213> ORGANISM: Artificial Sequence
<220> FEATURE:
<223> OTHER INFORMATION: Envelope; FPV

<400> SEQUENCE: 48

```
atgaacactc aaatcctggt tttcgccctt gtggcagtca tccccacaaa tgcagacaaa     60
atttgtcttg gacatcatgc tgtatcaaat ggcaccaaag taaacacact cactgagaga    120
ggagtagaag ttgtcaatgc aacggaaaca gtggagcgga caaacatccc caaaatttgc    180
tcaaaaggga aaagaaccac tgatcttggc caatgcggac tgttagggac cattaccgga    240
ccacctcaat gcgaccaatt tctagaattt tcagctgatc taataatcga gagacgagaa    300
ggaaatgatg tttgttaccc ggggaagttt gttaatgaag aggcattgcg acaaatcctc    360
agaggatcag gtgggattga caaagaaaca atgggattca catatagtgg aataaggacc    420
aacggaacaa ctagtgcatg tagaagatca gggtcttcat tctatgcaga aatggagtgg    480
ctcctgtcaa atacagacaa tgctgctttc ccacaaatga caaaatcata caaaaacaca    540
aggagagaat cagctctgat agtctgggga atccaccatt caggatcaac caccgaacag    600
accaaactat atgggagtgg aaataaactg ataacagtcg ggagttccaa atatcatcaa    660
tcttttgtgc cgagtccagg aacacgaccg cagataaatg gccagtccgg acggattgat    720
tttcattggt tgatcttgga tcccaatgat acagttactt ttagtttcaa tggggctttc    780
atagctccaa atcgtgccag cttcttgagg ggaaagtcca tggggatcca gagcgatgtg    840
caggttgatg ccaattgcga aggggaatgc taccacagtg gagggactat aacaagcaga    900
ttgccttttc aaaacatcaa tagcagagca gttggcaaat gcccaagata tgtaaaacag    960
gaaagtttat tattggcaac tggtatgaag aacgttcccg aaccttccaa aaaaaggaaa   1020
aaaagaggcc tgtttggcgc tatagcaggg tttattgaaa atggttggga aggtctggtc   1080
gacgggtggt acggtttcag gcatcagaat gcacaaggag aaggaactgc agcagactac   1140
aaaagcaccc aatcggcaat tgatcagata accggaaagt taaatagact cattgagaaa   1200
accaaccagc aatttgagct aatagataat gaattcactg aggtggaaaa gcagattggc   1260
aatttaatta actggaccaa agactccatc acagaagtat ggtcttacaa tgctgaactt   1320
cttgtggcaa tggaaaacca gcacactatt gatttggctg attcagagat gaacaagctg   1380
tatgagcgag tgaggaaaca attaagggaa aatgctgaag aggatggcac tggttgcttt   1440
gaaatttttc ataaatgtga cgatgattgt atggctagta taaggaacaa tacttatgat   1500
cacagcaaat acagagaaga agcgatgcaa aatagaatac aaattgaccc agtcaaattg   1560
agtagtggct acaaagatgt gatactttgg tttagcttcg ggcatcatg ctttttgctt   1620
cttgccattg caatgggcct tgttttcata tgtgtgaaga acggaaacat gcggtgcact   1680
atttgtatat aa                                                       1692
```

<210> SEQ ID NO 49
<211> LENGTH: 1266
<212> TYPE: DNA
<213> ORGANISM: Artificial Sequence
<220> FEATURE:
<223> OTHER INFORMATION: Envelope; RRV

<400> SEQUENCE: 49

```
agtgtaacag agcactttaa tgtgtataag gctactagac catacctagc acattgcgcc     60
gattgcgggg acgggtactt ctgctatagc ccagttgcta tcgaggagat ccgagatgag    120
gcgtctgatg gcatgcttaa gatccaagtc tccgcccaaa taggtctgga caaggcaggc    180
```

```
acccacgccc acacgaagct ccgatatatg gctggtcatg atgttcagga atctaagaga      240
gattccttga gggtgtacac gtccgcagcg tgctccatac atgggacgat gggacacttc      300
atcgtcgcac actgtccacc aggcgactac ctcaaggttt cgttcgagga cgcagattcg      360
cacgtgaagg catgtaaggt ccaatacaag cacaatccat tgccggtggg tagagagaag      420
ttcgtggtta gaccacactt tggcgtagag ctgccatgca cctcatacca gctgacaacg      480
gctcccaccg acgaggagat tgacatgcat acaccgccag atataccgga tcgcaccctg      540
ctatcacaga cggcgggcaa cgtcaaaata acagcaggcg gcaggactat caggtacaac      600
tgtacctgcg gccgtgacaa cgtaggcact accagtactg acaagaccat caacacatgc      660
aagattgacc aatgccatgc tgccgtcacc agccatgaca aatggcaatt tacctctcca      720
tttgttccca gggctgatca gacagctagg aaaggcaagg tacacgttcc gttccctctg      780
actaacgtca cctgccgagt gccgttggct cgagcgccgg atgccaccta tggtaagaag      840
gaggtgaccc tgagattaca cccagatcat ccgacgctct tctcctatag gagtttagga      900
gccgaaccgc acccgtacga ggaatgggtt gacaagttct ctgagcgcat catcccagtg      960
acggaagaag ggattgagta ccagtggggc aacaacccgc cggtctgcct gtgggcgcaa      1020
ctgacgaccg agggcaaacc ccatggctgg ccacatgaaa tcattcagta ctattatgga      1080
ctataccccg ccgccactat tgccgcagta tccggggcga gtctgatggc cctcctaact      1140
ctggcggcca catgctgcat gctggccacc gcgaggagaa agtgcctaac accgtacgcc      1200
ctgacgccag gagcggtggt accgttgaca ctggggctgc tttgctgcgc accgagggcg      1260
aatgca                                                                1266

<210> SEQ ID NO 50
<211> LENGTH: 1938
<212> TYPE: DNA
<213> ORGANISM: Artificial Sequence
<220> FEATURE:
<223> OTHER INFORMATION: Envelope; MLV 10A1

<400> SEQUENCE: 50
atggaaggtc cagcgttctc aaaccccctt aaagataaga ttaacccgtg gaagtcctta       60
atggtcatgg gggtctattt aagagtaggg atggcagaga gcccccatca ggtctttaat      120
gtaacctgga gagtcaccaa cctgatgact gggcgtaccg ccaatgccac ctccctttta      180
ggaactgtac aagatgcctt cccaagatta tattttgatc tatgtgatct ggtcggagaa      240
gagtgggacc cttcagacca ggaaccatat gtcgggtatg gctgcaaata ccccggaggg      300
agaaagcgga cccggacttt tgacttttac gtgtgccctg gcataccgt aaaatcgggg     360 tgtgggggc aagagaggg ctactgtggt gaatgggggtt gtgaaaccac cggacaggct     420
tactggaagc ccacatcatc atgggaccta atctccctta agcgcggtaa cacccccctgg    480 gacacgggat gctccaaaat ggcttgtggc ccctgctacg acctctccaa agtatccaat      540
tccttccaag gggctactcg aggggcaga tgcaaccctc tagtcctaga attcactgat      600
gcaggaaaaa aggctaattg gacgggccc aaatcgtggg gactgagact gtaccggaca      660
ggaacagatc ctattaccat gttctccctg acccgccagg tcctcaatat agggcccgc      720 atccccattg ggcctaatcc cgtgatcact ggtcaactac cccctcccg acccgtgcag      780 atcaggctcc ccaggcctcc tcagcctcct cctacaggcg cagcctctat agtccctgag      840
actgccccac cttctcaaca acctgggacg ggagacaggc tgctaaacct ggtagaagga      900
gcctatcagg cgcttaacct caccaatccc gacaagaccc aagaatgttg gctgtgctta      960
```

```
gtgtcgggac ctccttatta cgaaggagta gcggtcgtgg gcacttatac caatcattct   1020
accgccccgg ccagctgtac ggccacttcc aacataagc ttaccctatc tgaagtgaca   1080
ggacagggcc tatgcatggg agcactacct aaaactcacc aggccttatg taacaccacc   1140
caaagtgccg gctcaggatc ctactacctt gcagcaccg ctggaacaat gtgggcttgt   1200
agcactggat tgactccctg cttgtccacc acgatgctca atctaaccac agactattgt   1260
gtattagttg agctctggcc cagaataatt taccactccc ccgattatat gtatggtcag   1320
cttgaacagc gtaccaaata taagagggag ccagtatcgt tgaccctggc ccttctgcta   1380
ggaggattaa ccatgggagg gattgcagct ggaataggga cggggaccac tgccctaatc   1440
aaaacccagc agtttgagca gcttcacgcc gctatccaga cagacctcaa cgaagtcgaa   1500
aaatcaatta ccaacctaga aaagtcactg acctcgttgt ctgaagtagt cctacagaac   1560
cgaagaggcc tagatttgct cttcctaaaa gagggaggtc tctgcgcagc cctaaaagaa   1620
gaatgttgtt tttatgcaga ccacacggga ctagtgagag acagcatggc caaactaagg   1680
gaaaggctta atcagagaca aaactatttt gagtcaggcc aaggttggtt cgaagggcag   1740
tttaatagat cccctggtt taccaccta atctccacca tcatgggacc tctaatagta   1800
ctcttactga tcttactctt tggaccctgc attctcaatc gattggtcca atttgttaaa   1860
gacaggatct cagtggtcca ggctctggtt ttgactcaac aatatcacca gctaaaacct   1920
atagagtacg agccatga                                                 1938

<210> SEQ ID NO 51
<211> LENGTH: 2030
<212> TYPE: DNA
<213> ORGANISM: Artificial Sequence
<220> FEATURE:
<223> OTHER INFORMATION: Envelope; Ebola

<400> SEQUENCE: 51
atgggtgtta caggaatatt gcagttacct cgtgatcgat tcaagaggac atcattcttt     60
ctttgggtaa ttatccttt ccaaagaaca ttttccatcc cacttggagt catccacaat    120
agcacattac aggttagtga tgtcgacaaa ctggttttgcc gtgacaaact gtcatccaca    180
aatcaattga gatcagttgg actgaatctc gaagggaatg gagtggcaac tgacgtgcca    240
tctgcaacta aaagatgggg cttcaggtcc ggtgtcccac caaaggtggt caattatgaa    300
gctggtgaat gggctgaaaa ctgctacaat cttgaaatca aaaaacctga cgggagtgag    360
tgtctaccag cagcgccaga cgggattcgg gcttccccc ggtgccggta tgtgcacaaa    420
gtatcaggaa cgggaccgtg tgccggagac tttgccttcc acaaagaggg tgctttcttc    480
ctgtatgacc gacttgcttc cacagttatc taccgaggaa cgactttcgc tgaaggtgtc    540
gttgcatttc tgatactgcc ccaagctaag aaggacttct tcagctcaca ccccttgaga    600
gagccggtca tgcaacgga ggacccgtct agtggctact attctaccac aattagatat    660
caagctaccg gttttggaac caatgagaca gagtatttgt tcgaggttga caatttgacc    720
tacgtccaac ttgaatcaag attcacacca cagtttctgc tccagctgaa tgagacaata    780
tatacaagtg gaaaaggag caataccacg ggaaaactaa tttggaaggt caaccccgaa    840
attgatacaa caatcgggga gtgggccttc tgggaaacta aaaaaacctc actagaaaaa    900
ttcgcagtga gagttgtct ttcacagctg tatcaaacag agccaaaaac atcagtggtc    960
agagtccggc gcgaacttct tccgacccag ggaccaacac aacaactgaa gaccacaaaa   1020
```

```
tcatggcttc agaaaattcc tctgcaatgg ttcaagtgca cagtcaagga agggaagctg    1080
cagtgtcgca tctgacaacc cttgccacaa tctccacgag tcctcaaccc cccacaacca    1140
aaccaggtcc ggacaacagc acccacaata cacccgtgta taaacttgac atctctgagg    1200
caactcaagt tgaacaacat caccgcagaa cagacaacga cagcacagcc tccgacactc    1260
cccccgccac gaccgcagcc ggaccccgaa aagcagagaa caccaacacg agcaagggta    1320
ccgacctcct ggaccccgcc accacaacaa gtccccaaaa ccacagcgag accgctggca    1380
acaacaacac tcatcaccaa gataccggag aagagagtgc cagcagcggg aagctaggct    1440
taattaccaa tactattgct ggagtcgcag gactgatcac aggcgggagg agagctcgaa    1500
gagaagcaat tgtcaatgct caacccaaat gcaaccctaa tttacattac tggactactc    1560
aggatgaagg tgctgcaatc ggactggcct ggataccata tttcgggcca gcagccgagg    1620
gaatttacat agaggggctg atgcacaatc aagatggttt aatctgtggg ttgagacagc    1680
tggccaacga gacgactcaa gctcttcaac tgttcctgag agccacaacc gagctacgca    1740
ccttttcaat cctcaaccgt aaggcaattg atttcttgct gcagcgatgg ggcggcacat    1800
gccacatttt gggaccggac tgctgtatcg aaccacatga ttggaccaag aacataacag    1860
acaaaattga tcagattatt catgattttg ttgataaaac ccttccggac caggggggaca   1920 atgacaattg gtggacagga tggagacaat ggataccggc aggtattgga gttacaggcg    1980
ttataattgc agttatcgct ttattctgta tatgcaaatt tgtcttttag                2030
```

<210> SEQ ID NO 52
<211> LENGTH: 237
<212> TYPE: DNA
<213> ORGANISM: Artificial Sequence
<220> FEATURE:
<223> OTHER INFORMATION: Polymerase III shRNA promoters; U6 promoter

<400> SEQUENCE: 52

```
tttcccatga ttccttcata tttgcatata cgatacaagg ctgttagaga gataattgga      60
attaatttga ctgtaaacac aaagatatta gtacaaaata cgtgacgtag aaagtaataa     120
tttcttgggt agtttgcagt tttaaaatta tgttttaaaa tggactatca tatgcttacc     180
gtaacttgaa agtatttcga tttccttggct ttatatatct tgtggaaagg acgaaac        237
```

<210> SEQ ID NO 53
<211> LENGTH: 243
<212> TYPE: DNA
<213> ORGANISM: Artificial Sequence
<220> FEATURE:
<223> OTHER INFORMATION: Polymerase III shRNA promoters; 7SK promoter

<400> SEQUENCE: 53

```
ctgcagtatt tagcatgccc cacccatctg caaggcattc tggatagtgt caaaacagcc      60
ggaaatcaag tccgtttatc tcaaacttta gcattttggg aataaatgat atttgctatg     120
ctggttaaat tagattttag ttaaatttcc tgctgaagct ctagtacgat aagcaacttg     180
acctaagtgt aaagttgaga tttccttcag gtttatatag cttgtgcgcc gcctggctac     240
ctc                                                                    243
```

<210> SEQ ID NO 54
<211> LENGTH: 21
<212> TYPE: DNA
<213> ORGANISM: Artificial Sequence
<220> FEATURE:
<223> OTHER INFORMATION: FDPS target sequence #1

<400> SEQUENCE: 54
gtcctggagt acaatgccat t                                           21

<210> SEQ ID NO 55
<211> LENGTH: 21
<212> TYPE: DNA
<213> ORGANISM: Artificial Sequence
<220> FEATURE:
<223> OTHER INFORMATION: FDPS target sequence #2

<400> SEQUENCE: 55
gcaggatttc gttcagcact t                                           21

<210> SEQ ID NO 56
<211> LENGTH: 21
<212> TYPE: DNA
<213> ORGANISM: Artificial Sequence
<220> FEATURE:
<223> OTHER INFORMATION: FDPS target sequence #3

<400> SEQUENCE: 56
gccatgtaca tggcaggaat t                                           21

<210> SEQ ID NO 57
<211> LENGTH: 21
<212> TYPE: DNA
<213> ORGANISM: Artificial Sequence
<220> FEATURE:
<223> OTHER INFORMATION: FDPS target sequence #4

<400> SEQUENCE: 57
gcagaaggag gctgagaaag t                                           21

<210> SEQ ID NO 58
<211> LENGTH: 49
<212> TYPE: DNA
<213> ORGANISM: Artificial Sequence
<220> FEATURE:
<223> OTHER INFORMATION: Non-targeting sequence

<400> SEQUENCE: 58
gccgctttgt aggatagagc tcgagctcta tcctacaaag cggctttt              49

<210> SEQ ID NO 59
<211> LENGTH: 20
<212> TYPE: DNA
<213> ORGANISM: Artificial Sequence
<220> FEATURE:
<223> OTHER INFORMATION: Forward primer

<400> SEQUENCE: 59
aggaattgat ggcgagaagg                                             20

<210> SEQ ID NO 60
<211> LENGTH: 22
<212> TYPE: DNA
<213> ORGANISM: Artificial Sequence
<220> FEATURE:
<223> OTHER INFORMATION: Reverse primer

<400> SEQUENCE: 60
cccaaagagg tcaaggtaat ca                                          22

<210> SEQ ID NO 61

```
<211> LENGTH: 18
<212> TYPE: DNA
<213> ORGANISM: Artificial Sequence
<220> FEATURE:
<223> OTHER INFORMATION: Forward primer

<400> SEQUENCE: 61
agcgcggcta cagcttca                                                   18

<210> SEQ ID NO 62
<211> LENGTH: 20
<212> TYPE: DNA
<213> ORGANISM: Artificial Sequence
<220> FEATURE:
<223> OTHER INFORMATION: Reverse primer

<400> SEQUENCE: 62
ggcgacgtag cacagcttct                                                 20

<210> SEQ ID NO 63
<211> LENGTH: 130
<212> TYPE: DNA
<213> ORGANISM: Artificial Sequence
<220> FEATURE:
<223> OTHER INFORMATION: Left Inverted Terminal Repeat (Left ITR)

<400> SEQUENCE: 63
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact    120
aggggttcct                                                           130

<210> SEQ ID NO 64
<211> LENGTH: 151
<212> TYPE: DNA
<213> ORGANISM: Artificial Sequence
<220> FEATURE:
<223> OTHER INFORMATION: Right Inverted Terminal Repeat (Right ITR)

<400> SEQUENCE: 64
gagcggccgc aggaacccct agtgatggag ttggccactc cctctctgcg cgctcgctcg     60
ctcactgagg ccgggcgacc aaaggtcgcc cgacgcccgg gctttgcccg gcggcctca    120 gtgagcgagc gagcgcgcag ctgcctgcag g                                   151

<210> SEQ ID NO 65
<211> LENGTH: 1227
<212> TYPE: DNA
<213> ORGANISM: Artificial Sequence
<220> FEATURE:
<223> OTHER INFORMATION: RRE/rabbit poly A beta globin

<400> SEQUENCE: 65
tctagaagga gctttgttcc ttgggttctt gggagcagca ggaagcacta tgggcgcagc     60
gtcaatgacg ctgacggtac aggccagaca attattgtct ggtatagtgc agcagcagaa    120
caatttgctg agggctattg aggcgcaaca gcatctgttg caactcacag tctggggcat    180
caagcagctc caggcaagaa tcctggctgt ggaaagatac ctaaaggatc aacagctcct    240
agatcttttt ccctctgcca aaaattatgg ggacatcatg aagccccttg agcatctgac    300
ttctggctaa taaaggaaat ttattttcat tgcaatagtg tgttggaatt ttttgtgtct    360
ctcactcgga aggacatatg ggagggcaaa tcatttaaaa catcagaatg agtatttggt    420
ttagagtttg gcaacatatg ccatatgctg ctgccatga acaaaggtgg ctataaagag    480
```

```
gtcatcagta tatgaaacag cccctgctg tccattcctt attccataga aaagccttga    540
cttgaggtta gatttttttt atattttgtt ttgtgttatt tttttcttta acatccctaa    600
aattttcctt acatgtttta ctagccagat ttttcctcct ctcctgacta ctcccagtca    660
tagctgtccc tcttctctta tgaagatccc tcgacctgca gcccaagctt ggcgtaatca    720
tggtcatagc tgtttcctgt gtgaaattgt tatccgctca caattccaca caacatacga    780 gccgaagca taaagtgtaa agcctggggt gcctaatgag tgagctaact cacattaatt    840
gcgttgcgct cactgcccgc tttccagtcg ggaaacctgt cgtgccagcg gatccgcatc    900
tcaattagtc agcaaccata gtcccgcccc taactccgcc catcccgccc ctaactccgc    960
ccagttccgc ccattctccg ccccatggct gactaatttt ttttatttat gcagaggccg    1020
aggccgcctc ggcctctgag ctattccaga agtagtgagg aggcttttt ggaggcctag    1080 gcttttgcaa aaagctaact tgtttattgc agcttataat ggttacaaat aaagcaatag    1140
catcacaaat ttcacaaata aagcattttt ttcactgcat tctagttgtg gtttgtccaa    1200
actcatcaat gtatcttatc acccggg                                       1227
```